United States Patent
Ohkubo et al.

(10) Patent No.: US 7,834,018 B2
(45) Date of Patent: Nov. 16, 2010

(54) AMINOPYRIDINE DERIVATIVES HAVING AURORA A SELECTIVE INHIBITORY ACTION

(75) Inventors: Mitsuru Ohkubo, Ushiku (JP); Tetsuya Kato, Tsukuba (JP); Nobuhiko Kawanishi, Moriya (JP); Takashi Mita, Tsukuba (JP); Toshiyasu Shimomura, Tsukuba (JP)

(73) Assignee: Banyu Pharmaceutical Co., Ltd, Chiyoda-Ku Tokyo (JP)

( * ) Notice: Subject to any disclaimer, the term of this patent is extended or adjusted under 35 U.S.C. 154(b) by 57 days.

(21) Appl. No.: 12/315,425

(22) Filed: Dec. 3, 2008

(65) Prior Publication Data
US 2009/0149470 A1 Jun. 11, 2009

Related U.S. Application Data

(62) Division of application No. 11/258,447, filed on Oct. 25, 2005, now Pat. No. 7,491,720.

(60) Provisional application No. 60/692,537, filed on Jun. 21, 2005.

(30) Foreign Application Priority Data

Oct. 29, 2004 (JP) ............................. 2004-315152
Jun. 1, 2005 (JP) ............................. 2005-161156

(51) Int. Cl.
*A61K 31/497* (2006.01)
*C07D 241/04* (2006.01)
*C07D 295/00* (2006.01)

(52) U.S. Cl. .................. 514/252.12; 544/358

(58) Field of Classification Search ............ None
See application file for complete search history.

(56) References Cited

U.S. PATENT DOCUMENTS

| | | | |
|---|---|---|---|
| 6,653,300 B2 | 11/2003 | Bebbington et al. | |
| 6,841,579 B1 | 1/2005 | Plowman et al. | |
| 2002/0065270 A1 | 5/2002 | Moriarty et al. | |
| 2008/0027042 A1* | 1/2008 | Ohkubo et al. | 514/221 |

FOREIGN PATENT DOCUMENTS

| | | |
|---|---|---|
| WO | WO 99/41253 | 8/1999 |
| WO | WO 01/17995 | 3/2001 |
| WO | WO 02/18346 | 3/2002 |
| WO | WO 02/45652 | 6/2002 |
| WO | WO 02/50066 | 6/2002 |
| WO | WO 02/059112 | 8/2002 |
| WO | WO 02/066461 | 8/2002 |
| WO | WO 02/068415 | 9/2002 |
| WO | WO 03/078423 | 9/2003 |
| WO | WO 03/078426 | 9/2003 |
| WO | WO 03/078427 | 9/2003 |
| WO | WO 2005/002571 | 1/2005 |

* cited by examiner

*Primary Examiner*—James O Wilson
*Assistant Examiner*—Noble Jarrell
(74) *Attorney, Agent, or Firm*—Matthew A. Leff; David A. Muthard

(57) ABSTRACT

The present invention relates to a compound represented by the general formula (I):

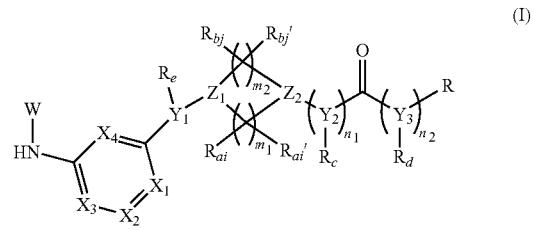

wherein $m_1$ and $m_2$ are 1, 2, or 3; $n_1$ and $n_2$ are 0 or 1; i is an integer of any of 1 to $m_1$; j is an integer of 1 to $m_2$; R is aryl, heteroaryl, or cycloalkyl any of which may be substituted; $R_{ai}$ and $R_{ai}'$ is hydrogen atom, etc. and $R_{bj}$ and $R_{bj}'$ is hydrogen atom, etc.; $R_c$, $R_d$, and $R_e$ are hydrogen atom, etc; $X_1$ is CH, $CX_{1a}$, or N; $X_2$ is CH, N, etc.; $X_3$ is CH, N, etc.; $X_4$ is CH or N; $Y_1$, $Y_2$, and $Y_3$ are each independently CH or N; $Z_1$ and $Z_2$ are each independently CH or N; W is a 5-membered aromatic heterocyclic group such as pyrazolyl, thiazolyl, etc., or a pharmaceutically acceptable salt or ester thereof; a pharmaceutical composition or antitumor agent containing the same; and combinations of the antitumor agent with other antitumor agent(s).

8 Claims, No Drawings

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Completely Synthetic Amino Acid Sequence

<400> SEQUENCE: 1

Lys Arg Arg Ala Ser Lys Gly
 1               5
```

AMINOPYRIDINE DERIVATIVES HAVING AURORA A SELECTIVE INHIBITORY ACTION

PRIORITY CLAIM

This application is a divisional of U.S. Ser. No. 11/258,447 that was filed on Oct. 25, 2005, now U.S. Pat. No. 7,491,720 which claims priority from U.S. Provisional Application No. 60/692,537, filed on Jun. 21, 2005; Japanese Application No. 2005-161156 filed on Jun. 1, 2005 and Japanese Application No. 2004-315152 filed on Oct. 29, 2004.

BACKGROUND OF THE INVENTION

The present invention relates to novel aminopyridine derivatives which are useful in the pharmaceutical field, and more particularly, to those which inhibit the growth of tumor cells based on an Aurora A selective inhibitory action and exhibit an antitumor effect, and also to an Aurora A selective inhibitor and an antitumor agent containing them.

Aurora kinase is a serine/threonine kinase involved in cell division. With regard to the Aurora kinase, three subtypes of A, B and C are known at present, and they have very high homology to each other. Aurora A participates in the maturation and distribution of centrosome or in the formation of spindle body. On the other hand, it is believed that Aurora B participates in the aggregation and pairing of chromosome, a spindle checkpoint and cytoplasm division [*Nat. Rev. Mol. Cell. Biol.*, No. 4, pp. 842-854]. Also, it is believed that Aurora C acts similarly as a result of interaction with Aurora B [*J. Biol. Chem.*, Epub ahead (2004)]. From the fact that high expression of Aurora A has been hitherto confirmed in many cancer cells; that high expression of Aurora A in normal cells leads to transformation of normal cell strains of rodent; and the like, Aurora A, being one of oncogenes, is recognized to be an adequate target for an antitumor agent [*EMBO J.*, No. 17, pp. 3052-3065 (1998)].

There is another report that cancer cells in which Aurora A is highly expressed have a resistance to paclitaxel [*Cancer Cell*, Vol. 3, pp. 51-62 (2003)]. Meanwhile, with regard to the Aurora kinase inhibitor, development of subtype-selective drugs has been thought to be difficult in view of high homology among subtypes, protein structure analysis and the like; and although there have been known reports on drugs such as ZM447-439 which inhibit both Aurora A and Aurora B at the same time [*J. Cell Biol.*, No. 161, pp. 267-280 (2003); *J. Cell Biol.*, No. 161, pp. 281-294, (2003); *Nat. Med.*, No. 10, pp. 262-267, (2004)], no report concerning Aurora A selective drugs have been known. Thus, in those reports, disclosed is the antitumor effect only for the case where a drug which inhibits both Aurora A and Aurora B at the same time is solely administered. In addition, there has been also reported a result that in a drug which inhibits both Aurora A and Aurora B at the same time, the Aurora kinase inhibiting action attenuates the action of paclitaxel [*J. Cell Biol.*, No. 161, pp. 281-294, (2003)].

Now, patent applications concerning compounds having an Aurora kinase inhibiting action have been previously filed (WO 02/057259, U.S. Pat. No. 6,664,247, etc.), and patent applications concerning aminopyridine derivatives has been filed as well (U.S. Pat. No. 6,586,424, etc.). However, there has been no report on an aminopyridine derivative having an excellent Aurora A selective inhibitory action thus far.

DETAILED DESCRIPTION OF THE INVENTION

The problems that the present invention should solve are to create novel aminopyridine derivatives which show an excellent Aurora A selective inhibitory action and cell-growth inhibitory action based on the foregoing, as well as achieve a synergistic action by a combined use with other antitumor agent(s).

In order to solve the above problems, the present inventors have synthesized a variety of novel aminopyridine derivatives and found that the compound represented by the following Formula (I) shows an excellent Aurora A selective inhibitory action and cell-growth inhibitory action based on the foregoing, and also achieves a synergistic action by a combined use with other antitumor agents, thus completing the invention. With regard to those cancers which have been unable to be completely treated with known antitumor agents such as paclitaxel because it has been impossible to use a sufficient amount of the agents owing to side-effects or drug resistance thereof, the administration of the compound according to the invention or the combined administration of the compound according to the invention with other antitumor agent is expected to exhibit an excellent antitumor effect (including potentiation of action due to the other antitumor agent) and an effect of attenuating side-effects.

Thus, the invention relates to a compound represented by Formula (I):

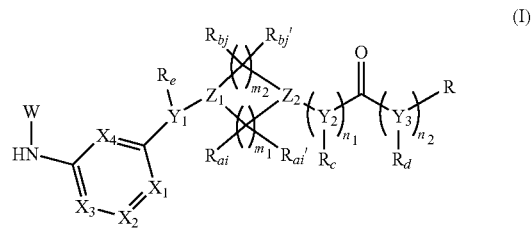

(I)

wherein:
$m_1$ is 1, 2 or 3;
$m_2$ is 1, 2 or 3;
$n_1$ is 0 or 1;
$n_2$ is 0 or 1;
i is an integer of any of 1 to $m_1$;
j is an integer of any of 1 to $m_2$;
R is aryl, heteroaryl or cycloalkyl, any of which may be substituted;
$R_{ai}$ and $R_{ai}'$, which may be the same or different, are each hydrogen atom or lower alkyl;
$R_{bj}$ and $R_{bj}'$, which may be the same or different, are each hydrogen atom or lower alkyl;
  wherein if $m_1$ is 2 or 3 and i is $i_0$ (wherein $i_0$ is an integer of any of 1 to $m_1$), and further if $m_2$ is 2 or 3 and j is $j_0$ (wherein $j_0$ is an integer of any of 1 to $m_2$), then either of $R_{ai0}$ and $R_{ai0}'$, and either of $R_{bj0}$ and $R_{bj0}'$ may be combined to form —$(CH_2)_n$— (wherein n is 1 or 2); and
$R_c$, $R_d$ and $R_e$, which may be the same or different, are each hydrogen atom or lower alkyl;
$X_1$ is CH, $CX_{1a}$ or N (wherein $X_{1a}$ is lower alkyl which may be substituted);
$X_2$ is CH, $CX_{2a}$ or N (wherein:
$X_{2a}$ is lower alkyl;

$X_{2a}$ is a substituent selected from <Substituent group $A_1$>, or lower alkyl which is substituted with one or more of the same or different substituents selected from <Substituent group $A_1$> (wherein <Substituent group $A_1$> is halogen atom; cyano; hydroxyl; lower alkylamino; di-lower alkylamino; lower alkoxy which may be substituted with one or more hydroxyl groups; lower alkylthio; and lower alkylsulfonyl); or $X_{2a}$ is $COOR_1$, $CONR_2R_3$, $NHCOR_1$, $NHCONR_2R_3$, $NHSO_2NR_2R_3$, $NR_5$ or $CH_2NR_4R_5$ (wherein:

$R_1$ is hydrogen atom or lower alkyl which may be substituted;

$R_2$ and $R_3$, which may be the same or different, are each hydrogen atom, lower alkyl which may be substituted or cycloalkyl, or alternatively $R_2$ and $R_3$, together with the nitrogen atom to which they bond, form a 5- or 6-membered aliphatic heterocyclic group which contains at least one atom selected from N, O and S and which may be substituted; and $R_4$ and $R_5$, which may be the same or different, are each hydrogen atom, lower alkyl that may be substituted or cycloalkyl); or $X_{2a}$ is a 5- or 6-membered aliphatic heterocyclic group which contains at least one atom selected from N, O and S and which may be substituted (wherein two hydrogen atoms that are bonded to the same carbon atom of the aliphatic heterocyclic group may be substituted with oxo and neighboring two carbon atoms constituting the aliphatic heterocyclic ring may be double-bonded), or lower alkyl which is substituted with the aliphatic heterocyclic group; or $X_{2a}$ is a 5- or 6-membered aromatic heterocyclic group which contains at least one atom selected from N, O and S and which may be substituted, or lower alkyl which is substituted with the aromatic heterocyclic group;

$X_3$ is CH, $CX_{3a}$ or N (wherein $X_{3a}$ is lower alkyl which may be substituted);

$X_4$ is CH or N;

The number of nitrogen atoms in $X_1$, $X_2$ and $X_3$ and $X_4$ is one or two;

$Y_1$, $Y_2$ and $Y_3$, which may be the same or different, are each CH or N, provided that if $Y_1$ is CH and $R_e$ is hydrogen atom, then the two hydrogen atoms may be substituted with oxo;

$Z_1$ and $Z_2$, which may be the same or different, are each CH or N;

W is the following group:

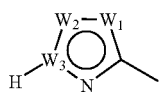

wherein:

$W_1$ is CH, N, NH, O or S;

$W_2$ is CH, $CW_{2a}$, N, $NW_{2b}$, O or S (wherein $W_{2a}$ and $W_{2b}$, which may be the same or different, are each hydrogen atom, halogen atom, cyano, $C_{1-2}$ lower alkyl, $C_{3-5}$ cycloalkyl, or $C_{1-2}$ lower alkyl which may be substituted with one or more halogen atoms);

$W_3$ is C or N; and at least one of $W_1$, $W_2$ and $W_3$ is carbon atom, provided that two of $W_1$, $W_2$ and $W_3$ are not simultaneously O and S;

(with the proviso that any compound in which $m_1$ is 1, $m_2$ is 1, and both of $Z_1$ and $Z_2$ are nitrogen atoms is excluded), or a pharmaceutically acceptable salt or ester thereof.

In another embodiment, the invention relates to a compound of general formula (I):

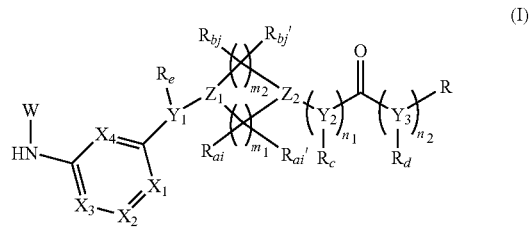

wherein:

$m_1$ is 1, 2, or 3;

$m_2$ is 1, 2, or 3;

$n_1$ is 0 or 1;

$n_2$ is 0 or 1;

i is an integer of any of 1 to $m_1$;

j is an integer of any of 1 to $m_2$;

R is aryl, heteroaryl, or cycloalkyl any of which may be substituted;

$R_{ai}$ and $R_{ai}'$ are each independently hydrogen atom and lower alkyl;

$R_{bj}$ and $R_{bj}'$ are each independently hydrogen atom and lower alkyl;

wherein:

if $m_1$ is 2 or 3 and i is $i_0$ wherein $i_0$ is an integer of any of 1 to $m_1$, and further if $m_2$ is 2 or 3 and j is $j_0$ wherein $j_0$ is an integer of any of 1 to $m_2$, then one of $R_{ai0}$ and $R_{ai0}'$ and one of $R_{bj0}$ and $R_{bj0}'$ may be combined to form —$(CH_2)_n$— wherein n is 1 or 2; and $R_c$, $R_d$, and $R_e$ are each independently hydrogen atom or lower alkyl;

$X_1$ is CH, $CX_{1a}$, or N wherein $X_{1a}$ is lower alkyl which may be substituted;

$X_2$ is CH or N;

$X_3$ is CH, $CX_{3a}$, or N wherein $X_{3a}$ is lower alkyl which may be substituted;

$X_4$ is CH or N;

the number of nitrogen atoms among $X_1$, $X_2$, and $X_3$, and $X_4$ is one or two;

$Y_1$, $Y_2$, and $Y_3$ are each independently CH or N; however, if $Y_1$ is CH and $R_e$ is hydrogen atom, then the two hydrogen atoms may be substituted with oxo;

$Z_1$ and $Z_2$ are each independently CH or N;

W is the following residue:

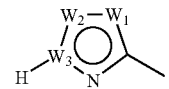

wherein:

$W_1$ is CH, N, NH, O, or S;

$W_2$ is CH, $CW_{2a}$, N, $NW_{2b}$, O or S, wherein $W_{2a}$ and $W_{2b}$ are each independently hydrogen atom, halogen atom, cyano, $C_{1-2}$ lower alkyl, $C_{3-5}$ cycloalkyl, or $C_{1-2}$ lower alkyl which may be substituted with one or more halogen atoms;

$W_3$ is C or N; and at least one of $W_1$, $W_2$, and $W_3$ is carbon atom; however two of $W_1$, $W_2$, and $W_3$ are not simultaneously O and S, with the proviso that any compound in which $m_1$ is 1, $m_2$ is 1, and both of $Z_1$ and $Z_2$ are nitrogen atom is excluded; and with the further proviso that when $W_1$ is CH, $W_2$ is CH or $CW_{2a}$, and $W_3$ is N, then $X_1$ is CH or $CX_{1a}$, $X_2$ is N, and $X_3$ is CH or $CX_{3a}$.

The invention also relates to a combined preparation for simultaneous, separate or sequential administration in the treatment of cancer, comprising two separate preparations which are:

a preparation comprising, together with a pharmaceutically acceptable carrier or diluent, a compound represented by the above-described Formula (I) or a pharmaceutically acceptable salt or ester thereof, and a preparation comprising, together with a pharmaceutically acceptable carrier or diluent, one antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents as well as pharmaceutically acceptable salt(s) or ester(s) thereof, wherein:

the antitumor alkylating agent is nitrogen mustard N-oxide, cyclophosphamide, ifosfamide, melphalan, busulfan, mitobronitol, carboquone, thiotepa, ranimustine, nimustine, temozolomide or carmustin;

the antitumor antimetabolite is methotrexate, 6-mercaptopurine riboside, mercaptopurine, 5-fluorouracil, tegafur, doxyfluridine, carmofur, cytarabine, cytarabine ocfosfate, enocitabine, S-1, gemcitabine, fludarabine or pemetrexed disodium;

the antitumor antibiotic is actinomycin D, doxorubicin, daunorubicin, neocarzinostatin, bleomycin, peplomycine, mitomycin C, aclarubicin, pirarubicin, epirubicin, zinostatin stimalamer, idarubicin, sirolimus or valrubicin;

the plant-derived antitumor agent is vincristine, vinblastine, vindesine, etoposide, sobuzoxane, docetaxel, paclitaxel or vinorelbine;

the antitumor platinum coordination compound is cisplatin, carboplatin, nedaplatin or oxaliplatin;

the antitumor camptothecin derivative is irinotecan, topotecan or camptothecin;

the antitumor tyrosine kinase inhibitor is gefitinib, imatinib or erlotinib;

the monoclonal antibody is cetuximab, bevacizumab, rituximab, bevacizumab, alemtuzumab or trastuzumab;

the interferon is interferon $\alpha$, interferon $\alpha$-2a, interferon $\alpha$-2b, interferon $\beta$, interferon $\gamma$-1a or interferon $\gamma$-n1;

the biological response modifier is krestin, lentinan, sizofuran, picibanil or ubenimex; and the other antitumor agent is mitoxantrone, L-asparaginase, procarbazine, dacarbazine, hydroxycarbamide, pentostatin, tretinoin, alefacept, darbepoetin alfa, anastrozole, exemestane, bicalutamide, leuprolelin, flutamide, fulvestrant, pegaptanib octasodium, denileukin diftitox, aldesleukin, thyrotropin alfa, arsenic trioxide, bortezomib, capecitabine or goserelin.

The invention further relates to a pharmaceutical composition comprising, together with a pharmaceutically acceptable carrier or diluent, a compound represented by the above-described Formula (I) or a pharmaceutically acceptable salt or ester thereof, and an antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, biological response modifiers and other antitumor agents (here, the definition of each antitumor agent is the same as that defined hereinabove) or a pharmaceutically acceptable salt or ester thereof.

The invention still further relates to a method for the treatment of cancer, comprising administering simultaneously, separately or sequentially a therapeutically effective amount of a compound represented by the above-described Formula (I) or a pharmaceutically acceptable salt or ester thereof in combination with a therapeutically effective amount of an antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents (here, definition of each antitumor agent is the same as that defined hereinabove) or a pharmaceutically acceptable salt or ester thereof.

Furthermore, the invention relates to the use of an Aurora selective A inhibitor for the manufacture of a medicament for the treatment of cancer; and the use of an Aurora selective A inhibitor in combination with an antitumor agent for the manufacture of a medicament for the treatment of cancer; and also relates to a method of treating cancer to a mammal (particularly a human) which comprises administering to said mammal a therapeutically effective amount of an Aurora selective A inhibitor; and a method of treating cancer in a mammal (particularly a human) which comprises administering to said mammal a therapeutically effective amount of an Aurora selective A inhibitor in combination with a therapeutically effective amount of an antitumor agent.

The invention relates to a pharmaceutical composition comprising as active ingredient an Aurora selective A inhibitor; and a pharmaceutical composition comprising as active ingredient an Aurora selective A inhibitor, together with an antitumor agent.

Next, symbols and terms used in the present specification will be explained.

The term "lower alkyl" in the above Formula (I) denotes a linear or branched alkyl group having 1 to 6 carbon atoms, and examples thereof include, for example, methyl, ethyl, propyl, isopropyl, butyl, isobutyl, sec-butyl, tert-butyl, pentyl and hexyl, among these methyl being preferred.

The term "aryl" in the above Formula (I) denotes a monocyclic, bicycle or tricyclic aromatic hydrocarbon group having 6 to 14 carbon atoms, and specifical examples thereof include phenyl, naphthyl, indenyl and anthranyl, among these phenyl being particularly preferred.

The term "heteroaryl" in the above Formula (I) denotes an aromatic heterocyclic group containing at least one atom selected from nitrogen atom, oxygen atom and sulfur atom in addition to carbon atoms, and examples thereof include 5- to 7-membered monocyclic heterocyclic groups, and condensed heterocyclic groups in which a 3- to 8-membered ring is condensed with the foregoing monocyclic heterocyclic group, specifically such as thienyl, pyrrolyl, furyl, thiazolyl, imidazolyl, pyrazolyl, oxazolyl, pyridyl, pyrazinyl, pyrimidinyl, pyridazinyl, isoxazolyl, isoquinolyl, isoindolyl, indazolyl, indolyl, quinoxalinyl, quinolyl, benzimidazolyl and benzofuranyl.

The term "cycloalkyl" in the above Formula (I) denotes a 3- to 8-membered aliphatic cyclic group such as, for example, cyclopropyl, cyclobutyl, cyclopentyl, cyclohexyl, cycloheptyl and cyclooctyl.

The term "5- or 6-membered aliphatic heterocyclic group" in the above Formula (I) denotes a 5- or 6-membered aliphatic cyclic group containing at least one atom selected from nitrogen atom, oxygen atom and sulfur atom in addition to carbon atoms, and examples thereof include pyrrolidinyl, piperidinyl, piperazinyl, morpholino, tetrahydrofuranyl, imidazolidinyl and thiomorpholino. Further, for the aliphatic heterocyclic group, two hydrogen atoms which are bonded to the same carbon atom may be substituted with an oxo group, and also, adjacent carbon atoms constituting the ring of the aliphatic heterocyclic group may be double-bonded.

The term "5- or 6-membered aromatic heterocyclic group" in the above Formula (I) denotes a 5- or 6-membered aromatic cyclic group containing at least one atom selected from nitrogen atom, oxygen atom and sulfur atom in addition to carbon atoms, and examples thereof include thienyl, pyrrolyl, furyl, thiazolyl, imidazolyl and oxazolyl.

The term "halogen atom" in the above Formula (I) is, for example, fluorine atom, chlorine atom, bromine atom or iodine atom. Among them, for example, fluorine atom, chlorine atom or bromine atom is preferred.

The term "lower alkoxy" in the above Formula (I) denotes a group in which "lower alkyl" is bonded to oxygen atom, and examples thereof include methoxy, ethoxy, propoxy, isopropoxy, butoxy, isobutoxy, sec-butoxy, tert-butoxy, pentyloxy, neopentyloxy, hexyloxy and isohexyloxy.

The term "lower alkylthio" in the above Formula (I) denotes a substituent in which the above-described "lower alkyl" is bonded to sulfur atom, and examples thereof include methylthio, ethylthio and butylthio.

The term "lower alkylsulfonyl" in the above Formula (I) denotes a substituent in which the above-described "lower alkyl" is bonded to sulfonyl, and examples thereof include methylsulfonyl, ethylsulfonyl and butylsulfonyl.

The term "lower alkylamino" in the above Formula (I) denotes a substituent in which amino is N-substituted with the above-described "lower alkyl", and examples thereof include N-methylamino, N-ethylamino, N-propylamino, N-isopropylamino, N-butylamino, N-isobutylamino, N-tert-butylamino, N-pentylamino and N-hexylamino.

The term "di-lower alkylamino" in the above Formula (I) denotes a substituent in which amino is N,N-disubstituted with the above-described "lower alkyl", and examples thereof include N,N-dimethylamino, N,N-diethylamino, N,N-dipropylamino, N,N-diisopropylamino, N,N-dibutylamino, N,N-diisobutylamino, N,N-di-tert-butylamino, N,N-dipentylamino, N,N-dihexylamino, N-ethyl-N-methylamino and N-methyl-N-propylamino.

The term "lower alkanoyl" in the above Formula (I) denotes a group in which the above-described "lower alkyl" is bonded to carbonyl, and examples thereof include acetyl, propionyl, butyryl, isobutyryl, valeryl, isovaleryl, pivaloyl and pentanoyl.

The term "lower alkanoylamino" in the above-described Formula (I) denotes a group in which the above-described "lower alkanoyl" is bonded to amino, and examples thereof include acetylamino, propionylamino, butyrylamino, isobutyrylamino, valerylamino, isovalerylamino, pivaloylamino and pentanoylamino.

The term "lower alkylcarbamoyl" in the above Formula (I) denotes a substituent in which carbamoyl is N-substituted with the above-described "lower alkyl", and examples thereof include N-methylcarbamoyl, N-ethylcarbamoyl, N-propylcarbamoyl, N-isopropylcarbamoyl, N-butylcarbamoyl, N-isobutylcarbamoyl, N-tert-butylcarbamoyl, N-pentylcarbamoyl and N-hexylcarbamoyl.

The term "selective inhibitor of Aurora A" used in the present specification is a compound or a drug which selectively inhibits Aurora A as compared with Aurora B. The "selective inhibitor of Aurora A" is preferably a compound or a drug of which inhibitory activities against Aurora A are at least ten times the activities against Aurora B; and more preferably a compound or a drug of which inhibitory activities against Aurora A are at least hundred times the activities against Aurora B.

Explanation for the term "pharmaceutically acceptable salt of ester thereof" or the term "pharmaceutically acceptable carrier or diluent" used in the specification still will be given later.

The term "treatment of cancer" as used in the specification means inhibition of cancer cell growth by administering an antitumor agent to a cancer patient. Preferably, this treatment enables retrogression of cancer growth, that is, reduction in the measurable cancer size. More preferably, such treatment completely eliminates cancer.

The term "cancer" as used in the specification refers to solid cancer and hematopoietic cancer. Here, examples of solid cancer include cerebral tumor, head and neck cancer, esophageal cancer, thyroid cancer, small cell lung cancer, non-small cell lung cancer, breast cancer, stomach cancer, gallbladder and bile duct cancer, liver cancer, pancreas cancer, colon cancer, rectal cancer, ovarian cancer, chorioepithelioma, uterine cancer, cervical cancer, renal pelvic and ureteral cancer, bladder cancer, prostate cancer, penile cancer, testicular cancer, embryonal cancer, wilms tumor, skin cancer, malignant melanoma, neuroblastoma, osteosarcoma, Ewing's tumor and soft tissue sarcoma. On the other hand, examples of hematopoietic cancer include acute leukemia, chronic lymphatic leukemia, chronic myelocytic leukemia, polycythemia vera, malignant lymphoma, multiple myeloma and non-Hodgkins' lymphoma.

The term "preparation" as used in the specification includes oral preparations and parenteral preparations. Examples of oral preparations include tablets, capsules, powders and granules, while examples of parenteral preparations include sterilized liquid preparations such as solutions or suspensions, specifically injections or drip infusions. Preferably, they are intravenous injections or intravenous drip infusions, and more preferably intravenous drip infusions.

The term "combined preparation" as used in the specification refers to those comprising two or more preparations for simultaneous, separate or sequential administration in the treatment, and such preparation may be a so-called kit type preparation or pharmaceutical composition. The term "combined preparation" also includes those having one or more preparations further combined with the combined preparation comprising two separate preparations used in the treatment of cancer.

The two separate preparations described above can be further combined with, in combination with a pharmaceutically acceptable carrier or diluent, at least one preparation comprising at least one antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents (here, definition of each antitumor agent is the same as that defined above), or a pharmaceutically acceptable salt or ester thereof. In this case, the above-mentioned at least one preparation that has been further combined can be administered simultaneously, separately or sequentially with respect to the two separate preparations. For example, a combined preparation comprising three preparations may include that is comprised of a preparation including a preparation containing the compound represented by the above Formula (I), a preparation containing 5-fluorouracil and a preparation containing leucovorin.

Here, in the above-mentioned combined preparation, either or both of the two separate preparations may be parenteral preparations, preferably injections or drip infusions, and more preferably intravenous drip infusions.

The term "preparation" according to the invention may usually comprise a therapeutically effective amount of a compound according to the invention, together with a pharmaceutically acceptable carrier or diluent. This technique of formulation is considered to be a technical common knowledge to those having ordinary skill in the pertinent art and is well known. Preferably, intravenous drip infusions or injections can be prepared in combination with a pharmaceutically acceptable carrier or diluent, by various methods that are well known in the art.

In the case of using the combined preparation according to the invention, the term "administration" as used in the present specification refers to parenteral administration and/or oral administration, and preferably parenteral administration. Thus, when a combined preparation is administered, both administrations may be parenteral; one administration may be parenteral while the other may be oral; or both administrations may be oral. Preferably, both preparations in the combined preparation are administered parenterally. Here, the term "parenteral administration" is, for example, intravenous administration, subcutaneous administration or intramuscular administration, and preferably it is intravenous administration. Even when three or more preparations are combined and administered, at least one preparation may be parenterally administered, preferably intravenously administered, and more preferably intravenously infused or intravenously injected.

In the embodiment of the present invention, a compound represented by the above Formula (I) may be administered simultaneously with other antitumor agent(s). Further, it is possible to administer the compound represented by the above Formula (I) first and then another antitumor agent consecutively, or alternatively it is possible to administer another antitumor agent first and then the compound represented by the above Formula (I) consecutively. It is also possible to administer the compound represented by the above Formula (I) first and then separately administer another antitumor agent after a while, or alternatively it is possible to administer another antitumor agent first and then separately administer the compound represented by the above Formula (I) after a while. The order and the time interval for the administration may be appropriately selected by a person skilled in the art in accordance with, for example, a preparation containing the compound represented by the above Formula (I) used and a preparation containing an antitumor agent that is used in combination therewith, the type of the cancer cells to be treated and the condition of the patient. For example, in the case of administering the compound represented by the above Formula (I) and paclitaxel, preferably paclitaxel is administered first, and then the compound represented by the above Formula (I) is administered sequentially or separately after a while.

The term "simultaneously" as used in the specification refers to the use of preparations for the treatment substantially at the same time, whereas the term "separately" refers to the separate use of preparations for the treatment at different times such that, for example, one agent is used on the first day and another agent is used on the second day for the treatment. The term "sequentially" refers to the use of preparations in such an order that, for example, one agent is first used and another agent is used after a predetermined period of time for the treatment.

The term "antitumor alkylating agent" as used in the present specification refers to an alkylating agent having antitumor activity, and the term "alkylating agent" herein generally refers to an agent giving an alkyl group in the alkylation reaction in which a hydrogen atom of an organic compound is substituted with an alkyl group. The term "antitumor alkylating agent" may be exemplified by nitrogen mustard N-oxide, cyclophosphamide, ifosfamide, melphalan, busulfan, mitobronitol, carboquone, thiotepa, ranimustine, nimustine, temozolomide or carmustine.

The term "antitumor antimetabolite" as used in the specification refers to an antimetabolite having antitumor activity, and the term "antimetabolite" herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). The term "antitumor antimetabolites" may be exemplified methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine or pemetrexed disodium, and preferred are 5-fluorouracil, S-1, gemcitabine and the like.

The term "antitumor antibiotic" as used in the specification refers to an antibiotic having antitumor activity, and the "antibiotic" herein includes substances that are produced by microorganisms and inhibit cell growth and other functions of microorganisms and of other living organisms. The term "antitumor antibiotic" may be exemplified by actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus or valrubicin.

The term "plant-derived antitumor agent" as used in the specification includes compounds having antitumor activities which originate from plants, or compounds prepared by applying chemical modification to the foregoing compounds. The term "plant-derived antitumor agent" may be exemplified by vincristine, vinblastine, vindesine, etoposide, sobuzoxane, docetaxel, paclitaxel and vinorelbine, and preferred and docetaxel and paclitaxel.

The term "antitumor camptothecin derivative" as used in the specification refers to compounds that are structurally related to camptothecin and inhibit cancer cell growth, including camptothecin per se. The term "antitumor camptothecin derivative" is not particularly limited to, but may be exemplified by, camptothecin, 10-hydroxycamptothecin, topotecan, irinotecan or 9-aminocamptothecin, with camptothecin, topotecan and irinotecan being preferred. Further, irinotecan is metabolized in vivo and exhibits antitumor effect as SN-38. The action mechanism and the activity of the camptothecin derivatives are believed to be virtually the same as those of camptothecin (e.g., Nitta, et al., *Gan to Kagaku Ryoho*, 14, 850-857 (1987)).

The term "antitumor platinum coordination compound" as used in the specification refers to a platinum coordination compound having antitumor activity, and the term "platinum coordination compound" herein refers to a platinum coordination compound which provides platinum in ion form. Preferred platinum compounds include cisplatin; cis-diamminediaquoplatinum (II)-ion; chloro(diethylenetriamine)-platinum (II) chloride; dichloro(ethylenediamine)-platinum (II); diammine(1,1-cyclobutanedicarboxylato) platinum (II) (carboplatin); spiroplatin; iproplatin; diammine(2-ethylmalonato)platinum (II); ethylenediaminemalonatoplatinum (II); aqua(1,2-diaminodicyclohexane)sulfatoplatinum (II); aqua (1,2-diaminodicyclohexane)malonatoplatinum (II); (1,2-diaminocyclohexane)malonatoplatinum (II); (4-carboxyphthalato)(1,2-diaminocyclohexane) platinum (II); (1,2-diaminocyclohexane)-(isocitrato)platinum (II); (1,2-diaminocyclohexane)oxalatoplatinum (II); ormaplatin; tetraplatin; carboplatin, nedaplatin and oxaliplatin, and preferred is carboplatin or oxaliplatin. Further, other antitumor platinum coordination compounds mentioned in the specification are known and are commercially available and/or producible by a person having ordinary skill in the art by conventional techniques.

The term "antitumor tyrosine kinase inhibitor" as used in the specification refers to a tyrosine kinase inhibitor having antitumor activity, and the term "tyrosine kinase inhibitor" herein refers to a chemical substance inhibiting "tyrosine kinase" which transfers a γ-phosphate group of ATP to a hydroxyl group of a specific tyrosine in protein. The term "antitumor tyrosine kinase inhibitor" may be exemplified by gefitinib, imatinib or erlotinib.

The term "monoclonal antibody" as used in the specification, which is also known as single clonal antibody, refers to an antibody produced by a monoclonal antibody-producing cell, and examples thereof include cetuximab, bevacizumab, rituximab, alemtuzumab and trastuzumab.

The term "interferon" as used in the specification refers to an interferon having antitumor activity, and it is a glycoprotein having a molecular weight of about 20,000 which is produced and secreted by most animal cells upon viral infection. It has not only the effect of inhibiting viral growth but also various immune effector mechanisms including inhibition of growth of cells (in particular, tumor cells) and enhancement of the natural killer cell activity, thus being designated as one type of cytokine. Examples of "interferon" include interferon α, interferon α-2a, interferon α-2b, interferon β, interferon γ-1a and interferon γ-n1.

The term "biological response modifier" as used in the specification is the so-called biological response modifier or BRM and is generally the generic term for substances or drugs for modifying the defense mechanisms of living organisms or biological responses such as survival, growth or differentiation of tissue cells in order to direct them to be useful for an individual against tumor, infection or other diseases. Examples of the "biological response modifier" include krestin, lentinan, sizofuran, picibanil and ubenimex.

The term "other antitumor agent" as used in the specification refers to an antitumor agent which does not belong to any of the above-described agents having antitumor activities. Examples of the "other antitumor agent" include mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

The above-described terms "antitumor alkylating agent", "antitumor antimetabolite", "antitumor antibiotic", "plant-derived antitumor agent", "antitumor platinum coordination compound", "antitumor camptothecin derivative", "antitumor tyrosine kinase inhibitor", "monoclonal antibody", "interferon", "biological response modifier" and "other antitumor agent" are all known and are either commercially available or producible by a person skilled in the art by methods known per se or by well-known or conventional methods. The process for preparation of gefitinib is described, for example, in U.S. Pat. No. 5,770,599; the process for preparation of cetuximab is described, for example, in WO 96/40210; the process for preparation of bevacizumab is described, for example, in WO 94/10202; the process for preparation of oxaliplatin is described, for example, in U.S. Pat. Nos. 5,420,319 and 5,959,133; the process for preparation of gemcitabine is described, for example, in U.S. Pat. Nos. 5,434,254 and 5,223,608; and the process for preparation of camptothecin is described in U.S. Pat. Nos. 5,162,532, 5,247,089, 5,191,082, 5,200,524, 5,243,050 and 5,321,140; the process for preparation of irinotecan is described, for example, in U.S. Pat. No. 4,604,463; the process for preparation of topotecan is described, for example, in U.S. Pat. No. 5,734,056; the process for preparation of temozolomide is described, for example, in JP-B No. 4-5029; and the process for preparation of rituximab is described, for example, in JP-W No. 2-503143.

The above-mentioned antitumor alkylating agents are commercially available, as exemplified by the following: nitrogen mustard N-oxide from Mitsubishi Pharma Corp. as Nitromin (tradename); cyclophosphamide from Shionogi & Co., Ltd. as Endoxan (tradename); ifosfamide from Shionogi & Co., Ltd. as Ifomide (tradename); melphalan from Glaxo-SmithKline Corp. as Alkeran (tradename); busulfan from Takeda Pharmaceutical Co., Ltd. as Mablin (tradename); mitobronitol from Kyorin Pharmaceutical Co., Ltd. as Myebrol (tradename); carboquone from Sankyo Co., Ltd. as Esquinon (tradename); thiotepa from Sumitomo Pharmaceutical Co., Ltd. as Tespamin (tradename); ranimustine from Mitsubishi Pharma Corp. as Cymerin (tradename); nimustine from Sankyo Co., Ltd. as Nidran (tradename); temozolomide from Schering Corp. as Temodar (tradename); and carmustine from Guilford Pharmaceuticals Inc. as Gliadel Wafer (tradename).

The above-mentioned antitumor antimetabolites are commercially available, as exemplified by the following: methotrexate from Takeda Pharmaceutical Co., Ltd. as Methotrexate (tradename); 6-mercaptopurine riboside from Aventis Corp. as Thioinosine (tradename); mercaptopurine from Takeda Pharmaceutical Co., Ltd. as Leukerin (tradename); 5-fluorouracil from Kyowa Hakko Kogyo Co., Ltd. as 5-FU (tradename); tegafur from Taiho Pharmaceutical Co., Ltd. as Futraful (tradename); doxyfluridine from Nippon Roche Co., Ltd. as Furutulon (tradename); carmofur from Yamanouchi Pharmaceutical Co., Ltd. as Yamafur (tradename); cytarabine from Nippon Shinyaku Co., Ltd. as Cylocide (tradename); cytarabine ocfosfate from Nippon Kayaku Co., Ltd. as Strasid (tradename); enocitabine from Asahi Kasei Corp. as Sanrabin (tradename); S-1 from Taiho Pharmaceutical Co., Ltd. as TS-1 (tradename); gemcitabine from Eli Lilly & Co. as Gemzar (tradename); fludarabine from Nippon Schering Co., Ltd. as Fludara (tradename); and pemetrexed disodium from Eli Lilly & Co. as Alimta (tradename).

The above-mentioned antitumor antibiotics are commercially available, as exemplified by the following: actinomycin D from Banyu Pharmaceutical Co., Ltd. as Cosmegen (tradename); doxorubicin from Kyowa Hakko Kogyo Co., Ltd. as adriacin (tradename); daunorubicin from Meiji Seika Kaisha Ltd. as Daunomycin; neocarzinostatin from Yamanouchi Pharmaceutical Co., Ltd. as Neocarzinostatin (tradename); bleomycin from Nippon Kayaku Co., Ltd. as Bleo (tradename); pepromycin from Nippon Kayaku Co, Ltd. as Pepro (tradename); mitomycin C from Kyowa Hakko Kogyo Co., Ltd. as Mitomycin (tradename); aclarubicin from Yamanouchi Pharmaceutical Co., Ltd. as Aclacinon (tradename); pirarubicin from Nippon Kayaku Co., Ltd. as Pinorubicin (tradename); epirubicin from Pharmacia Corp. as Pharmorubicin (tradename); zinostatin stimalamer from Yamanouchi Pharmaceutical Co., Ltd. as Smancs (tradename); idarubicin from Pharmacia Corp. as Idamycin (tradename); sirolimus from Wyeth Corp. as Rapamune (tradename); and valrubicin from Anthra Pharmaceuticals Inc. as Valstar (tradename).

The above-mentioned plant-derived antitumor agents are commercially available, as exemplified by the following: vincristine from Shionogi & Co., Ltd. as Oncovin (tradename); vinblastine from Kyorin Pharmaceutical Co., Ltd. as Vinblastine (tradename); vindesine from Shionogi & Co., Ltd. as Fildesin (tradename); etoposide from Nippon Kayaku Co., Ltd. as Lastet (tradename); sobuzoxane from Zenyaku Kogyo Co., Ltd. as Perazolin (tradename); docetaxel from Aventis Corp. as Taxsotere (tadename); paclitaxel from Bristol-Myers Squibb Co. as Taxol (tradename); and vinorelbine from Kyowa Hakko Kogyo Co., Ltd. as Navelbine (tradename).

The above-mentioned antitumor platinum coordination compounds are commercially available, as exemplified by the following: cisplatin from Nippon Kayaku Co., Ltd. as Randa (tradename); carboplatin from Bristol-Myers Squibb Co. as Paraplatin (tradename); nedaplatin from Shionogi & Co., Ltd. as Aqupla (tradename); and oxaliplatin from Sanofi-Synthelabo Co. as Eloxatin (tradename).

The above-mentioned antitumor camptothecin derivatives are commercially available, as exemplified by the following: irinotecan from Yakult Honsha Co., Ltd. as Campto (tradename); topotecan from GlaxoSmithKline Corp. as Hycamtin (tradename); and camptothecin from Aldrich Chemical Co., Inc., U.S.A.

The above-mentioned antitumor tyrosine kinase inhibitors are commercially available, as exemplified by the following: gefitinib from AstraZeneca Corp. as Iressa (tradename); imatinib from Novartis AG as Gleevec (tradename); and erlotinib from OSI Pharmaceuticals Inc. as Tarceva (tradename).

The above-mentioned monoclonal antibodies are commercially available, as exemplified by the following: cetuximab from Bristol-Myers Squibb Co. as Erbitux (tradename); bevacizumab from Genentech, Inc. as Avastin (tradename); rituximab from Biogen Idec Inc. as Rituxan (tradename); alemtuzumab from Berlex Inc. as Campath (tradename); and trastuzumab from Chugai Pharmaceutical Co., Ltd. as Herceptin (tradename).

The above-mentioned interferons are commercially available, as exemplified by the following: interferon α from Sumitomo Pharmaceutical Co., Ltd. as Sumiferon (tradename); interferon α-2a from Takeda Pharmaceutical Co., Ltd. as Canferon-A (tradename); interferon α-2b from Schering-Plough Corp. as Intron A (tradename); interferon β from Mochida Pharmaceutical Co., Ltd. as IFNβ (tradename); interferon γ-1a from Shionogi & Co., Ltd. as Immunomax-γ (tradename); and interferon γ-n1 from Otsuka Pharmaceutical Co., Ltd. as Ogamma (tradename).

The above-mentioned biological response modifiers are commercially available, as exemplified by the following: krestin from Sankyo Co., Ltd. as krestin (tradename); lentinan from Aventis Corp. as Lentinan (tradename); sizofuran from Kaken Seiyaku Co., Ltd. as Sonifuran (tradename); picibanil from Chugai Pharmaceutical Co., Ltd. as Picibanil (tradename); and ubenimex from Nippon Kayaku Co., Ltd. as Bestatin (tradename).

The above-mentioned other antitumor agents are commercially available, as exemplified by the following: mitoxantrone from Wyeth Lederle Japan, Ltd. as Novantrone (tradename); L-asparaginase from Kyowa Hakko Kogyo Co., Ltd. as Leunase (tradename); procarbazine from Nippon Roche Co., Ltd. as Natulan (tradename); dacarbazine from Kyowa Hakko Kogyo Co., Ltd. as Dacarbazine (tradename); hydroxycarbamide from Bristol-Myers Squibb Co. as Hydrea (tradename); pentostatin from Kagaku Oyobi Kessei Ryoho Kenkyusho as Coforin (tradename); tretinoin from Nippon Roche Co., Ltd. As Vesanoid (tradename); alefacept from Biogen Idec Inc. as Amevive (tradename); darbepoetin alfa from Amgen Inc. as Aranesp (tradename); anastrozole from AstraZeneca Corp. as Arimidex (tradename); exemestane from Pfizer Inc. as Aromasin (tradename); bicalutamide from AstraZeneca Corp. as Casodex (tradename); leuprorelin from Takeda Pharmaceutical Co., Ltd. as Leuplin (tradename); flutamide from Schering-Plough Corp. as Eulexin (tradename); fulvestrant from AstraZeneca Corp. as Faslodex (tradename); pegaptanib octasodium from Gilead Sciences, Inc. as Macugen (tradename); denileukin diftitox from Ligand Pharmaceuticals Inc. as Ontak (tradename); aldesleukin from Chiron Corp. as Proleukin (tradename); thyrotropin alfa from Genzyme Corp. as Thyrogen (tradename); arsenic trioxide from Cell Therapeutics, Inc. as Trisenox (tradename); bortezomib from Millennium Pharmaceuticals, Inc. as Velcade (tradename); capecitabine from Hoffmann-La Roche, Ltd. as Xeloda (tradename); and goserelin from AstraZeneca Corp. as Zoladex (tradename).

The term "antitumor agent" as used in the specification includes the above-described "antitumor alkylating agent", "antitumor antimetabolite", "antitumor antibiotic", "plant-derived antitumor agent", "antitumor platinum coordination compound", "antitumor camptothecin derivative", "antitumor tyrosine kinase inhibitor", "monoclonal antibody", "interferon", "biological response modifier" and "other antitumor agent".

The term "aminopyridine derivative" as used in the specification includes, but is not limited to, any compound having a pyridyl group substituted with an amino group. It is exemplified by a compound of the above General Formula (I), and preferably any one compound of the below-mentioned (a) to (cc).

Embodiments of the compound represented by the above General Formula (I) will be illustrated in more detail.

$m_1$ is 1, 2 or 3; preferably $m_1$ is 2 or 3; and more preferably $m_1$ is 2.

$m_2$ is 1, 2 or 3; and preferably $m_2$ is 2.

$n_1$ is 0 or 1; and preferably $n_1$ is 0.

$n_2$ is 0 or 1; and preferably $n_2$ is 0.

i is an integer of any of 1 to $m_1$, and j is an integer of any of 1 to $m_2$.

R is aryl, heteroaryl or cycloaryl, any of which may be substituted.

R is preferably phenyl, or a 5- or 6-membered aromatic heterocyclic group containing at least one atom selected from N, O and S (wherein the phenyl or aromatic heterocyclic group may be substituted with one or more of identical or different substituents selected from:

1) lower alkyl,
2) a substituent selected from <Substituent group $A_2$>, and
3) lower alkyl which is substituted with one or more of identical or different substituents selected from <Substituent group $A_2$>), wherein:

<Substituent group $A_2$> consists of halogen atom, cyano, hydroxyl, amino, lower alkylamino, di-lower alkylamino, lower alkanoyl, lower alkanoylamino, carbamoyl, lower alkylcarbamoyl and lower alkylsulfonyl. Here, when R is a 5-membered aromatic heterocyclic group, preferred are, for example, pyrrolyl, furyl, thienyl, thiazolyl, pyrazolyl, pyridyl and pyrazinyl, any of which may be appropriately substituted.

R is more preferably phenyl which is substituted with identical or different halogen atoms at the 2- and 3-positions, or alternatively phenyl which is substituted with halogen atom, and methyl substituted with one to three of identical or different halogen atoms at the 2- and 3-positions, respectively.

$R_{ai}$ and $R_{ai}'$ (wherein i is an integer of 1 to $m_1$), which may be identical or different, is hydrogen atom or lower alkyl, and $R_{bj}$ and $R_{bj}'$ (wherein j is an integer of 1 to $m_2$), which may be identical or different, is hydrogen atom or lower alkyl. Here, if $m_1$ is 2 or 3 and i is $i_0$ (wherein $i_0$ is an integer of any of 1 to $m_1$), and further if $m_2$ is 2 or 3 and j is $j_0$ (wherein $j_0$ is an integer of any of 1 to $m_2$), then either of $R_{ai0}$ and $R_{ai0}'$ and either of $R_{bj0}$ and $R_{bj0}'$ may be combined to form —$(CH_2)_n$— (wherein n is 1 or 2). For example, with regard to $R_{ai}$ and $R_{ai}'$ (wherein i is an integer of 1 to $m_1$), and $R_{bj}$ and $R_{bj}'$ (wherein j is an integer of 1 to $m_2$), if $m_1$ is 2 and $m_2$ is 2, then either of $R_{a2}$ and $R_{a2}'$ and either of $R_{b1}$ and $R_{b1}'$ are combined to form —$CH_2$—.

With regard to $R_{ai}$ and $R_{ai}'$ (wherein i is an integer of 1 to $m_1$), and $R_{bj}$ and $R_{bj}'$ (wherein j is an integer of 1 to $m_2$), if $m_1$ is 2 or 3 and $m_2$ is 2, then $R_{ai}$, $R_{ai}'$, $R_{bj}$ and $R_{bj}'$, preferably all of $R_{ai}$, $R_{ai}'$, $R_{bj}$ and $R_{bj}'$, are hydrogen atom, or any one of $R_{ai}$, $R_{ai}'$, $R_{bj}$ and $R_{bj}'$ is methyl while the others are hydrogen atom; more preferably, all of $R_{a1}$, $R_{a1}'$, $R_{bj}$ and $R_{bj}'$ are hydrogen atom. For example, if $m_1$ is 2 and $m_2$ is 2, $R_{a1}$, $R_{a1}'$, $R_{a2}$, $R_{a2}'$, $R_{b1}$, $R_{b1}'$, $R_{b2}$ and $R_{b2}'$ are preferably all hydrogen atom.

$R_c$, $R_d$ and $R_e$, which may be identical or different, are hydrogen atom or lower alkyl.

$R_e$ is preferably hydrogen atom.

$X_1$ is CH, $CX_{1a}$ or N, wherein $X_{1a}$ is lower alkyl which may be substituted. $X_1$ is preferably CH.

$X_2$ is CH, $CX_{2a}$ or N (wherein:
$X_{2a}$ is lower alkyl;
$X_{2a}$ is a substituent selected from <Substituent group $A_1$>, or lower alkyl which is substituted with one or more of identical or different substituents selected from <Substituent group $A_1$> (wherein <Substituent group $A_1$> consists of halogen atom; cyano; hydroxyl; lower alkylamino; di-lower alkylamino; lower alkoxy which may be substituted with one or more hydroxyl groups; lower alkylthio; and lower alkylsulfonyl); or
$X_{2a}$ is $COOR_1$, $CONR_2R_3$, $NHCOR_1$, $NHCONR_2R_3$, $NHSO_2NR_2R_3$, $NR_5$ or $CH_2NR_4R_5$ (wherein:
$R_1$ is hydrogen atom or lower alkyl which may be substituted;
$R_2$ and $R_3$, which may be identical or different, are each hydrogen atom, lower alkyl which may be substituted, or cycloalkyl, or alternatively $R_2$ and $R_3$ together with the nitrogen atom to which they bond, form a 5- or 6-membered aliphatic heterocyclic group which contains at least one atom selected from N, O and S and which may be substituted; and
$R_4$ and $R_5$, which may be identical or different, are each hydrogen atom, lower alkyl that may be substituted, or cycloalkyl); or
$X_{2a}$ is a 5- or 6-membered aliphatic heterocyclic group which contains at least one atom selected from N, O and S and which may be substituted (wherein two hydrogen atoms that are bonded to the same carbon atom of the aliphatic heterocyclic group may be substituted with oxo and neighboring two carbon atoms constituting the aliphatic heterocyclic ring may be double-bonded), or lower alkyl which is substituted with the aliphatic heterocyclic group; or
$X_{2a}$ is a 5- or 6-membered aromatic heterocyclic group which contains at least one atom selected from N, O and S and which may be substituted or lower alkyl which is substituted with the aromatic heterocyclic group.

$X_2$ is preferably CH, $CX_{2a}$ or N (wherein:
$X_{2a}$ is a substituent selected from <Substituent group $A_1$>, or lower alkyl which is substituted with one or more substituents selected from <Substituent group $A_1$>; or
$X_{2a}$ is $COOR_1$, $CONR_2R_3$, $NHCOR_1$, $NHCONR_2R_3$, $NHSO_2NR_2R_3$, $NR_5$ or $CH_2NR_4R_5$ (wherein:
$R_1$ is hydrogen atom or lower alkyl which may be substituted;
$R_2$ and $R_3$, which may be identical or different, are each hydrogen atom, lower alkyl which may be substituted, or cycloalkyl, or alternatively $R_2$ and $R_3$, together with the nitrogen atom to which they bond, form a 5- or 6-membered aliphatic heterocyclic group which contains at least one atom selected from N, O and S and which may be substituted; and
$R_4$ and $R_5$, which may be identical or different, are each hydrogen atom, lower alkyl which may be substituted, or cycloalkyl); or
$X_{2a}$ is a 5-membered aromatic heterocyclic group which may be substituted with lower alkyl and which is selected from <Substituent group $A_3$>; or lower alkyl which is substituted with the aromatic heterocyclic group; or
$X_{2a}$ is a 5- or 6-membered aliphatic heterocyclic group which may be substituted with lower alkyl and which is selected from <Substituent group $A_4$>; or lower alkyl which is substituted with the aliphatic heterocyclic group;
wherein <Substituent group $A_3$> consists of the following:

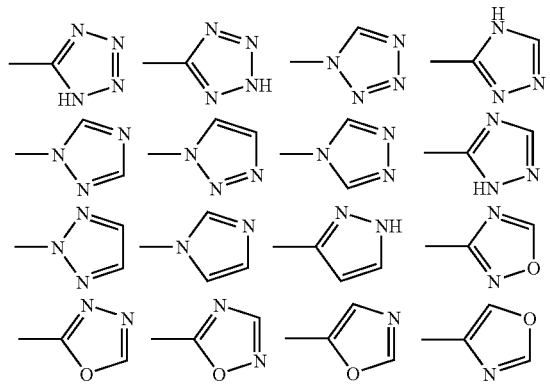

and <Substituent group $A_4$> consists of the following:

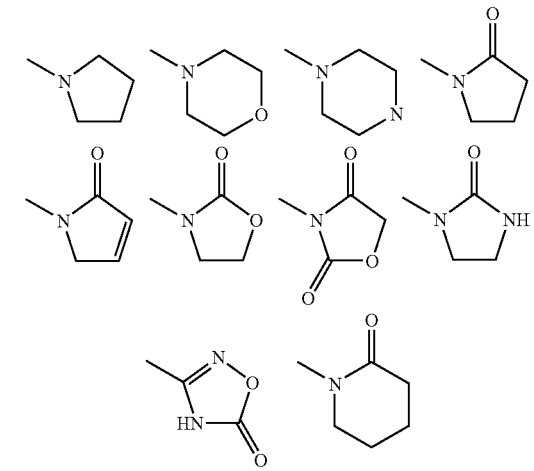

<Substituent group $A_4$> preferably consists of the following:

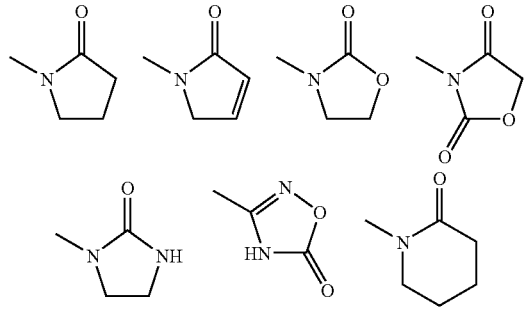

$X_2$ is even more preferably CH or N.

$X_3$ is CH, $CX_{3a}$ or N (wherein $X_{3a}$ is lower alkyl which may be substituted).

$X_3$ is preferably CH.

$X_4$ is CH or N, and preferably N.

The number of nitrogen atoms among $X_1$, $X_2$ and $X_3$ and $X_4$ is one or two; preferably $X_4$ is N, while the number of N among $X_1$ to $X_3$ is at most 1; more preferably $X_1$ and $X_3$ are each CH, $X_2$ is CH or N, and $X_4$ is N; and particularly preferably $X_1$, $X_2$ and $X_3$ are all CH, while $X_4$ is N.

When $W_1$ is CH, $W_2$ is CH or $CW_{2a}$, and $W_3$ is N, then $X_1$ is preferably CH or $CX_{1a}$, $X_2$ is preferably N, and $X_3$ is preferably CH or $CX_{3a}$.

$Y_1$, $Y_2$ and $Y_3$, which may be identical or different, are each CH or N, provided that if $Y_1$ is CH and $R_e$ is hydrogen atom, then the two hydrogen atoms may be substituted with oxo.

$Y_1$ is preferably CH.

$Z_1$ and $Z_2$, which may be identical or different, are each CH or N.

Preferably, at least one of $Z_1$ and $Z_2$ is N.

More preferably, $Z_1$ is N, and $Z_2$ is CH or N.

Particularly preferably, both $Z_1$ and $Z_2$ are N.

W is the following group:

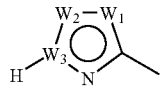

wherein:

$W_1$ is CH, N, NH, O or S;

$W_2$ is CH, $CW_{2a}$, N, $NW_{2b}$, O or S (wherein $W_{2a}$ and $W_{2b}$, which may be identical or different, are each hydrogen atom, halogen atom, cyano, $C_{1-2}$ lower alkyl, $C_{3-5}$ cycloalkyl or $C_{1-2}$ lower alkyl which may be substituted with one or more halogen atoms);

$W_3$ is C or N; and

At least one of $W_1$, $W_2$ and $W_3$ is carbon atom; however, two of $W_1$, $W_2$ and $W_3$ are not simultaneously O and S.

W is preferably selected from the following:

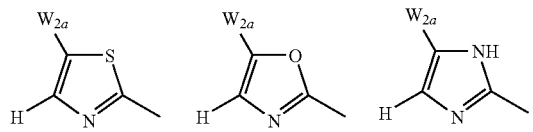

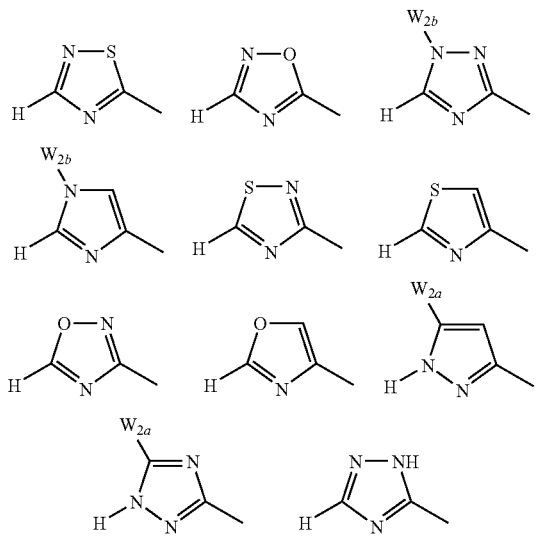

W is more preferably selected from the following:

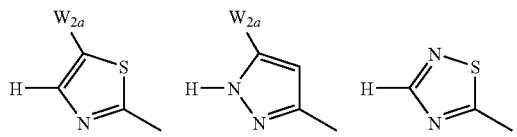

wherein $W_{2a}$ is hydrogen atom, halogen atom, cyano, or methyl which may be substituted with one to three fluorine atoms.

W is particularly preferably selected from the following:

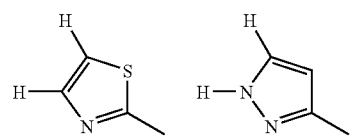

A preferred embodiment of the compound represented by the above General Formula (I) can be also expressed as follows:

(1) A compound of General Formula (I) or a pharmaceutically acceptable salt or ester thereof, wherein W is selected from the following:

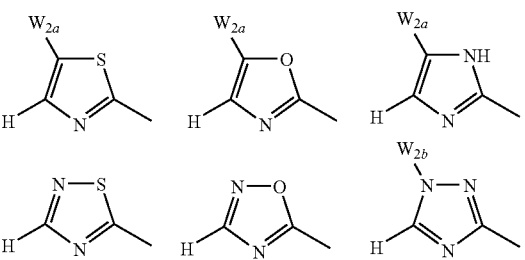

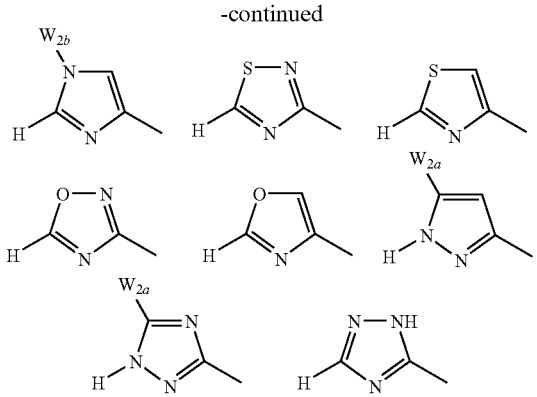

or (2) the compound as described in the above (1) or a pharmaceutically acceptable salt or ester thereof, wherein:
  $m_1$ is 2 or 3;
  $m_2$ is 2;
  $n_1$ is 0;
  $n_2$ is 0;
  $Z_1$ is N;
  $Z_2$ is CH or N; and
  R is phenyl, or a 5- or 6-membered aromatic heterocyclic group which contains at least one atom selected from N, O and S (wherein the phenyl or aromatic heterocyclic group may be substituted with one or more of identical or different substituents selected from the following:
    1) lower alkyl,
    2) a substituent selected from <Substituent group $A_2$>, and
    3) lower alkyl which is substituted with a substituent selected from <Substituent group $A_2$>, wherein:
  <Substituent group $A_2$> consists of halogen atom, cyano, hydroxyl, amino, lower alkylamino, di-lower alkylamino, lower alkanoyl, lower alkanoylamino, carbamoyl, lower alkylcarbamoyl and lower alkylsulfonyl); or (3) the compound as described in the above (2) or a pharmaceutically acceptable salt or ester thereof, wherein $Y_1$ is CH, and $R_e$ is hydrogen atom; or (4) the compound as described in the above (3) or a pharmaceutically acceptable salt or ester thereof, wherein $m_1$ is 2, and $R_{a1}$, $R_{a1}'$, $R_{a2}$, $R_{a2}'$, $R_{b1}$, $R_{b1}'$, $R_{b2}$ and $R_{b2}'$ are each hydrogen atom; or (5) the compound as described in the above (4) or a pharmaceutically acceptable salt or ester thereof, wherein $X_4$ is N, while the number of N among $X_1$ to $X_3$ is at most 1; and R is phenyl which is substituted with identical or different halogen atoms at the 2- and 3-positions, or alternatively phenyl which is substituted with halogen atom, and methyl substituted with one to three of identical or different halogen atoms at the 2- and 3-positions, respectively; or (6) the compound as described in the above (5) or a pharmaceutically acceptable salt or ester thereof, wherein:
  $X_2$ is preferably CH, $CX_{2a}$ or N (wherein:
  $X_{2a}$ is a substituent selected from <Substituent group $A_1$>, or lower alkyl which is substituted with one or more substituents selected from <Substituent group $A_1$>; or
  $X_{2a}$ is $COOR_1$, $CONR_2R_3$, $NHCOR_1$, $NHCONR_2R_3$, $NHSO_2NR_2R_3$, $NR_5$ or $CH_2NR_4R_5$ (wherein:
  $R_1$ is hydrogen atom or lower alkyl which may be substituted;
  $R_2$ and $R_3$, which may be identical or different, are each hydrogen atom, lower alkyl which may be substituted, or cycloalkyl, or alternatively $R_2$ and $R_3$, together with the nitrogen atom to which they bond, form a 5- or 6-membered aliphatic heterocyclic group which contains at least one atom selected from N, O and S and which may be substituted; and
  $R_4$ and $R_5$, which may be identical or different, are each hydrogen atom, lower alkyl which may be substituted, or cycloalkyl); or
  $X_{2a}$ is a 5-membered aromatic heterocyclic group which may be substituted with lower alkyl and which is selected from <Substituent group $A_3$>; or lower alkyl which is substituted with the aromatic heterocyclic group; or
  $X_{2a}$ is a 5- or 6-membered aliphatic heterocyclic group which may be substituted with lower alkyl and which is selected from <Substituent group $A_4$>; or lower alkyl which is substituted with the aliphatic heterocyclic group;
  wherein <Substituent group $A_3$> consists of the following:

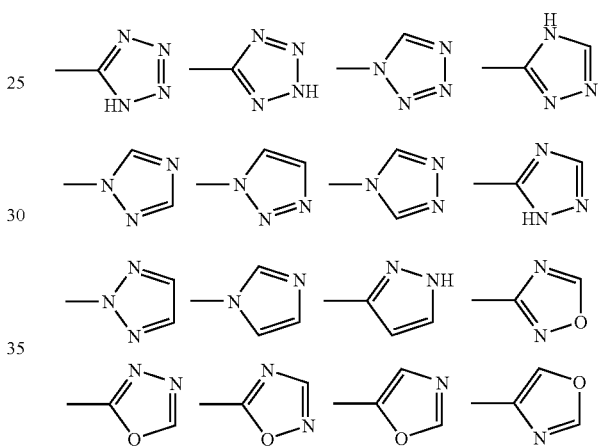

and <Substituent group $A_4$> consists of the following:

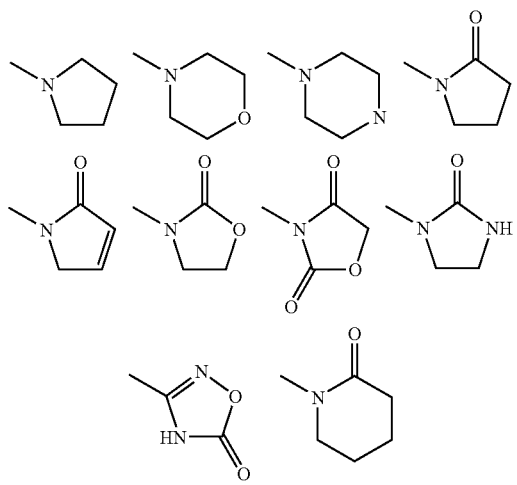

or (7) the compound as described in the above (6) or a pharmaceutically acceptable salt or ester, wherein:

W is selected from the following:

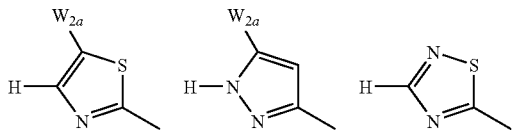

wherein $W_{2a}$ is hydrogen atom, halogen atom, cyano, or methyl which may be substituted with one to three fluorine atoms; or (8) the compound as described in the above (7) or a pharmaceutically acceptable salt or ester, wherein all of $X_1$, $X_2$ and $X_3$ are CH, and both $Z_1$ and $Z_2$ are N.

The compound of the above General Formula (I) is preferably:

(a) 6-((4-(3-chloro-2-fluorobenzoyl)piperazin-1-yl)methyl)-N-thiazol-2-ylpyridin-2-amine, (b) 6-((4-(2,3-dichlorobenzoyl)piperazin-1-yl)methyl)-N-thiazol-2-ylpyridin-2-amine, (c) 6-(((1S,4S)-5-(3-chloro-2-fluorobenzoyl)-2,5-diazabicyclo[2.2.1]hept-2-yl)methyl)-N-thiazol-2-ylpyridin-2-amine, (d) 6-((4-(3-chloro-2-fluorobenzoyl)piperazin-1-yl)methyl)-N-(1H-pyrazol-3-yl)pyridin-2-amine, (e) 6-((4-(2-fluoro-3-(trifluoromethyl)benzoyl)piperazin-1-yl)methyl)-N-1H-pyrazol-3-ylpyridin-2-amine, (f) 6-((4-(3-(difluoromethyl)-2-fluorobenzoyl)piperazin-1-yl)methyl)-N-1H-pyrazol-3-ylpyridin-2-amine, (g) 6-((4-(3-chloro-2-fluorobenzoyl)piperazin-1-yl)methyl)-N-(5-methyl-1H-pyrazol-3-yl)pyridin-2-amine, (h) 6-((4-(2-fluoro-3-(trifluoromethyl)benzoyl)piperazin-1-yl)methyl)-N-(5-methyl-1H-pyrazol-3-yl)pyridin-2-amine, (i) 6-((4-(2-chloro-3-(trifluoromethyl)benzoyl)piperazin-1-yl)methyl)-N-(5-methyl-1H-pyrazol-3-yl)pyridin-2-amine, (j) 6-((4-(2,3-dichlorobenzoyl)piperazin-1-yl)methyl)-N-1,2,4-thiadiazol-5-ylpyridin-2-amine, (k) 6-((4-(2-fluoro-3-(trifluoromethyl)benzoyl)piperazin-1-yl)methyl)-N-1,2,4-thiadiazol-5-ylpyridin-2-amine, (l) 6-((4-(3-chloro-2-fluorobenzoyl)piperazin-1-yl)methyl)-N-1H-pyrazol-3-ylpyrazin-2-amine, (m) 6-(((1S,4S)-5-(3-chloro-2-fluorobenzoyl)-2,5-diazabicyclo[2.2.1]hept-2-yl)methyl)-N-1H-pyrazol-3-ylpyrazin-2-amine, (n) 6-((4-(2-fluoro-3-(trifluoromethyl)benzoyl)piperazin-1-yl)methyl)-N-1H-pyrazol-3-ylpyrazin-2-amine, (q) 6-((4-(3-chloro-2-fluorobenzoyl)piperazin-1-yl)methyl)-N-(5-methyl-1H-pyrazol-3-yl)pyrazin-2-amine, (p) 6-((4-(2-fluoro-3-(trifluoromethyl)benzoyl)piperazin-1-yl)methyl)-N-1,2,4-thiadiazol-5-ylpyrazin-2-amine, (q) 6-((4-(3-chloro-2-fluorobenzoyl)piperazin-1-yl)methyl)-N-thiazol-2-ylpyrazin-2-amine, (r) 6-((4-(3-chloro-2-fluorobenzoyl)piperazin-1-yl)methyl)-N-(5-chlorothiazol-2-yl)pyridin-2-amine, (s) 2-((4-(3-chloro-2-fluorobenzoyl)piperazin-1-yl)methyl)-N,N-dimethyl-6-(thiazol-2-yl)aminoisonicotinic amide, (t) (2-((4-(3-chloro-2-fluorobenzoyl)piperazin-1-yl)methyl)-6-(thiazol-2-ylamino)pyridin-4-yl)methanol, (u) 6-((4-(3-chloro-2-fluorobenzoyl)piperazin-1-yl)methyl)-4-(methoxymethyl)-N-thiazol-2-ylpyridin-2-amine, (v) 1-(2-((4-(3-chloro-2-fluorobenzoyl)piperazin-1-yl)methyl)-6-(thiazol-2-ylamino) pyridin-4-yl)-3-methylimidazolidin-2-one, (w) 2-((4-(3-chloro-2-fluorobenzoyl)piperazin-1-yl)methyl)-6-(thiazol-2-ylamino) isonicotinonitrile, (x) 6-((4-(3-chloro-2-fluorobenzoyl)piperazin-1-yl)methyl)-4-(1-methyl-1H-tetrazol-5-yl)-N-thiazol-2-ylpyridin-2-amine, (y) 6-((4-(3-chloro-2-fluorobenzoyl)piperazin-1-yl)methyl)-4-(2-methyl-2H-tetrazol-5-yl)-N-thiazol-2-ylpyridin-2-amine, (z) 6-((4-(3-chloro-2-fluorobenzoyl)piperazin-1-yl)methyl)-N-thiazol-2-yl-4-(1H-1,2,4-triazol-5-yl)pyridin-2-amine, (aa) 6-((4-(3-chloro-2-fluorobenzoyl)piperazin-1-yl)methyl)-N-(5-fluorothiazol-2-yl)pyridin-2-amine;

(bb) 6-((4-(2-fluoro-3-trifluoromethylbenzoyl)piperazin-1-yl)methyl)-N-(5-methyl-1H-pyrazol-3-yl)pyrazin-2-amine; or (cc) 2-{[4-(3-chloro-2-fluorobenzoyl)piperazin-1-yl]methyl}-N,N-dimethyl-6-(1H-pyrazol-3-ylamino)isonicotinamide, or a pharmaceutically acceptable salt or ester thereof.

In another embodiment, the present invention relates to a compound which is:

(a) 6-((4-(3-chloro-2-fluorobenzoyl)piperazin-1-yl)methyl)-N-thiazol-2-ylpyridin-2-amine, (b) 6-((4-(2,3-dichlorobenzoyl)piperazin-1-yl)methyl)-N-thiazol-2-ylpyridin-2-amine, (c) 6-(((1S,4S)-5-(3-chloro-2-fluorobenzoyl)-2,5-diazabicyclo[2.2.1]hept-2-yl)methyl)-N-thiazol-2-ylpyridin-2-amine, (d) 6-((4-(3-chloro-2-fluorobenzoyl)piperazin-1-yl)methyl)-N-(1H-pyrazol-3-yl)pyrazin-2-amine, (e) 6-((4-(2-fluoro-3-(trifluoromethyl)benzoyl)piperazin-1-yl)methyl)-N-1H-pyrazol-3-ylpyridin-2-amine, (f) 6-((4-(3-(difluoromethyl)-2-fluorobenzoyl)piperazin-1-yl)methyl)-N-1H-pyrazol-3-ylpyridin-2-amine, (g) 6-((4-(3-chloro-2-fluorobenzoyl)piperazin-1-yl)methyl)-N-(5-methyl-1H-pyrazol-3-yl)pyridin-2-amine, (h) 6-((4-(2-fluoro-3-(trifluoromethyl)benzoyl)piperazin-1-yl)methyl)-N-(5-methyl-1H-pyrazol-3-yl)pyridin-2-amine, (i) 6-((4-(2-chloro-3-(trifluoromethyl)benzoyl)piperazin-1-yl)methyl)-N-(5-methyl-1H-pyrazol-3-yl)pyridin-2-amine, (j) 6-((4-(2,3-dichlorobenzoyl)piperazin-1-yl)methyl)-N-1,2,4-thiadiazol-5-ylpyridin-2-amine, (k) 6-((4-(2-fluoro-3-(trifluoromethyl)benzoyl)piperazin-1-yl)methyl)-N-1,2,4-thiadiazol-5-ylpyridin-2-amine, (l) 6-((4-(3-chloro-2-fluorobenzoyl)piperazin-1-yl)methyl)-N-1H-pyrazol-3-ylpyrazin-2-amine, (m) 6-(((1S,4S)-5-(3-chloro-2-fluorobenzoyl)-2,5-diazabicyclo[2.2.1]hept-2-yl)methyl)-N-1H-pyrazol-3-ylpyrazin-2-amine, (n) 6-((4-(2-fluoro-3-(trifluoromethyl)benzoyl)piperazin-1-yl)methyl)-N-1H-pyrazol-3-ylpyrazin-2-amine, (o) 6-((4-(3-chloro-2-fluorobenzoyl)piperazin-1-yl)methyl)-N-(5-methyl-1H-pyrazol-3-yl)pyrazin-2-amine, (p) 6-((4-(2-fluoro-3-(trifluoromethyl)benzoyl)piperazin-1-yl)methyl)-N-1,2,4-thiadiazol-5-ylpyrazin-2-amine, (q) 6-((4-(3-chloro-2-fluorobenzoyl)piperazin-1-yl)methyl)-N-thiazol-2-ylpyrazin-2-amine, (r) 6-((4-(3-chloro-2-fluorobenzoyl)piperazin-1-yl)methyl)-N-(5-chlorothiazol-2-yl)pyridin-2-amine, (s) 6-((4-(3-chloro-2-fluorobenzoyl)piperazin-1-yl)methyl)-N-(5-fluorothiazol-2-yl)pyridin-2-amine; or (t) 6-((4-(2-fluoro-3-trifluoromethylbenzoyl)piperazin-1-yl)methyl)-N-(5-methyl-1H-pyrazol-3-yl)pyrazin-2-amine;

or a pharmaceutically acceptable salt or ester thereof.

Further, in the combined preparation comprising two separate preparations according to the invention, preferably either or both of the two separate preparations are parenteral preparations, and more preferably either or both of the two separate preparations are injections or drip infusions.

The combined preparation comprising two separate preparations according to the invention is preferably such that one of the preparations is a preparation containing the following:

(a) 6-((4-(3-chloro-2-fluorobenzoyl)piperazin-1-yl)methyl)-N-thiazol-2-ylpyridin-2-amine, (b) 6-((4-(2,3-dichlorobenzoyl)piperazin-1-yl)methyl)-N-thiazol-2-ylpyridin-2-amine, (c) 6-(((1S,4S)-5-(3-chloro-2-fluorobenzoyl)-2,5-diazabicyclo[2.2.1]hept-2-yl)methyl)-N-thiazol-2-ylpyridin-2-amine, (d) 6-((4-(3-chloro-2-fluorobenzoyl)piperazin-1-yl)methyl)-N-(1H-pyrazol-3-yl)pyridin-2-amine, (e) 6-((4-(2-fluoro-3-(trifluoromethyl)benzoyl)piperazin-1-yl)methyl)-N-1H-pyrazol-3-ylpyridin-2-amine, (f) 6-((4-(3-(difluoromethyl)-2-fluorobenzoyl)piperazin-1-yl)methyl)-N-1H-pyrazol-3-ylpyridin-2-amine, (g) 6-((4-(3-chloro-2-fluorobenzoyl)piperazin-1-yl)methyl)-N-(5-methyl-1H-pyrazol-3-yl)pyridin-2-amine, (h) 6-((4-(2-fluoro-3-(trifluoromethyl)benzoyl)piperazin-1-yl)methyl)-N-(5-methyl-1H-pyrazol-3-yl)pyridin-2-amine, (i) 6-((4-(2-chloro-3-(trifluoromethyl)benzoyl)piperazin-1-yl)methyl)-N-(5-methyl-1H-pyrazol-3-yl)pyridin-2-amine, (j) 6-((4-(2,3-dichlorobenzoyl)piperazin-1-yl)methyl)-N-1,2,4-thiadiazol-5-ylpyridin-2-amine, (k) 6-((4-(2-fluoro-3-(trifluoromethyl)benzoyl)piperazin-1-yl)methyl)-N-1,2,4-thiadiazol-5-ylpyridin-2-amine, (l) 6-((4-(3-chloro-2-fluorobenzoyl)piperazin-1-yl)methyl)-N-1H-pyrazol-3-ylpyrazin-2-amine, (m) 6-(((1S,4S)-5-(3-chloro-2-fluorobenzoyl)-2,5-diazabicyclo[2.2.1]hept-2-yl)methyl)-N-1H-pyrazol-3-ylpyrazin-2-amine, (n) 6-((4-(2-fluoro-3-(trifluoromethyl)benzoyl)piperazin-1-yl)methyl)-N-1H-pyrazol-3-ylpyrazin-2-amine, (o) 6-((4-(3-chloro-2-fluorobenzoyl)piperazin-1-yl)methyl)-N-(5-methyl-1H-pyrazol-3-yl)pyrazin-2-amine, (p) 6-((4-(2-fluoro-3-(trifluoromethyl)benzoyl)piperazin-1-yl)methyl)-N-1,2,4-thiadiazol-5-ylpyrazin-2-amine, (q) 6-((4-(3-chloro-2-fluorobenzoyl)piperazin-1-yl)methyl)-N-thiazol-2-ylpyrazin-2-amine, (r) 6-((4-(3-chloro-2-fluorobenzoyl)piperazin-1-yl)methyl)-N-(5-chlorothiazol-2-yl)pyridin-2-amine, (s) 2-((4-(3-chloro-2-fluorobenzoyl)piperazin-1-yl)methyl)-N,N-dimethyl-6-(thiazol-2-yl)aminoisonicotinic amide, (t) (2-((4-(3-chloro-2-fluorobenzoyl)piperazin-1-yl)methyl)-6-(thiazol-2-ylamino)pyridin-4-yl)methanol, (u) 6-((4-(3-chloro-2-fluorobenzoyl)piperazin-1-yl)methyl)-4-(methoxymethyl)-N-thiazol-2-ylpyridin-2-amine, (v) 1-(2-((4-(3-chloro-2-fluorobenzoyl)piperazin-1-yl)methyl)-6-(thiazol-2-ylamino) pyridin-4-yl)-3-methylimidazolidin-2-one, (w) 2-((4-(3-chloro-2-fluorobenzoyl)piperazin-1-yl)methyl)-6-(thiazol-2-ylamino) isonicotinonitrile, (x) 6-((4-(3-chloro-2-fluorobenzoyl)piperazin-1-yl)methyl)-4-(1-methyl-1H-tetrazol-5-yl)-N-thiazol-2-ylpyridin-2-amine, (y) 6-((4-(3-chloro-2-fluorobenzoyl)piperazin-1-yl)methyl)-4-(2-methyl-2H-tetrazol-5-yl)-N-thiazol-2-ylpyridin-2-amine, (z) 6-((4-(3-chloro-2-fluorobenzoyl)piperazin-1-yl)methyl)-N-thiazol-2-yl-4-(1H-1,2,4-triazol-5-yl)pyridin-2-amine, (aa) 6-((4-(3-chloro-2-fluorobenzoyl)piperazin-1-yl)methyl)-N-(5-fluorothiazol-2-yl)pyridin-2-amine;

(bb) 6-((4-(2-fluoro-3-trifluoromethylbenzoyl)piperazin-1-yl)methyl)-N-(5-methyl-1H-pyrazol-3-yl)pyrazin-2-amine; or (cc) 2-{[4-(3-chloro-2-fluorobenzoyl)piperazin-1-yl]methyl}-N,N-dimethyl-6-(1H-pyrazol-3-ylamino)isonicotinamide, or a pharmaceutically acceptable salt or ester thereof, and the other preparation is a preparation containing paclitaxel or docetaxel, or a pharmaceutically acceptable salt or ester thereof, together with a pharmaceutically acceptable carrier or diluent.

In another embodiment, the combined preparation comprising two separate preparations according to the invention is more preferably such that one of the preparations is a preparation containing the following:

(a) 6-((4-(3-chloro-2-fluorobenzoyl)piperazin-1-yl)methyl)-N-thiazol-2-ylpyridin-2-amine, (b) 6-((4-(2,3-dichlorobenzoyl)piperazin-1-yl)methyl)-N-thiazol-2-ylpyridin-2-amine, (c) 6-(((1S,4S)-5-(3-chloro-2-fluorobenzoyl)-2,5-diazabicyclo [2.2.1]hept-2-yl)methyl)-N-thiazol-2-ylpyridin-2-amine, (d) 6-((4-(3-chloro-2-fluorobenzoyl)piperazin-1-yl)methyl)-N-(1H-pyrazol-3-yl)pyridin-2-amine, (e) 6-((4-(2-fluoro-3-(trifluoromethyl)benzoyl)piperazin-1-yl)methyl)-N-1H-pyrazol-3-ylpyridin-2-amine, (f) 6-((4-(3-(difluoromethyl)-2-fluorobenzoyl)piperazin-1-yl)methyl)-N-1H-pyrazol-3-ylpyridin-2-amine, (g) 6-((4-(3-chloro-2-fluorobenzoyl)piperazin-1-yl)methyl)-N-(5-methyl-1H-pyrazol-3-yl)pyridin-2-amine, (h) 6-((4-(2-fluoro-3-(trifluoromethyl)benzoyl)piperazin-1-yl)methyl)-N-(5-methyl-1H-pyrazol-3-yl)pyridin-2-amine, (i) 6-((4-(2-chloro-3-(trifluoromethyl)benzoyl)piperazin-1-yl)methyl)-N-(5-methyl-1H-pyrazol-3-yl)pyridin-2-amine, (j) 6-((4-(2,3-dichlorobenzoyl)piperazin-1-yl)methyl)-N-1,2,4-thiadiazol-5-ylpyridin-2-amine, (k) 6-((4-(2-fluoro-3-(trifluoromethyl)benzoyl)piperazin-1-yl)methyl)-N-1,2,4-thiadiazol-5-ylpyridin-2-amine, (l) 6-((4-(3-chloro-2-fluorobenzoyl)piperazin-1-yl)methyl)-N-1H-pyrazol-3-ylpyrazin-2-amine, (m) 6-(((1S,4S)-5-(3-chloro-2-fluorobenzoyl)-2,5-diazabicyclo[2.2.1]hept-2-yl)methyl)-N-1H-pyrazol-3-ylpyrazin-2-amine, (n) 6-((4-(2-fluoro-3-(trifluoromethyl)benzoyl)piperazin-1-yl)methyl)-N-1H-pyrazol-3-ylpyrazin-2-amine, (o) 6-((4-(3-chloro-2-fluorobenzoyl)piperazin-1-yl)methyl)-N-(5-methyl-1H-pyrazol-3-yl)pyrazin-2-amine, (p) 6-((4-(2-fluoro-3-(trifluoromethyl)benzoyl)piperazin-1-yl)methyl)-N-1,2,4-thiadiazol-5-ylpyrazin-2-amine, (q) 6-((4-(3-chloro-2-fluorobenzoyl)piperazin-1-yl)methyl)-N-thiazol-2-ylpyrazin-2-amine, (r) 6-((4-(3-chloro-2-fluorobenzoyl)piperazin-1-yl)methyl)-N-(5-chlorothiazol-2-yl)pyridin-2-amine, (s) 6-((4-(3-chloro-2-fluorobenzoyl)piperazin-1-yl)methyl)-N-(5-fluorothiazol-2-yl)pyridin-2-amine; or (t) 6-((4-(2-fluoro-3-trifluoromethylbenzoyl)piperazin-1-yl)methyl)-N-(5-methyl-1H-pyrazol-3-yl)pyrazin-2-amine;

or a pharmaceutically acceptable salt or ester thereof, and the other preparation is a preparation containing paclitaxel or docetaxel, or a pharmaceutically acceptable salt or ester thereof, together with a pharmaceutically acceptable carrier or diluent.

Moreover, the combined preparation comprising, together with a pharmaceutically acceptable carrier or diluent, two separate preparations according to the invention may be further combined with at least one preparation containing an antitumor agent selected from the group consisting of antitumor alkylating agents, antitumor antimetabolites, antitumor antibiotics, plant-derived antitumor agents, antitumor platinum coordination compounds, antitumor camptothecin derivatives, antitumor tyrosine kinase inhibitors, monoclonal antibodies, interferons, biological response modifiers and other antitumor agents (here, definition of each antitumor agent is the same as that defined above), or a pharmaceutically acceptable salt or ester thereof.

Also, the pharmaceutical composition according to the invention preferably contains the following:

(a) 6-((4-(3-chloro-2-fluorobenzoyl)piperazin-1-yl)methyl)-N-thiazol-2-ylpyridin-2-amine, (b) 6-((4-(2,3-dichlorobenzoyl)piperazin-1-yl)methyl)-N-thiazol-2-ylpyridin-2-amine, (c) 6-(((1S,4S)-5-(3-chloro-2-fluorobenzoyl)-2,5-diazabicyclo[2.2.1]hept-2-yl)methyl)-N-thiazol-2-ylpyridin-2-amine, (d) 6-((4-(3-chloro-2-fluorobenzoyl)piperazin-1-yl)methyl)-N-(1H-pyrazol-3-yl)pyridin-2-amine, (e) 6-((4-(2-fluoro-3-(trifluoromethyl)benzoyl)piperazin-1-yl)methyl)-N-1H-pyrazol-3-ylpyridin-2-amine, (f) 6-((4-(3-(difluoromethyl)-2-fluorobenzoyl)piperazin-1-yl)methyl)-N-1H-pyrazol-3-ylpyridin-2-amine, (g) 6-((4-(3-chloro-2-fluorobenzoyl)piperazin-1-yl)methyl)-N-(5-methyl-1H-pyrazol-3-yl)pyridin-2-amine, (h) 6-((4-(2-fluoro-3-(trifluoromethyl)benzoyl)piperazin-1-yl)methyl)-N-(5-methyl-1H-pyrazol-3-yl)pyridin-2-amine, (i) 6-((4-(2-chloro-3-(trifluoromethyl)benzoyl)piperazin-1-yl)methyl)-N-(5-methyl-1H-pyrazol-3-yl)pyridin-2-amine, (j) 6-((4-(2,3-dichlorobenzoyl)piperazin-1-yl)methyl)-N-1,2,4-thiadiazol-5-ylpyridin-2-amine, (k) 6-((4-(2-fluoro-3-(trifluoromethyl)benzoyl)piperazin-1-yl)methyl)-N-1,2,4-thiadiazol-5-ylpyridin-2-amine, (l) 6-((4-(3-chloro-2-fluorobenzoyl)piperazin-1-yl)methyl)-N-1H-pyrazol-3-ylpyrazin-2-amine, (m) 6-(((1S,4S)-5-(3-chloro-2-fluorobenzoyl)-2,5-diazabicyclo[2.2.1]hept-2-yl)methyl)-N-1H-pyrazol-3-ylpyrazin-2-amine, (n) 6-((4-(2-fluoro-3-(trifluoromethyl)benzoyl)piperazin-1-yl)methyl)-N-1H-pyrazol-3-ylpyrazin-2-amine, (o) 6-((4-(3-chloro-2-fluorobenzoyl)piperazin-1-yl)methyl)-N-(5-methyl-1H-pyrazol-3-yl)pyrazin-2-amine, (p) 6-((4-(2-fluoro-3-(trifluoromethyl)benzoyl)piperazin-1-yl)methyl)-N-1,2,4-thiadiazol-5-ylpyrazin-2-amine, (q) 6-((4-(3-chloro-2-fluorobenzoyl)piperazin-1-yl)methyl)-N-thiazol-2-ylpyrazin-2-amine, (r) 6-((4-(3-chloro-2-fluorobenzoyl)piperazin-1-yl)methyl)-N-(5-chlorothiazol-2-yl)pyridin-2-amine, (s) 2-((4-(3-chloro-2-fluorobenzoyl)piperazin-1-yl)methyl)-N,N-dimethyl-6-(thiazol-2-yl)aminoisonicotinic amide, (t) (2-((4-(3-chloro-2-fluorobenzoyl)piperazin-1-yl)methyl)-6-(thiazol-2-ylamino)pyridin-4-yl)methanol, (u) 6-((4-(3-chloro-2-fluorobenzoyl)piperazin-1-yl)methyl)-4-(methoxymethyl)-N-thiazol-2-ylpyridin-2-amine, (v) 1-(2-((4-(3-chloro-2-fluorobenzoyl)piperazin-1-yl)methyl)-6-(thiazol-2-ylamino) pyridin-4-yl)-3-methylimidazolidin-2-one, (w) 2-((4-(3-chloro-2-fluorobenzoyl)piperazin-1-yl)methyl)-6-(thiazol-2-ylamino) isonicotinonitrile, (x) 6-((4-(3-chloro-2-fluorobenzoyl)piperazin-1-yl)methyl)-4-(1-methyl-1H-tetrazol-5-yl)-N-thiazol-2-ylpyridin-2-amine, (y) 6-((4-(3-chloro-2-fluorobenzoyl)piperazin-1-yl)methyl)-4-(2-methyl-2H-tetrazol-5-yl)-N-thiazol-2-ylpyridin-2-amine, (z) 6-((4-(3-chloro-2-fluorobenzoyl)piperazin-1-yl)methyl)-N-thiazol-2-yl-4-(1H-1,2,4-triazol-5-yl)pyridin-2-amine, (aa) 6-((4-(3-chloro-2-fluorobenzoyl)piperazin-1-yl)methyl)-N-(5-fluorothiazol-2-yl)pyridin-2-amine;

(bb) 6-((4-(2-fluoro-3-trifluoromethylbenzoyl)piperazin-1-yl)methyl)-N-(5-methyl-1H-pyrazol-3-yl)pyrazin-2-amine; or (cc) 2-{[4-(3-chloro-2-fluorobenzoyl)piperazin-1-yl]methyl}-N,N-dimethyl-6-(1H-pyrazol-3-ylamino)isonicotinamide, or a pharmaceutically acceptable salt or ester thereof; and paclitaxel or docetaxel, or a pharmaceutically acceptable salt or ester thereof, together with a pharmaceutically acceptable carrier or diluent.

Description of the Process for Preparation of Compound of General Formula (I)

Among the compounds represented by the General Formula (I):

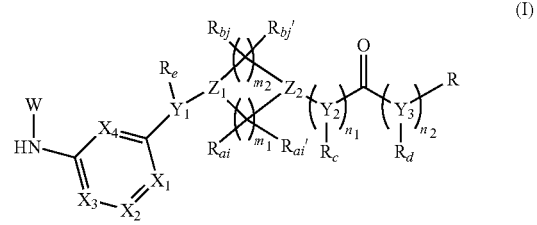

(wherein $m_1$, $m_2$, $n_1$, $n_2$, i, j, R, $R_{ai}$, $R_{ai}'$, $R_{bj}$, $R_{bj}'$, $R_c$, $R_d$, $R_e$, $X_1$, $X_2$, $X_3$, $X_4$, $Y_1$, $Y_2$, $Y_3$, $Z_1$, $Z_2$ and W have the same meaning as defined in the above) according to the invention, the compound of Formula (I-1) in which $Y_1$ is CH and $Z_1$ is N:

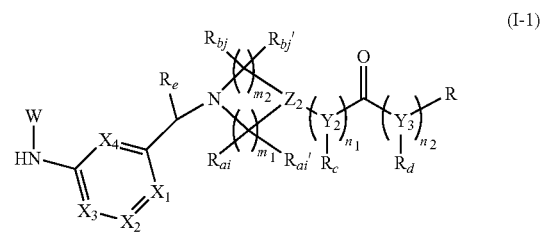

(wherein the symbols have the same meaning as the symbols for the above Formula (I)) can be prepared by, for example, the following method. Hereinafter, it is meant by the term "symbols for the above Formula (I)" in the phrase "same meaning as the symbols for the above Formula (I)," that "the respective symbols as described for General Formula (I) initially described in the present specification."

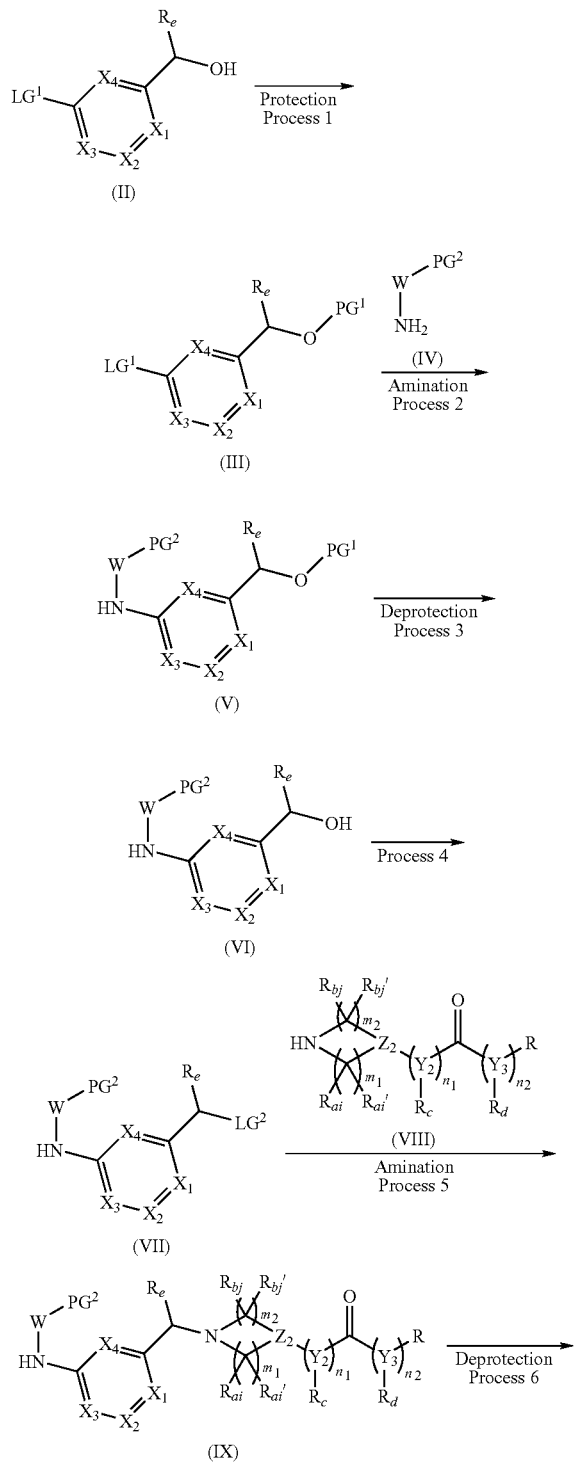

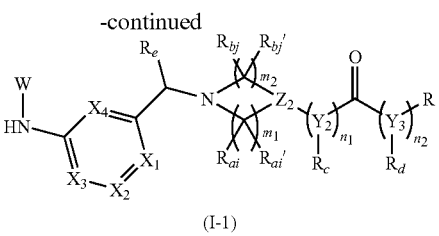

(Process 1) The present process is a method of introducing a protective group $PG^1$ such as a tert-butyldimethylsilyl group to Compound (II) (wherein $LG^1$ represents a leaving group such as halogen, and $X_1$, $X_2$, $X_3$, $X_4$ and $R_e$ have the same meaning as the symbols for the above Formula (I)), to produce Compound (III) (wherein $LG^1$ and $PG^1$ have the same meaning as defined above, and $X_1$, $X_2$, $X_3$, $X_4$ and $R_e$ have the same meaning as the symbols for the above Formula (I)).

The above-mentioned Compound (II) used in this process may be exemplified by (6-bromopyridin-2-yl)methanol, 1-(6-bromopyridin-2-yl)ethanol or (3-iodophenyl)methanol. The above-mentioned Compound (II) is commercially available or can be prepared by known methods.

As to the protective group $PG^1$, a method of protection may vary depending on the type of the protective group, but methods described in the literature [See T. W. Greene, *Protective Groups in Organic Synthesis*, John Wiley & Sons (1981)] or methods equivalent thereto can be utilized. For example, the Compound (II) can be synthesized by using tert-butyldimethylsilyl chloride in a solvent such as N,N-dimethylformamide in the presence of a base such as imidazole. When tert-butyldimethylsilyl chloride is used in a protection reaction, tert-butyldimethylsilyl chloride is used in an amount of from 1 to 10 mol, preferably from 1 to 3 mol, and the base is used in an amount of from 1 to 20 mol, preferably from 1 to 5 mol, relative to 1 mol of Compound (II). In this case, the reaction temperature may be appropriately selected by a person skilled in the art in accordance with the starting compound or reaction solvent used, but it is typically from 0° to the boiling point of the solvent. Also, the reaction is typically completed within 1 hour to 24 hours, but the reaction time can be appropriately extended or reduced.

Thus obtained Compound (III) is subjected to isolation and purification by known separation and purification means such as, for example, concentration, concentration under reduced pressure, crystallization, solvent extraction, reprecipitation or chromatography, or is subjected to the next process without isolation and purification.

(Process 2) The present process is a method of subjecting Compound (III) obtained by the above-described Process 1 (wherein $LG^1$ and $PG^1$ have the same meaning as defined above, and $X_1$, $X_2$, $X_3$, $X_4$ and $R_e$ have the same meaning as the symbols for the above Formula (I)) and Compound (IV) (wherein $PG^2$ may be absent, or if present, it is a protective group such as 4-methoxybenzyl, 2,4-dimethoxybenzyl, benzyl, methoxymethyl, (2-(trimethylsilyl)ethoxy)methyl or tert-butyl, preferably (2-(trimethylsilyl)ethoxy)methyl, methoxymethyl or tert-butyl, and W has the same meaning as the symbol for the above Formula (I)) to an amination reaction to produce Compound (V) (wherein $PG^1$ and $PG^2$ have the same meaning as defined above, and $X_1$, $X_2$, $X_3$, $X_4$ and $R_e$ have the same meaning as the symbols for the above Formula (I)).

The above-mentioned Compound (IV) used in this process may be exemplified by 2-aminothiazol-5-carbonitrile, 2-aminothiazole, 2-amino-5-methylthiazole, 5-amino-1,2,4-thiadiazole, 5-methyl-1-((2-(trimethylsilyl)ethoxy)methyl)-1H-pyrazol-3-amine, 1-((2-(trimethylsilyl)ethoxy)methyl)-1H-pyrazol-3-amine, or 1-tert-butyl-3-methyl-1H-pyrazol-5-amine. The Compound (IV) is commercially available or can be prepared by known methods (e.g., *Phosphorus, Sulfur and Silicon and the Related Elements*, Vol. 177, No. 11, pages 2651-2659 (2002), and *Journal of Chemical Research, Synopses*, Vol. 6, page 198 (1979)).

The amination reaction used in this process employs methods well known to those skilled in the art. In the amination reaction used in the process, specifically, for example, synthesis can be performed by reacting the above-mentioned Compound (III) and Compound (IV) in a solvent such as 1,4-dioxane, 1,2-dimethoxyethane, tetrahydrofuran, methylene chloride, chloroform or toluene, using a palladium catalyst such as trisdibenzylideneacetone dipalladium (0) or palladium acetate, a ligand such as 2,2'-bisdiphenylphosphino-1,1'-binaphthyl or 4,5-bis(diphenylphosphino)-9,9-dimethylxanthene, and a base such as cesium carbonate or sodium t-butoxide. In the reaction, with respect to 1 mol of compound (III), 0.5 to 3 mol, preferably 1 mol, of Compound (IV) is used; 0.001 to 1 mol, preferably 0.05 to 0.5 mol, of palladium catalyst is used; 0.002 to 2 mol, preferably 0.1 to 1.0 mol, of ligand is used; and 1 to 10 mol, preferably 1 to 3 mol, of base is used. The reaction temperature is appropriately selected by a person skilled in the art in accordance with the starting compound or reaction solvent used, but it is typically from 50° to the boiling point of the solvent used in the reaction. Also, the reaction is typically completed within 1 hour to 24 hours, but the reaction time can be appropriately extended or reduced. Thus obtained Compound (V) is subjected to isolation and purification by known separation and purification means such as, for example, concentration, concentration under reduced pressure, crystallization, solvent extraction, reprecipitation or chromatography, or subjected to the next process without isolation and purification.

(Process 3) The present process is a method of deprotecting Compound (V) obtained in the above-described Process 2 (wherein $PG^1$ and $PG^2$ have the same meaning as defined above, and $X_1$, $X_2$, $X_3$, $X_4$, $R_e$ and W have the same meaning as the symbols for the above Formula (I)) by removing protective group $PG^1$ to produce Compound (VI) (wherein $PG^2$ has the same meaning as defined above, and $X_1$, $X_2$, $X_3$, $X_4$, $R_e$ and W have the same meaning as the symbols for the above Formula (I)).

For removal of the protective group $PG^1$ used in this process, the method of removal may vary depending on the type of the protective group and stability of the compound, but methods described in the literature [See T. W. Greene, *Protective Groups in Organic Synthesis*, John Wiley & Sons (1981)] or methods equivalent thereto can be carried out. For example, Compound (V) in which $PG^1$ is tert-butyldimethylsilyl can be deprotected in a solvent such as tetrahydrofuran using tetrabutylammonium fluoride. When tetrabutylammonium fluoride is used in the deprotection reaction, tetrabutylammonium fluoride is used in an amount of from 1 to 10 mol, preferably from 1 to 3 mol, relative to 1 mol of Compound (V). The reaction temperature can be appropriately selected by a person having ordinary skill in the art in accordance with the starting compound or reaction solvent used, but it is typically from 0° to the boiling point of the solvent. Also, the reaction is typically completed within 1 hour to 24 hours, but the reaction time can be appropriately extended or reduced.

Thus obtained Compound (VI) is subjected to isolation and purification by known separation and purification means such as, for example, concentration, concentration under reduced pressure, crystallization, solvent extraction, reprecipitation or chromatography, or subjected to the next process without isolation and purification.

(Process 4) The present process is a method of converting a hydroxyl group of Compound (VI) obtained in the above-described Process 3 (wherein $PG^2$ has the same meaning as defined above, and $X_1$, $X_2$, $X_3$, $X_4$, $R_e$ and W have the same meaning as the symbols for the above Formula (I)) to a leaving group such as methanesulfonyloxy or chloro to produce Compound (VII) (wherein $LG^2$ represents a leaving group such as methanesulfonyloxy or halogen atom, $PG^2$ has the same meaning as defined above, and $X_1$, $X_2$, $X_3$, $X_4$, $R_e$ and W have the same meaning as the symbols for the above Formula (I)).

The reaction used in this process employs methods well known to those skilled in the art. In the reaction used in this process, specifically, for example, Compound (VII) in which $LG^2$ is methanesulfonyloxy can be obtained by reacting Compound (VI) with methanesulfonyl chloride in a solvent such as chloroform, methylene chloride, tetrahydrofuran, N,N-dimethylformamide, diethyl ether or ethyl acetate, in the presence of a base such as triethylamine or diisopropylethylamine. In this case, with respect to 1 mol of Compound (VI), methanesulfonyl chloride is used in an amount of from 1 to 10 mol, preferably from 1 to 3 mol; and the base is used in an amount of from 1 to 20 mol, preferably from 1 to 6 mol. The reaction temperature can be appropriately selected by a person having ordinary skill in the art in accordance with the starting compound or reaction solvent used, but it is typically from 0° to room temperature. Also, the reaction is typically completed within 10 minutes to 2 hours, but the reaction time can be appropriately extended or reduced.

Thus obtained Compound (VII) is subjected to isolation and purification by known separation and purification means such as, for example, concentration, concentration under reduced pressure, crystallization, solvent extraction, reprecipitation or chromatography, or subjected to the next process without isolation and purification.

(Process 5) The present process is a method of subjecting Compound (VII) obtained in the above-described Process 4 (wherein $LG^2$ and $PG^2$ have the same meaning as defined above, and $X_1$, $X_2$, $X_3$, $X_4$, $R_e$ and W have the same meaning as the symbols for the above Formula (I)) and Compound (VIII) (wherein $m_1$, $m_2$, $n_1$, $n_2$, R, $R_{ai}$, $R_{ai}'$, $R_{bj}$, $R_{bj}'$, $R_c$, $R_d$, $Y_2$, $Y_3$ and $Z_2$ have the same meaning as the symbols for the above Formula (I)) to an amination reaction to produce Compound (IX) (wherein $PG^2$ has the same meaning as defined above, and $X_1$, $X_2$, $X_3$, $X_4$, $R_e$ and W, and $m_1$, $m_2$, n1, n2, R, $R_{ai}$, $R_{ai}'$, $R_{bj}$, $R_{bj}'$, $R_c$, $R_d$, $Y_2$, $Y_3$ and $Z_2$ have the same meaning as the symbols for the above Formula (I)).

The aforementioned Compound (VIII) used in this process may be exemplified by 1-(3-chloro-2-fluorobenzoyl)piperazine, 1-(3-(trifluoromethyl)-2-fluorobenzoyl)piperazine, 1-((6-fluoropyridin-2-yl)carbonyl)piperazine, phenyl(piperidin-4-yl)methanone, 2-benzoyl-2,5-diazabicyclo[2.2.1]heptane or 1-benzoyl-1,4-diazepan. Compound (VIII) is commercially available or can be prepared by known methods (e.g., *Journal of Medicinal Chemistry*, Vol. 29, No. 5, pages 630-634 (1986)).

The amination reaction used in this process employs methods well known to those skilled in the art. In the amination reaction used in this process, specifically, for example, synthesis can be performed by reacting Compound (VII) and Compound (VIII) in a solvent such as tetrahydrofuran, dimethylsulfoxide, N,N-dimethylformamide, 1,4-dioxane, dichloromethane or chloroform, using a base such as sodium hydrogen carbonate, triethylamine, diisopropylethylamine or sodium hydroxide. In this case, with respect to 1 mol of Compound (VII), Compound (VIII) is used in an amount of from 1 to 10 mol, preferably from 1 to 3 mol; and the base is used in an amount of from 1 to 20 mol, preferably from 1 to 5 mol. The reaction temperature can be appropriately selected by a person having ordinary skill in the art in accordance with the starting compound or reaction solvent used, but it is typically from room temperature to the boiling point of the solvent. Also, the reaction is typically completed within 1 hour to 24 hours, but the reaction time can be appropriately extended or reduced.

Thus obtained Compound (IX) is subjected to isolation and purification by known separation and purification means such as, for example, concentration, concentration under reduced pressure, crystallization, solvent extraction, reprecipitation or chromatography, or subjected to the next process without isolation and purification.

In addition, if Compound (IX) does not necessitate deprotection, this Compound (IX) is used as the compound according to the invention without further performing the following Process 6.

(Process 6) The present process is a method of subjecting Compound (IX) obtained in the above-described Process 5 (wherein $PG^2$ has the same meaning as defined above, and $X_1$, $X_2$, $X_3$, $X_4$, $R_e$ and W, and $m_1$, $m_2$, $n_1$, $n_2$, R, $R_{ai}$, $R_{ai}'$, $R_{bj}$, $R_{bj}'$, $R_c$, $R_d$, $Y_2$, $Y_3$ and $Z_2$ have the same meaning as the symbols for the above Formula (I)) to a deprotection reaction to produce Compound (I-1) (wherein $X_1$, $X_2$, $X_3$, $X_4$, $R_e$ and W, and $m_1$, $m_2$, $n_1$, $n_2$, R, $R_{ai}$, $R_{ai}'$, $R_{bj}$, $R_{bj}'$, $R_c$, $R_d$, $Y_2$, $Y_3$ and $Z_2$ have the same meaning as the symbols for the above Formula (I)).

For the deprotection reaction of $PG^2$, the method may vary depending on the type of the protective group or stability of the compound, but methods described in the literature [See T. W. Greene, *Protective Groups in Organic Synthesis*, John Wiley & Sons (1981)] or methods equivalent thereto can be carried out, for example, by solvolysis using acid.

For example, specifically, synthesis can be performed by subjecting Compound (IX) (wherein W is 1H-pyrazol-3-yl, $PG^2$ is (2-(trimethylsilyl)ethoxy)methyl, the pyrazole of W is substituted with $PG^2$ at the 1-position, and $X_1$, $X_2$, $X_3$, $X_4$, $R_e$ and W, and $m_1$, $m_2$, $n_1$, $n_2$, R, $R_{ai}$, $R_{ai}'$, $R_{bj}$, $R_{bj}'$, $R_c$, $R_d$, $Y_2$, $Y_3$ and $Z_2$ have the same meaning as the symbols for the above Formula (I)) to deprotection reaction by solvolysis using a solvent mixture of trifluoroacetic acid and water, to produce the corresponding Compound (1-1) (wherein W has the same meaning as defined above, and $X_1$, $X_2$, $X_3$, $X_4$, $R_e$ and W, and $m_1$, $m_2$, $n_1$, $n_2$, R, $R_{ai}$, $R_{ai}'$, $R_{bj}$, $R_{bj}'$, $R_c$, $R_d$, $Y_2$, $Y_3$ and $Z_2$ have the same meaning as the symbols for the above Formula (I)). In this case, the reaction temperature can be appropriately selected by a person having ordinary skill in the art in accordance with the starting compound or reaction solvent used, but it is typically from 0° to the boiling point of the solvent. Also, the reaction is typically completed within 1 hour to 24 hours, but the reaction time can be appropriately extended or reduced.

Thus obtained Compound (I-1) is subjected to isolation and purification by known separation and purification means such as, for example, concentration, concentration under reduced pressure, crystallization, solvent extraction, reprecipitation or chromatography, or subjected to the next process without isolation and purification.

Among the Compounds (VIII) (wherein $m_1$, $m_2$, $n_1$, $n_2$, R, $R_{ai}$, $R_{ai}'$, $R_{bj}$, $R_{bj}'$, $R_c$, $R_d$, $Y_2$, $Y_3$ and $Z_2$ have the same meaning as the symbols for the above Formula (I)) according to the invention, Compound (VIII-1) (wherein $Z_2$ is N, $n_1$ is 0, and $m_1$, $m_2$, $n_2$, R, $R_{ai}$, $R_{ai}'$, $R_{bj}$, $R_{bj}'$, $R_d$ and $Y_3$ have the same meaning as the symbols for the above Formula (I)) can be prepared, for example, by the following method.

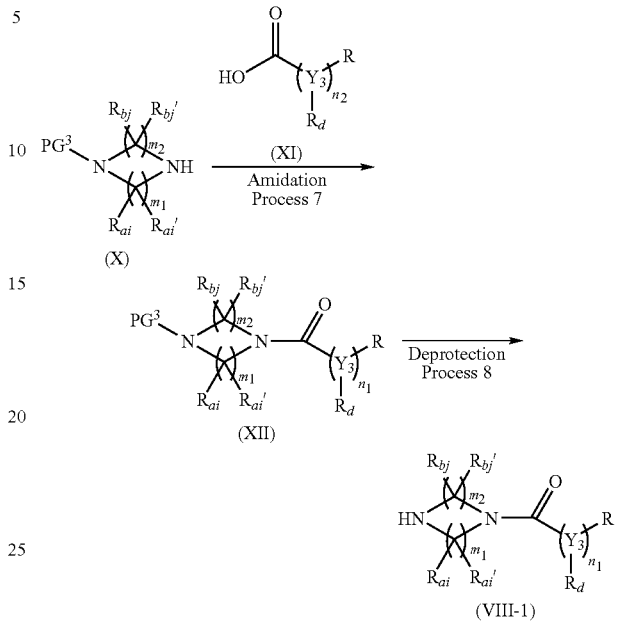

(Process 7) The present process is a method of subjecting Compound (X) (wherein $PG^3$ is a protective group such as tert-butyloxycarbonyl, and $m_1$, $m_2$, $R_{ai}$, $R_{ai}'$, $R_{bj}$ and $R_{bj}'$ have the same meaning as the symbols for the above Formula (I)) and Compound (XI) (wherein $n_2$, R, $R_d$ and $Y_3$ have the same meaning as the symbols for the above Formula (I)) to an amidation reaction to produce Compound (XII) (wherein $PG^3$ has the same meaning as defined above, and $m_1$, $m_2$, $R_{ai}$, $R_{ai}'$, $R_{bj}$ and $R_{bj}'$, and $n_2$, $R_c$, $R_d$ and $Y_3$ have the same meaning as the symbols for the above Formula (I)).

The aforementioned Compound (X) used in this process may be exemplified by tert-butylpiperazin-1-carboxylic acid ester, tert-butyl-2-methylpiperazin-1-carboxylic acid ester, tert-butyl-2,5-diazabicyclo[2.2.1]heptane-2-carboxylic acid ester, or tert-butyl-1,4-diazepan-1-carboxylic acid ester. This Compound (X) is commercially available or can be prepared by known methods (e.g., *Journal of Medicinal Chemistry*, Vol. 29, No. 5, pages 630-634 (1986)).

The aforementioned Compound (XI) used in this process may be exemplified by 6-fluoropyridine-2-carboxylic acid, thiophene-2-carboxylic acid, 2,3-dichlorobenzoic acid, 3-chloro-2-fluorobenzoic acid, 3-(trifluoromethyl)-2-fluorobenzoic acid, furan-3-carboxylic acid or 2-fluoropyridine-3-carboxylic acid. This Compound (XI) is commercially available or can be produced by known methods.

The amidation reaction used in this process can be carried out by using a carboxylic acid represented by the above-described Compound (XI) or its reactive derivatives and the above-described Compound (X). Examples of the "reactive derivatives" of Compound (XI) may include mixed acid anhydrides, active esters and active amides, and these can be obtained according to the method described in, for example, WO 98/05641. Specifically, for example, synthesis can be performed by condensing the above Compound (X) and Compound (XI) in a solvent such as tetrahydrofuran, dimethylsulfoxide, N,N-dimethylformamide, 1,4-dioxane, dichloromethane or chloroform, using a condensing agent such as 1-(3-dimethylaminopropyl)-3-ethylcarbodiimide, and 1-hydroxybenzotriazole. In this case, with respect to 1 mol of Compound (X), Compound (XI) is used in an amount of from 1 to 3 mol, preferably 1 mol, and the condensing agent is used in an amount from 1 to 10 mol, preferably from 1 to 3 mol. The reaction temperature is appropriately selected by a person skilled in the art in accordance with the starting compound or reaction solvent used, but it is typically from room temperature to the boiling point of the solvent used in the reaction. Also, the reaction is typically completed within 1 hour to 24 hours, but the reaction time can be appropriately extended or reduced.

Thus obtained Compound (XII) is subjected to isolation and purification by known separation and purification means such as, for example, concentration, concentration under reduced pressure, crystallization, solvent extraction, reprecipitation or chromatography, or subjected to the next process without isolation and purification.

compound represented by Formula (XII) (wherein $PG^3$ is tert-butyloxycarbonyl) can be carried out by solvolysis using acid.

Thus obtained Compound (VIII-1) is subjected to isolation and purification by known separation and purification means such as, for example, concentration, concentration under reduced pressure, crystallization, solvent extraction, reprecipitation or chromatography, or subjected to the next process without isolation and purification.

Among the Compounds (VI) (wherein $PG^2$ has the same meaning as defined above, and $R_e$, $X_1$, $X_2$, $X_3$, $X_4$ and W have the same meaning as the symbols for the above Formula (I)) according to the invention, Compound (VI-1) (wherein $R_e$ is hydrogen atom, PG has the same meaning as defined above, and $X_1$, $X_2$, $X_3$, $X_4$ and W have the same meaning as the symbols for the above Formula (I)) can be also prepared, for example, by the following method.

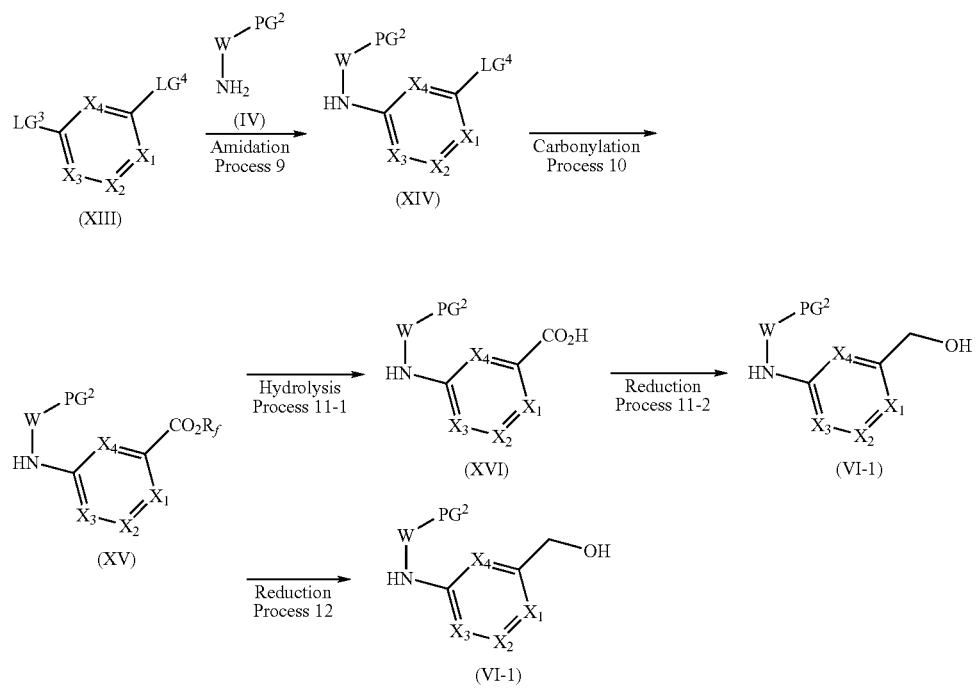

(Process 8) The present process is a method of deprotecting Compound (XII) obtained in the above-described Process 7 (wherein $PG^3$ has the same meaning as defined above, and $m_1$, $m_2$, $R_{ai}$, $R_{ai}'$, $R_{bj}$ and $R_{bj}'$, and $n_2$, $R_c$, $R_d$ and $Y_3$ have the same meaning as the symbols for the above Formula (I)) by removing protective group $PG^3$ to produce a compound represented by Formula (VIII-1) (wherein $m_1$, $m_2$, $R_{ai}$, $R_{ai}'$, $R_{bj}$ and $R_{bj}'$, and $n_2$, $R_c$, $R_d$ and $Y_3$ have the same meaning as the symbols for the above Formula (I)).

The deprotection reaction used in this process employs methods well known to those skilled in the art. For removal of the protective group of the above-mentioned Compound (XII) in this process, the method of removal may vary depending on the type of the protective group and stability of the compound, but methods described in the literature [See T. W. Greene, *Protective Groups in Organic Synthesis*, John Wiley & Sons (1981)] or methods equivalent thereto can be carried out. For example, the deprotection reaction for the (Process 9) The present process is a method of subjecting Compound (XIII) (wherein $LG^3$ and $LG^4$ each represent a leaving group such as halogen atom, and $X_1$, $X_2$, $X_3$ and $X_4$ have the same meaning as the symbols for the above Formula (I)) and Compound (IV) (wherein $PG^2$ have the same meaning as defined above, and W has the same meaning as the symbol for the above Formula (I)) to an amination reaction to produce Compound (XIV) (wherein $PG^2$ and $LG^4$ have the same meaning as defined above, and $X_1$, $X_2$, $X_3$, X and W have the same meaning as the symbols for the above Formula (I)).

The above-described Compound (IV) used in this process may be exemplified by 2-aminothiazole, 5-amino-1,2,4-thiadiazole, 5-methyl-1-((2-(trimethylsilyl)ethoxy)methyl)-1H-pyrazol-3-amine, 1-((2-(trimethylsilyl)ethoxy)methyl)-1H-pyrazol-3-amine, or 1-tert-butyl-3-methyl-1H-pyrazol-5-amine. The Compound (IV) is commercially available or can be prepared by known methods (e.g., *Phosphorus, Sulfur and*

*Silicon and the Related Elements*, Vol. 177, No. 11, pages 2651-2659 (2002), and *Journal of Chemical Research, Synopses*, Vol. 6, page 198 (1979)).

The above-described Compound (XIII) used in this process may be exemplified by 2,6-dichloropyridine, 2,4-dichloropyrimidine or 2,6-dichloropyrazine. Compound (XIII) is commercially available or can be prepared by known methods.

This process can be carried out according to a method similar to the aforementioned Process 2, a method equivalent to that, or a combination of these methods with conventional methods.

Thus obtained Compound (XIV) (wherein $PG^2$ and $LG^4$ have the same meaning as defined above, and $X_1$, $X_2$, $X_3$, $X_4$ and W have the same meaning as the symbols for the above Formula (I)) is subjected to isolation and purification by known separation and purification means such as, for example, concentration, concentration under reduced pressure, crystallization, solvent extraction, reprecipitation or chromatography, or subjected to the next process without isolation and purification.

(Process 10) The present process is a method of subjecting Compound (XIV) obtained in the above-described Process 9 (wherein $PG^2$ and $LG^4$ have the same meaning as defined above, and $X_1$, $X_2$, $X_3$, $X_4$ and W have the same meaning as the symbols for the above Formula (I)) to a carbonylation reaction to produce Compound (XV) (wherein $R_f$ is lower alkyl, $PG^2$ has the same meaning as defined above, and $X_1$, $X_2$, $X_3$, $X_4$ and W have the same meaning as the symbols for the above Formula (I)).

The carbonylation reaction used in this process employs methods well known to those skilled in the art. In the carbonylation reaction used in this process, specifically, for example, Compound (XV) can be synthesized by reacting Compound (XIV) with carbon monoxide in a solvent mixture in which alcohol such as methanol or ethanol is added to a solvent such as N,N-dimethylacetamide, N-methylpyrrolidone or N,N-dimethylformamide, in the presence of a ligand such as 1,1'-bis(diphenylphosphino)ferrocene, a palladium catalyst such as palladium (II) acetate, and a base such as sodium hydrogen carbonate or triethylamine. In this case, with respect to 1 mol of Compound (XIV), the palladium catalyst is used in an amount of from 0.01 to 1 mol, preferably from 0.05 to 0.5 mol; the ligand is used in an amount of from 0.02 to 1 mol, preferably from 0.1 to 1 mol; and the base is used in an amount of from 1 to 10 mol, preferably from 1 to 3 mol. The reaction temperature can be appropriately selected by a person skilled in the art in accordance with the starting compound and reaction solvent used, but it is typically from 50° to the boiling point of the solvent used in the reaction. Also, the reaction is typically completed within 1 hour to 24 hours, but the reaction time can be appropriately extended or reduced.

Thus obtained Compound (XV) is subjected to isolation and purification by known separation and purification means such as, for example, concentration, concentration under reduced pressure, crystallization, solvent extraction, reprecipitation or chromatography, or subjected to the next process without isolation and purification.

(Process 11-1) The present process is a method of subjecting Compound (XV) obtained in the above-described Process 10 (wherein $R_f$ and $PG^2$ have the same meaning as defined above, and $X_1$, $X_2$, $X_3$, $X_4$ and W have the same meaning as the symbols for the above Formula (I)) to a hydrolysis reaction to produce Compound (XVI) (wherein $PG^2$ has the same meaning as defined above and $X_1$, $X_2$, $X_3$, $X_4$ and W have the same meaning as the symbols for the above Formula (I)).

The hydrolysis reaction used in this process employs methods well known to those skilled in the art. In the hydrolysis reaction used in this process, specifically, for example, Compound (XVI) can be synthesized by hydrolyzing Compound (XV) in a solvent such as methanol, ethanol or tetrahydrofuran, using an aqueous solution of sodium hydroxide as the base. In this case, with respect to 1 mol of Compound (XV), the base is used in an amount of from 1 to 1000 mol, preferably from 1 to 100 mol. The reaction temperature can be appropriately selected by a person skilled in the art in accordance with the starting compound and reaction solvent used, but it is typically from room temperature to the boiling point of the solvent. Also, the reaction is typically completed within 1 hour to 24 hours, but the reaction time can be appropriately extended or reduced.

Thus obtained Compound (XVI) is subjected to isolation and purification by known separation and purification means such as, for example, concentration, concentration under reduced pressure, crystallization, solvent extraction, reprecipitation or chromatography, or subjected to the next process without isolation and purification.

(Process 11-2) The present process is a method of subjecting Compound (XVI) obtained in the above-described Process 11-1 (wherein $PG^2$ has the same meaning as defined above, and $X_1$, $X_2$, $X_3$, $X_4$ and W have the same meaning as the symbols for the above Formula (I)) to a reduction reaction to produce Compound (VI-1) (wherein $PG^2$ has the same meaning as defined above, and $X_1$, $X_2$, $X_3$, $X_4$ and W have the same meaning as the symbols for the above Formula (I)).

The reduction reaction used in this process employs methods well known to those skilled in the art. In the reduction reaction used in this process, specifically, for example, Compound (VI-1) can be synthesized by reacting Compound (XVI) with N,N'-carbonyldiimidazole in a solvent such as N,N-dimethylformamide or tetrahydrofuran at room temperature for 12 to 24 hours, and then reacting again with a reducing agent such as sodium borohydride. In this case, with respect to 1 mol of Compound (XVI), N,N'-carbonyldiimidazole is used in an amount of from 1 to 10 mol, preferably from 1 to 3 mol; and the reducing agent is used in an amount of from 1 to 20 mol, preferably from 1 to 5 mol. The reaction temperature can be appropriately selected by a person skilled in the art in accordance with the starting compound and reaction solvent used, but it is typically from 0° to room temperature. Also, the reaction is typically completed within 10 minutes to 24 hours, but the reaction time can be appropriately extended or reduced.

Thus obtained Compound (VI-1) is subjected to isolation and purification by known separation and purification means such as, for example, concentration, concentration under reduced pressure, crystallization, solvent extraction, reprecipitation or chromatography, or subjected to the next process without isolation and purification.

(Process 12) The present process is a method of subjecting Compound (XV) obtained in the above-described Process 10 (wherein $R_f$ and $PG^2$ have the same meaning as defined above, and $X_1$, $X_2$, $X_3$, $X_4$ and W have the same meaning as the symbols for the above Formula (I)) to a reduction reaction to produce Compound (VI-1) (wherein $PG^2$ has the same meaning as defined above, and $X_1$, $X_2$, $X_3$, $X_4$ and W have the same meaning as the symbols for the above Formula (I)).

The reduction reaction used in this process employs methods well known to those skilled in the art. In the reduction reaction used in this process, specifically, for example, Compound (VI-1) can be synthesized by reacting Compound (XV) with a reducing agent such as lithium borohydride or lithium aluminum hydride in a solvent such as tetrahydrofuran or 1,4-dioxane. In this case, with respect to 1 mol of Compound (XV), the reducing agent is used in an amount of from 1 to 20 mol, preferably from 1 to 5 mol. The reaction temperature can be appropriately selected by a person skilled in the art in accordance with the starting compound and reaction solvent used, but it is typically from 0° to the boiling point of the solvent used in the reaction. Also, the reaction is typically completed within 10 minutes to 24 hours, but the reaction time can be appropriately extended or reduced.

Thus obtained Compound (VI-1) is subjected to isolation and purification by known separation and purification means such as, for example, concentration, concentration under reduced pressure, crystallization, solvent extraction, reprecipitation or chromatography, or subjected to the next process without isolation and purification.

Compound (XV) (wherein $R_f$ is a lower alkyl group, $PG^2$ has the same meaning as defined above, and $X_1$, $X_2$, $X_3$, $X_4$ and W have the same meanings as the symbols for the above Formula (I)) according to the invention can be also prepared by, for example, the following method.

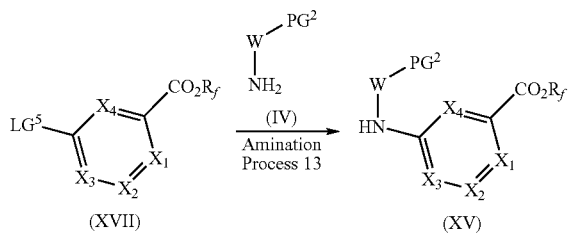

(Process 13) The present process is a method of subjecting Compound (XVII) (wherein $R_f$ is a lower alkyl group, $LG^5$ is a leaving group such as halogen atom, and $X_1$, $X_2$, $X_3$ and $X_4$ have the same meanings as the symbols for the above Formula (I)) and Compound (IV) (wherein $PG^2$ has the same meaning as defined above, and W has the same meaning as the symbol for the above Formula (I)) to an amination reaction to produce Compound (XV) (wherein $R_f$ is a lower alkyl group, $PG^2$ has the same meaning as defined above, and $X_1$, $X_2$, $X_3$, $X_4$ and W have the same meanings as the symbols for the above Formula (I)).

The above-described Compound (IV) that is used in this process may be exemplified by 2-aminothiazole, 5-amino-1,2,4-thiadiazole, 5-methyl-1-((2-(trimethylsilyl)ethoxy)methyl)-1H-pyrazol-3-amine, 1-((2-(trimethylsilyl)ethoxy)methyl)-1H-pyrazol-3-amine, 1-tert-butyl-3-methyl-1H-pyrazol-5-amine and the like. The above-described Compound (IV) is commercially available or can be produced by known methods (for example, Phosphorus, Sulfur and Silicon and the Related Elements, Vol. 177 (11) pp. 2651-2659 (2002); and Journal of Chemical Research, Synopses, Vol. 6, p. 198 (1979)).

The above-mentioned Compound (XVII) that is used in the present process may be exemplified by 6-chloro-2-pyridinecarboxylic acid methyl ester, 6-chloro-4-methoxy-2-pyridinecarboxylic acid methyl ester or the like. Compound (XVII) is commercially available or can be produced by known methods.

This process can be carried out by a method similar to the above-described Process 2, a method equivalent to this, or a combination of these methods and conventional methods.

Thus obtained, aforementioned Compound (XV) (wherein $R_f$ is a lower alkyl group, $PG^2$ has the same meaning as defined above, and $X_1$, $X_2$, $X_3$, $X_4$ and W have the same meanings as the symbols for the above Formula (I)) can be either subjected to isolation and purification by known separation and purification means such as, for example, concentration, concentration under reduced pressure, crystallization, solvent extraction, reprecipitation or chromatography, or subjected to the next process without isolation and purification.

The aforementioned introduction of a protective group into a compound can be carried out in a number of stages for producing the above-described synthetic intermediates as needed. In obtaining the protection product, reaction can be carried out in a manner similar to the corresponding process as described above. Further, such compound can be deprotected by removing the introduced protective group according to a method similar to the aforementioned Process 6, a method equivalent to that, or a combination of these methods and conventional methods.

Hereinunder, examples of introducing protective groups to Compound (IV) and to Compound (XV) will be illustrated. In addition, a person having ordinary skill in the art can perform introduction of protective groups into the above-mentioned synthetic intermediates by using commercially available, known compounds and using any appropriate, known method, and/or the below-described methods or methods equivalent to these.

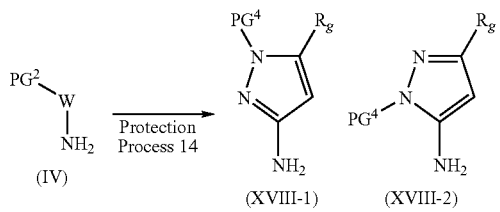

(Process 14) The present process is a method of producing Compound (XVIII-1) or Compound (XVIII-2) (wherein $PG^4$ is a protective group such as methoxymethyl or (2-(trimethylsilyl)ethoxy)methyl, and $R_g$ is a substituent such as hydrogen atom, methyl or cyclopropyl) by introducing a protective group into Compound (IV) (wherein —W-$PG^1$ is 5-methyl-1H-pyrazol-3-yl, 5-cyclopropyl-1H-pyrazol-3-yl or 1-H-pyrazol-3-yl).

In the protection reaction used in this process, for example, Compound (IV) is protected in a solvent such as tetrahydrofuran, N,N-dimethylformamide, 1,4-dioxane, toluene, dichloromethane or chloroform, using a base such as sodium hydride together with chloromethyl methyl ether, chloromethyl 2-(trimethylsilyl)ethyl ether or the like, to synthesize the corresponding Compound (XVIII-1) or Compound (XVIII-2). In this case, with respect to 1 mol of Compound (IV), the base is used in an amount of from 1 to 20 mol, preferably from 1 to 5 mol; and the protective reagent is used in an amount of from 1 to 10 mol, preferably from 1 to 3 mol. The reaction temperature can be appropriately selected by a person skilled in the art in accordance with the starting compound or reaction solvent used, but it is typically from 0° to room temperature. Also, the reaction is typically completed within 10 minutes to 24 hours, but the reaction time can be appropriately extended or reduced.

Thus obtained Compound (XVIII-1) or Compound (XVIII-2) is subjected to isolation and purification by known separation and purification means such as, for example, concentration, concentration under reduced pressure, crystallization, solvent extraction, reprecipitation or chromatography, or subjected to the next process without isolation and purification.

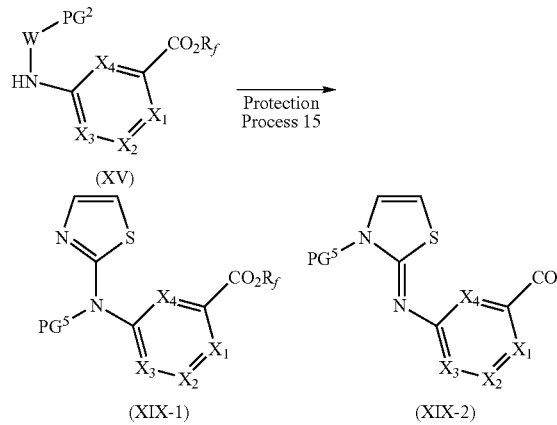

(Process 15) The present process is a method of producing Compound (XIX-1) or Compound (XIX-2) (wherein $R_f$ and $PG^5$ have the same meaning as defined above, and $X_1$, $X_2$, $X_3$, $X_4$ and W have the same meaning as the symbols for the above Formula (I)) by introducing a protective group $PG^5$ such as methoxymethyl or (2-(trimethylsilyl)ethoxy)methyl into Compound (XV) (wherein $R_f$ and $PG^2$ have the same meaning as defined above, and $X_1$, $X_2$, $X_3$, $X_4$ and W have the same meaning as the symbols for the above Formula (I)).

The protection reaction used in this process can be carried out, for example, by protecting Compound (XV) in a solvent such as tetrahydrofuran, N,N-dimethylformamide, 1,4-dioxane, toluene, dichloromethane or chloroform, using a base such as sodium hydride or diisopropylethylamine together with chloromethyl methyl ether, chloromethyl 2-(trimethylsilyl)ethyl ether or the like. In this case, with respect to 1 mol of Compound (XV), the base is used in an amount of from 1 to 20 mol, preferably from 1 to 5 mol, and the protective reagent is used in an amount of from 1 to 10 mol, preferably from 1 to 3 mol. The reaction temperature can be appropriately selected by a person skilled in the art in accordance with the starting compound or reaction solvent used, but it is typically from 0° to room temperature. Also, the reaction is typically completed within 10 minutes to 24 hours, but the reaction time can be appropriately extended or reduced.

Thus obtained Compound (XIX-1) or Compound (XIX-2) is subjected to isolation and purification by known separation and purification means such as, for example, concentration, concentration under reduced pressure, crystallization, solvent extraction, reprecipitation or chromatography, or subjected to the next process without isolation and purification.

Furthermore, introduction or conversion of $X_{1a}$, $X_{2a}$ or $X_{3a}$ can be carried out at any step for producing the above-mentioned synthetic intermediates which may have appropriate protective groups. Hereinafter, examples of introduction or conversion of a substituent for $X_{2a}$ in the compound represented by Formula (I) (wherein $X_1$ is CH, $X_2$ is $CX_{2a}$, $X_3$ is CH, $X_4$ is N, and $m_1$, $m_2$, $n_1$, $n_2$, i, j, R, $R_{ai}$, $R_{ai}'$, $R_{bj}$, $R_{bj}'$, $R_c$, $R_d$, $R_e$, $Y_1$, $Y_2$, $Y_3$, $Z_1$, $Z_2$ and W have the same meanings as the symbols for the above Formula (I)), the above-mentioned Compound (XV) (wherein $R_f$, $PG^2$, $X_1$, $X_2$, $X_3$, $X_4$ and W have the same meanings as defined above) and the above-mentioned Compound (V) (wherein $PG^1$, $PG^2$, $X_1$, $X_2$, $X_3$, $X_4$, $R_e$ and W have the same meanings as defined above) will be illustrated. Here, the compound of Formula (I) mentioned in the description of the following Processes (16-1) to (16-7), the compound of Formula (XV) mentioned in the description of Process (17), and the compound of Formula (V) mentioned in the description of Processes (18-1) and (18-2) may have an appropriate protective group at a substitutable position to which a protective group can be introduced. Further, a person skilled in the art can perform introduction or conversion of a substituent for $X_{1a}$, $X_{2a}$ or $X_{3a}$ by using commercially available, known compounds and using any appropriate, known method, and/or the below-described methods or methods equivalent to these.

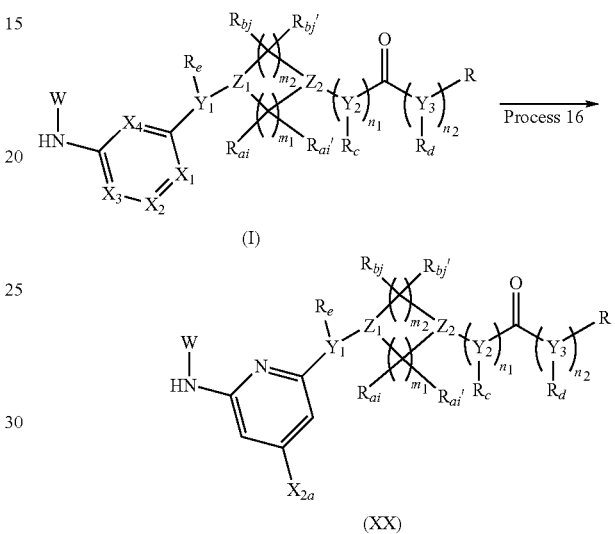

Process 16 relates to a method of synthesizing Compound (XX) from Compound (I). Hereafter, it is exemplified in Processes 16-1 to 16-7.

(Process 16-1) The present process is a method of subjecting Compound (I) (wherein $X_1$ is CH, $X_2$ is $CX_{2a}$, $X_{2a}$ is bromine atom, $X_3$ is CH, $X_4$ is N, and $m_1$, $m_2$, $n_1$, $n_2$, i, j, R, $R_{ai}$, $R_{ai}'$, $R_{bj}$, $R_{bj}'$, $R_c$, $R_d$, $R_e$, $Y_1$, $Y_2$, $Y_3$, $Z_1$, $Z_2$ and W have the same meaning as the symbols for the above Formula (I)) to a carbonylation reaction to produce Compound (XIX) (wherein $X_1$ is CH, $X_2$ is $CX_{2a}$, $X_{2a}$ is alkoxycarbonyl, $X_3$ is CH, $X_4$ is N, and $m_1$, $m_2$, $n_1$, $n_2$, i, j, R, $R_{ai}$, $R_{ai}'$, $R_{bj}$, $R_{bj}'$, $R_c$, $R_d$, $R_e$, $Y_1$, $Y_2$, $Y_3$, $Z_1$, $Z_2$ and W have the same meaning as the symbols for the above Formula (I)).

This process can be carried out by a method similar to the above-described Process 10, a method equivalent to this, or a combination of these methods and conventional methods.

Thus obtained Compound (XIX) according to the invention can be subjected to isolation and purification by known separation and purification means such as, for example, concentration, concentration under reduced pressure, crystallization, solvent extraction, reprecipitation or chromatography.

(Process 16-2) The present process is a method of subjecting Compound (I) (wherein $X_1$ is CH, $X_2$ is $CX_{2a}$, $X_{2a}$ is alkoxycarbonyl, $X_3$ is CH, $X_4$ is N, and $m_1$, $m_2$, $n_1$, $n_2$, i, j, R, $R_{ai}$, $R_{ai}'$, $R_{bj}$, $R_{bj}'$, $R_c$, $R_d$, $R_e$, $Y_1$, $Y_2$, $Y_3$, $Z_1$, $Z_2$ and W have the same meaning as the symbols for the above Formula (I)) to a hydrolysis reaction to produce Compound (XIX) (wherein $X_1$ is CH, $X_2$ is $CX_{2a}$, $X_{2a}$ is carboxyl, $X_3$ is CH, $X_4$ is N, and $m_1$, $m_2$, $n_1$, $n_2$, i, j, R, $R_{ai}$, $R_{ai}'$, $R_{bj}$, $R_{bj}'$, $R_c$, $R_d$, $R_e$, $Y_1$, $Y_2$, $Y_3$, $Z_1$, $Z_2$ and W have the same meaning as the symbols for the above Formula (I)).

This process can be carried out by a method similar to the above-described Process 11, a method equivalent to this, or a combination of these methods and conventional methods.

Thus obtained Compound (XIX) according to the invention can be subjected to isolation and purification by known separation and purification means such as, for example, concentration, concentration under reduced pressure, crystallization, solvent extraction, reprecipitation or chromatography.

(Process 16-3) The present process is a method of subjecting Compound (I) (wherein $X_1$ is CH, $X_2$ is $CX_{2a}$, $X_{2a}$ is carboxyl, $X_3$ is CH, $X_4$ is N, and $m_1, m_2, n_1, n_2, i, j, R, R_{ai}, R_{ai}'$, $R_{bj}, R_{bj}', R_c, R_d, R_e, Y_1, Y_2, Y_3, Z_1, Z_2$ and W have the same meaning as the symbols for the above Formula (I)) to an amidation reaction to produce Compound (XIX) (wherein $X_{2a}$ is carbamoyl, and $m_1, m_2, n_1, n_2, i, j, R, R_{ai}, R_{ai}', R_{bj}, R_{bj}'$, $R_c, R_d, R_e, Y_1, Y_2, Y_3, Z_1, Z_2$ and W have the same meaning as the symbols for the above Formula (I)).

This process can be carried out by a method similar to the above-described Process 7, a method equivalent to this, or a combination of these methods and conventional methods. The amine used in this process may be exemplified by dimethylamine, methylamine, pyrrolidine and 2-hydroxyethylamine.

Thus obtained Compound (XIX) according to the invention can be subjected to isolation and purification by known separation and purification means such as, for example, concentration, concentration under reduced pressure, crystallization, solvent extraction, reprecipitation or chromatography.

(Process 16-4) The present process is a method of subjecting Compound (I) (wherein $X_1$ is CH, $X_2$ is $CX_{2a}$, $X_{2a}$ is carboxyl, $X_3$ is CH, $X_4$ is N, and $m_1, m_2, n_1, n_2, i, j, R, R_{ai}, R_{ai}'$, $R_{bj}, R_{bj}', R_c, R_d, R_e, Y_1, Y_2, Y_3, Z_1, Z_2$ and W have the same meaning as the symbols for the above Formula (I)) to a reduction reaction to produce Compound (XIX) (wherein $X_{2a}$ is hydroxymethyl, and $m_1, m_2, n_1, n_2, i, j, R, R_{ai}, R_{ai}', R_b, R_{bj}'$, $R_c, R_d, R_e, Y_1, Y_2, Y_3, Z_1, Z_2$ and W have the same meaning as the symbols for the above Formula (I)).

This process can be carried out by a method similar to the above-described Process 11-2, a method equivalent to this, or a combination of these methods and conventional methods.

Thus obtained Compound (XIX) according to the invention can be subjected to isolation and purification by known separation and purification means such as, for example, concentration, concentration under reduced pressure, crystallization, solvent extraction, reprecipitation or chromatography.

(Process 16-5) The present process is a method of subjecting Compound (I) (wherein $X_1$ is CH, $X_2$ is $CX_{2a}$, $X_{2a}$ is hydroxymethyl, $X_3$ is CH, $X_4$ is N, and $m_1, m_2, n_1, n_2, i, j, R, R_{ai}, R_{ai}', R_{bj}, R_{bj}', R_c, R_d, R_e, Y_1, Y_2, Y_3, Z_1, Z_2$ and W have the same meaning as the symbols for the above Formula (I)) to a reaction to produce Compound (XIX) (wherein $X_{2a}$ is methanesulfonyloxymethyl, and $m_1, m_2, n_1, n_2, i, j, R, R_{ai}, R_{ai}', R_b, R_{bj}', R_c, R_d, R_e, Y_1, Y_2, Y_3, Z_1, Z_2$ and W have the same meaning as the symbols for the above Formula (I)).

This process can be carried out by a method similar to the above-described Process 4, a method equivalent to this, or a combination of these methods and conventional methods.

Thus obtained Compound (XIX) according to the invention can be subjected to isolation and purification by known separation and purification means such as, for example, concentration, concentration under reduced pressure, crystallization, solvent extraction, reprecipitation or chromatography.

(Process 16-6) The present process is a method of subjecting Compound (I) (wherein $X_1$ is CH, $X_2$ is $CX_{2a}$, $X_{2a}$ is methanesulfonyloxymethyl, $X_3$ is CH, $X_4$ is N, and $m_1, m_2$, $n_1, n_2, i, j, R, R_{ai}, R_{ai}', R_b, R_{bj}', R_c, R_d, R_e, Y_1, Y_2, Y_3, Z_1, Z_2$ and W have the same meaning as the symbols for the above Formula (I)) to a substitution reaction to produce Compound (XIX) [wherein $X_{2a}$ is $R_iR_hNCH_2$— (wherein $R_i$ and $R_h$, which may be identical or different, are each hydrogen atom or lower alkyl which may be substituted, or $R_i$ and $R_h$ may be combined to form an aliphatic heterocyclic group which may be substituted), and $m_1, m_2, n1, n2, i, j, R, R_{ai}, R_{ai}', R_{bj}, R_{bj}'$, $R_c, R_d, R_e, Y_1, Y_2, Y_3, Z_1, Z_2$ and W have the same meaning as the symbols for the above Formula (I)].

In the substitution reaction used in this process, for example, synthesis can be performed by reacting Compound (I) (wherein $X_1$ is CH, $X_2$ is $CX_{2a}$, $X_{2a}$ is methanesulfonyloxymethyl, $X_3$ is CH, $X_4$ is N, and $m_1, m_2, n_1, n_2, i, j, R, R_{ai}$, $R_{ai}', R_b, R_{bj}', R_c, R_d, R_e, Y_1, Y_2, Y_3, Z_1, Z_2$ and W have the same meaning as the symbols for the above Formula (I)) with a nucleophilic agent represented by $R_iR_hNH$ such as dimethylamine, 1,2,3-triazole or 1,2,4-triazole, in a solvent such as chloroform, methylene chloride, tetrahydrofuran, N,N-dimethylformamide or dimethylsulfoxide, in the presence of a base such as potassium carbonate, triethylamine, diisopropylethylamine, or 1,8-diazabicyclo[5.4.0]undec-7-ene. In this case, with respect to 1 mol of Compound (I), the base is used in an amount of from 1 to 20 mol, preferably from 1 to 5 mol; and the nucleophilic agent is used in an amount of from 1 to 10 mol, preferably from 1 to 3 mol. The reaction temperature can be appropriately selected by a person skilled in the art in accordance with the starting compound or reaction solvent used, but it is typically from room temperature to the boiling point of the solvent used in the reaction. Also, the reaction is typically completed within 1 hour to 24 hours, but the reaction time can be appropriately extended or reduced.

Thus obtained Compound (XIX) according to the invention can be subjected to isolation and purification by known separation and purification means such as, for example, concentration, concentration under reduced pressure, crystallization, solvent extraction, reprecipitation or chromatography.

(Process 16-7) The present process is a method of subjecting Compound (I) (wherein $X_1$ is CH, $X_2$ is $CX_{2a}$, $X_{2a}$ is bromine atom, $X_3$ is CH, $X_4$ is N, and $m_1, m_2, n_1, n_2, i, j, R$, $R_{ai}, R_{ai}', R_{bj}, R_{bj}', R_c, R_d, R_e, Y_1, Y_2, Y_3, Z_1, Z_2$ and W have the same meaning as the symbols for the above Formula (I)) to a coupling reaction to produce Compound (XIX) [wherein $X_{2a}$ is $R_jR_kN$— (wherein $R_j$ and $R_k$, which may be identical or different, are each hydrogen atom, lower alkyl which may be substituted, lower acyl, lower carbamoyl or lower alkoxycarbonyl, or $R_j$ and $R_k$ may be combined to form a heterocyclic group which may be substituted), and $m_1, m_2, n_1, n_2, i, j, R$, $R_{ai}, R_{ai}', R_b, R_{bj}', R_c, R_d, R_e, Y_1, Y_2, Y_3, Z_1, Z_2$ and W have the same meaning as the symbols for the above Formula (I)].

This process can be carried out by a method similar to the above-described Process 2, a method equivalent to this, or a combination of these methods and conventional methods. The nucleophilic agent used in this process may be exemplified by amine represented by $R_jR_kNH$ such as 1-methyl-2-imidazolidinone, 2-pyrrolidone, 2-oxazolidone, piperazine or morpholine, amide, urea or carbamate.

Thus obtained Compound (XIX) according to the invention can be subjected to isolation and purification by known separation and purification means such as, for example, concentration, concentration under reduced pressure, crystallization, solvent extraction, reprecipitation or chromatography.

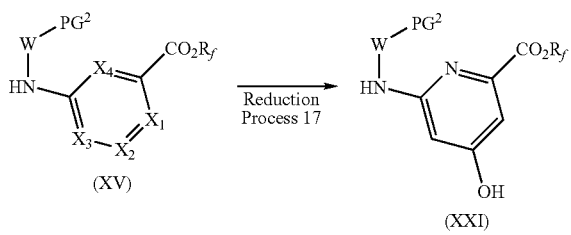

(Process 17) The present process is a method of removing a benzyl group that is a protective group of the hydroxyl group of Compound (XV) (wherein $R_f$ is a lower alkyl group, $PG^2$ has the same meaning as defined above, $X_1$ is CH, $X_2$ is $CX_{2a}$, $X_{2a}$ is a benzyloxy group, $X_3$ is CH, $X_4$ is N, and W has the same meaning as the symbol for the above Formula (I)) to produce Compound (XXI) (wherein $R_f$, $PG^2$ and W have the same meanings as defined above).

Removal of a protective group in this process can be carried out by methods described in the literature (for example, T. W. Green, Protective Groups in Organic Synthesis, $2^{nd}$ Ed., John Wiley & Sons (1991), etc.), methods equivalent to these or combinations of these methods and conventional methods, for example, by catalytic hydrogenation using a palladium hydroxide-carbon catalyst, or the like.

In the case of using a palladium hydroxide-carbon catalyst in removal of the benzyl group, the amount of the catalyst is usually 0.01 to 1000 equivalents, and preferably 0.1 to 10 equivalents.

The reaction solvent used in the present process is not particularly limited as long as it does not affect the reaction, and may be exemplified by methanol, ethanol or the like.

Thus obtained, above-described Compound (XXI) according to the invention can be subjected to isolation and purification by known separation and purification means such as, for example, concentration, concentration under reduced pressure, crystallization, solvent extraction, reprecipitation or chromatography.

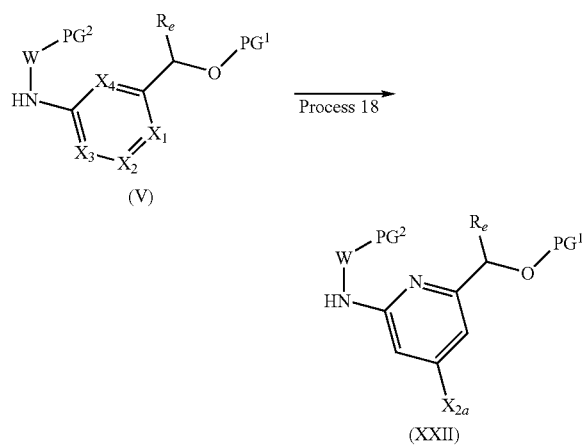

Process 18 relates to a method of synthesizing Compound (XXII) from Compound (V). Hereafter, it is exemplified in Processes 18-1 and 18-2.

(Process 18-1) The present process is a method of producing Compound (XXII) (wherein $R_c$, W, $PG^1$ and $PG^2$ have the same meanings as defined above, and $X_{2a}$ is a trifluoromethanesulfonyloxy group) from Compound (V) (wherein $R_c$, W, $PG^1$ and $PG^2$ have the same meanings as defined above, $X_1$ is CH, $X_2$ is $CX_{2a}$, $X_{2a}$ is a hydroxyl group, $X_3$ is CH, and $X_4$ is N).

The reaction used in this process employs a method well-known to a person skilled in the art. In the reaction used in this process, specifically, for example, the above-described Compound (V) can be reacted with anhydrous trifluoromethanesulfonic acid in a solvent such as chloroform, methylene chloride, tetrahydrofuran, N,N-dimethylformamide, diethyl ether and ethyl acetate, in the presence of a base such as 4-dimethylaminopyridine, triethylamine and diisopropylethylamine, to obtain Compound (XXII) (wherein $R_c$, W, $PG^1$ and PG have the same meanings as defined above, and $X_{2a}$ is a trifluoromethanesulfonyloxy group). In this case, with respect to 1 mole of Compound (V), anhydrous trifluoromethanesulfonic acid is used in an amount of 1 to 10 moles, and preferably 1 to 3 moles, and the base is used in an amount of 1 to 20 moles, and preferably 1 to 6 moles. The reaction temperature can be appropriately selected by a person skilled in the art in accordance with the starting compound used, and it is usually 0° C. to room temperature. Also, the reaction is typically completed in 10 minutes to 2 hours, but the reaction time can be appropriately extended or reduced.

Thus obtained, above-mentioned Compound (XXII) can be either subjected to isolation and purification by known separation and purification means such as, for example, concentration, concentration under reduced pressure, crystallization, solvent extraction, reprecipitation and chromatography, or subjected to the next process without isolation and purification.

(Process 18-2) The present process is a method of subjecting Compound (V) (wherein $R_c$, W, $PG^1$ and $PG^2$ have the same meanings as defined above, $X_1$ is CH, $X_2$ is $CX_{2a}$, $X_{2a}$ is a trifluoromethanesulfonyloxy group, $X_3$ is CH, and $X_4$ is N) to a carbonylation reaction to produce Compound (XXII) (wherein $R_c$, W, $PG^1$ and $PG^2$ have the same meanings as defined above, and $X_{2a}$ is an alkoxycarbonyl group).

The present process can be carried out by a method similar to the above-described Process 10, a method equivalent to this, or a combination of these methods and conventional methods.

Thus obtained, above-described Compound (XXII) according to the invention can be subjected to isolation and purification by known separation and purification means such as, for example, concentration, crystallization, solvent extraction, reprecipitation and chromatography.

Introduction or conversion of substituent for W can be carried out in any one of stages for producing the above-mentioned synthetic intermediates or protection products thereof. Hereinunder, an example of introducing a substituent for W in the compound represented by Formula (V) (wherein W is thiazol-2-yl, $PG^1$ and $PG^2$ have the same meaning as defined above, and $R_c$, $X_1$, $X_2$, $X_3$, $X_4$ and W have the same meaning as the symbols for the above Formula (I)) will be illustrated. In addition, a person having ordinary skill in the art can carry out introduction or conversion of substituent for W in a number of stages for producing the above-mentioned synthetic intermediates or protection products thereof by using commercially available, known compounds and using any appropriate, known method, and/or the below-described method or a method equivalent to this.

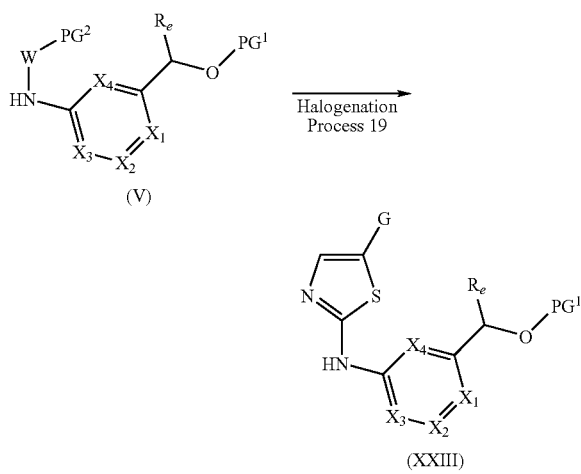

(V)

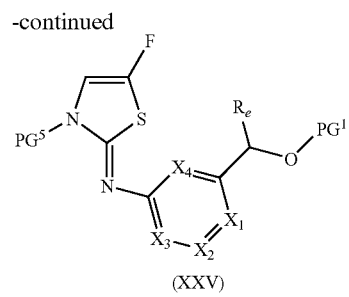

(XXV)

(Process 20) The present process is a method of subjecting Compound (XXIV) (wherein $PG^5$ is a protective group such as methoxymethyl or (2-(trimethylsilyl)ethoxy)methyl, $PG^1$ has the same meaning as defined above, and $R_e$, $X_1$, $X_2$, $X_3$ and $X_4$ have the same meaning as the symbols for the above Formula (I)) to a fluorination reaction to produce Compound (XXV) (wherein $PG^5$ is a protective group such as methoxymethyl or (2-(trimethylsilyl)ethoxy)methyl, $PG^1$ has the same meaning as defined above, and $R_e$, $X_1$, $X_2$, $X_3$ and $X_4$ have the same meaning as the symbols for the above Formula (I)).

The fluorination reaction used in this process can be carried out, for example, by adding dropwise a hexane solution of n-butyllithium to a solution of Compound (XXIV) (wherein $PG^5$ is a protective group such as methoxymethyl or (2-(trimethylsilyl)ethoxy)methyl, $PG^1$ has the same meaning as defined above, and $R_e$, $X_1$, $X_2$, $X_3$ and $X_4$ have the same meaning as the symbols for the above Formula (I)) in tetrahydrofuran or toluene, and then adding dropwise a tetrahydrofuran solution of N-fluorobenzenesulfonimide again. In the reaction, with respect to 1 mol of Compound (XXIV), the fluorinating reagent is used in an amount of from 1 to 3 mol, preferably 1 mol. In this case, the reaction temperature is appropriately selected in accordance with the starting compound or reaction solvent used, but it is typically from −78° to −20°. Also, the reaction is typically completed within 15 minutes to 2 hours, but the reaction time can be appropriately extended or reduced.

Thus obtained Compound (XXV) is subjected to isolation and purification by known separation and purification means such as, for example, concentration, concentration under reduced pressure, crystallization, solvent extraction, reprecipitation or chromatography, or subjected to the next process without isolation and purification.

(XXIII)

(Process 19) The present process is a method of subjecting Compound (V) (wherein —W-$PG^2$ is thiazol-2-yl, $PG^1$ has the same meaning as defined above, and $R_e$, $X_1$, $X_2$, $X_3$ and $X_4$ have the same meaning as the symbols for the above Formula (I)) to a halogenation reaction to produce Compound (XXIII) (wherein G is halogen atom such as chlorine, bromine or iodine, $PG^1$ has the same meaning as defined above, and $R_e$, $X_1$, $X_2$, $X_3$ and $X_4$ have the same meaning as the symbols for the above Formula (I)).

The halogenation reaction used in this process can be carried out, for example, by reacting Compound (V) (wherein —W-$PG^2$ is thiazol-2-yl, $PG^1$ has the same meaning as defined above, and $R_e$, $X_1$, $X_2$, $X_3$ and $X_4$ have the same meaning as the symbols for the above Formula (I)) with a halogenating reagent such as N-chlorosuccinimide, N-bromosuccinimide or N-iodosuccinimide, in a solvent such as tetrahydrofuran, water, acetic acid, methanol, ethanol, 1,4-dioxane, methylene chloride, chloroform or toluene. In the reaction, with respect to 1 mol of Compound (V), the halogenating reagent is used in an amount of from 1 to 3 mol, preferably 1 mol. In this case, the reaction temperature is appropriately selected in accordance with the starting compound or reaction solvent used, but it is typically from 0° to the boiling point of the solvent. Also, the reaction is typically completed within 1 hour to 24 hours, but the reaction time can be appropriately extended or reduced.

Thus obtained Compound (XXIII) is subjected to isolation and purification by known separation and purification means such as, for example, concentration, concentration under reduced pressure, crystallization, solvent extraction, reprecipitation or chromatography, or subjected to the next process without isolation and purification.

Next, the Aurora A and Aurora B inhibitory actions of the compound of General Formula (I) according to the invention will be explained below.

Aurora A Inhibitory Action (1) Purification of Aurora A cDNA of Aurora A having histidine tag fused at the amino terminal was integrated into an expression vector, which was then highly expressed in *Escherichia coli* BL21-CodonPlus (DE3)-RIL cells. The *Escherichia coli* cells were recovered and solubilized, and then the histidine-tagged Aurora A protein was adsorbed onto a nickel chelate column and eluted from the column with imidazole. The active fraction was desalted with a desalting column to give a pure enzyme.

(2) Measurement of Activity of Aurora A

For measurement of the activity of Aurora A, the substrate used was Kemptide (Lys-Arg-Arg-Ala-Ser-Lys-Gly) (SEQ.ID.NO.: 1), a synthetic peptide purchased from Sigma-Aldrich, Inc. [Certificate of analysis (Upstate, Inc.)].

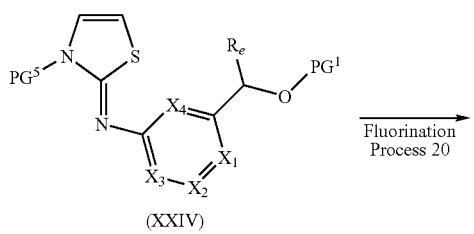

(XXIV)

Reaction was conducted by a partial modification of a method by Upstate, Inc. [Kinase Profiler™ Assay Protocols]. The amount of the reaction liquid was 21.1 µL, and the composition of the reaction buffer (R2 buffer) was 50 mM Tris-hydrochloride buffer (pH 7.4)/15 mM magnesium acetate/0.2 mM ethylenediamine-N,N,N',N'-tetraacetate (EDTA). To this, purified Aurora A, 100 µM of a substrate peptide, 20 µM of unlabeled adenosine triphosphate (ATP) and 0.5 µCi of [γ-$^{33}$P] labeled ATP (2,500 Ci/mmole or more) were added, and the mixture was reacted at 30° C. for 20 minutes. Then, 10 µL of 350 mM phosphate buffer was added to the reaction system to stop the reaction. The substrate peptide was adsorbed on a P81 paper filter 96-well plate and then washed with 130 mM phosphate buffer for several times. The radiation activity of the peptide was measured with a liquid scintillation counter. The [γ-$^{33}$P] labeled ATP was purchased from Amersham Biosciences Co., Ltd.

The compound to be tested was added to the reaction system such that a dilution series of the compound in dimethylsulfoxide was first prepared, and 1.1 µL of this solution was added. A control was provided by adding 1.1 µL of DMSO to the reaction system.

Aurora B Inhibitory Action (1) Purification of Aurora B cDNA of Aurora B having histidine tag fused at the amino terminal was integrated into an expression vector, which was then highly expressed in *Escherichia coli* BL21-CodonPlus (DE3)-RIL cells. The *Escherichia coli* cells were recovered and solubilized, and then the histidine-tagged Aurora A protein was adsorbed onto a nickel chelate column and eluted from the column with imidazole. The active fraction was desalted with a desalting column to give a pure enzyme.

(2) Measurement of Activity of Aurora B

For measurement of the activity of Aurora B, the substrate used was Kemptide (Lys-Arg-Arg-Ala-Ser-Lys-Gly) (SEQ.ID.NO.: 1), a synthetic peptide purchased from Sigma-Aldrich, Inc. [Certificate of analysis (Upstate, Inc.)].

Reaction was conducted by a partial modification of the method of activity measurement for Aurora A. The amount of the reaction liquid was 21.1 µL, and the composition of the reaction buffer (R2 buffer) was 50 mM Tris-hydrochloride buffer (pH 7.4)/15 mM magnesium acetate/0.2 mM ethylenediamine-N,N,N',N'-tetraacetate (EDTA). To this, purified Aurora B, 100 µM of a substrate peptide, 100 µM of unlabeled adenosine triphosphate (ATP) and 1 µCi of [γ-$^{33}$P] labeled ATP (2,500 Ci/mmole or more) were added, and the mixture was reacted at 30° C. for 20 minutes. Then, 10 µL of 350 mM phosphate buffer was added to the reaction system to stop the reaction. The substrate peptide was adsorbed on a P81 paper filter 96-well plate and then washed with 130 mM phosphate buffer for several times. The radiation activity of the peptide was measured with a liquid scintillation counter. The [γ-$^{33}$P] labeled ATP was purchased from Amersham Biosciences Co., Ltd.

The compound to be tested was added to the reaction system such that a dilution series of the compound in dimethylsulfoxide was first prepared, and 1.1 µL of this solution was added. A control was provided by adding 1.1 µL of DMSO to the reaction system.

The compound according to the invention exhibits excellent Aurora A selective inhibitory activity, as shown in Table 1.

TABLE 1

| Example | Aurora A inhibitory action (IC$_{50}$, nM) | Aurora B inhibitory action (IC$_{50}$, nM) |
|---|---|---|
| Example 5 | 0.67 | 440 |
| Example 6 | 0.5 | 200 |
| Example 8 | 1.9 | 1400 |
| Example 9 | 1.3 | 760 |
| Example 10 | 0.49 | 92 |
| Example 11 | 1.3 | 570 |
| Example 12 | 0.52 | 400 |
| Example 13 | 0.89 | 380 |
| Example 15 | 1.4 | 1000 |
| Example 16 | 1.8 | 1300 |
| Example 17 | 1.2 | 3200 |
| Example 18 | 1.8 | 830 |
| Example 19 | 0.9 | 530 |
| Example 20 | 1.1 | 1800 |
| Example 21 | 16 | 6800 |
| Example 22 | 2.9 | 1500 |
| Example 23 | 3.6 | 1200 |
| Example 24 | 23 | 26000 |
| Example 25 | 1.1 | 770 |
| Example 26 | 1.1 | 450 |
| Example 27 | 3.3 | 1700 |
| Example 28 | 0.52 | 310 |
| Example 29 | 0.97 | 590 |
| Example 30 | 1.1 | 320 |
| Example 31 | 37 | 760 |
| Example 32 | 3.7 | 4800 |
| Example 33 | 50 | 3000 |
| Example 35 | 31 | 3400 |
| Example 36 | 2.6 | 3200 |
| Example 37 | 4.9 | 8800 |
| Example 38 | 9.1 | 9500 |
| Example 39 | 67 | 9100 |
| Example 40 | 0.99 | 1900 |
| Example 41 | 2.9 | 5000 |
| Example 42 | 1 | 530 |
| Example 43 | 1.1 | 460 |
| Example 44 | 0.89 | 1100 |
| Example 45 | 2.5 | 4800 |
| Example 46 | 6.1 | 1400 |
| Example 47 | 5.5 | 2200 |
| Example 48 | 2.8 | 2900 |
| Example 49 | 1.4 | 4400 |
| Example 50 | 2.2 | 5400 |
| Example 51 | 0.98 | 930 |
| Example 55 | 20 | 7400 |
| Example 56 | 2.1 | 2900 |
| Example 57 | 15 | 28000 |
| Example 58 | 4.8 | 9900 |
| Example 61 | 17 | 530 |
| Example 62 | 12 | 380 |
| Example 63 | 1.3 | 570 |
| Example 64 | 110 | 2500 |
| Example 65 | 2.4 | 160 |
| Example 66 | 3.4 | 250 |
| Example 67 | 17 | 320 |
| Example 68 | 11 | 670 |
| Example 69 | 32 | 920 |
| Example 70 | 2.4 | 96 |
| Example 71 | 3 | 370 |
| Example 72 | 27 | 170 |
| Example 73 | 17 | 410 |
| Example 74 | 47 | 850 |
| Example 75 | 0.44 | 89 |
| Example 76 | 0.44 | 47 |
| Example 77 | 4.1 | 1300 |
| Example 78 | 2 | 240 |
| Example 79 | 26 | 2200 |
| Example 81 | 0.33 | 300 |
| Example 82 | 0.51 | 210 |
| Example 83 | 0.64 | 800 |
| Example 84 | 0.72 | 400 |
| Example 85 | 1 | 610 |
| Example 86 | 0.66 | 560 |
| Example 87 | 1.2 | 1400 |
| Example 88 | 0.72 | 1000 |

TABLE 1-continued

| Example | Aurora A inhibitory action (IC$_{50}$, nM) | Aurora B inhibitory action (IC$_{50}$, nM) |
|---|---|---|
| Example 89 | 0.38 | 200 |
| Example 90 | 1.5 | 860 |
| Example 91 | 1.4 | 1200 |
| Example 92 | 0.93 | 830 |
| Example 93 | 0.36 | 250 |
| Example 94 | 1.1 | 1100 |
| Example 95 | 0.59 | 250 |
| Example 96 | 0.57 | 690 |
| Example 97 | 0.62 | 830 |
| Example 98 | 0.36 | 230 |
| Example 99 | 0.77 | 460 |
| Example 100 | 2.6 | 1300 |
| Example 103 | 0.76 | 250 |
| Example 104 | 1.1 | 1400 |
| Example 105 | 1.4 | 1000 |
| Example 106 | 0.88 | 400 |
| Example 107 | 0.32 | 190 |
| Example 108 | 0.59 | 800 |
| Example 109 | 0.42 | 520 |
| Example 110 | 0.59 | 750 |
| Example 112 | 0.81 | 230 |

Next, the cell growth suppressive action of the compound of the General Formula (I) according to the invention will be explained below.

Method for Judging the Pharmaceutical Effect Using Cells a) Reagent

Fetal calf serum (FCS) was purchased from Moregate Biotech, and DMEM medium was purchased from Invitrogen Corp. WST-8 was purchased from Kishida Chemical Co., Ltd.

b) Cells

Human cervical cancer cells (HeLa S3) were obtained from the American Type Culture Collection (ATCC).

c) Method of Judging the Effect

Cells were suspended in a DMEM medium containing 10% FCS, and the cell suspension was dispensed to a 96-well plastic plate at a rate of 750 cells/100 microliters per well. The plate was incubated overnight in 5% CO$_2$-95% air at 37° C. A drug was subjected to graded dilution in dimethylsulfoxide and further diluted with a DMEM medium containing 10% FCS. Then, the dilution was dispensed to the plate on which cells had been disseminated, at a rate of 100 microliters per well. The plate was incubated for further three days in 5% CO$_2$-95% air at 37° C. Cell growth after incubation was measured by the WST-8 method (H. Tominaga, et al., *Anal. Commun.*, 36, 47-50 (1999)). Here, the WST-8 method refers to a method in which 20 microliters of a WST-8 reagent solution is added to each well, incubation is conducted at 37° C. for 45 minutes, the plate is stirred, and the amount of formazan produced is measured by a calorimetric method to determine the inhibitory rate of the drug. The concentration for 50% growth inhibition (EC$_{50}$, μM) of the compound was determined.

The compound according to the invention exhibits excellent cell growth inhibitory effect against human-derived cancer cells (HeLa S3), as shown in Table 2.

TABLE 2

| Example | Cell growth inhibitory effect (IC$_{50}$, μM) |
|---|---|
| Example 5 | 11.00 |
| Example 6 | 0.40 |
| Example 8 | 0.25 |
| Example 17 | 1.10 |
| Example 19 | 0.92 |
| Example 22 | 3.50 |
| Example 25 | 0.80 |
| Example 28 | 1.10 |
| Example 29 | 3.30 |
| Example 30 | 2.50 |
| Example 36 | 6.80 |
| Example 39 | 11.00 |
| Example 40 | 6.50 |
| Example 44 | 2.40 |
| Example 46 | 4.10 |
| Example 50 | 3.60 |
| Example 56 | 1.40 |
| Example 58 | 3.00 |
| Example 62 | 0.86 |
| Example 66 | 2.90 |
| Example 68 | 5.10 |
| Example 71 | 3.00 |
| Example 75 | 11.00 |
| Example 77 | 1.60 |
| Example 86 | 0.51 |
| Example 89 | 0.36 |
| Example 95 | 0.22 |
| Example 104 | 0.99 |
| Example 106 | 0.40 |
| Example 107 | 0.21 |
| Example 108 | 1.20 |

Method for Judging the Effect by Combined Use of Drugs in Cells a) Reagent

Fetal calf serum (FCS) was purchased from Moregate Biotech, DMEM medium from Invitrogen Corp., paclitaxel (tradename: Taxol) from Sigma-Aldrich, Inc., and WST-8 from Kishida Chemical Co., Ltd.

b) Cells

Human cervical cancer cells (HeLa S3) were obtained from the American Type Culture Collection (ATCC).

c) Method of Judging the Effect

Cells were suspended in a DMEM medium containing 10% FCS, and the cell suspension was dispensed to two 96-well plastic plates at a rate of 750 cells/100 microliters per well. The plates were incubated overnight in 5% CO$_2$-95% air at 37° C. A drug was subjected to graded dilution in dimethylsulfoxide and further diluted with DMSO or with a DMEM medium containing 10% FCS and also containing 2 nM paclitaxel. Then, the dilutions were each dispensed to one of the plates on which cells had been disseminated, at a rate of 100 microliters per well. The final concentration of paclitaxel at this stage was 1 nM. Also, the concentrations in the case of sole administration of the compound according to the invention were 0.03, 0.1, 0.3, 1 and 3 μM. The plates were incubated for further three days in 5% CO$_2$-95% air at 37° C. Cell growth after incubation was measured by the WST-8 method (H. Tominaga, et al., *Anal. Commun.*, 36, 47-50 (1999)). Here, the WST-8 method refers to a method in which 20 microliters of a WST-8 reagent solution is added to each well, incubation is conducted at 37° C. for 45 minutes, the plate is stirred, and the amount of formazan produced is measured by a calorimetric method to determine the inhibitory rate of the drug. The growth inhibitory effects of paclitaxel and of the compound according to the invention were determined, with the value obtained in sole treatment of DMSO being defined as 0%.

The compound according to the invention exhibits excellent cell growth inhibitory effect as well as a synergistic action with paclitaxel against human-derived cancer cells (HeLa S3), as shown in Table 3.

TABLE 3

| Example | Cell growth inhibitory effect by sole administration of paclitaxel (1 nM) (%) | Conc. of the compound of Example (μM) | Cell growth inhibitory effect by sole administration of the compound of Example (%) | Cell growth inhibitory effect by combined administration of paclitaxel and the compound of Example (%) |
|---|---|---|---|---|
| Example 5 | 44.1 | 0.1 | 0.0 | 72.8 |
| Example 6 | 44.1 | 0.3 | 19.6 | 89.0 |
| Example 8 | 37.8 | 0.1 | 4.6 | 87.1 |
| Example 17 | 45.4 | 0.3 | 0.0 | 73.8 |
| Example 19 | 44.1 | 0.1 | 0.0 | 77.6 |
| Example 22 | 43.3 | 1.0 | 18.5 | 80.9 |
| Example 25 | 45.4 | 0.1 | 0.0 | 65.1 |
| Example 28 | 45.4 | 0.3 | 0.0 | 84.5 |
| Example 29 | 45.4 | 0.3 | 0.0 | 77.3 |
| Example 30 | 36.8 | 1.0 | 29.1 | 90.1 |
| Example 36 | 45.4 | 3.0 | 17.2 | 83.4 |
| Example 39 | 43.3 | 3.0 | 5.4 | 72.2 |
| Example 40 | 43.3 | 1.0 | 6.5 | 76.9 |
| Example 44 | 44.1 | 0.3 | 7.1 | 86.5 |
| Example 46 | 36.8 | 1.0 | 8.5 | 75.0 |
| Example 50 | 45.4 | 1.0 | 6.0 | 82.0 |
| Example 56 | 37.8 | 0.3 | 6.5 | 81.8 |
| Example 58 | 45.4 | 1.0 | 0.0 | 81.4 |
| Example 62 | 36.8 | 0.1 | 2.9 | 68.0 |
| Example 66 | 36.8 | 1.0 | 7.2 | 60.9 |
| Example 68 | 36.8 | 3.0 | 27.3 | 71.8 |
| Example 71 | 36.8 | 1.0 | 13.2 | 60.7 |
| Example 75 | 45.4 | 0.3 | 27.1 | 91.5 |
| Example 77 | 36.8 | 0.3 | 2.2 | 51.8 |
| Example 86 | 43.3 | 0.03 | 6.2 | 71.6 |
| Example 89 | 43.3 | 0.1 | 19.1 | 85.8 |
| Example 95 | 44.1 | 0.03 | 0.0 | 73.5 |
| Example 104 | 43.3 | 0.3 | 6.3 | 81.6 |
| Example 106 | 43.3 | 0.1 | 6.1 | 76.7 |
| Example 107 | 43.3 | 0.03 | 11.5 | 74.1 |
| Example 108 | 44.1 | 1.0 | 17.2 | 86.4 |

From the above, the compound according to the invention is believed to be useful as an antitumor agent since it exhibits not only excellent cell growth inhibitory action based on Aurora A selective inhibitory activity, but also a synergistic action in combined use with other antitumor agent. Thus, it is believed that a pharmaceutical composition or Aurora A selective inhibitor containing the novel aminopyridine derivative according to the invention or a pharmaceutically acceptable salt or ester thereof, or an antitumor agent containing the compound according to the invention or a pharmaceutically acceptable salt or ester thereof is effective in the treatment of cancer patients.

The above-mentioned pharmaceutical composition and inhibitor, and the above-mentioned antitumor agent may contain a pharmaceutically acceptable carrier or diluent. Here, the "pharmaceutically acceptable carrier or diluent" refers to excipients [e.g., fats, beeswax, semi-solid and liquid polyols, natural or hydrogenated oils, etc.]; water (e.g., distilled water, particularly distilled water for injection, etc.), physiological saline, alcohol (e.g., ethanol), glycerol, polyols, aqueous glucose solution, mannitol, plant oils, etc.); additives [e.g., extending agent, disintegrating agent, binder, lubricant, wetting agent, stabilizer, emulsifier, dispersant, preservative, sweetener, colorant, seasoning agent or aromatizer, concentrating agent, diluent, buffer substance, solvent or solubilizing agent, chemical for achieving storage effect, salt for modifying osmotic pressure, coating agent or antioxidant], and the like.

A suitable tumor for which the therapeutic effect of the compound according to the invention is expected may be exemplified by human solid cancer. Examples of human solid cancer include brain cancer, head and neck cancer, esophageal cancer, thyroid cancer, small cell carcinoma, non-small cell carcinoma, breast cancer, stomach cancer, gallbladder and bile duct cancer, liver cancer, pancreas cancer, colon cancer, rectal cancer, ovarian cancer, chorioepithelioma, uterine cancer, cervical cancer, renal pelvic and ureteral cancer, bladder cancer, prostate cancer, penile cancer, testicular cancer, embryonal cancer, Wilms' tumor, skin cancer, malignant melanoma, neuroblastoma, osteosarcoma, Ewing's tumor, soft tissue sarcoma, and the like.

Next, the above-described "pharmaceutically acceptable salt or ester" will be explained below.

When the compound according to the invention is used as an antitumor agent or the like, it may be also used in a form of pharmaceutically acceptable salt. Typical examples of the pharmaceutically acceptable salt include a salt with an alkali metal such as sodium and potassium; a salt with an inorganic acid, such as hydrochloride, sulfate, nitrate, phosphate, carbonate, hydrogen carbonate, and perchlorate; a salt with an organic acid, such as acetate, propionate, lactate, maleate, fumarate, tartrate, malate, citrate, and ascorbate; a salt with sulfonic acid, such as methanesulfonate, isethionate, benzenesulfonate, and toluenesulfonate; a salt with acidic amino acid, such as aspartate and glutamate; and the like. A pharmaceutically acceptable salt of the Compound (I) is preferably a salt with an inorganic acid, such as hydrochloride, sulfate, nitrate, phosphate, carbonate, hydrogen carbonate, and perchlorate; more preferably hydrochloride.

The process for preparation of a pharmaceutically acceptable salt of the compound according to the invention may be carried out by an appropriate combination of those methods that are conventionally used in the field of organic synthetic chemistry. A specific example thereof is a method in which a solution of the compound according to the invention in its free form is subjected to neutralization titration with an alkaline solution or an acidic solution.

Examples of the ester of the compound according to the invention include methyl ester and ethyl ester. Such esters can be prepared by esterification of a free carboxyl group according to a conventional method.

With regard to each preparation of the combined preparation according to the invention, various preparation forms can be selected, and examples thereof include oral preparations such as tablets, capsules, powders, granules or liquids, or sterilized liquid parenteral preparations such as solutions or suspensions, suppositories, ointments and the like.

Solid preparations can be prepared in the forms of tablet, capsule, granule and powder without any additives, or prepared using appropriate carriers (additives). Examples of such carriers (additives) may include saccharides such as lactose or glucose; starch of corn, wheat or rice; fatty acids such as stearic acid; inorganic salts such as magnesium metasilicate aluminate or anhydrous calcium phosphate; synthetic polymers such as polyvinylpyrrolidone or polyalkylene glycol; alcohols such as stearyl alcohol or benzyl alcohol; synthetic cellulose derivatives such as methylcellulose, carboxymethylcellulose, ethylcellulose or hydroxypropylmethylcellulose; and other conventionally used additives such as gelatin, talc, plant oil and gum arabic.

These solid preparations such as tablets, capsules, granules and powders may generally contain, for example, 0.1 to 100% by weight, and preferably 5 to 98% by weight, of the compound of the above Formula (I) as an active ingredient, based on the total weight of the preparation.

Liquid preparations are produced in the forms of suspension, syrup, injection and drip infusion (intravenous fluid) using appropriate additives, such as water, alcohol or a plant-derived oil such as soybean oil, peanut oil and sesame oil.

In particular, when the preparation is administered parenterally in a form of intramuscular injection, intravenous injection or subcutaneous injection, appropriate solvent or diluent may be exemplified by distilled water for injection, an aqueous solution of lidocaine hydrochloride (for intramuscular injection), physiological saline, aqueous glucose solution, ethanol, polyethylene glycol, propylene glycol, liquid for intravenous injection (e.g., an aqueous solution of citric acid, sodium citrate and the like) or an electrolytic solution (for intravenous drip infusion and intravenous injection), or a mixed solution thereof.

Such injection may be in a form of a preliminarily dissolved solution, or in a form of powder per se or powder associated with a suitable carrier (additive) which is dissolved at the time of use. The injection liquid may contain, for example, 0.1 to 10% by weight of an active ingredient based on the total weight of the preparation.

Liquid preparations such as suspension or syrup for oral administration may contain, for example, 0.1 to 10% by weight of an active ingredient based on the total weight of the preparation.

Each preparation of the combined preparation according to the invention can be prepared by a person having ordinary skill in the art according to conventional methods or common techniques. For example, a preparation containing another antitumor agent that is used in combination with the compound represented by the above General Formula (I), can be prepared, if the preparation is an oral preparation, for example, by mixing an appropriate amount of the antitumor agent with an appropriate amount of lactose and filling this mixture into hard gelatin capsules which are suitable for oral administration. On the other hand, preparation can be carried out, if the preparation containing the antitumor agent is an injection, for example, by mixing an appropriate amount of the antitumor agent with an appropriate amount of 0.9% physiological saline and filling this mixture in vials for injection.

Also, in the case of a combination preparation containing the compound represented by the above General Formula (I) according to the invention and another antitumor agent, a person having ordinary skill in the art can easily prepare the preparation according to conventional methods or common techniques.

In the process according to the invention, preferred therapeutic unit may vary in accordance with, for example, the administration route of the compound represented by the General Formula (I), the type of the compound represented by the General Formula (I) used, and the dosage form of the compound represented by the General Formula (I) used; the type, administration route and dosage form of the other antitumor agent used in combination; and the type of cells to be treated, the condition of patient, and the like. The optimal treatment under the given conditions can be determined by a person skilled in the art, based on the set conventional therapeutic unit and/or based on the content of the present specification.

In the process according to the invention, the therapeutic unit for the compound represented by the above General Formula (I) may vary in accordance with, specifically, the type of compound used, the type of compounded composition, application frequency and the specific site to be treated, seriousness of the disease, age of the patient, doctor's diagnosis, the type of cancer, or the like. However, as an exemplary reference, the daily dose for an adult may be within a range of, for example, 1 to 1,000 mg in the case of oral administration. In the case of parenteral administration, preferably intravenous administration, and more preferably intravenous drip infusion, the daily dose may be within a range of, for example, 1 to 100 mg/m$^2$ (body surface area). Here, in the case of intravenous drip infusion, administration may be continuously carried out for, for example, 1 to 48 hours. Moreover, the administration frequency may vary depending on the administering method and symptoms, but it is, for example, once to five times a day. Alternatively, periodically intermittent administration such as administration every other day, administration every two days or the like may be employed as well in the administering method. The period of withdraw from medication in the case of parenteral administration is, for example, 1 to 6 weeks.

Although the therapeutic unit for the other antitumor agent used in combination with the compound represented by the General Formula (I) is not particularly limited, it can be determined, if needed, by those skilled in the art according to known literatures. Examples may be as follows.

The therapeutic unit of 5-fluorouracil (5-FU) is such that, in the case of oral administration, for example, 200 to 300 mg per day is administered in once to three times consecutively, and in the case of injection, for example, 5 to 15 mg/kg per day is administered once a day for the first 5 consecutive days by intravenous injection or intravenous drip infusion, and then 5 to 7.5 mg/kg is administered once a day every other day by intravenous injection or intravenous drip infusion (the dose may be appropriately increased or decreased).

The therapeutic unit of S-1 (Tegafur, Gimestat and Ostat potassium) is such that, for example, the initial dose (singe dose) is set to the following standard amount in accordance with the body surface area, and it is orally administered twice a day, after breakfast and after dinner, for 28 consecutive days, followed by withdrawal from medication for 14 days. This is set as one course of administration, which is repeated. The initial standard amount per unit body surface area (Tegafur equivalent) is 40 mg in one administration for an area less than 1.25 $m^2$; 50 mg in one administration for an area of 1.25 $m^2$ to less than 1.5 $m^2$; 60 mg in one administration for an area of 1.5 $m^2$ or more. This dose is appropriately increased or decreased depending on the condition of the patient.

The therapeutic unit for gemcitabine is, for example, 1 g as gemcitabine/$m^2$ in one administration, which is administered by intravenous drip infusion over a period of 30 minutes, and one administration per week is continued for 3 weeks, followed by withdrawal from medication on the fourth week. This is set as one course of administration, which is repeated. The dose is appropriately decreased in accordance with age, symptom or development of side-effects.

The therapeutic unit for doxorubicin (e.g., doxorubicin hydrochloride) is such that, for example, in the case of intravenous injection, 10 mg (0.2 mg/kg) (titer) is administered once a day by intravenous one-shot administration for 4 to 6 consecutive days, followed by withdrawal from medication for 7 to 10 days. This is set as one course of administration, which is repeated two or three times. Here, the total dose is preferably 500 mg (titer)/$m^2$ (body surface area) or less, and it may be appropriately increased or decreased within the range.

The therapeutic unit for etoposide is such that, for example, in the case of intravenous injection, 60 to 100 mg/$m^2$ (body surface area) per day is administered for 5 consecutive days, followed by withdrawal from medication for three weeks (the dose may be appropriately increased or decreased). This is set as one course of administration, which is repeated. Meanwhile, in the case of oral administration, for example, 175 to 200 mg per day is administered for 5 consecutive days, followed by withdrawal from medication for three weeks (the dose may be appropriately increased or decreased). This is set as one course of administration, which is repeated.

The therapeutic unit for docetaxel (docetaxel hydrate) is such that, for example, 60 mg as docetaxel/$m^2$ (body surface area) is administered once a day by intravenous drip infusion over a period of 1 hour or longer at an interval of 3 to 4 weeks (the dose may be appropriately increased or decreased).

The therapeutic unit of paclitaxel is such that, for example, 210 mg/$m^2$ (body surface area) is administered once a day by intravenous drip infusion over a period of 3 hours, followed by withdrawal from medication for at least 3 weeks. This is set as one course of administration, which is repeated. The dose may be appropriately increased or decreased.

The therapeutic unit for cisplatin is such that, for example, in the case of intravenous injection, 50 to 70 mg/$m^2$ (body surface area) is administered once a day, followed by withdrawal from medication for 3 weeks or longer (the dose may be appropriately increased or decreased). This is set as one course of administration, which is repeated.

The therapeutic unit for carboplatin is such that, for example, 300 to 400 mg/$m^2$ is administered once a day by intravenous drip infusion over a period of 30 minutes or longer, followed by withdrawal from medication for at least 4 weeks (the dose may be appropriately increased or decreased). This is set as one course of administration, which is repeated.

The therapeutic unit for oxaliplatin is such that 85 mg/$m^2$ is administered once a day by intravenous injection, followed by withdrawal from medication for two weeks. This is set as one course of administration, which is repeated.

The therapeutic unit for irinotecan (e.g., irinotecan hydrochloride) is such that, for example, 100 mg/$m^2$ is administered once a day by intravenous drip infusion for 3 or 4 times at an interval of one week, followed by withdrawal from medication for at least two weeks.

The therapeutic unit for topotecan is such that, for example, 1.5 mg/$m^2$ is administered once a day by intravenous drip infusion for 5 days, followed by withdrawal from medication for at least 3 weeks.

The therapeutic unit for cyclophosphamide is such that, for example, in the case of intravenous injection, 100 mg is administered once a day by intravenous injection for consecutive days. If the patient can tolerate, the daily dose may be increased to 200 mg. The total dose is 3,000 to 8,000 mg, which may be appropriately increased or decreased. If necessary, it may be injected or infused intramuscularly, intrathoracically or intratumorally. On the other hand, in the case of oral administration, for example, 100 to 200 mg is administered a day.

The therapeutic unit for gefitinib is such that 250 mg is orally administered once a day.

The therapeutic unit for cetuximab is such that, for example, 400 mg/$m^2$ is administered on the first day by intravenous drip infusion, and then 250 mg/$m^2$ is administered every week by intravenous drip infusion.

The therapeutic unit for bevacizumab is such that, for example, 3 mg/kg is administered every week by intravenous drip infusion.

The therapeutic unit for trastuzumab is such that, for example, typically for an adult, once a day, 4 mg as trastuzumab/kg (body weight) is administered initially, followed by intravenous drip infusion of 2 mg/kg over a period of 90 minutes or longer every week from the second administration.

The therapeutic unit for exemestane is such that, for example, typically for an adult, 25 mg is orally administered once a day after meal.

The therapeutic unit for leuprorelin (e.g., leuprorelin acetate) is such that, for example, typically for an adult, 11.25 mg is subcutaneously administered once in 12 weeks.

The therapeutic unit for imatinib is such that, for example, typically for an adult in the chronic phase of chronic myelogenous leukemia, 400 mg is orally administered once a day after meal.

The therapeutic unit for a combination of 5-FU and leucovorin is such that, for example, 425 mg/$m^2$ of 5-FU and 200 mg/$m^2$ of leucovorin are administered from the first day to the fifth day by intravenous drip infusion, and this course is repeated at an interval of 4 weeks.

WORKING EXAMPLES

In a thin-layer chromatography of Examples and Referential Examples, Silica gel60F254 (Merck) was used as a plate and a UV detector was used in a detecting method. As silica gel for the column, Wakogel™ C-300 or C-200 (Wako Pure Chemical) or NH (FUJI SILYSIA CHEMICAL) was used. In a reversed phase preparative liquid chromatography, Combi-Prep Pro C18 (YMC) was used as a column and a 0.1% aqueous trifluoroacetic acid solution and a 0.1% solution of trifluoroacetic acid in acetonitrile were used in a mobile phase. MS spectra were measured using JMS-SX102A (JEOL) or QUATTROII (Micro Mass). NMR spectra were measured using a spectrometer in a type of Gemini-200 (200 MHz; Varian), Gemini-300 (300 MHz; Varian), VXR-300 (300 MHz; Varian), Mercury 400 (400 MHz; Varian) or Inova 400 (400 MHz; Varian) and all δ values are represented in ppm.

Meanings of abbreviations used in the NMR measurement are as follows.

s: singlet
d: doublet
dd: double doublet
t: triplet
dt: double triplet
q: quartet
qui: quintet
m: multiplet
br: broad
J: coupling constant
Hz: Hertz
DMSO-d6: dimethylsulfoxide-d6
TBS: tert-butyldimethylsilyl group
Ms: methanesulfonyl group
SEM: 2-(trimethylsilyl)ethoxymethyl group
MOM: methoxymethyl group
THP: tetrahydropyran-2-yl group
Boc: tert-butoxycarbonyl group Example 1

Synthesis of (5-bromo-thiazol-2-yl)-(6-(4-benzoyl-piperazin-1-ylmethyl)-pyridin-2-yl)-amine (1) Synthesis of (6-chloro-pyridin-2-yl)-thiazol-2-yl-amine

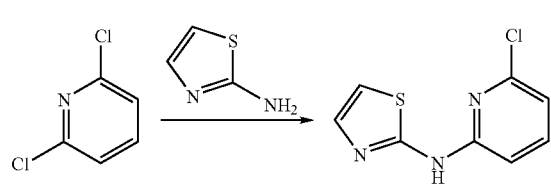

A mixture of 1.37 g (9.26 mmol) of 2-aminothiazole, 0.74 g (7.39 mmol) of 2,6-dichloropyridine, 387 mg (0.621 mmol) of (S)-(−)-2,2'-(bisdiphenylphosphino)-1,1'-binaphthyl, 322 mg (0.311 mmol) of tris(dibenzylideneacetone)dipalladium (0)-chloroform complex, 2.77 g (8.50 mmol) of cesium carbonate and 10 ml of toluene was heated under reflux for 1 hour and 30 minutes, cooled to room temperature and diluted with ethyl acetate. An insoluble matter was filtered off using Celite and the resulting ethyl acetate solution was washed with water and brine. The organic layer was dried over anhydrous magnesium sulfate and filtered, and the filtrate was concentrated. The residue was purified by a silica gel column chromatography to give 990 mg (4.68 mmol) of the title compound as a white solid.

(2) Synthesis of methyl 6-(thiazol-2-ylamino)-pyridine-2-carboxylate

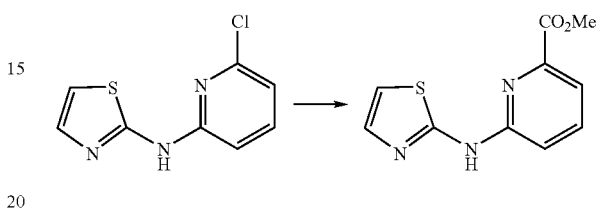

A mixture of 1.94 g (9.17 mmol) of (6-chloro-pyridin-2-yl)-thiazol-2-yl-amine, 206 mg (0.918 mmol) of palladium acetate, 508 mg (0.916 mmol) of 1,1'-bisdiphenylphosphino-ferrocene, 2.40 ml (13.8 mmol) of N,N-diisopropylethylamine, 10 ml of methanol and 15 ml of N,N-dimethylformamide was stirred at 100° C. for 3 hours and 15 minutes under 3 atmospheric pressure of carbon monoxide and cooled on an ice bath. The resulting solid was filtered and washed with ether to give 1.53 g (6.50 mmol) of the title compound as a light brown solid.

(3) Synthesis of methyl 6-(3-methoxymethyl-3H-thiazol-2-ylideneamino)-pyridine-2-carboxylate

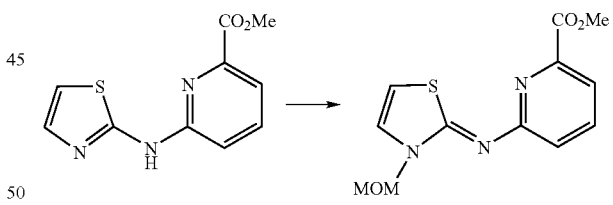

To a mixture of 4.85 g (20.6 mmol) of methyl 6-(thiazol-2-ylamino)-pyridine-2-carboxylate, 7.20 ml (41.2 mmol) of N,N-diisopropylethylamine and 100 ml of chloroform was added 2.35 ml (30.9 mmol) of chloromethylmethyl ether followed by stirring at room temperature for 1 hour. The reaction mixture was washed with 100 ml of water for three times and the organic layer was dried over anhydrous magnesium sulfate and filtered. The filtrate was concentrated to about 20 ml in total and the resulting solid was filtered. The resulting solid was washed with ether and dried in vacuo to give 6.38 g (20.6 mmol) of the title compound as a white solid.

(4) Synthesis of methyl 6-(5-bromo-3-methoxymethyl-3H-thiazol-2-ylideneamino)-pyridine-2-carboxylate

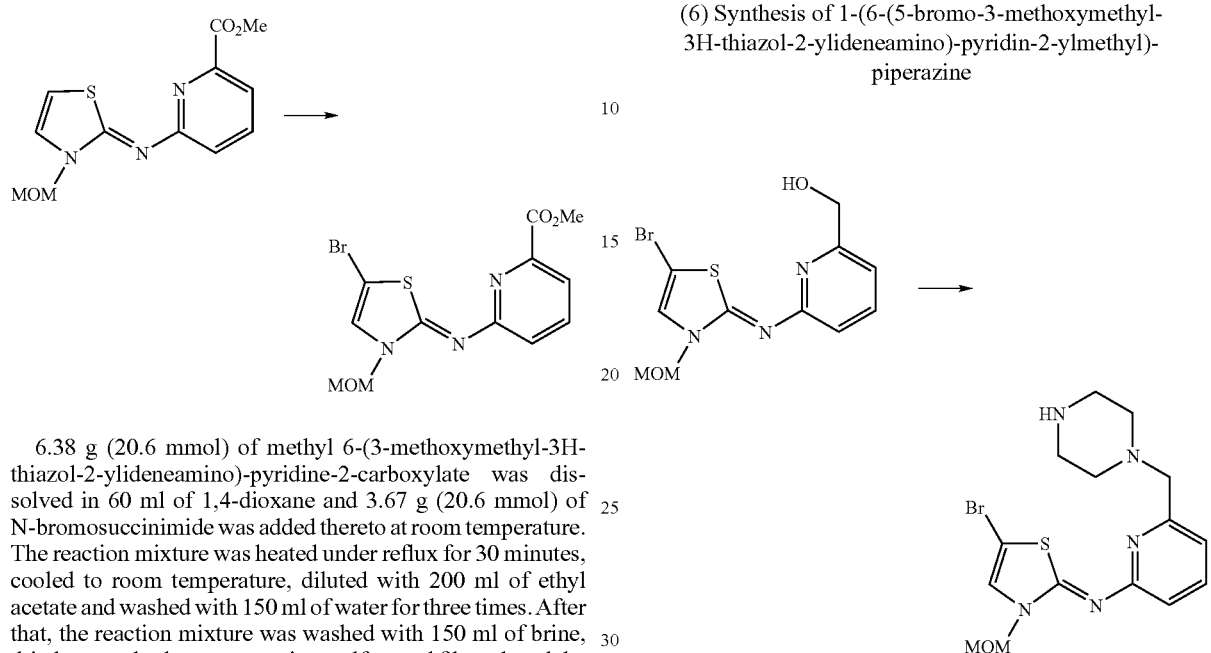

6.38 g (20.6 mmol) of methyl 6-(3-methoxymethyl-3H-thiazol-2-ylideneamino)-pyridine-2-carboxylate was dissolved in 60 ml of 1,4-dioxane and 3.67 g (20.6 mmol) of N-bromosuccinimide was added thereto at room temperature. The reaction mixture was heated under reflux for 30 minutes, cooled to room temperature, diluted with 200 ml of ethyl acetate and washed with 150 ml of water for three times. After that, the reaction mixture was washed with 150 ml of brine, dried over anhydrous magnesium sulfate and filtered, and the filtrate was concentrated in vacuo to give 7.10 g (19.8 mmol) of the title compound as a white solid.

(5) Synthesis of (6-(5-bromo-3-methoxymethyl-3H-thiazol-2-ylideneamino)-pyridin-2-yl)-methanol

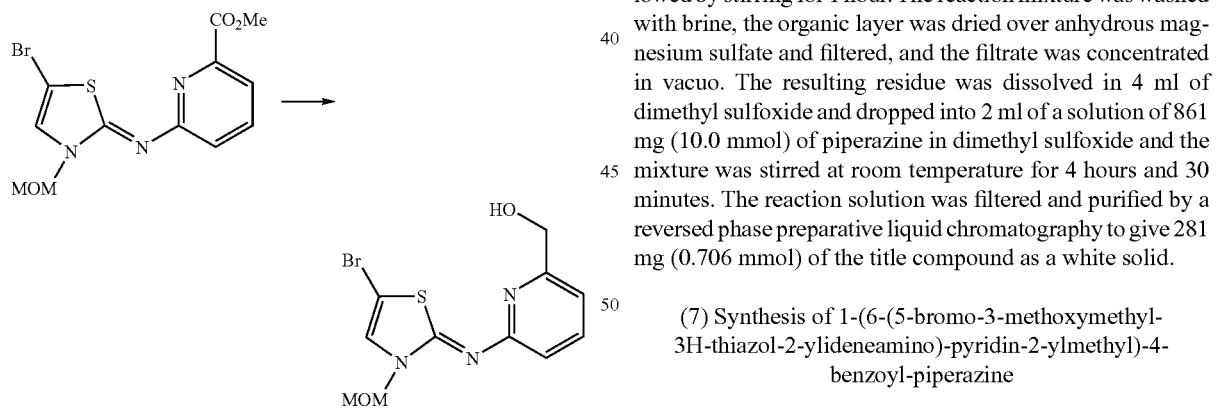

6.50 g (18.0 mmol) of methyl 6-(5-bromo-3-methoxymethyl-3H-thiazol-2-ylideneamino)-pyridine-2-carboxylate was dissolved in 80 ml of tetrahydrofuran, 790 mg (36.0 mmol) of lithium borohydride was added thereto and the mixture was heated under reflux. After 1 hour, 790 mg (36.0 mmol) of lithium borohydride was added thereto followed by further heating under reflux for 1 hour, the reaction mixture was cooled to room temperature and water was added thereto. After water was added until no more bubbling took place, the mixture was extracted with ethyl acetate. The resulting ethyl acetate solution was washed with 100 ml of water for two times and then washed with 100 ml of brine. The organic layer was dried over anhydrous magnesium sulfate and filtered, and the filtrate was concentrated in vacuo. The resulting residue was purified by a silica gel column chromatography to give 2.67 g (8.09 mmol) of the title compound as a white solid.

(6) Synthesis of 1-(6-(5-bromo-3-methoxymethyl-3H-thiazol-2-ylideneamino)-pyridin-2-ylmethyl)-piperazine To a mixture of 330 mg (1.00 mmol) of (6-(5-bromo-3-methoxymethyl-3H-thiazol-2-ylideneamino)-pyridin-2-yl)-methanol, 0.348 ml (2.00 mmol) of N,N-diisopropylethylamine and 15 ml of chloroform was added 0.116 ml (1.50 mmol) of methanesulfonyl chloride at room temperature followed by stirring for 1 hour. The reaction mixture was washed with brine, the organic layer was dried over anhydrous magnesium sulfate and filtered, and the filtrate was concentrated in vacuo. The resulting residue was dissolved in 4 ml of dimethyl sulfoxide and dropped into 2 ml of a solution of 861 mg (10.0 mmol) of piperazine in dimethyl sulfoxide and the mixture was stirred at room temperature for 4 hours and 30 minutes. The reaction solution was filtered and purified by a reversed phase preparative liquid chromatography to give 281 mg (0.706 mmol) of the title compound as a white solid.

(7) Synthesis of 1-(6-(5-bromo-3-methoxymethyl-3H-thiazol-2-ylideneamino)-pyridin-2-ylmethyl)-4-benzoyl-piperazine

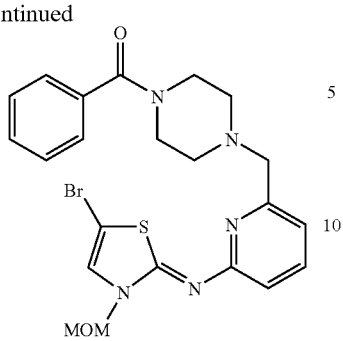

77 mg (0.217 mmol) of 1-(6-(5-bromo-3-methoxymethyl-3H-thiazol-2-ylideneamino)-pyridin-2-ylmethyl)-piperazine was dissolved in 10 ml of chloroform, 0.363 ml (2.60 mmol) of triethylamine was added thereto, 0.126 ml (1.09 mmol) of benzoyl chloride was gradually dropped thereinto and the mixture was stirred at room temperature for 30 minutes. The resulting mixture was diluted with ethyl acetate, washed with brine, dried over anhydrous magnesium sulfate and filtered, and the filtrate was concentrated in vacuo. The resulting residue was purified by a silica gel column chromatography to give 81 mg (0.161 mmol) of the title compound as a white solid.

(8) Synthesis of (5-bromo-thiazol-2-yl)-(6-(4-benzoyl-piperazin-1-ylmethyl)-pyridin-2-yl)-amine

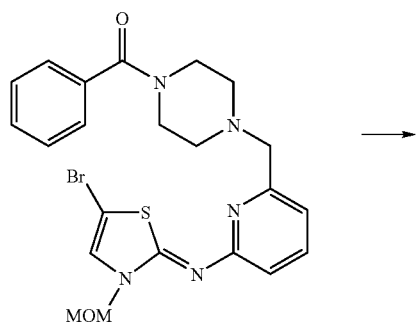

81 mg (0.161 mmol) of 1-(6-(5-bromo-3-methoxymethyl-3H-thiazol-2-ylideneamino)-pyridin-2-ylmethyl)-4-benzoyl-piperazine was dissolved in 10 ml of chloroform, a hydrochloric acid-1,4-dioxane solution (4 M, 4 ml) was added thereto and the mixture was stirred at room temperature for 18 hours. The reaction mixture was concentrated in vacuo, the residue was recrystallized from methanol-ether and filtered and the resulting white solid was dissolved in water (10 ml) and neutralized with sodium bicarbonate. The resulting precipitate was filtered to give 32 mg (0.070 mmol) of the title compound as a white solid.

Spectral data of the title compound are as follows.
$^1$H-NMR (DMSO-$d_6$) δ: 11.50 (brs, 1H), 7.78-7.62 (m, 1H), 7.50-7.30 (m, 6H), 7.02 (d, J=6.9 Hz, 1H), 6.90 (d, J=8.6 Hz, 1H), 3.80-3.20 (m, 10H)
Mass: 458, 460 (M+1)$^+$ Example 2

Synthesis of (5-methyl-1H-pyrazol-3-yl)-(6-(4-benzoyl-piperazin-1-yl-methyl)-pyridin-2-yl)-amine (1) Synthesis of 2-amino-6-(tert-butyldimethylsilyloxymethyl)pyridine

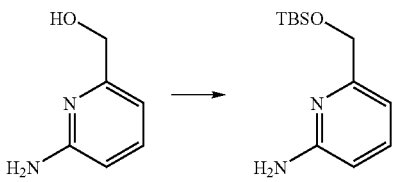

1.26 g (10.2 mmol) of 2-amino-6-hydroxymethylpyridine (Journal of Heterocyclic Chemistry, 2001, 38, 173) was dissolved in 5.1 mL of dimethylformamide and 1.7 g (25 mmol) of imidazole was added thereto. Under cooling with ice, 1.8 g (12 mmol) of tert-butyldimethylsilyl chloride was added thereto followed by stirring at room temperature for 1 hour. The reaction solution was diluted with ethyl acetate and the organic layer was washed with water and brine. This was dried over magnesium sulfate and filtered, and the filtrate was concentrated. The resulting residue was purified by a silica gel column chromatography to give 1.9 g of the title compound as an orange-colored oil.

Spectral data of the title compound are as follows.
$^1$H-NMR (CDCl$_3$) δ: 7.45 (dd, J=8.0, 7.6 Hz, 1H), 6.86 (dd, J=7.6, 0.8 Hz, 1H), 6.37 (dd, J=8.0, 0.8 Hz, 1H), 4.65 (s, 2H), 4.34 (brs, 2H), 0.95 (s, 9H), 0.11 (s, 6H)
Mass: 239 (M+1)$^+$ (2) Synthesis of N-(6-(tert-butyldimethylsilyloxymethyl)pyridin-2-yl)-3-oxobutanamide

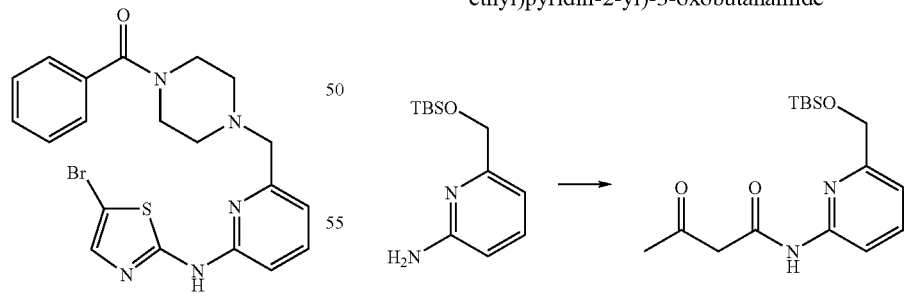

6.6 mL of tert-butyl acetoacetate was dissolved in 10 mL of toluene and the mixture was stirred at 100° C. for 1 hour. To the reaction solution was added a solution of 1.9 g (8.1 mmol) of 2-amino-6-(tert-butyldimethylsilyloxymethyl)pyridine in 5 mL of toluene and the mixture was stirred at the same temperature for 15 hours. The reaction solution was concentrated and the resulting residue was purified by a silica gel column chromatography to give 2.2 g of the title compound as a yellow oil.

Spectral data of the title compound are as follows.
¹H-NMR (CDCl₃) δ: 9.03 (brs, 1H), 7.99 (brd, J=7.6 Hz, 1H), 7.69 (dd, J=8.0, 7.6 Hz, 1H), 7.25 (brd, J=8.0 Hz, 1H), 4.72 (s, 2H), 3.58 (s, 2H), 2.33 (s, 3H), 0.96 (s, 9H), 0.12 (s, 6H)
Mass: 323 (M+1)⁺

(3) Synthesis of 3-(6-hydroxymethylpyridin-2-yl)amino-5-1H-methylpyrazole

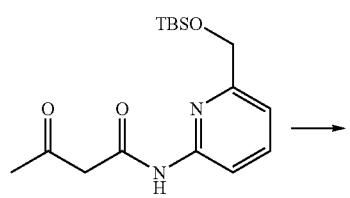

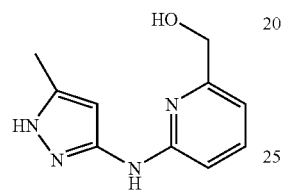

2.2 g (6.8 mmol) of N-(6-(tert-butyldimethylsilyloxymethyl)pyridin-2-yl)-3-oxobutanamide was dissolved in 68 mL of 1,2-dimethoxyethane and 8.9 mL (140 mmol) of methanesulfonic acid and 3.3 mL (68 mmol) of hydrazine monohydrate were added thereto successively at 0° C. After stirring at room temperature for 15 hours, the mixture was stirred at 80° C. for 6 hours. Under cooling with an ice bath, 30 mL of 25% aqueous ammonia and 30 mL of water were added to the reaction solution and the mixture was extracted with chloroform. The organic layer was concentrated and the resulting residue was purified by a silica gel column chromatography to give 630 mg of the title compound as an orange-colored oil.
Spectral data of the title compound are as follows.
¹H-NMR (CD₃OD) δ: 7.53 (t, J=7.6 Hz, 1H), 6.83 (brd, J=7.6 Hz, 2H), 4.57 (s, 2H), 2.23 (s, 3H)
Mass: 205 (M+1)⁺

(4) Synthesis of 3-(6-chloromethylpyridin-2-yl)amino-5-methyl-1H-pyrazole

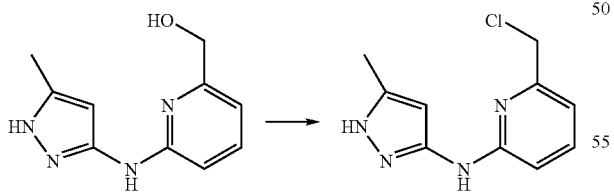

68 mg (340 μmol) of 3-(6-hydroxymethylpyridin-2-yl)amino-5-methyl-1H-pyrazole was dissolved in 4 mL of a 6:1 mixed solvent of chloroform and dimethylformamide. Under cooling on an ice bath, 250 μL (3.4 mmol) of thionyl chloride was added thereto. After stirring at room temperature for 18 hours, the reaction solution was concentrated. The resulting residue was purified by a silica gel thin-layer chromatography to give 87 mg of a brown oil. This oil was used as it was for the next reaction.

(5) Synthesis of 3-(6-(4-benzoyl-1H-piperazin-1-ylmethyl)pyridin-2-yl)amino-5-methylpyrazole

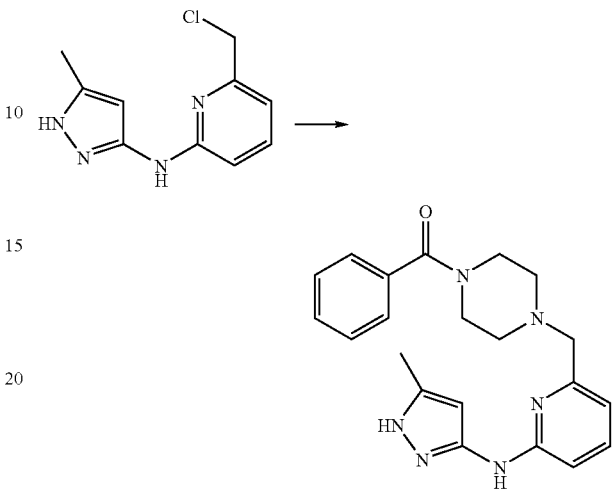

87 mg of the above-mentioned oil was dissolved in 2 mL of dimethyl sulfoxide and then 340 μL (1.95 mmol) of N,N-diisopropylethylamine and 134 mg (706 μmol) of N-benzoylpiperazine were added thereto successively. After the mixture was made to react at 90° C. for 30 minutes, the reaction solution was purified by a reversed phase preparative column chromatography to give 52 mg of the title compound as a light yellow solid.
Spectral data of the title compound are as follows.
¹H-NMR (CD₃OD) δ: 7.93 (dd, J=8.8, 7.6 Hz, 1H), 7.52-7.44 (m, 5H), 7.10 (d, J=7.6 Hz, 1H), 7.09 (d, J=8.8 Hz, 1H), 5.99 (s, 1H), 4.22 (s, 2H), 4.06-3.60 (m, 4H), 3.15-2.85 (m, 4H), 2.39 (s, 3H)
Mass: 377 (M+1)⁺

Example 3

Synthesis of (5-bromo-thiazol-2-yl)-(6-(4-(2,3-difluorobenzoyl)-piperazin-1-yl-methyl)-pyridin-2-yl)-amine (1) Synthesis of (5-bromo-thiazol-2-yl)-(6-(piperazin-1-ylmethyl)-pyridin-2-yl)-amine

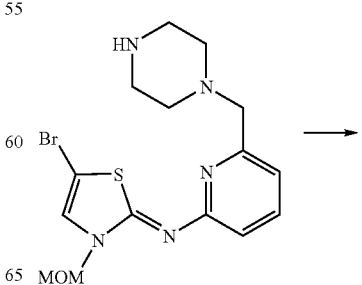

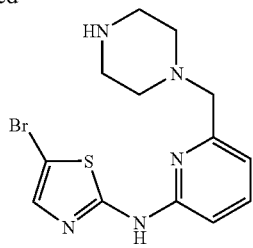

A hydrochloric acid-1,4-dioxane solution (4 M, 5 ml) was added to a mixture of 509 mg (1.28 mmol) of the compound obtained in Example 1-(6), 5 ml of chloroform and 14 ml of methanol and the mixture was stirred at room temperature for 10 hours. To the reaction solution was added 1 ml of a hydrochloric acid-1,4-dioxane solution followed by further stirring at room temperature for 18 hours. The reaction mixture was concentrated in vacuo and the residue was diluted with ethyl acetate and washed with a 1 M aqueous sodium hydroxide solution and brine. This was dried over magnesium sulfate, filtered and concentrated in vacuo to give 367 mg (1.04 mmol) of the title compound as a white solid.

(2) Synthesis of (5-bromo-thiazol-2-yl)-(6-(4-(2,3-difluorobenzoyl)-piperazin-1-ylmethyl)-pyridin-2-yl)-amine

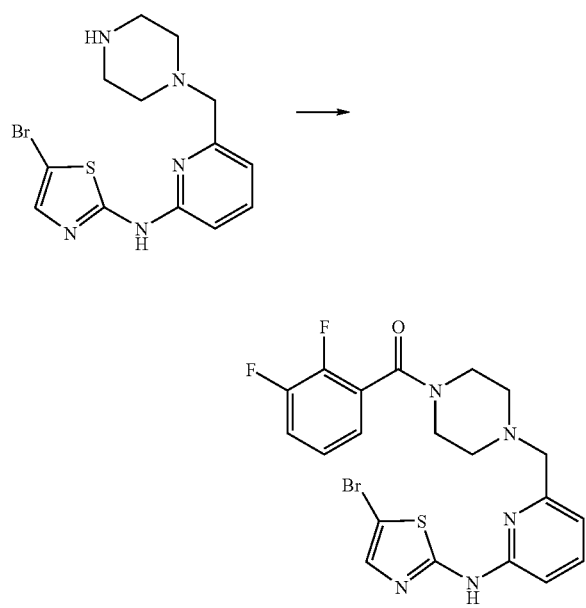

A mixture of 20 mg (0.056 mmol) of the compound obtained in the above (1), 32.5 mg (0.169 mmol) of 1-(3-dimethyl-aminopropyl)-3-ethylcarbodiimide hydrochloride, 22.9 mg (0.169 mmol) of 1-hydroxybenzotriazole, 26.8 mg (0.169 mmol) of 2,3-difluorobenzoic acid and 1 ml of chloroform was stirred at room temperature for 4 hours. Water was added thereto and the resulting mixture was extracted with ethyl acetate followed by washing with brine. The resulting mixture was dried over magnesium sulfate and filtered, the filtrate was concentrated in vacuo and the resulting residue was purified by a preparative thin-layer chromatography to give 17.0 mg (0.034 mmol) of the title compound as a colorless amorphous substance.

Spectral data of the title compound are as follows.

$^1$H-NMR (CDCl$_3$) δ: 7.63 (dd, J=7.8, 7.6 Hz, 1H), 7.34 (s, 1H), 7.32-7.09 (m, 3H), 7.06 (d, J=7.2 Hz, 1H), 6.76 (d, J=8.0 Hz, 1H), 3.90-3.82 (m, 2H), 3.76 (s, 2H), 3.47-3.37 (m, 2H), 2.76-2.63 (m, 2H), 2.63-2.50 (m, 2H)

Mass: 494, 496 (M+1)$^+$

Example 4

Synthesis of (thiazol-2-yl)-(6-(4-(2,3-difluorobenzoyl)-piperazin-1-ylmethyl)-pyridin-2-yl)-amine

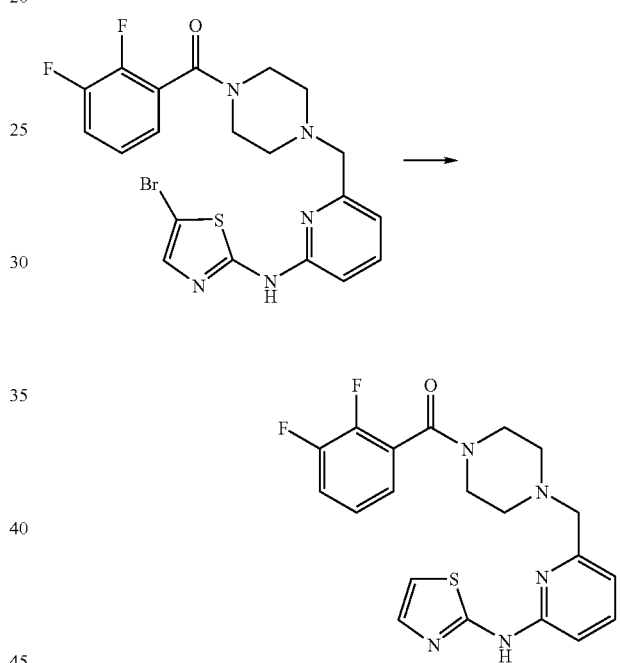

8.5 mg (0.017 mmol) of the compound obtained in Example 3-(2) was dissolved in 1 ml of methanol, 10 mg of 10% palladium-carbon was added thereto and the mixture was stirred under a hydrogen atmosphere at ordinary pressure and room temperature for 1 hour. The reaction solution was filtered, the solvent was concentrated in vacuo and the resulting residue was purified by a preparative thin-layer chromatography to give 4.1 mg (0.010 mmol) of the title compound as a colorless amorphous substance.

Spectral data of the title compound are as follows.

$^1$H-NMR (CD$_3$OD) δ: 7.65 (t, J=7.4 Hz, 1H), 7.32 (d, J=3.7 Hz, 1H), 7.40-7.30 (m, 1H), 7.28-7.22 (m, 1H), 7.19-7.14 (m, 1H), 7.04 (d, J=7.2 Hz, 1H), 6.92-6.85 (m, 2H), 3.82 (dd, J=5.3, 5.1 Hz, 2H), 3.74 (s, 2H), 3.39 (t, J=4.7 Hz, 2H), 2.69 (t, J=5.1 Hz, 2H), 2.58 (dd, J=5.7, 4.1 Hz, 2H)

Mass: 416 (M+1)$^+$

Example 5

Synthesis of 6-((4-(3-chloro-2-fluorobenzoyl)piperazin-1-yl)methyl)-N-thiazol-2-ylpyridin-2-amine

(1) Synthesis of 2-bromo-6-(((tert-butyl(dimethyl)silyl)oxy)methyl)pyridine

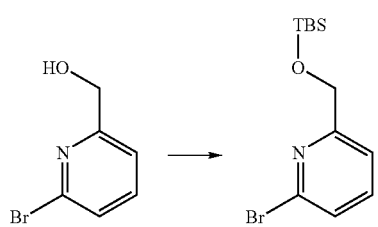

5.00 g of (6-bromo-pyridin-2-yl)-methanol was dissolved in 50 mL of dimethylformamide and 2.72 g of imidazole was added thereto. Under cooling with ice, 5.21 g of tert-butyldimethylsilyl chloride was added thereto followed by stirring at room temperature for 1 hour. The reaction solution was diluted with ethyl acetate and washed with water and brine. The resulting organic layer was dried over magnesium sulfate and filtered, and the filtrate was concentrated. The resulting residue was purified by a silica gel column chromatography (eluent: hexane/ethyl acetate=10/1 to 1/1) to give the title compound.

(2) Synthesis of 6-(((tert-butyl(dimethyl)silyl)oxy)methyl)-N-thiazol-2-ylpyridin-2-amine

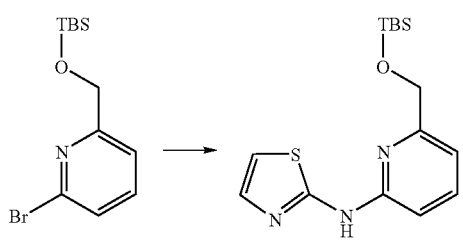

A mixture of 7.85 g of 2-bromo-6-(((tert-butyl(dimethyl)silyl)oxy)methyl)pyridine, 3.12 g of 2-aminothiazole, 1.50 g of 9,9-dimethyl-4,5-bis(diphenylphosphino)xanthene, 1.35 g of tris(dibenzylideneacetone)dipalladium(0)-chloroform complex, 13.8 g of potassium phosphate and 80 ml of 1,4-dioxane was stirred at 100° C. for 4.5 hours, cooled to room temperature and diluted with ethyl acetate. An insoluble matter was filtered off using Celite and the resulting ethyl acetate solution was washed with water and brine. The organic layer was dried over anhydrous magnesium sulfate and filtered, and the filtrate was concentrated. The residue was purified by a silica gel column chromatography (eluent: hexane/ethyl acetate=10/1 to 1/1) to give the title compound.

(3) Synthesis of (6-(thiazol-2-ylamino)pyridin-2-yl)methanol

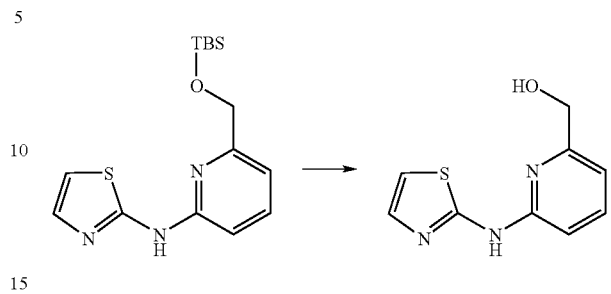

6.48 g of 6-(((tert-butyl(dimethyl)silyl)oxy)methyl)-N-thiazol-2-ylpyridin-2-amine was dissolved in 100 ml of tetrahydrofuran. Under cooling with ice, a tetrabutylammonium fluoride-tetrahydrofuran solution (1.0 M, 20.2 ml) was added followed by stirring at room temperature for 1 hour. The reaction solution was diluted with ethyl acetate and then washed with phosphate buffer (pH 6.8). The organic layer was dried over anhydrous magnesium sulfate and filtered, and the filtrate was concentrated to give the title compound.

(4) Synthesis of 6-(chloromethyl)-N-thiazol-2-ylpyridin-2-amine

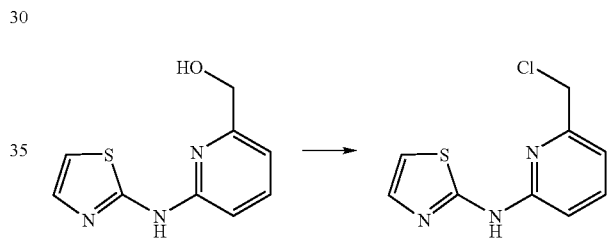

The entire amount of (6-(thiazol-2-ylamino)pyridin-2-yl)methanol obtained by the above operation was suspended in 150 ml of chloroform, and 7.37 ml of thionyl chloride was added thereto. After stirring at room temperature for 2 hours, the reaction solution was concentrated. The resulting residue was diluted with ethyl acetate, and then washed with a 2 M aqueous sodium hydroxide solution and brine. The organic layer was dried over anhydrous magnesium sulfate and filtered, and the filtrate was concentrated. The residue was purified by a silica gel column chromatography (eluent: chloroform to chloroform/methanol=20/1) to give the title compound.

(5) Synthesis of 6-((4-(3-chloro-2-fluorobenzoyl)piperazin-1-yl)methyl)-N-thiazol-2-ylpyridin-2-amine

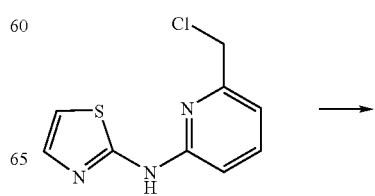

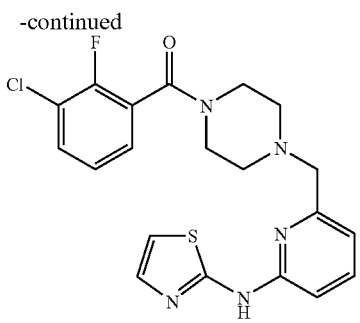

A mixture of 2.70 g of 6-(chloromethyl)-N-thiazol-2-ylpyridin-2-amine, 4.00 g of 1-(3-chloro-2-fluorobenzoyl)piperazine obtained in Reference Example 1, 6.25 ml of N,N-diisopropylethylamine and 30 ml of dimethylformamide was stirred at 90° C. for 2 hours. The reaction solution was diluted with ethyl acetate and then washed with water and brine. The resulting organic layer was dried over magnesium sulfate and filtered, and the filtrate was concentrated. The resulting residue was purified by a silica gel column chromatography (eluent: chloroform to chloroform/methanol=10/1). Then, the obtained compound was suspended in ethyl acetate, and filtered and collected to give the title compound as a colorless amorphous substance.

Spectral data of the title compound are as follows.

$^1$H-NMR (DMSO-$d_6$) δ: 11.20 (s, 1H), 7.65 (t, J=7.8 Hz, 2H), 7.41-7.33 (m, 2H), 7.29 (t, J=7.8 Hz, 1H), 7.00-6.87 (m, 3H), 3.72-3.61 (m, 4H), 3.27-3.20 (m, 2H), 2.60-2.36 (m, 4H).

Mass: 432 (M+1)$^+$

Examples 6 to 15, 32 to 43 and 63 were synthesized in the same manner as in Example 5 as follows.

Example 6

Synthesis of 6-((4-(2,3-dichlorobenzoyl)piperazin-1-yl)methyl)-N-thiazol-2-ylpyridin-2-amine $^1$H-NMR (DMSO-$d_6$) δ: 11.21 (s, 1H), 7.72-7.61 (m, 2H), 7.42 (t, J=7.8 Hz, 1H), 7.39-7.29 (m, 2H), 7.02-6.90 (m, 3H), 3.73-3.61 (m, 4H), 3.19-3.12 (m, 2H), 2.60-2.38 (m, 4H)

Mass: 448 (M+1)$^+$

Example 7

Synthesis of 6-((4-(3-chlorobenzoyl)piperazin-1-yl)methyl)-N-thiazol-2-ylpyridin-2-amine $^1$H-NMR (DMSO-$d_6$) δ: 11.20 (s, 1H), 7.65 (t, J=7.8 Hz, 1H), 7.54-7.39 (m, 3H), 7.38-7.28 (m, 2H), 7.00-6.88 (m, 3H), 3.64 (s, 4H), 3.48-3.19 (m, 2H), 2.62-2.34 (m, 4H)

Mass: 414 (M+1)$^+$

Example 8

Synthesis of 6-((4-(2-fluoro-3-methylbenzoyl)piperazin-1-yl)methyl)-N-thiazol-2-ylpyridin-2-amine $^1$H-NMR (DMSO-$d_6$) δ: 11.21 (s, 1H), 7.65 (t, J=7.8 Hz, 1H), 7.39-7.31 (m, 2H), 7.20-7.10 (m, 2H), 7.00-6.89 (m, 3H), 3.73-3.62 (m, 4H), 3.22 (t, J=4.7 Hz, 2H), 2.56-2.34 (m, 4H), 2.24 (d, J=1.6 Hz, 3H)

Mass: 412 (M+1)$^+$

Example 9

Synthesis of 6-((4-(2-chloro-3-fluorobenzoyl)piperazin-1-yl)methyl)-N-thiazol-2-ylpyridin-2-amine $^1$H-NMR (DMSO-$d_6$) δ: 11.21 (brs, 1H), 7.65 (t, J=7.8 Hz, 1H), 7.51-7.42 (m, 2H), 7.36 (d, J=3.9 Hz, 1H), 7.25-7.18 (m, 1H), 7.02-6.81 (m, 3H), 3.75-3.60 (m, 4H), 3.16 (t, J=4.3 Hz, 2H), 2.61-2.40 (m, 4H)

Mass: 432 (M+1)$^+$

Example 10

Synthesis of 6-(((1S,4S)-5-(3-chloro-2-fluorobenzoyl)-2,5-diazabicyclo[2.2.1]hept-2-yl)methyl)-N-thiazol-2-ylpyridin-2-amine Trifluoroacetate $^1$H-NMR (DMSO-$d_6$) δ: 7.84-7.71 (m, 2H), 7.48-7.40 (m, 2H), 7.38-7.30 (m, 1H), 7.19-7.07 (m, 3H), 5.00-3.36 (m, 8H), 2.54-2.14 (m, 2H)

Mass: 444 (M+1)$^+$

Example 11

Synthesis of 6-(((1R,4R)-5-(3-chloro-2-fluorobenzoyl)-2,5-diazabicyclo[2.2.1]hept-2-yl)methyl)-N-thiazol-2-ylpyridin-2-amine $^1$H-NMR (CDCl$_3$) δ: 7.63-7.57 (m, 1H), 7.50-7.44 (m, 2H), 7.37-7.31 (m, 1H), 7.19-7.13 (m, 1H), 7.04-6.99 (m, 1H), 6.87-6.77 (m, 2H), 4.93-2.82 (m, 8H), 2.05 and 1.99 (each d, J=10.0 Hz, total 1H), 1.83 (d, J=10.0 Hz, 1H)

Mass: 444, 446 (M+1)$^+$

Example 12

Synthesis of 6-((4-(3-bromo-2-fluorobenzoyl)piperazin-1-yl)methyl)-N-thiazol-2-ylpyridin-2-amine Trifluoroacetate $^1$H-NMR (CD$_3$OD) δ: 7.94 (dd, J=8.4, 7.2 Hz, 1H), 7.80-7.74 (m, 1H), 7.53 (d, J=3.6 Hz, 1H), 7.46-7.40 (m, 1H), 7.32 (d, J=7.2 Hz, 1H), 7.26 (d, J=8.4 Hz, 1H), 7.23 (t, J=8.0 Hz, 1H), 7.19 (d, J=3.6 Hz, 1H), 4.53 (s, 2H), 4.15-4.00 (m, 2H), 3.72-3.64 (m, 2H), 3.59-3.52 (m, 2H), 3.48-3.41 (m, 2H)

Mass: 478 (M+1)$^+$

Example 13

Synthesis of 6-((4-(2-fluoro-3-(trifluoromethyl)benzoyl)piperazin-1-yl)methyl)-N-thiazol-2-ylpyridin-2-amine Trifluoroacetate $^1$H-NMR (CD$_3$OD) δ: 7.95 (dd, J=8.4, 7.2 Hz, 1H), 7.86 (brt, J=7.6 Hz, 1H), 7.75 (brt, J=6.4 Hz, 1H), 7.55 (d, J=4.4 Hz, 1H), 7.49 (t, J=8.0 Hz, 1H), 7.34 (d, J=7.2 Hz, 1H), 7.27 (d, J=8.4 Hz, 1H), 7.20 (d, J=4.4 Hz, 1H) 4.54 (s, 2H), 4.16-4.00 (m, 2H), 3.74-3.66 (m, 2H), 3.61-3.53 (m, 2H), 3.50-3.42 (m, 2H)

Mass: 466 (M+1)$^+$

Example 14

Synthesis of 6-(((3R)-4-(3-chloro-2-fluorobenzoyl)-3-methylpiperazin-1-yl)methyl)-N-thiazol-2-ylpyridin-2-amine $^1$H-NMR (CDCl$_3$) δ: 7.60 (t, J=7.6 Hz, 1H), 7.49 (d, J=3.7 Hz, 1H), 7.43 (t, J=7.6 Hz, 1H), 7.26-7.11 (m, 2H), 7.06-7.01 (m, 1H), 6.85 (d, J=3.1 Hz, 1H), 6.80 (d, J=8.0 Hz, 1H), 5.00-2.20 (m, 9H), 1.50-1.25 (m, 3H)

Mass: 446, 448 (M+1)$^+$

Example 15

Synthesis of 6-((4-(3-(difluoromethyl)-2-fluorobenzoyl)piperazin-1-yl)methyl)-N-thiazol-2-ylpyridin-2-amine $^1$H-NMR (CDCl$_3$) δ: 7.65 (brt, J=7.6 Hz, 1H), 7.60 (dd, J=8.0, 7.2 Hz, 1H), 7.51 (brt, J=7.8 Hz, 1H), 7.48 (d, J=3.6 Hz, 1H), 7.31 (t, J=7.6 Hz, 1H), 7.00 (d, J=7.2 Hz, 1H), 6.89 (t, J=54.8 Hz, 1H), 6.85 (d, J=3.6 Hz, 1H), 6.82 (d, J=8.0 Hz, 1H), 3.90-3.83 (m, 2H), 3.76 (s, 2H), 3.41-3.33 (m, 2H), 2.71 (brt, J=4.8 Hz, 2H), 2.61-2.52 (m, 2H)

Mass: 448 (M+1)$^+$

Example 16

Synthesis of 6-((4-(3-chloro-2-fluorobenzoyl)piperazin-1-yl)methyl)-N-1H-pyrazol-3-ylpyridin-2-amine (1) Synthesis of (6-((1-((2-(trimethylsilyl)ethoxy)methyl)-1H-pyrazol-3-yl)amino)pyridin-2-yl)methnol

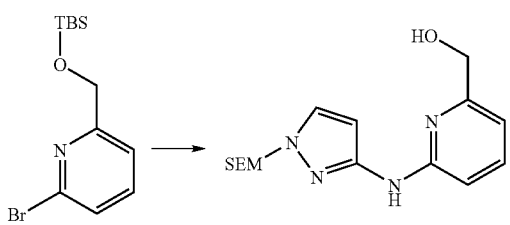

In the same manner as in Example 5-(2) to (3), the title compound was obtained using 2-bromo-6-(((tert-butyl(dimethyl)silyl)oxy)methyl)pyridine obtained in Example 5-(1) and 1-((2-(trimethylsilyl)ethoxy)methyl)-1-H-pyrazol-3-amine obtained in Reference Example 2.

(2) Synthesis of 6-(methanesulfonyloxymethyl)-N-(1-((2-(trimethylsilyl)ethoxy)methyl)-1H-pyrazol-3-yl)pyridin-2-amine

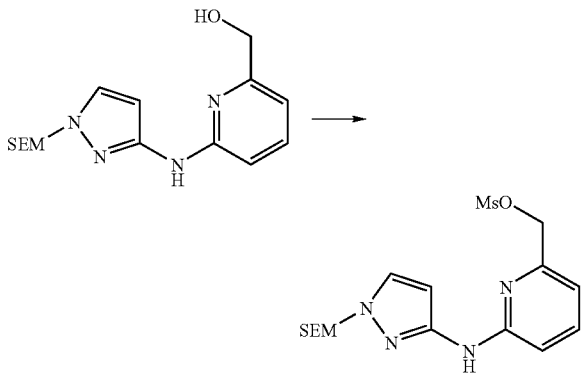

To a mixture of 10 mg of (6-((1-((2-(trimethylsilyl)ethoxy)methyl)-1H-pyrazol-3-yl)amino)pyridin-2-yl)methanol, 27 μl of N,N-diisopropylethylamine and 1 ml of chloroform was added 7.3 μl of methanesulfonyl chloride at room temperature followed by stirring for 1 hour. The reaction mixture was washed with brine, and the organic layer was dried over anhydrous magnesium sulfate and filtered. The filtrate was then concentrated in vacuo to give the title compound.

(3) Synthesis of 6-((4-(3-chloro-2-fluorobenzoyl)piperazin-1-yl)methyl)-N-(1-((2-(trimethylsilyl)ethoxy)methyl)-1H-pyrazol-3-yl)pyridin-2-amine

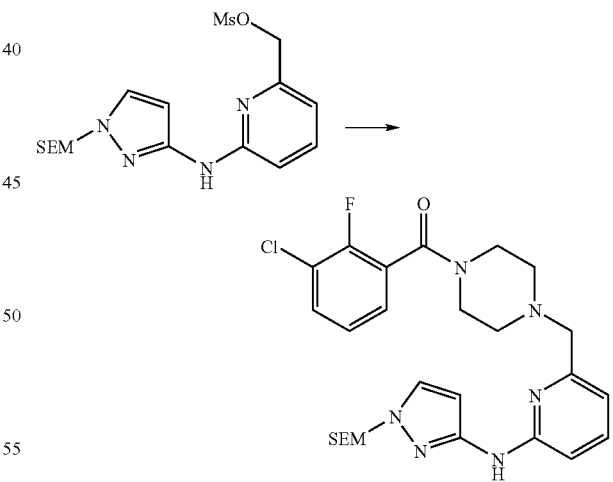

A mixture of 10 mg of 6-(methanesulfonyloxymethyl)-N-(1-((2-(trimethylsilyl)ethoxy)methyl)-1H-pyrazol-3-yl)pyridin-2-amine, 40 mg of 1-(3-chloro-2-fluorobenzoyl)piperazine hydrochloride obtained in Reference Example 1, 27 μl of N,N-diisopropylethylamine and 1 ml of chloroform was stirred at 60° C. for 5 hours. The reaction solution was diluted with chloroform, and then washed with water and brine. The resulting organic layer was dried over magnesium sulfate and filtered, and the filtrate was concentrated. The resulting resi- (4) Synthesis of 6-((4-(3-chloro-2-fluorobenzoyl)piperazin-1-yl)methyl)-N-1H-pyrazol-3-ylpyridin-2-amine

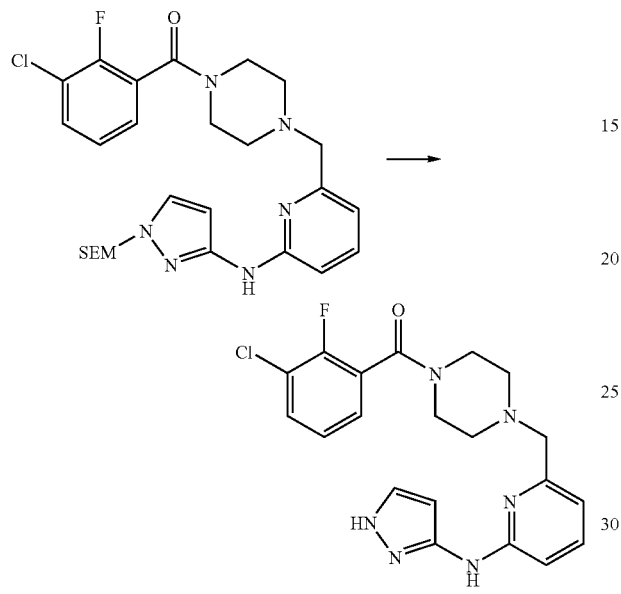

18 mg of (6-((4-(3-Chloro-2-fluorobenzoyl)piperazin-1-yl)methyl)-N-(1-((2-(trimethylsilyl)ethoxy)methyl)-1H-pyrazol-3-yl)pyridin-2-amine was dissolved in 900 µl of trifluoroacetate and 100 µl of water followed by stirring at room temperature for 5 hours. The reaction solution was concentrated in vacuo, diluted with ethyl acetate, and then washed with saturated sodium bicarbonate, water and brine. The resulting organic layer was dried over magnesium sulfate and filtered, and the filtrate was concentrated. The resulting residue was purified by a silica gel column chromatography (eluent: chloroform to chloroform/methanol=10/1) to give the title compound.

Spectral data of the title compound are as follows.

$^1$H-NMR (CDCl$_3$) δ: 7.51 (dd, J=8.2, 7.4 Hz, 1H), 7.48-7.39 (m, 2H), 7.36-7.20 (m, 2H) 7.17-7.10 (m, 1H), 6.90 (d, J=8.2 Hz, 1H), 6.82 (d, J=7.2 Hz, 1H), 5.98 (s, 1H), 3.87 (brs, 2H), 3.62 (s, 2H), 3.37 (brs, 2H), 2.63 (t, J=5.2 Hz, 2H), 2.51 (brs, 2H)

Mass: 415 (M+1)$^+$

Examples 17 to 31 were synthesized in the same manner as in Example 16 as follows.

Example 17

Synthesis of 6-((4-(2,3-dichlorobenzoyl)piperazin-1-yl)methyl)-N-1H-pyrazol-3-ylpyridin-2-amine $^1$H-NMR (CDCl$_3$) δ: 7.57-7.47 (m, 3H), 7.31-7.10 (m, 4H), 6.90 (d, J=8.0 Hz, 1H), 6.82 (d, J=7.4 Hz, 1H), 5.98 (d, J=2.0 Hz, 1H), 3.97-3.80 (m, 2H), 3.62 (s, 2H), 3.38-3.23 (m, 2H), 2.68-2.59 (m, 2H), 2.59-2.40 (m, 2H)

Mass: 431 (M+1)$^+$

Example 18

Synthesis of 6-((4-(2-chloro-3-(trifluoromethyl)benzoyl)piperazin-1-yl)methyl)-N-1H-pyrazol-3-ylpyridin-2-amine Trifluoroacetate $^1$H-NMR (CD$_3$OD) δ: 8.01 (dd, J=8.8, 7.2 Hz, 1H), 7.89 (dd, J=7.2, 2.4 Hz, 1H), 7.79 (d, J=2.4 Hz, 1H), 7.67-7.58 (m, 2H), 7.14 (d, J=8.8 Hz, 1H), 7.04 (brd, J=7.2 Hz, 1H), 6.16 (d, J=2.4 Hz, 1H), 4.13-4.03 (m, 1H), 4.00-3.89 (m, 1H), 3.97 (s, 2H), 3.44 (brt, J=5.2 Hz, 2H), 2.88-2.80 (m, 2H), 2.73-2.66 (m, 2H)

Mass: 465 (M+1)$^+$

Example 19

Synthesis of 6-((4-(2-fluoro-3-(trifluoromethyl)benzoyl)piperazin-1-yl)methyl)-N-1H-pyrazol-3-ylpyridin-2-amine Trifluoroacetate $^1$H-NMR (CD$_3$OD) δ: 8.01 (dd, J=8.8, 7.2 Hz, 1H), 7.84 (brt, J=7.2 Hz, 1H), 7.79 (d, J=2.4 Hz, 1H), 7.71 (brt, J=7.2 Hz, 1H), 7.49 (brt, J=7.6 Hz, 1H), 7.14 (d, J=8.8 Hz, 1H), 7.04 (dd, J=7.2, 1.2 Hz, 1H), 6.16 (d, J=2.4 Hz, 1H), 4.05-3.97 (m, 2H), 3.97 (s, 2H), 3.58-3.51 (m, 2H), 2.82 (brt, J=4.8 Hz, 2H), 2.70 (brt, J=4.8 Hz, 2H)

Mass: 449 (M+1)$^+$

Example 20

Synthesis of 6-((4-(3-bromo-2-fluorobenzoyl)piperazin-1-yl)methyl)-N-1H-pyrazol-3-ylpyridin-2-amine trifluoroacetate $^1$H-NMR (CD$_3$OD) δ: 8.01 (dd, J=8.8, 7.2 Hz, 1H), 7.81-7.73 (m, 2H), 7.43-7.37 (m, 1H), 7.23 (t, J=7.6 Hz, 1H), 7.14 (d, J=8.8 Hz, 1H), 7.04 (d, J=7.2 Hz, 1H), 6.16 (d, J=2.4 Hz, 1H), 4.05-3.93 (m, 4H), 3.57-3.50 (m, 2H), 2.82 (brt, J=4.8 Hz, 2H), 2.70 (brt, J=4.8 Hz, 2H)

Mass: 459 (M+1)$^+$

Example 21

Synthesis of 6-((4-((3,4-dichlorophenyl)acetyl)piperazin-1-yl)methyl)-N-1H-pyrazol-3-ylpyridin-2-amine Trifluoroacetate $^1$H-NMR (CD$_3$OD) δ: 7.97 (dd, J=8.8, 7.6 Hz, 1H), 7.80 (d, J=2.4 Hz, 1H), 7.47 (d, J=8.4 Hz, 1H) 7.44 (d, J=2.0 Hz, 1H), 7.19 (dd, J=8.4, 2.0 Hz, 1H), 7.13 (brd, J=8.8 Hz, 1H), 7.04 (brd, J=7.6 Hz, 1H), 6.17 (d, J=2.4 Hz, 1H), 4.02 (s, 2H), 3.97 (s, 1H), 3.86-3.76 (m, 6H), 2.83-2.74 (m, 4H)

Mass: 445 (M+1)$^+$

Example 22

Synthesis of 6-((4-(3-(difluoromethyl)-2-fluorobenzoyl)piperazin-1-yl)methyl)-N-1H-pyrazol-3-ylpyridin-2-amine $^1$H-NMR (CDCl$_3$) δ: 7.64 (brt, J=7.2 Hz, 1H), 7.55-7.44 (m, 3H), 7.31 (t, J=8.0 Hz, 1H), 6.91 (d, J=8.0 Hz, 1H), 6.89 (t, J=54.8 Hz, 1H), 6.82 (d, J=7.6 Hz, 1H), 5.99 (s, 1H), 3.92-3.84 (m, 2H), 3.62 (s, 2H), 3.42-3.34 (m, 2H), 2.66-2.60 (m, 2H), 2.55-2.47 (m, 2H)

Mass: 431 (M+1)$^+$

Example 23

Synthesis of 6-(((1S,4S)-5-(3-chloro-2-fluorobenzoyl)-2,5-diazabicyclo[2.2.1]hept-2-yl)methyl)-N-1H-pyrazol-3-ylpyridin-2-amine $^1$H-NMR (CDCl$_3$) δ: 7.58-7.42 (m, 3H), 7.36-7.28 (m, 1H), 7.28-7.10 (m, 2H), 6.97-6.81 (m, 2H), 6.06-5.96 (m, 1H), 4.95-2.72 (m, 8H), 2.10-2.00 (m, 1H), 1.86-1.78 (m, 1H)

Mass: 427 (M+1)$^+$

Example 24

Synthesis of 6-(1-(4-(3-chloro-2-fluorobenzoyl)piperazin-1-yl)ethyl)-N-1H-pyrazol-3-ylpyridin-2-amine $^1$H-NMR (CDCl$_3$) δ: 7.52 (dd, J=8.2, 7.6 Hz, 1H), 7.50-7.40 (m, 2H), 7.27-7.21 (m, 1H) 7.17-7.11 (m, 1H), 6.87 (d, J=8.4 Hz, 1H), 6.80 (d, J=7.2 Hz, 1H), 6.01 (d, J=1.8 Hz, 1H), 3.83 (brs, 2H), 3.58-3.52 (m, 1H), 3.34 (brs, 2H), 2.72-2.40 (m, 4H), 1.42 (d, J=6.8 Hz, 3H)

Mass: 429 (M+1)$^+$

Example 25

Synthesis of 6-((4-(3-chloro-2-fluorobenzoyl)piperazin-1-yl)methyl)-N-(5-methyl-1H-pyrazol-3-yl)pyridin-2-amine $^1$H-NMR (CD$_3$OD) δ: 7.99 (dd, J=8.8, 7.2 Hz, 1H), 7.64-7.57 (m, 1H), 7.38-7.26 (m, 2H), 7.11 (d, J=8.8 Hz, 1H), 7.01 (d, J=7.2 Hz, 1H), 5.91 (s, 1H), 4.03-3.95 (m, 2H), 3.94 (s, 2H), 3.56-3.50 (m, 2H), 2.82-2.75 (m, 2H), 2.69-2.64 (m, 2H), 2.35 (s, 3H)

Mass: 429 (M+1)$^+$

Example 26

Synthesis of 6-((4-(2,3-dichlorobenzoyl)piperazin-1-yl)methyl)-N-(5-methyl-1H-pyrazol-3-yl)pyridin-2-amine Trifluoroacetate $^1$H-NMR (CD$_3$OD) δ: 7.96 (dd, J=8.8, 7.2 Hz, 1H), 7.64 (dd, J=8.0, 1.6 Hz, 1H), 7.42 (t, J=8.0 Hz, 1H), 7.32 (dd, J=8.0, 1.6 Hz, 1H), 7.09 (dd, J=8.0, 0.8 Hz, 1H), 7.05 (dd, J=7.2, 0.8 Hz, 1H), 5.95 (d, J=0.8 Hz, 1H), 4.13-4.03 (m, 1H), 4.07 (s, 2H), 3.98-3.88 (m, 1H), 3.47 (brt, J=5.2 Hz, 2H), 3.03-2.89 (m, 2H), 2.82 (brt, J=5.2 Hz, 2H), 2.37 (s, 3H)

Mass: 445 (M+1)$^+$

Example 27

Synthesis of 6-(((1S,4S)-5-(3-chloro-2-fluorobenzoyl)-2,5-diazabicyclo[2.2.1]hept-2-yl)methyl)-N-(5-methyl-1H-pyrazol-3-yl)pyridin-2-amine $^1$H-NMR (CD$_3$OD) δ: 7.85-7.81 (m, 1H), 7.67-7.60 (m, 1H), 7.45-7.38 (m, 1H), 7.33-7.25 (m, 1H), 7.15-7.08 (m, 1H), 7.04 (d, J=8.8 Hz, 1H), 6.02 (s, 1H), 4.63-4.51 (m, 1H), 4.49-4.36 (m, 3H), 4.00-3.93 (m, 1H), 3.81-3.75 (m, 1H), 3.68-3.58 (m, 1H), 3.56-3.50 (m, 1H), 3.38-3.31 (m, 1H), 2.40 (s, 3H), 2.30-2.20 (m, 1H)

Mass: 441 (M+1)$^+$

Example 28

Synthesis of 6-((4-(3-bromo-2-fluorobenzoyl)piperazin-1-yl)methyl)-N-(5-methyl-1H-pyrazol-3-yl)pyridin-2-amine $^1$H-NMR (CD$_3$OD) δ: 7.90 (d, J=0.8 Hz, 1H), 7.75-7.69 (m, 1H), 7.53 (dd, J=8.0, 7.2 Hz, 1H), 7.40-7.33 (m, 1H), 7.20 (t, J=8.0 Hz, 1H), 6.82 (d, J=7.2 Hz, 1H), 3.90-3.78 (m, 2H), 3.67-3.55 (m, 2H), 3.44-3.34 (m, 2H), 2.64 (brt, J=4.8 Hz, 2H), 2.53 (brt, J=4.8 Hz, 2H), 2.23 (s, 3H)

Mass: 473 (M+1)$^+$

Example 29

Synthesis of 6-((4-(2-fluoro-3-(trifluoromethyl)benzoyl)piperazin-1-yl)methyl)-N-(5-methyl-1H-pyrazol-3-yl)pyridin-2-amine 1H-NMR (CD$_3$OD) δ: 7.90 (s, 1H), 7.81 (brt, J=7.2 Hz, 1H), 7.68 (brt, J=6.8 Hz, 1H), 7.53 (t, J=8.0 Hz, 1H), 7.46 (t, J=7.6 Hz, 1H), 6.82 (d, J=7.2 Hz, 1H), 3.89-3.82 (m, 2H), 3.65-3.57 (m, 2H), 3.43-3.37 (m, 2H), 2.65 (brt, J=4.8 Hz, 2H), 2.54 (brt, J=4.8 Hz, 2H), 2.23 (s, 3H)

Mass: 463 (M+1)$^+$

Example 30

Synthesis of 6-((4-(2-chloro-3-(trifluoromethyl)benzoyl)piperazin-1-yl)methyl)-N-(5-methyl-1H-pyrazol-3-yl)pyridin-2-amine $^1$H-NMR (CD$_3$OD) δ: 7.91-7.84 (m, 2H), 7.64-7.50 (m, 3H), 6.82 (brd, J=7.2 Hz, 1H), 3.90-3.80 (m, 2H), 3.65-3.56 (m, 2H), 2.66 (brt, J=4.8 Hz, 2H), 2.63-2.49 (m, 2H), 2.23 (s, 3H)

Mass: 479 (M+1)$^+$

Example 31

Synthesis of 6-((4-benzoylpiperazin-1-yl)methyl)-N-(5-cyclopropyl-1H-pyrazol-3-yl)pyridin-2-amine $^1$H-NMR (CD$_3$OD) δ: 7.96 (dd, J=8.8, 7.6 Hz, 1H), 7.53-7.43 (m, 5H), 7.09 (brd, J=8.8 Hz, 1H), 7.02 (brd, J=7.6 Hz, 1H), 5.76 (s, 1H), 4.04-3.60 (m, 4H), 3.99 (s, 2H), 2.95-2.65 (m, 4H), 2.02-1.93 (m, 1H), 1.10-1.05 (m, 2H), 0.82-0.77 (m, 2H)

Mass: 403 (M+1)$^+$

Example 32

Synthesis of 6-((4-(3-chloro-2-fluorobenzoyl)piperazin-1-yl)methyl)-N-1,2,4-thiadiazol-5-ylpyridin-2-amine Mass: 433 (M+1)$^+$

Example 33

Synthesis of 6-(((3R)-4-benzoyl-3-methylpiperazin-1-yl)methyl)-N-1,2,4-thiadiazol-5-ylpyridin-2-amine Trifluoroacetate $^1$H-NMR (DMSO-d$_6$) δ: 12.31 (brs, 1H), 8.34 (s, 1H), 7.99-7.82 (m, 1H), 7.50-7.10 (m, 7H), 4.60-2.80 (m, 9H), 1.31 (d, J=7.0 Hz, 3H)
Mass: 395 (M+1)$^+$

Example 34

Synthesis of phenyl (1-((6-(1,2,4-thiadiazol-5-ylamino)pyridin-2-yl)methyl)piperidin-4-yl)methanone Trifluoroacetate $^1$H-NMR (DMSO-d$_6$) δ: 12.39 (s, 1H), 9.94 (brs, 1H), 8.36 (s, 1H), 8.02-7.90 (m, 3H), 7.70-7.61 (m, 1H), 7.60-7.50 (m, 2H), 7.38-7.20 (m, 2H), 4.60-4.20 (m, 2H), 4.00-3.20 (m, 5H), 2.10-1.75 (m, 4H)
Mass: 380 (M+1)$^+$

Example 35

Synthesis of 6-((4-benzoyl-1,4-diazepan-1-yl)methyl)-N-1,2,4-thiadiazol-5-ylpyridin-2-amine Mass: 395 (M+1)$^+$

Example 36

Synthesis of 6-((4-(2,3-dichlorobenzoyl)piperazin-1-yl)methyl)-N-1,2,4-thiadiazol-5-ylpyridin-2-amine Trifluoroacetate $^1$H-NMR (DMSO-d$_6$) δ: 12.35 (brs, 1H), 8.35 (s, 1H), 7.99-7.90 (m, 1H), 7.75-7.70 (m, 1H), 7.55-7.40 (m, 2H), 7.38-7.20 (m, 2H), 4.60-3.10 (m, 10H)
Mass: 449 (M+1)$^+$

Example 37

Synthesis of 6-((4-(3-(trifluoromethyl)benzoyl)piperazin-1-yl)methyl)-N-1,2,4-thiadiazol-5-ylpyridin-2-amine Mass: 449 (M+1)$^+$

Example 38

Synthesis of 6-((4-(3-bromobenzoyl)piperazin-1-yl)methyl)-N-1,2,4-thiadiazol-5-ylpyridin-2-amine Mass: 459, 461 (M+1)$^+$

Example 39

Synthesis of 6-((4-(2-(trifluoromethyl)benzoyl)piperazin-1-yl)methyl)-N-1,2,4-thiadiazol-5-ylpyridin-2-amine Mass: 449 (M+1)$^+$

Example 40

Synthesis of 6-((4-(2-fluoro-3-(trifluoromethyl)benzoyl)piperazin-1-yl)methyl)-N-1,2,4-thiadiazol-5-ylpyridin-2-amine $^1$H-NMR (DMSO-d$_6$) δ: 12.18 (brs, 1H), 8.30 (s, 1H), 7.83-7.75 (m, 3H), 7.55-7.45 (m, 1H), 7.13 (d, J=7.3 Hz, 1H), 7.05 (d, J=8.3 Hz, 1H), 3.78-3.65 (m, 4H), 3.32-3.22 (m, 2H), 2.62-2.52 (m, 2H), 2.51-2.43 (m, 2H)
Mass: 467 (M+1)$^+$

Example 41

Synthesis of 6-((4-(2-fluoro-3-(difluoromethyl)benzoyl)piperazin-1-yl)methyl)-N-1,2,4-thiadiazol-5-ylpyridin-2-amine Trifluoroacetate $^1$H-NMR (CD$_3$OD) δ: 8.27 (s, 1H), 7.94 (dd, J=8.0, 7.2 Hz, 1H), 7.76 (brt, J=7.2 Hz, 1H), 7.64 (brt, J=6.8 Hz, 1H), 7.44 (t, J=7.6 Hz, 1H), 7.32 (d, J=7.2 Hz, 1H), 7.24 (d, J=8.0 Hz, 1H), 7.02 (t, J=54.8 Hz, 1H), 4.58 (s, 2H), 3.73-3.46 (m, 6H)
Mass: 449 (M+1)$^+$

Example 42

Synthesis of 6-((4-(3-chloro-2-fluorobenzoyl)piperazin-1-yl)methyl)-N-(5-methyl-thiazol-2-yl)pyridin-2-amine Trifluoroacetate $^1$H-NMR (CD$_3$OD) δ: 7.98 (dd, J=8.4, 7.2 Hz, 1H), 7.62 (dt, J=8.0, 1.2 Hz, 1H), 7.44-7.37 (m, 2H), 7.32-7.25 (m, 3H), 4.58 (s, 2H), 4.20-3.92 (m, 2H), 3.69 (brs, 2H), 3.57 (brs, 2H), 3.45 (brs, 2H), 2.45 (d, J=1.2 Hz, 3H)
Mass: 446 (M+1)$^+$

Example 43

Synthesis of 6-((4-(3-chloro-2-fluorobenzoyl)piperazin-1-yl)methyl)-N-(5-cyano-thiazol-2-yl)pyridin-2-yl)amine $^1$H-NMR (CDCl$_3$) δ: 11.06 (brs, 1H), 8.00 (s, 1H), 7.72 (dd, J=8.0, 7.2 Hz, 1H), 7.47-7.42 (m, 1H), 7.33-7.25 (m, 1H), 7.20-7.12 (m, 2H), 6.82 (d, J=8.0 Hz, 1H), 3.92-3.83 (m, 2H), 3.79 (s, 2H), 3.45-3.29 (m, 2H), 2.71-2.45 (m, 4H)
Mass: 457 (M+1)$^+$

Example 44

Synthesis of 6-((4-(2-fluoro-3-(trifluoromethyl)benzoyl)piperazin-1-yl)methyl)-N-1H-pyrazol-3-ylpyrazin-2-amine (1) Synthesis of 6-chloro-N-(1-((2-(trimethylsilyl)ethoxy)methyl)-1H-pyrazol-3-yl)pyrazin-2-amine

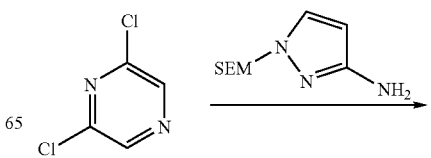

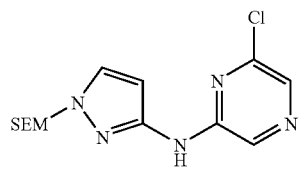

A mixture of 1.78 g of 2,6-dichloropyrazine, 2.84 g of 1-((2-(trimethylsilyl)ethoxy)methyl)-1H-pyrazol-3-amine obtained in Reference Example 2, 690 mg of 9,9-dimethyl-4,5-bis(diphenylphosphino)xanthene, 620 mg of tris(dibenzylideneacetone)dipalladium(0)-chloroform complex, 5.07 g of potassium phosphate, 25 ml of 1,4-dioxane was stirred at 100° C. for 2 hours, cooled to room temperature, and then diluted with ethyl acetate. An insoluble matter was filtered off using Celite and the resulting ethyl acetate solution was washed with water and brine. The organic layer was dried over anhydrous magnesium sulfate and filtered, and the filtrate was concentrated. The residue was purified by a silica gel column chromatography (eluent: hexane/ethyl acetate=10/1 to 1/1) to give the title compound.

(2) Synthesis of methyl 6-((1-((2-(trimethylsilyl)ethoxy)methyl)-1H-pyrazol-3-yl)amino)pyrazine-2-carboxylate

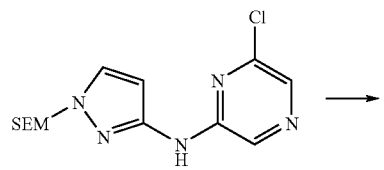

A mixture of 2.41 g of 6-chloro-N-(1-((2-(trimethylsilyl)ethoxy)methyl)-1H-pyrazol-3-yl)pyrazin-2-amine, 320 mg of palladium acetate, 790 mg of 1,1'-bisdiphenylphosphinoferrocene, 890 mg of sodium hydrogen carbonate, 10 ml of methanol and 10 ml of N,N-dimethylformamide was stirred at 100° C. for 15 hours under 3 atmospheric pressure of carbon monoxide, cooled to room temperature, and then diluted with ethyl acetate. An insoluble matter was filtered off using Celite and the resulting ethyl acetate solution was washed with water and brine. The organic layer was dried over anhydrous magnesium sulfate and filtered, and the filtrate was concentrated. The residue was purified by a silica gel column chromatography (eluent: hexane/ethyl acetate=10/1 to 1/1) to give the title compound.

(3) Synthesis of 6-((1-((2-(trimethylsilyl)ethoxy)methyl)-1H-pyrazol-3-yl)amino)pyrazine-2-carboxylic Acid

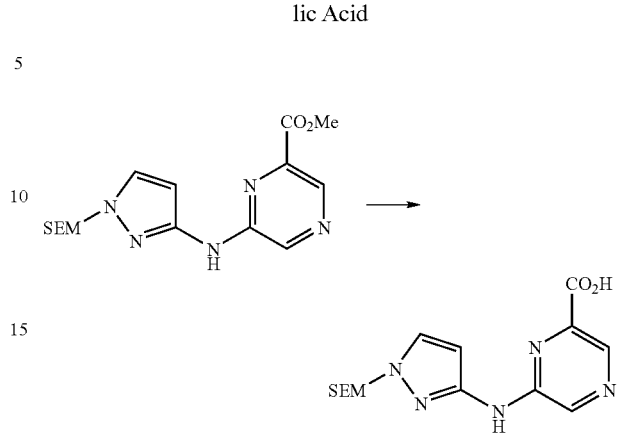

To a mixture of 52 mg of methyl 6-((1-((2-(trimethylsilyl)ethoxy)methyl)-1H-pyrazol-3-yl)amino)pyrazine-2-carboxylate, 0.5 ml of tetrahydrofuran and 1 ml of methanol was added an aqueous sodium hydroxide solution (1.0 M, 0.5 ml), followed by stirring at room temperature for 15 hours. The obtained reaction solution was diluted with ethyl acetate, and then washed with aqueous ammonium chloride and brine. The organic layer was dried over anhydrous magnesium sulfate and filtered, and filtrate was concentrated to give the title compound.

(4) Synthesis of (6-((1-((2-(trimethylsilyl)ethoxy)methyl)-1H-pyrazol-3-yl)amino)pyrazin-2-yl)methanol

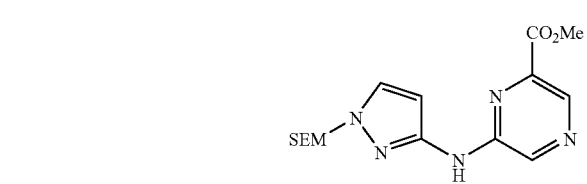

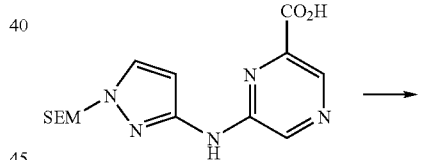

To a mixture of 28 mg of 6-((1-((2-(trimethylsilyl)ethoxy)methyl)-1H-pyrazol-3-yl)amino)pyrazine-2-carboxylic acid and 1 ml of N,N-dimethylformamide was added 84 mg of N,N'-carbonyldiimidazole, followed by stirring at room temperature for 15 hours. Then, 200 μl of an aqueous solution of 20 mg of sodium borohydride was added thereto and the resulting mixture was stirred. Water was added to the reaction mixture, and then the mixture was extracted with ethyl acetate. The resulting ethyl acetate solution was dried over anhydrous magnesium sulfate and filtered, and the filtrate was concentrated. The residue was purified by a silica gel column chromatography (eluent: chloroform to chloroform/methanol=10/1) to give the title compound.

(5) Synthesis of 6-((4-(2-fluoro-3-(trifluoromethyl)benzoyl)piperazin-1-yl)methyl)-N-(1-((2-(trimethylsilyl)ethoxy)methyl)-1H-pyrazol-3-yl)pyrazin-2-amine

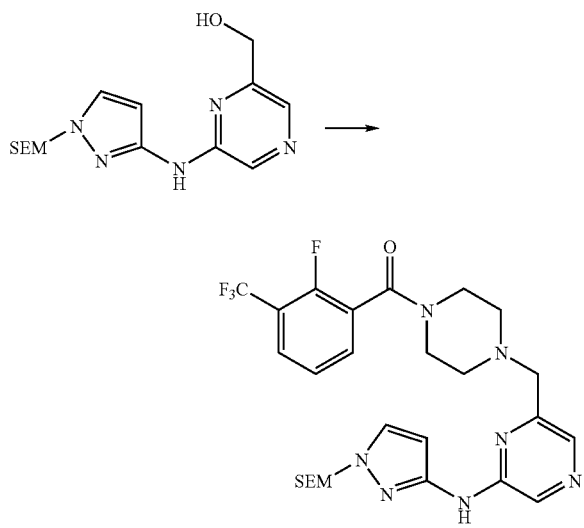

To a mixture of 2.14 g of (6-((1-((2-(trimethylsilyl)ethoxy)methyl)-1H-pyrazol-3-yl)amino)pyrazin-2-yl)methanol, 2.32 ml of N,N-diisopropylethylamine and 40 ml of chloroform was added 619 μl of methanesulfonyl chloride at room temperature followed by stirring for 1 hour. To the reaction mixture was added 2.32 ml of N,N-diisopropylethylamine, and then 3.13 g of 1-(2-fluoro-3-(trifluoromethyl)benzoyl)piperazine hydrochloride obtained in Reference Example 7 was added thereto followed by stirring at 50° C. for 2 hours. The resulting reaction mixture was washed with aqueous sodium bicarbonate and brine. The resulting organic layer was dried over anhydrous magnesium sulfate and filtered, and then the filtrate was concentrated in vacuo. The resulting residue was purified by a silica gel column chromatography (eluent: chloroform to chloroform/methanol=20/1) to obtain the title compound.

(6) Synthesis of 6-((4-(2-fluoro-3-(trifluoromethyl)benzoyl)piperazin-1-yl)methyl)-N-1H-pyrazol-3-ylpyrazin-2-amine

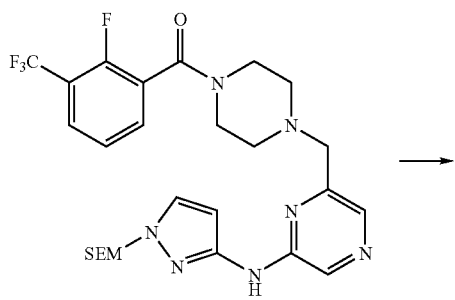

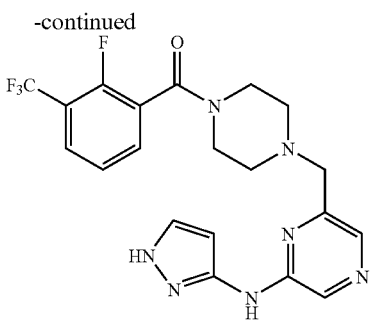

2.49 g of 6-((4-(2-fluoro-3-(trifluoromethyl)benzoyl)piperazin-1-yl)methyl)-N-(1-((2-(trimethylsilyl)ethoxy)methyl)-1H-pyrazol-3-yl)pyrazin-2-amine was dissolved in 25 ml of trifluoroacetic acid and 2.5 ml of water followed by stirring at room temperature for 2 hours. The reaction solution was concentrated in vacuo, diluted with ethyl acetate, and then washed with saturated sodium bicarbonate, water and brine. The resulting organic layer was dried over magnesium sulfate and filtered, and the filtrate was concentrated. The resulting residue was purified by a silica gel column chromatography (eluent: chloroform to chloroform/methanol=5/1) to give the title compound as a solid. The resulting solid was dissolved in ethanol by heating to 80° C. The solution was charged with heptane, and heating was stopped. Then the solution was cooled slowly to room temperature. After heptane was further added, the precipitate was filtered and dried to give a crystal of the title compound.

Spectral data of the title compound are as follows.

$^1$H-NMR (CDCl$_3$) δ: 8.51 (s, 1H), 8.09 (s, 1H), 7.70-7.56 (m, 2H), 7.52 (s, 1H), 7.37-7.20 (m, 2H), 6.26 (s, 1H), 3.89 (brs, 2H), 3.64 (s, 2H), 3.37 (brs, 2H), 2.66 (dd, J=5.1, 4.9 Hz, 2H), 2.54 (brs, 2H)

Mass: 450 (M+1)$^+$ m.p.: 160-163° C.

Examples 45 to 54, 56 to 60 and 113 to 115 were synthesized in the same manner as in Example 44 as follows.

Example 45

Synthesis of 6-((4-(2,3-dichlorobenzoyl)piperazin-1-yl)methyl)-N-1H-pyrazol-3-ylpyrazin-2-amine $^1$H-NMR (CDCl$_3$) δ: 8.45 (s, 1H), 8.06 (s, 1H), 7.77 (s, 1H), 7.51-7.47 (m, 2H), 7.28-7.17 (m, 2H), 6.26 (s, 1H), 3.96-3.78 (m, 4H), 3.63 (s, 2H), 2.72-2.43 (m, 4H)

Mass: 432 (M+1)+

Example 46

Synthesis of 6-(((1S,4S)-5-(3-chloro-2-fluorobenzoyl)-2,5-diazabicyclo[2.2.1]hept-2-yl)methyl)-N-1H-pyrazol-3-ylpyrazin-2-amine $^1$H-NMR (CDCl$_3$) δ: 8.44 (s, 1H), 8.11-8.03 (m, 1H), 7.87-7.65 (m, 1H), 7.57-7.42 (m, 2H), 7.40-7.30 (m, 1H), 7.22-7.13 (m, 1H), 6.34-6.22 (m, 1H), 4.97-2.70 (m, 8H), 2.10-1.80 (m, 2H)

Mass: 428 (M+1)$^+$

Example 47

Synthesis of 6-(((1S,4S)-5-(2-fluoro-3-(trifluoromethyl)benzoyl)-2,5-diazabicyclo [2.2.1]hept-2-yl)methyl)-N-1H-pyrazol-3-ylpyrazin-2-amine $^1$H-NMR (CDCl$_3$) δ: 8.46 (s, 1H), 8.08 and 8.05 (each s, total 1H), 8.02-7.80 (m, 1H), 7.72-7.61 (m, 2H), 7.51 and 7.48 (each d, J=2.3 Hz, total 1H), 7.33 (t, J=7.8 Hz, 1H), 6.30 and 6.26 (each s, total 1H), 4.95-2.72 (m, 8H), 2.07 and 2.02 (each d, J=10.0 Hz, total 1H), 1.85 (d, J=10.0 Hz, 1H)

Mass: 462 (M+1)$^+$

Example 48

Synthesis of 6-(((1R,4R)-5-(2-fluoro-3-(trifluoromethyl)benzoyl)-2,5-diazabicyclo [2.2.1]hept-2-yl)methyl)-N-1H-pyrazol-3-ylpyrazin-2-amine $^1$H-NMR (CDCl$_3$) δ: 8.46 (s, 1H), 8.08 and 8.05 (each s, total 1H), 8.02-7.80 (m, 1H), 7.72-7.61 (m, 2H), 7.51 and 7.48 (each d, J=2.3 Hz, total 1H), 7.33 (t, J=7.8 Hz, 1H), 6.30 and 6.26 (each s, total 1H), 4.95-2.72 (m, 8H), 2.07 and 2.02 (each d, J=10.0 Hz, total 1H), 1.85 (d, J=10.0 Hz, 1H)

Mass: 462 (M+1)$^+$

Example 49

Synthesis of 6-((4-(3-bromo-2-fluorobenzoyl)piperazin-1-yl)methyl)-N-1H-pyrazol-3-ylpyrazin-2-amine Trifluoroacetate $^1$H-NMR (DMSO-d$_6$) δ: 10.05 (s, 1H), 8.45 (s, 1H), 8.01 (s, 1H), 7.85-7.80 (m, 1H), 7.64 (s, 1H), 7.47 (dd, J=6.3, 6.0 Hz, 1H), 7.27 (dd, J=8.0, 7.6 Hz, 1H), 6.52 (s, 1H), 4.40 (s, 2H), 3.58-3.24 (m, 4H), 2.55-2.48 (m, 4H)

Mass: 460, 462 (M+1)$^+$

Example 50

Synthesis of 6-((4-(3-chloro-2-fluorobenzoyl)piperazin-1-yl)methyl)-N-1H-pyrazol-3-ylpyrazin-2-amine $^1$H-NMR (CDCl$_3$) δ: 8.51 (s, 1H), 8.09 (s, 1H), 7.52 (s, 1H), 7.45 (dd, J=7.0, 6.3 Hz, 1H), 7.37-7.24 (m, 2H), 7.15 (t, J=7.8 Hz, 1H), 6.26 (s, 1H), 3.86 (brs, 2H), 3.64 (s, 2H), 3.38 (brs, 2H), 2.65 (dd, J=5.3, 4.7 Hz, 2H), 2.53 (brs, 2H)

Mass: 415 (M+1)$^+$

Example 51

Synthesis of 6-((4-(2-chloro-3-(trifluoromethyl)benzoyl)piperazin-1-yl)methyl)-N-1H-pyrazol-3-ylpyrazin-2-amine Trifluoroacetate $^1$H-NMR (DMSO-d$_6$) δ: 10.05 (s, 1H), 8.45 (s, 1H), 8.01 (s, 1H), 7.98-7.93 (m, 1H), 7.80-7.74 (m, 1H), 7.70-7.62 (m, 2H), 6.52 (s, 1H), 4.41 (s, 2H), 3.60-3.20 (m, 4H), 2.55-2.40 (m, 4H)

Mass: 466 (M+1)$^+$

Example 52

Synthesis of 6-(((3R)-4-(2-fluoro-3-(trifluoromethyl)benzoyl)-3-methylpiperazin-1-yl)methyl)-N-1H-pyrazol-3-ylpyrazin-2-amine $^1$H-NMR (CDCl$_3$) δ: 8.42 (s, 1H), 8.12 (s, 1H), 7.79 (s, 1H), 7.66 (t, J=7.0 Hz, 1H), 7.63-7.51 (m, 1H), 7.50 (d, J=2.4 Hz, 1H), 7.31 (t, J=7.8 Hz, 1H), 6.31 (s, 1H), 5.00-2.20 (m, 9H), 1.50-1.25 (m, 3H)

Mass: 464 (M+1)$^+$

Example 53

Synthesis of 6-((4-(3-cyclopropyl-2-fluorobenzoyl)piperazin-1-yl)methyl)-N-1H-pyrazol-3-ylpyrazin-2-amine $^1$H-NMR (CDCl$_3$) δ: 8.50 (s, 1H), 8.10 (s, 1H), 7.51 (d, J=2.0 Hz), 7.30-7.05 (m, 4H), 6.94-6.90 (m, 1H), 6.24 (s, 1H), 4.00-3.80 (m, 2H), 3.64 (s, 2H), 3.50-3.30 (m, 2H), 2.65 (t, J=5.1 Hz, 2H), 2.60-2.40 (m, 2H), 2.11-2.07 (m, 1H), 1.00 (dd, J=8.5, 1.7 Hz, 2H), 0.72 (d, J=5.9 Hz, 2H)

Mass: 422 (M+1)$^+$

Example 54

Synthesis of 6-((4-(2-fluoro-3-(trifluoromethyl)benzoyl)-1,4-diazepan-1-yl)methyl)-N-1H-pyrazol-3-ylpyrazin-2-amine $^1$H-NMR (CDCl$_3$) δ: 8.47-8.42 (m, 1H), 8.12-8.02 (m, 1H), 7.92-7.79 (m, 1H), 7.68-7.50 (m, 3H), 7.35-7.25 (m, 1H), 6.27 (s, 1H), 3.93-3.71 (m, 4H), 3.48-3.36 (m, 2H), 2.93 (t, J=4.8 Hz, 1H), 2.83 (dd, J=5.6, 5.2 Hz, 1H), 2.78-2.68 (m, 2H), 2.07-1.98 (m, 1H), 1.91-1.80 (m, 1H)

Mass: 464 (M+1)$^+$

Example 55

Synthesis of 6-((4-(2-fluoro-3-(trifluoromethyl)benzoyl)-6-hydroxy-1,4-diazepan-1-yl)methyl)-N-1H-pyrazol-3-ylpyrazin-2-amine (1) Synthesis of 6-((6-(tetrahydro-2H-pyran-2-yloxy)-1,4-diazepan-1-yl)methyl)-N-(1-((2-(trimethylsilyl)ethoxy)methyl)-1H-pyrazol-3-yl)pyrazin-2-amine

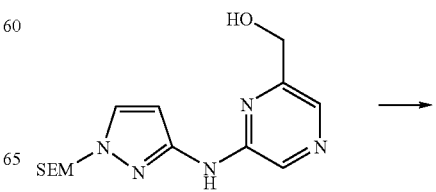

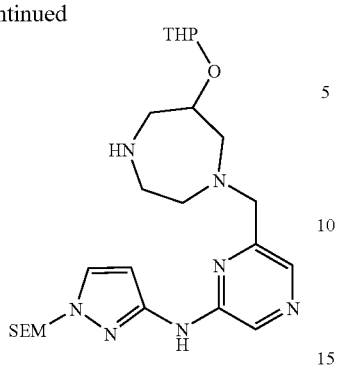

To a mixture of 44.9 mg of (6-((1-((2-(trimethylsilyl)ethoxy)methyl)-1H-pyrazol-3-yl)amino)pyrazin-2-yl)methanol, 73 μl of N,N-diisopropylethylamine and 4 ml of chloroform was added 16 μl of methanesulfonyl chloride at room temperature followed by stirring for 1 hour. The reaction mixture was dropped into a solution of 6-(tetrahydro-2H-pyran-2-yloxy)-1,4-diazepane obtained in Reference Example 5 in 2 ml of chloroform, and the reaction mixture was stirred at room temperature for 15 hours. The resulting reaction mixture was washed with water and brine. The resulting organic layer was dried over anhydrous magnesium sulfate and filtered, and the filtrate was concentrated in vacuo. The resulting residue was purified by a basic thin-layer chromatography (eluent: chloroform/methanol=30/1) to give the title compound.

(2) Synthesis of 6-((4-(2-fluoro-3-(trifluoromethyl)benzoyl)-6-hydroxy-1,4-diazepan-1-yl)methyl)-N-1H-pyrazol-3-ylpyrazin-2-amine

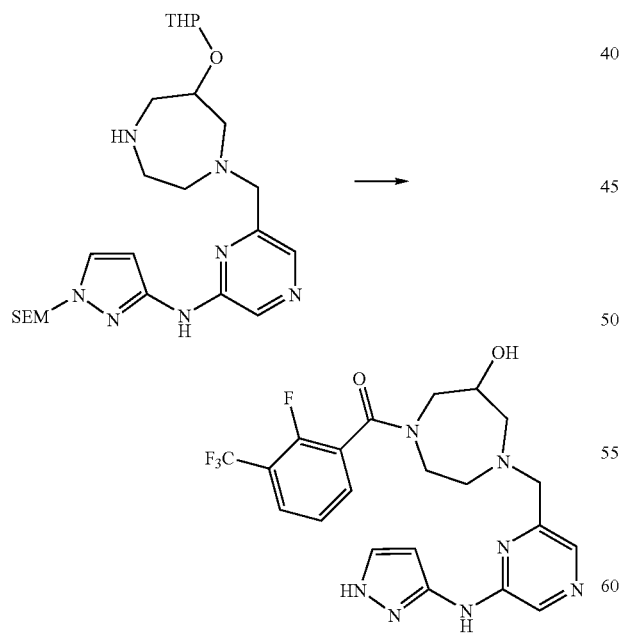

The amidation reaction was performed in the same manner as in Example 3-(2) using 6-((6-(tetrahydro-2H-pyran-2-yloxy)-1,4-diazepan-1-yl)methyl)-N-(1-((2-(trimethylsilyl)ethoxy)methyl)-1H-pyrazol-3-yl)pyrazin-2-amine and 2-fluoro-3-(trifluoromethyl)benzoic acid. Next, the deprotection reaction was performed in the same manner as in Example 16-(4) using trifluoroacetic acid to give the title compound.

Spectral data of the title compound are as follows.
$^1$H-NMR (CDCl$_3$) δ: 8.48-8.39 (m, 1H), 7.93 (s, 1H), 7.70-7.43 (m, 3H), 7.22-7.10 (m, 1H), 6.37-6.27 (m, 1H), 4.17-2.67 (m, 11H)
Mass: 480 (M+1)$^+$ Example 56

Synthesis of 6-((4-(3-chloro-2-fluorobenzoyl)piperazin-1-yl)methyl)-N-(5-methyl-1H-pyrazol-3-yl)pyrazin-2-amine $^1$H-NMR (CDCl$_3$) δ: 8.48 (s, 1H), 8.06 (s, 1H), 7.48-7.33 (m, 2H), 7.33-7.25 (m, 1H), 7.15 (dd, J=8.0, 7.6 Hz, 1H), 6.02 (s, 1H), 3.87 (brs, 2H), 3.62 (s, 2H), 3.37 (brs, 2H), 2.64 (t, J=5.1 Hz, 2H), 2.52 (brs, 2H), 2.31 (s, 3H)
Mass: 430 (M+1)$^+$ Example 57

Synthesis of 6-((4-(2-fluoro-(3-trifluoromethyl))benzoyl)piperazin-1-yl)methyl)-N-1,2,4-thiadiazol-5-ylpyrazin-2-amine $^1$H-NMR (CDCl$_3$) δ: 12.16 (brs, 1H), 8.49 (s, 1H), 8.44-8.39 (m, 2H), 7.72-7.59 (m, 2H), 7.33 (dd, J=8.0, 7.6 Hz, 1H), 3.96-3.80 (m, 4H), 3.40 (brs, 2H), 2.78-2.51 (m, 4H)
Mass: 468 (M+1)$^+$ Example 58

Synthesis of 6-((4-(3-chloro-2-fluorobenzoyl)piperazin-1-yl)methyl)-N-thiazol-2-ylpyrazin-2-amine $^1$H-NMR (CDCl$_3$) δ: 8.33 (s, 1H), 8.24 (s, 1H), 7.56 (d, J=3.5 Hz, 1H), 7.49-7.42 (m, 1H), 7.30-7.23 (m, 2H), 7.14 (t, J=8.1 Hz, 1H), 6.95 (d, J=3.7 Hz, 1H), 3.87 (brs, 2H), 3.79 (s, 2H), 3.34 (brs, 2H), 2.72 (t, J=5.2 Hz, 2H), 2.59 (brs, 2H)
Mass: 433 (M+1)$^+$ Example 59

Synthesis of 2-((4-(3-chloro-2-fluorobenzoyl)piperazin-1-yl)methyl)-N-1H-pyrazol-3-ylpyrimidin-4-amine $^1$H-NMR (CDCl$_3$) δ: 8.35 (d, J=5.9 Hz, 1H), 7.53 (d, J=2.4 Hz, 2H), 7.46-7.42 (m, 1H), 7.28-7.26 (m, 1H), 7.15 (t, J=7.8 Hz, 1H), 7.10-7.00 (m, 1H), 6.23 (s, 1H), 4.00-3.80 (m, 2H), 3.73 (s, 2H), 3.60-3.30 (m, 2H), 2.71 (t, J=5.1 Hz, 2H), 2.71-2.51 (m, 2H)
Mass: 416 (M+1)$^+$ Example 60

Synthesis of 2-((4-(2-fluoro-3-(trifluoromethyl)benzoyl)piperazin-1-yl)methyl)-N-1H-pyrazol-3-ylpyrimidin-4-amine $^1$H-NMR (CDCl$_3$) δ: 8.35 (d, J=5.9 Hz, 1H), 7.66 (t, J=7.1 Hz, 1H), 7.64-7.50 (m, 3H), 7.53 (d, J=2.0 Hz, 1H), 7.32 (t, J=7.8 Hz, 1H), 7.05 (s, 1H), 6.24 (s, 1H), 4.00-3.80 (m, 2H), 3.73 (s, 2H), 3.50-3.35 (m, 2H), 2.72 (t, J=5.1 Hz, 2H), 2.70-2.55 (m, 2H)

Mass: 450 (M+1)+

Example 61

Synthesis of 6-((4-(3-furoyl)piperazin-1-yl)methyl)-N-(5-chlorothiazol-2-yl)pyridin-2-amine (1) Synthesis of 6-(((tert-butyl(dimethyl)silyl)oxy)methyl)-N-(5-chlorothiazol-2-yl)pyridin-2-amine

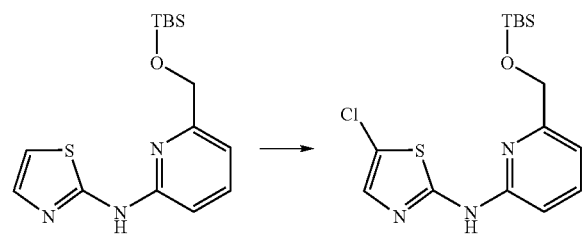

2 g of 6-(((tert-butyl(dimethyl)silyl)oxy)methyl)-N-thiazol-2-ylpyridin-2-amine obtained in Example 5-(2) was dissolved in 20 ml of 1,4-dioxane, and then 832 mg of N-chlorosuccinimide was added thereto at room temperature. The reaction mixture was heated under reflux for 2 hours, cooled to room temperature, diluted with ethyl acetate, and then washed with water and brine. The resulting organic layer was dried over anhydrous magnesium sulfate and filtered, and the filtrate was concentrated in vacuo to give the title compound.

(2) Synthesis of 6-(chloromethyl)-N-(5-chlorothiazol-2-yl)pyridin-2-amine

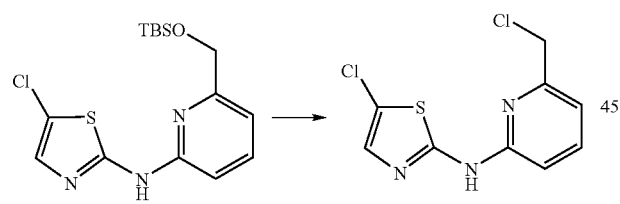

In the same manner as in Example 5-(3) and (4), the title compound was obtained using 6-(((tert-butyl(dimethyl)silyl)oxy)methyl)-N-(5-chlorothiazol-2-yl)pyridin-2-amine.

(3) Synthesis of 6-((4-(3-furoyl)piperazin-1-yl)methyl)-N-(5-chlorothiazol-2-yl)pyridin-2-amine

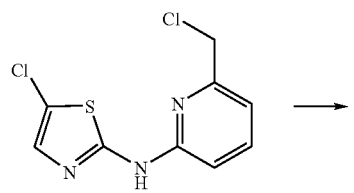

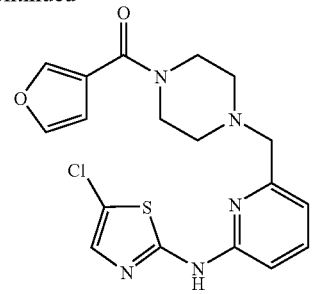

In the same manner as in Example 5-(5), the title compound was obtained using 6-(chloromethyl)-N-(5-chlorothiazol-2-yl)pyridin-2-amine and 1-(3-furoyl)piperazine synthesized in reference with the disclosed method in the process (7) to (8), similar to Reference Example 1.

Spectral data of the title compound are as follows.

1H-NMR (DMSO-d6) δ: 11.47 (s, 1H), 8.01 (s, 1H), 7.72-7.68 (m, 2H), 7.37 (s, 1H), 7.02 (d, J=7.4 Hz, 1H), 6.89 (d, J=8.2 Hz, 1H), 6.64-6.63 (m, 1H), 3.66 (s, 2H), 3.60-3.58 (m, 4H), 2.50-2.48 (m, 4H)

Mass: 404 (M+1)+

Examples 62 and 64 to 77 were synthesized in the same manner as in Example 61 as follows.

Example 62

Synthesis of 6-((4-(2-furoyl)piperazin-1-yl)methyl-N-(5-chlorothiazol-2-yl)pyridin-2-amine 1H-NMR (DMSO-d6) δ: 11.48 (s, 1H), 7.82-7.80 (m, 1H), 7.71 (t, J=7.8 Hz, 1H), 7.37 (s, 1H), 7.03 (d, J=7.0 Hz, 1H), 6.97 (dd, J=3.5, 0.8 Hz, 1H), 6.90 (d, J=8.2 Hz, 1H), 6.61-6.59 (m, 1H), 3.73-3.64 (m, 6H), 2.53-2.47 (m, 4H)

Mass: 404 (M+1)+

Example 63

Synthesis of 6-((4-(3-chloro-2-fluorobenzoyl)-1,4-diazepan-1-yl)methyl)-N-thiazol-2-ylpyridin-2-amine 1H-NMR (CDCl3) δ: 7.64-7.55 (m, 1H), 7.55-7.37 (m, 2H), 7.33-7.22 (m, 1H), 7.18-6.98 (m, 2H), 6.86-6.81 (m, 1H), 6.78 (dd, J=9.2, 8.6 Hz, 1H), 3.92-3.78 (m, 4H), 3.49-3.36 (m, 2H), 2.96 (dd, J=5.7, 4.1 Hz, 1H), 2.85 (t, J=5.5 Hz, 1H), 2.81-2.70 (m, 2H), 2.07-1.78 (m, 2H)

Mass: 446 (M+1)+

Example 64

Synthesis of 6-((4-(pyrazin-2-ylcarbonyl)piperazin-1-yl)methyl)-N-(5-chlorothiazol-2-yl)pyridin-2-amine 1H-NMR (DMSO-d6) δ: 11.48 (s, 1H), 8.83 (d, J=1.2 Hz, 1H), 8.73 (d, J=2.3 Hz, 1H), 8.65 (dd, J=2.7, 1.6 Hz, 1H), 7.69 (t, J=7.4 Hz, 1H), 7.38 (s, 1H), 7.02 (d, J=7.4 Hz, 1H), 6.90 (d, J=7.4 Hz, 1H), 3.74-3.64 (m, 4H), 3.48-3.40 (m, 2H), 2.62-2.53 (m, 2H), 2.51-2.44 (m, 2H)

Mass: 416 (M+1)+

Example 65

Synthesis of 6-((4-(3-thienylcarbonyl)piperazin-1-yl) methyl)-N-(5-chlorothiazol-2-yl)pyridin-2-amine ¹H-NMR (DMSO-d₆) δ: 11.48 (s, 1H), 7.76 (d, J=1.6 Hz, 1H), 7.70 (t, J=7.6 Hz, 1H), 7.59 (dd, J=4.7, 2.7 Hz, 1H), 7.37 (s, 1H), 7.18 (dd, J=5.1, 1.2 Hz, 1H), 7.02 (d, J=7.4 Hz, 1H), 6.90 (d, J=8.2 Hz, 1H), 3.74 (s, 2H), 3.65-3.45 (m, 2H), 3.39-3.37 (m, 2H), 2.54-2.41 (m, 4H)

Mass: 420 (M+1)⁺

Example 66

Synthesis of 6-((4-(2-thienylcarbonyl)piperazin-1-yl) methyl)-N-(5-chlorothiazol-2-yl)pyridin-2-amine ¹H-NMR (DMSO-d₆) δ: 11.48 (s, 1H), 7.76-7.67 (m, 2H), 7.15-7.05 (m, 2H), 7.10 (dd, J=5.1, 3.9 Hz, 1H), 7.03 (d, J=6.6 Hz, 1H), 6.90 (d, J=8.6 Hz, 1H), 3.76-3.60 (m, 4H), 3.39-3.24 (m, 2H), 2.58-2.42 (m, 4H)

Mass: 420 (M+1)⁺

Example 67

Synthesis of 6-((4-(thiazol-2-ylcarbonyl)piperazin-1-yl)methyl)-N-(5-chlorothiazol-2-yl)pyridin-2-amine ¹H-NMR (DMSO-d₆) δ: 11.48 (s, 1H), 8.03-7.97 (m, 2H), 7.71 (t, J=7.8 Hz, 1H), 7.37 (s, 1H), 7.04 (d, J=7.0 Hz, 1H), 6.90 (d, J=8.2 Hz, 1H), 4.31 (brs, 2H), 3.68 (brs, 4H), 2.64-2.51 (m, 4H)

Mass: 421 (M+1)⁺

Example 68

Synthesis of 6-((4-((2-methyl-thiazol-4-yl)carbonyl) piperazin-1-yl)methyl)-N-(5-chlorothiazol-2-yl)pyridin-2-amine ¹H-NMR (DMSO-d₆) δ: 11.48 (s, 1H), 7.90 (brs, 1H), 7.75-7.66 (m, 1H), 7.38 (s, 1H), 7.02 (d, J=6.2 Hz, 1H), 6.89 (d, J=8.6 Hz, 1H), 3.66 (brs, 4H), 3.36-3.25 (m, 2H), 2.66 (s, 3H), 2.51-2.45 (m, 4H)

Mass: 435 (M+1)⁺

Example 69

Synthesis of 6-((4-((1-methyl-1H-pyrazol-3-yl)carbonyl)piperazin-1-yl)methyl)-N-(5-chlorothiazol-2-yl)pyridin-2-amine ¹H-NMR (DMSO-d₆) δ: 11.50 (brs, 1H), 7.75-7.69 (m, 2H), 7.38 (s, 1H), 7.04 (brs, 1H), 6.91 (brs, 1H), 6.52 (s, 1H), 4.07-3.80 (m, 2H), 3.86 (s, 3H), 3.79-3.56 (m, 2H), 3.38-3.21 (m, 2H), 2.51-2.38 (m, 4H)

Mass: 418 (M+1)⁺

Example 70

Synthesis of 6-((4-(2-cyanobenzoyl)piperazin-1-yl) methyl)-N-(5-chlorothiazol-2-yl)pyridin-2-amine ¹H-NMR (DMSO-d₆) δ: 11.47 (s, 1H), 7.93 (dd, J=7.8, 0.8 Hz, 1H), 7.77 (dt, J=1.2, 7.6 Hz, 1H), 7.70 (dd, J=8.2, 7.4 Hz, 1H), 7.62 (dt, J=1.2, 7.6 Hz, 1H), 7.56 (dd, J=7.8, 0.8 Hz, 1H), 7.37 (s, 1H), 7.02 (d, J=7.0 Hz, 1H), 6.89 (d, J=8.2 Hz, 1H), 3.74-3.64 (m, 4H), 3.26-3.20 (m, 2H), 2.60-2.53 (m, 2H), 2.51-2.43 (m, 2H)

Mass: 439 (M+1)⁺

Example 71

Synthesis of 6-((4-(3-cyanobenzoyl)piperazin-1-yl) methyl)-N-(5-chlorothiazol-2-yl)pyridin-2-amine ¹H-NMR (DMSO-d₆) δ: 11.47 (s, 1H), 7.93-7.86 (m, 2H), 7.74-7.61 (m, 3H), 7.37 (s, 1H), 7.01 (d, J=7.4 Hz, 1H), 6.89 (d, J=8.2 Hz, 1H), 3.66 (s, 4H), 3.41-3.25 (m, 2H), 2.60-2.38 (m, 4H)

Mass: 439 (M+1)⁺

Example 72

Synthesis of 6-((4-(3-(acetylamino)benzoyl)piperazin-1-yl)methyl)-N-(5-chlorothiazol-2-yl)pyridin-2-amine ¹H-NMR (DMSO-d₆) δ: 11.47 (s, 1H), 10.05 (s, 1H), 7.70 (dd, J=8.2, 7.4 Hz, 1H), 7.65 (t, J=1.6 Hz, 1H), 7.59-7.54 (m, 1H), 7.37 (s, 1H), 7.33 (t, J=8.0 Hz, 1H), 7.01 (d, J=7.4 Hz, 2H), 6.88 (d, J=8.2 Hz, 1H), 3.77-3.56 (m, 4H), 3.48-3.22 (m, 2H), 2.59-2.37 (m, 4H), 2.03 (s, 3H)

Mass: 471 (M+1)⁺

Example 73

Synthesis of 6-((4-(3-(dimethylamino)benzoyl)piperazin-1-yl)methyl)-N-(5-chlorothiazol-2-yl)pyridin-2-amine ¹H-NMR (DMSO-d₆) δ: 11.47 (s, 1H), 7.69 (t, J=7.8 Hz, 1H), 7.37 (s, 1H), 7.20 (t, J=8.0 Hz, 1H), 7.01 (d, J=7.4 Hz, 1H), 6.88 (t, J=8.4 Hz, 1H), 6.75 (dd, J=8.6, 2.7 Hz, 1H), 6.63-6.56 (m, 2H), 3.73-3.53 (m, 4H), 3.48-3.20 (m, 2H), 2.87 (s, 6H), 2.53-2.46 (m, 4H)

Mass: 422 (M+1)⁺

Example 74

Synthesis of 6-((4-(3-(methanesulfonyl)benzoyl) piperazin-1-yl)methyl)-N-(5-chlorothiazol-2-yl)pyridin-2-amine ¹H-NMR (DMSO-d₆) δ: 11.47 (s, 1H), 7.99 (dt, J=7.4, 1.8 Hz, 1H), 7.91 (t, J=1.4 Hz, 1H), 7.76-7.68 (m, 3H), 7.37 (s, 1H), 7.02 (d, J=7.4 Hz, 1H), 6.89 (d, J=8.2 Hz, 1H), 3.67 (s, 4H), 3.48-3.29 (m, 2H), 3.26 (s, 3H), 2.62-2.40 (m, 4H)

Mass: 492 (M+1)⁺

Example 75

Synthesis of 6-((4-(3-chloro-2-fluorobenzoyl)piperazin-1-yl)methyl)-N-(5-chlorothiazol-2-yl)pyridin-2-amine ¹H-NMR (DMSO-d₆) δ: 11.46 (s, 1H), 7.73-7.62 (m, 2H), 7.41-7.33 (m, 2H), 7.29 (t, J=8.0 Hz, 1H), 7.01 (d, J=7.4 Hz, 1H), 6.89 (d, J=8.2 Hz, 1H), 3.73-3.62 (m, 4H), 3.36-3.20 (m, 2H), 2.59-2.39 (m, 4H)

Mass: 466 (M+1)⁺

Example 76

Synthesis of 6-((4-(2,3-dichlorobenzoyl)piperazin-1-yl)methyl)-N-(5-chlorothiazol-2-yl)pyridin-2-amine $^1$H-NMR (DMSO-d$_6$) δ: 11.46 (s, 1H), 7.72-7.64 (m, 2H), 7.43 (t, J=7.8 Hz, 1H), 7.37-7.34 (m, 2H), 7.01 (d, J=7.4 Hz, 1H), 6.89 (d, J=8.2 Hz, 1H), 3.76-3.59 (m, 4H), 3.21-3.11 (m, 2H), 2.61-2.37 (m, 4H)

Mass: 482 (M+1)$^+$

Example 77

Synthesis of 6-((4-((4-chlorophenyl)acetyl)piperazin-1-yl)methyl)-N-(5-chlorothiazol-2-yl)pyridin-2-amine Trifluoroacetate $^1$H-NMR (CD$_3$OD) δ: 7.81 (dd, J=8.4, 7.6 Hz, 1H), 7.29 (d, J=8.4 Hz, 2H), 7.28 (s, 1H), 7.21 (d, J=8.4 Hz, 2H), 7.17 (d, J=7.6 Hz, 1H), 7.10 (d, J=8.4 Hz, 1H), 4.46 (s, 2H), 4.10-3.70 (m, 4H), 3.80 (s, 2H), 3.52-3.34 (m, 4H)

Mass: 462 (M+1)$^+$

Example 78

Synthesis of 6-((4-((2-fluoropyridin-3-yl)carbonyl)piperazin-1-yl)methyl)-N-(5-bromothiazol-2-yl)pyridin-2-amine (1) Synthesis of 6-(((tert-butyl(dimethyl)silyl)oxy)methyl)-N-(5-bromothiazol-2-yl)pyridin-2-amine

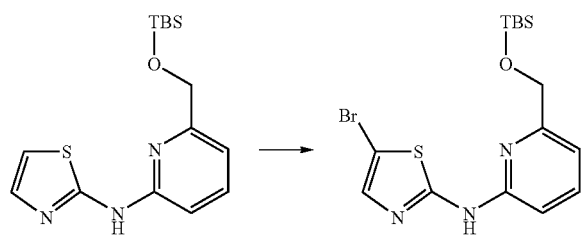

In the same manner as in Example 61-(1), the title compound was obtained using 6-(((tert-butyl(dimethyl)silyl)oxy)methyl)-N-thiazol-2-ylpyridin-2-amine obtained in Example 5-(2) and N-bromosuccinimide.

(2) Synthesis of 6-(chloromethyl)-N-(5-bromothiazol-2-yl)pyridin-2-amine

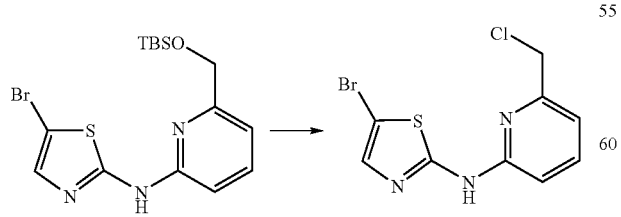

In the same manner as in Examples 5-(3) and (4), the title compound was synthesized using 6-(((tert-butyl(dimethyl)silyl)oxy)methyl)-N-(5-bromothiazol-2-yl)pyridin-2-amine.

(3) Synthesis of 6-((4-((2-fluoropyridin-3-yl)carbonyl)piperazin-1-yl)methyl)-N-(5-bromothiazol-2-yl)pyridin-2-amine

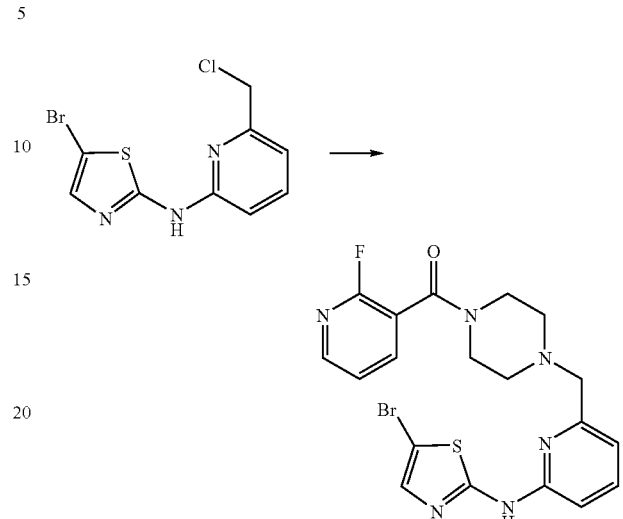

In the same manner as in Example 5-(5), the title compound was obtained using 6-(((tert-butyl(dimethyl)silyl)oxy)methyl)-N-(5-bromothiazol-2-yl)pyridin-2-amine and 1-((2-fluoropyridin-3-yl)carbonyl)piperazine synthesized with reference to the disclosed method in the processes (7) to (8), similar to Reference Example 1.

Spectral data of the title compound are as follows.

$^1$H-NMR (CDCl$_3$) δ: 8.29 (d, J=3.5 Hz, 1H), 7.89 (t, J=7.6 Hz, 1H), 7.63 (t, J=7.6 Hz, 1H), 7.35 (s, 1H), 7.33-7.20 (m, 1H), 7.05 (d, J=7.4 Hz, 1H), 6.72 (d, J=8.2 Hz, 1H), 3.87 (s, 2H), 3.77 (s, 2H), 3.39 (s, 2H), 2.69 (s, 2H), 2.58 (s, 2H)

Mass: 477, 479 (M+1)$^+$

Examples 79 and 80 were synthesized in the same manner as in Example 78 as follows.

Example 79

Synthesis of 6-((4-(2-fluoroisonicotinoyl)piperazin-1-yl)methyl)-N-(5-bromothiazol-2-yl)pyridin-2-amine $^1$H-NMR (CDCl$_3$) δ: 8.30 (d, J=4.9 Hz, 1H), 7.64 (dd, J=7.6, 7.2 Hz, 1H), 7.37 (s, 1H), 7.19 (d, J=4.9 Hz, 1H), 7.03 (d, J=7.2 Hz, 1H), 6.95 (s, 1H), 6.74 (d, J=8.0 Hz, 1H), 3.85 (s, 2H), 3.77 (s, 2H), 3.41 (s, 2H), 2.70 (s, 2H), 2.55 (s, 2H)

Mass: 477, 479 (M+1)$^+$

Example 80

Synthesis of 6-((4-((6-fluoropyridin-2-yl)carbonyl)piperazin-1-yl)methyl)-N-(5-bromothiazol-2-yl)pyridin-2-amine $^1$H-NMR (CDCl$_3$) δ: 7.95-7.88 (m, 1H), 7.63 (dd, J=8.2, 7.6 Hz, 1H), 7.57 (d, J=7.4 Hz, 1H), 7.35 (s, 1H), 7.06 (d, J=8.0 Hz, 1H), 7.00 (d, J=7.2 Hz, 1H), 6.72 (d, J=7.6 Hz, 1H), 3.89-3.81 (m, 2H), 3.77 (s, 2H), 3.70-3.63 (m, 2H), 2.74-2.67 (m, 2H), 2.67-2.55 (m, 2H)

Mass: 477, 479 (M+1)$^+$

Example 81

Synthesis of 4-bromo-6-((4-(3-chloro-2-fluorobenzoyl)piperazin-1-yl)methyl)-N-thiazol-2-ylpyridin-2-amine

(1) Synthesis of dimethyl 4-bromopyridine-2,6-dicarboxylate

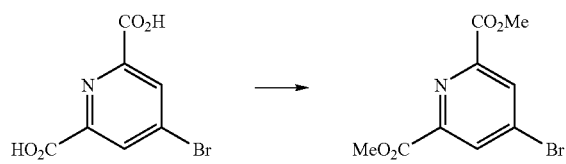

A mixture of 7.38 g of 4-bromopyridine-2,6-dicarboxylic acid synthesized in the method of Tetrahedron lett., 42 (29), 4849 (2001), 10 ml of a hydrochloric acid-methanol reagent and 100 ml of methanol was stirred at room temperature for 15 hours, and the reaction mixture was concentrated in vacuo. Ethyl acetate was added to the residue and the mixture was washed three times with a mixed solution of brine-saturated sodium bicarbonate (1:1). The organic layer was dried over anhydrous magnesium sulfate and filtered. The filtrate was then concentrated in vacuo to give the title compound.

(2) Synthesis of methyl hydrogen 4-bromopyridine-2,6-dicarboxylate

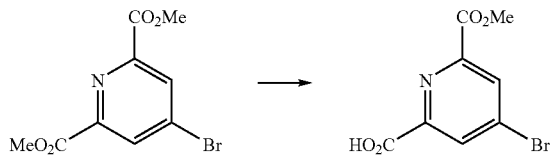

A mixture of 6.09 g of dimethyl 4-bromopyridine-2,6-dicarboxylate, 1.08 g of potassium hydroxide, 200 ml of methanol and 20 ml of dichloromethane was stirred at room temperature for 3 hours, and 200 ml of ether was added thereto. The resulting white solid was filtered, and then washed with ether. The obtained white solid was dissolved in water, and then 12 ml of hydrochloric acid (2 M) was added thereto. The resulting mixture was extracted with chloroform. The organic layer was dried over anhydrous magnesium sulfate and filtered, and the filtrate was concentrated in vacuo to give the title compound.

(3) Synthesis of methyl 4-bromo-6-tert-butoxycarbonylaminopyridine-2-carboxylate

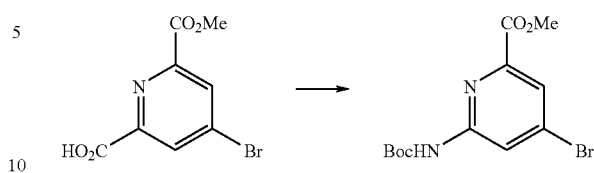

To a mixture of 4.62 g of methyl hydrogen 4-bromopyridine-2,6-dicarboxylate, 2.97 ml of triethylamine, 25 ml of t-butanol and 70 ml of 1,4-dioxane was added 4.59 ml of diphenylphosphoryl azide at room temperature. The reaction mixture was heated under reflux for 3 hours and cooled to room temperature. Water was added thereto and the resulting mixture was extracted with ethyl acetate. The obtained ethyl acetate solution was washed with water and brine, dried over anhydrous sodium sulfate and filtered. The filtrate was concentrated in vacuo to give the title compound.

(4) Synthesis of methyl 6-amino-4-bromopyridine-2-carboxylate

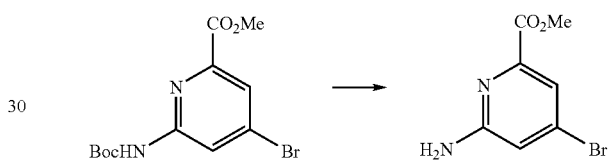

7.23 g of methyl 4-bromo-6-t-butoxycarbonylamino-pyridine-2-carboxylate was dissolved in 30 ml of chloroform, and then 15 ml of trifluoroacetic acid was added thereto, followed by stirring at room temperature for 1 hour. After concentrating the reaction mixture, the residue was dissolved in ethyl acetate and washed with saturated sodium bicarbonate and brine. The organic layer was dried over anhydrous magnesium sulfate, filtered, and then concentrated in vacuo. The residue was purified by a silica gel column chromatography (eluent: chloroform to chloroform/methanol=20/1) to give the title compound.

(5) Synthesis of methyl 6-(3-benzoylthioureido)-4-bromopyridine-2-carboxylate

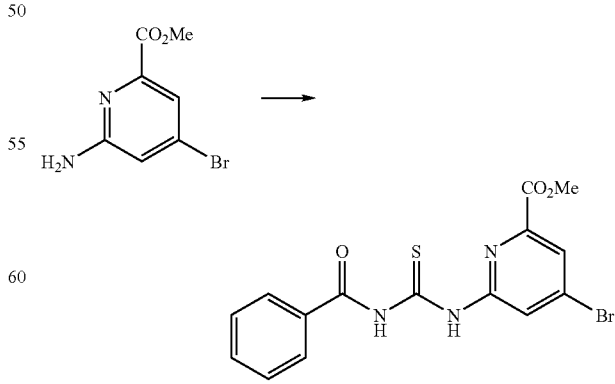

2.74 g of methyl 6-amino-4-bromopyridine-2-carboxylate was dissolved in 15 ml of tetrahydrofuran and 1.63 ml of benzoyl isothiocyanate was added thereto, followed by stirring at room temperature for 13 hours. To the reaction mixture was added 40 ml of hexane. The resulting solid was filtered and washed with hexane. The obtained solid was dried in vacuo to give the title compound.

(6) Synthesis of methyl 4-bromo-6-(thiazol-2-ylamino)pyridine-2-carboxylate

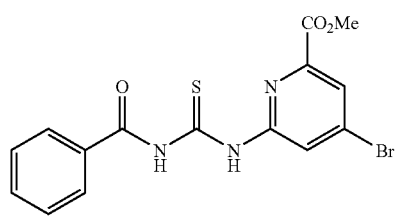

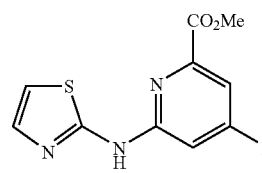

To a mixture of 2.37 g of methyl 6-(3-benzoylthioureido)-4-bromopyridine-2-carboxylate, 20 ml of tetrahydrofuran and 40 ml of methanol was added 673 mg of potassium hydroxide. The reaction mixture was stirred at room temperature for 1.5 hours, and acidified with a hydrochloric acid-methanol solution. The solvents were concentrated in vacuo. The resulting residue was dissolved in 60 ml of 1,4-dioxane and 3.53 ml of a 40% chloroacetaldehyde aqueous solution was added thereto. After the reaction mixture was heated under reflux for 1 hour, 40 ml of a hydrochloric acid-methanol solution and 60 ml of methanol were added thereto at room temperature, and the resulting mixture was stirred overnight. The reaction mixture was concentrated in vacuo and the residue was recrystallized from methanol-diethyl ether to give the title compound.

(7) Synthesis of (4-bromo-6-((3-(methoxymethyl)-thiazol-2(3H)-ylidene)amino)pyridin-2-yl)methanol

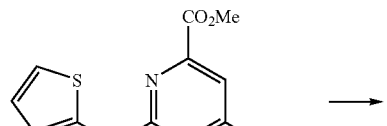

In the same manner as in Examples 1-(3) and (5), the title compound was obtained using methyl 4-bromo-6-(thiazol-2-ylamino)pyridine-2-carboxylate.

(8) Synthesis of 4-bromo-6-(methanesulfonyloxymethyl)-N-(3-(methoxymethyl)-thiazol-2(3H)-ylidene)amino)pyridin-2-amine

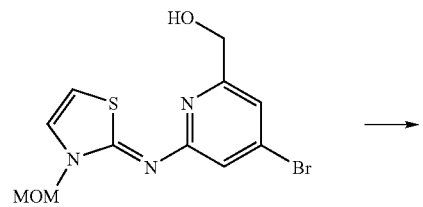

In the same manner as in Example 16-(2), the title compound was obtained using (4-bromo-6-((3-(methoxymethyl)-thiazol-2(3H)-ylidene)amino)pyridin-2-yl)methanol.

(9) Synthesis of 4-bromo-6-((4-(3-chloro-2-fluorobenzoyl)piperazin-1-yl)methyl)-N-(3-(methoxymethyl)-thiazol-2(3H)-ylidene)amino)pyridin-2-amine

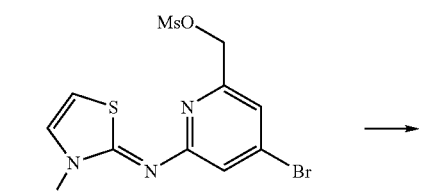

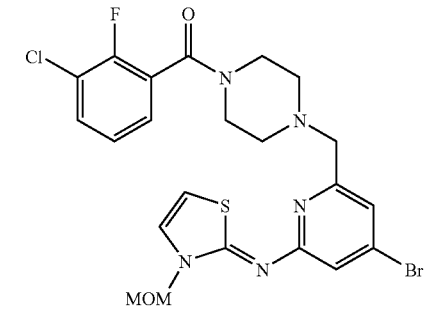

In the same manner as in example 16-(3), the title compound was obtained using 4-bromo-6-(methanesulfonyloxymethyl)-N-(3-(methoxymethyl)-thiazol-2(3H)-ylidene)amino)pyridin-2-amine.

(10) Synthesis of 4-bromo-6-((4-(3-chloro-2-fluorobenzoyl)piperazin-1-yl)methyl)-N-thiazol-2-ylpyridin-2-amine

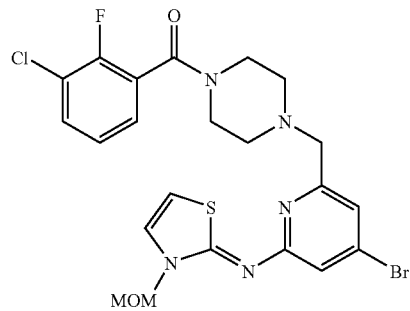

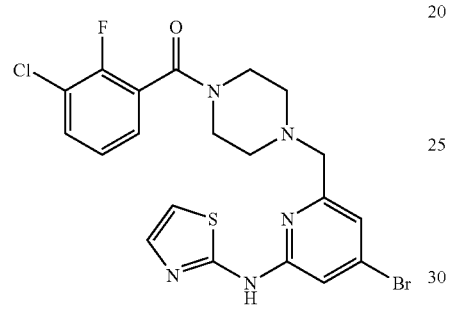

In the same manner as in Example 1-(8), the title compound was obtained using 4-bromo-6-((4-(3-chloro-2-fluorobenzoyl)piperazin-1-yl)methyl)-N-(3-(methoxymethyl)-thiazol-2(3H)-ylidene)amino)pyridin-2-amine.

Spectral data of the title compound are as follows.

Mass: 510, 512 (M+1)$^+$

Example 82

Synthesis of methyl 2-((4-(3-chloro-2-fluorobenzoyl)piperazin-1-yl)methyl)-6-(thiazol-2-ylamino)isonicotinate (1) Synthesis of methyl 2-((4-(3-chloro-2-fluorobenzoyl)piperazin-1-yl)methyl)-6-((3-(methoxymethyl)-thiazol-2(3H)-ylidene)amino)isonicotinate

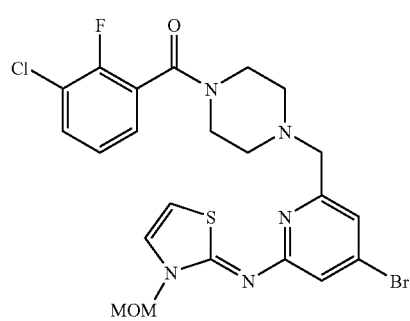

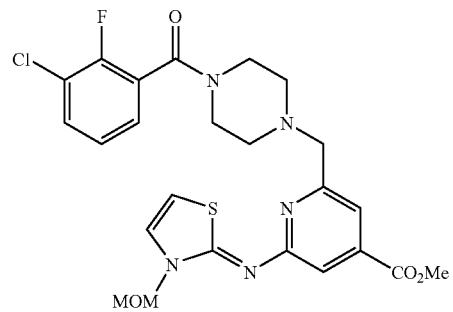

In the same manner as in Example 1-(2), the title compound was obtained using 4-bromo-6-((4-(3-chloro-2-fluorobenzoyl)piperazin-1-yl)methyl)-N-(3-(methoxymethyl)-thiazol-2(3H)-ylidene)amino)pyridin-2-amine obtained in Example 81-(9).

(2) Synthesis of methyl 2-((4-(3-chloro-2-fluorobenzoyl)piperazin-1-yl)methyl)-6-(thiazol-2-ylamino)isonicotinate

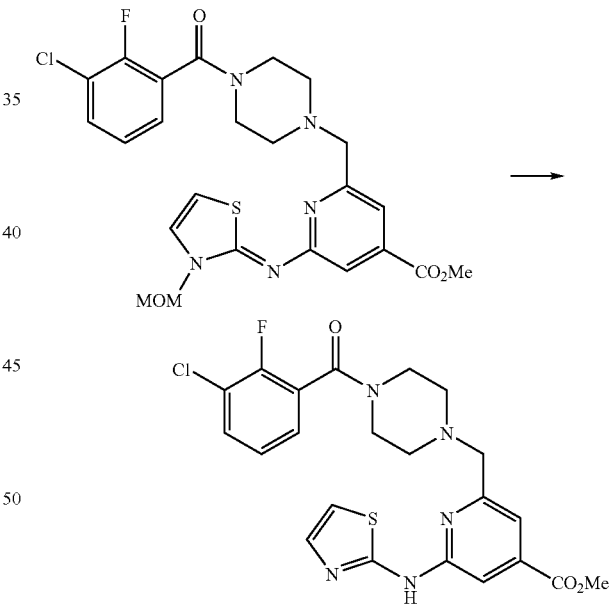

In the same manner as in Example 1-(8), the title compound was obtained using methyl 2-((4-(3-chloro-2-fluorobenzoyl)piperazin-1-yl)methyl)-6-((3-(methoxymethyl)-thiazol-2(3H)-ylidene)amino)isonicotinate.

Spectral data of the title compound are as follows.

$^1$H-NMR (CDCl$_3$) δ: 7.57-7.52 (m, 2H), 7.47-7.42 (m, 2H), 7.30-7.25 (m, 1H), 7.15 (t, J=8.0 Hz, 1H), 6.91 (d, J=3.6 Hz, 1H), 3.98 (s, 3H), 3.91-3.85 (m, 2H), 3.81 (s, 2H), 3.43-3.32 (m, 2H), 2.71 (brt, J=4.8 Hz, 2H), 2.63-2.52 (m, 2H)

Mass: 490 (M+1)$^+$

Example 83

Synthesis of 2-((4-(3-chloro-2-fluorobenzoyl)piperazin-1-yl)methyl)-6-(thiazol-2-ylamino)isonicotinic acid (1) Synthesis of 2-((4-(3-chloro-2-fluorobenzoyl)piperazin-1-yl)methyl)-6-((3-(methoxymethyl)-thiazol-2(3H)-ylidene)amino)isonicotinic Acid

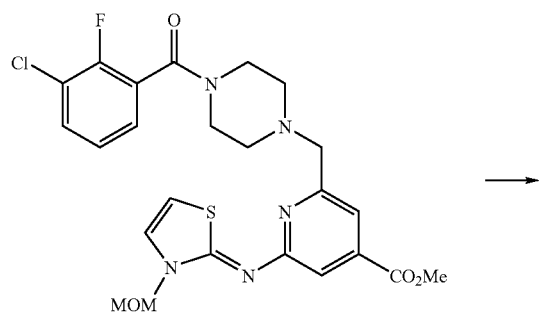

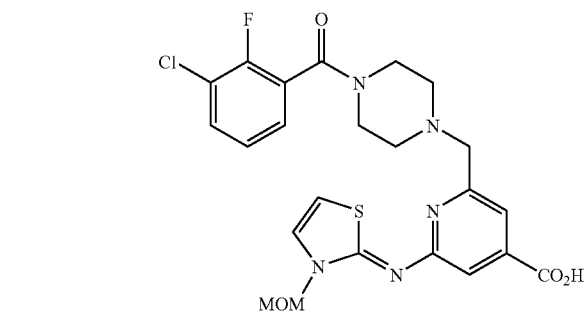

In the same manner as in Example 44-(3), the title compound was obtained using methyl 2-((4-(3-chloro-2-fluorobenzoyl)piperazin-1-yl)methyl)-6-((3-(methoxymethyl)-thiazol-2(3H)-ylidene)amino)isonicotinate obtained in Example 82-(1).

(2) Synthesis of 2-((4-(3-chloro-2-fluorobenzoyl)piperazin-1-yl)methyl)-6-(thiazol-2-ylamino)isonicotinic acid trifluoroacetate

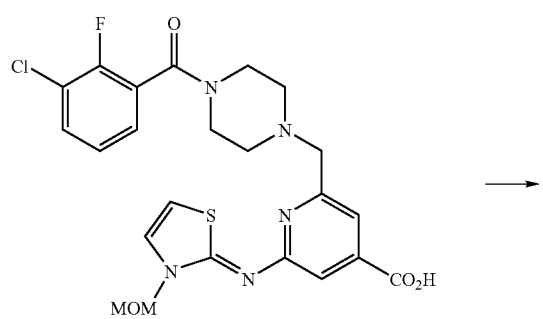

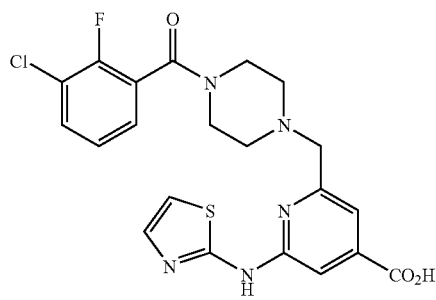

In the same manner as in Example 16-(4), the title compound was obtained using 2-((4-(3-chloro-2-fluorobenzoyl)piperazin-1-yl)methyl)-6-((3-(methoxymethyl)-thiazol-2(3H)-ylidene)amino)isonicotinic acid.

Spectral data of the title compound are as follows.

$^1$H-NMR (DMSO-$d_6$) δ: 7.74-7.68 (m, 1H), 7.63 (s, 1H), 7.61 (s, 1H), 7.47-7.41 (m, 2H), 7.33 (t, J=8.0 Hz, 1H), 7.13 (d, J=4.0 Hz, 1H), 4.49 (brs, 2H)

Mass: 476 (M+1)$^+$

Example 84

Synthesis of 6-((4-(3-chloro-2-fluorobenzoyl)piperazin-1-yl)methyl)-4-(pyrrolidin-1-ylcarbonyl)-N-thiazol-2-ylpyridin-2-amine Trifluoroacetate

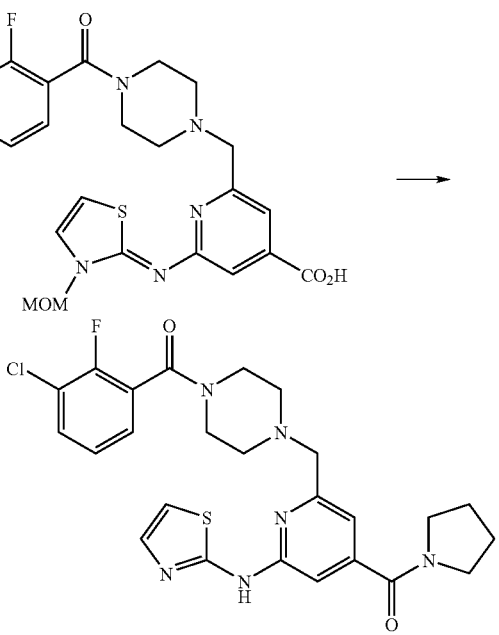

The amidation reaction was performed in the same manner as in Example 3-(2) using 2-((4-(3-chloro-2-fluorobenzoyl)piperazin-1-yl)methyl)-6-((3-(methoxymethyl)-thiazol-2(3H)-ylidene)amino)isonicotinic acid obtained in Example 83-(1) and pyrrolidine. The deprotection reaction was then performed to give the title compound.

Spectral data of the title compound are as follows.

¹H-NMR (CD₃OD) δ: 7.67-7.61 (m, 1H), 7.52-7.49 (m, 1H), 7.43-7.37 (m, 1H), 7.33-7.26 (m, 3H), 7.18-7.14 (m, 1H), 4.57 (s, 2H), 4.17-4.00 (m, 2H), 3.70 (brs, 2H), 3.64-3.57 (m, 4H), 3.52-3.43 (m, 4H), 2.06-1.90 (m, 4H)

Mass: 490 (M+1)⁺

Examples 85 to 88 were synthesized in the same manner as in Example 84 as follows.

Example 85

Synthesis of 2-((4-(3-chloro-2-fluorobenzoyl)piperazin-1-yl)methyl)-N-methyl-6-(thiazol-2-ylamino) isonicotinamide Trifluoroacetate ¹H-NMR (CD₃OD) δ: 7.67-7.60 (m, 1H), 7.54 (s, 1H), 7.52 (s, 1H), 7.51 (d, J=4.0 Hz, 1H), 7.43-7.37 (m, 1H), 7.30 (t, J=8.0 Hz, 1H), 7.16 (d, J=4.0 Hz, 1H), 4.57 (s, 2H), 4.15-4.01 (m, 2H), 3.70 (brs, 2H), 3.60 (brs, 2H), 3.48 (brs, 2H), 2.95 (s, 3H)

Mass: 489 (M+1)⁺

Example 86

Synthesis of 2-((4-(3-chloro-2-fluorobenzoyl)piperazin-1-yl)methyl)-N,N-dimethyl-6-(thiazol-2-ylamino)isonicotinamide Trifluoroacetate ¹H-NMR (CD₃OD) δ: 7.66-7.60 (m, 1H), 7.54 (d, J=4.0 Hz, 1H), 7.43-7.37 (m, 1H), 7.30 (t, J=8.0 Hz, 1H), 7.29 (d, J=1.2 Hz, 1H), 7.24 (d, J=1.2 Hz, 1H), 7.20 (d, J=4.0 Hz, 1H), 4.58 (s, 2H), 4.09 (brs, 2H), 3.70 (brs, 2H), 3.61 (brs, 2H), 3.49 (brs, 2H), 3.12 (s, 3H), 3.01 (s, 3H)

Mass: 503 (M+1)⁺

Example 87

Synthesis of 2-((4-(3-chloro-2-fluorobenzoyl)piperazin-1-yl)methyl)-6-(thiazol-2-ylamino)isonicotinamide Trifluoroacetate ¹H-NMR (CD₃OD) δ: 7.67-7.59 (m, 3H), 7.55 (d, J=4.0 Hz, 1H), 7.43-7.37 (m, 1H), 7.30 (t, J=8.0 Hz, 1H), 7.20 (d, J=4.0 Hz, 1H), 4.60 (s, 2H), 4.09 (brs, 2H), 3.70 (brs, 2H), 3.60 (brs, 2H), 3.49 (brs, 2H)

Mass: 475 (M+1)⁺

Example 88

Synthesis of 2-((4-(3-chloro-2-fluorobenzoyl)piperazin-1-yl)methyl)-N-(2-hydroxyethyl)-6-(thiazol-2-ylamino)isonicotinamide Trifluoroacetate ¹H-NMR (CD₃OD) δ: 7.66-7.60 (m, 1H), 7.49 (s, 2H), 7.45 (d, J=3.6 Hz, 1H), 7.42-7.37 (m, 1H), 7.29 (t, J=8.0 Hz, 1H), 7.09 (d, J=3.6 Hz, 1H), 4.52 (s, 2H), 4.07 (brs, 2H), 3.72 (t, J=5.6 Hz, 2H), 3.68 (brs, 2H), 3.56 (brs, 2H), 3.52 (t, J=5.6 Hz, 2H), 3.44 (brs, 2H)

Mass: 519 (M+1)⁺

Example 89

Synthesis of (2-((4-(3-chloro-2-fluorobenzoyl)piperazin-1-yl)methyl)-6-(thiazol-2-ylamino)pyridin-4-yl)methanol (1) Synthesis of (2-((4-(3-chloro-2-fluorobenzoyl)piperazin-1-yl)methyl)-6-((3-(methoxymethyl)-thiazol-2(3H)-ylidene)amino)pyridin-4-yl)methanol

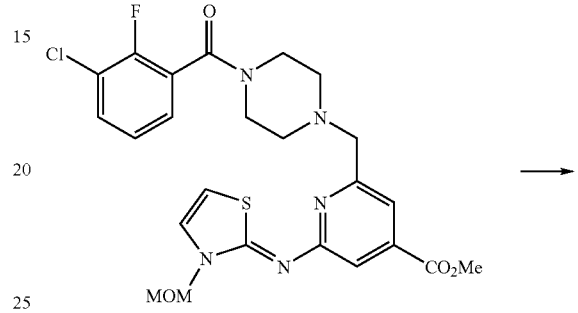

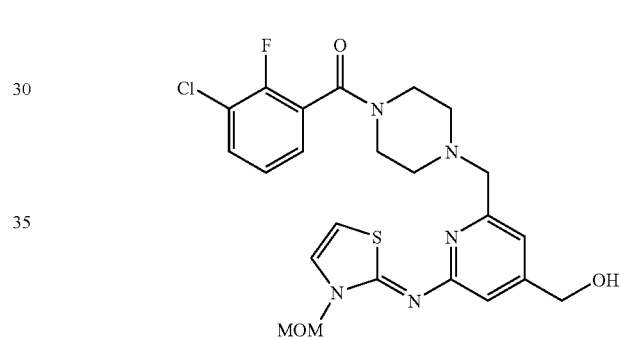

In the same manner as in Example 1-(5), the title compound was obtained using methyl 2-((4-(3-chloro-2-fluorobenzoyl)piperazin-1-yl)methyl)-6-((3-(methoxymethyl)-thiazol-2(3H)-ylidene)amino)isonicotinate obtained in Example 82-(1).

(2) Synthesis of (2-((4-(3-chloro-2-fluorobenzoyl)piperazin-1-yl)methyl)-6-(thiazol-2-ylamino)pyridin-4-yl)methanol

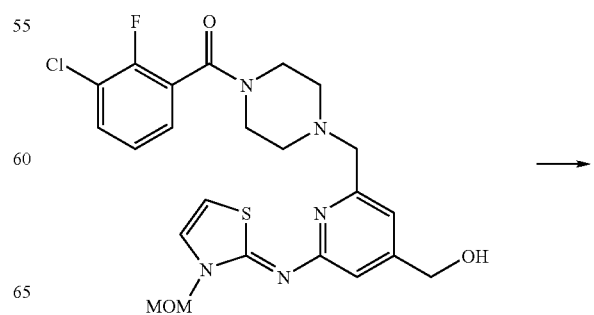

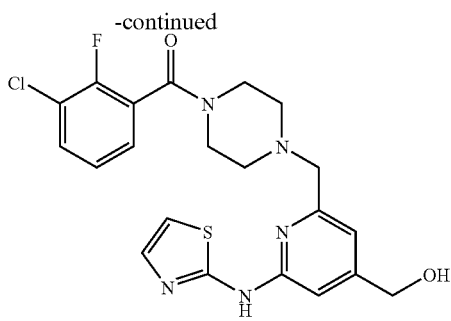

In the same manner as in Example 16-(4), the title compound was obtained using (2-((4-(3-chloro-2-fluorobenzoyl)piperazin-1-yl)methyl)-6-((3-(methoxymethyl)-thiazol-2(3H)-ylidene)amino)pyridin-4-yl)methanol.

Spectral data of the title compound are as follows.

$^1$H-NMR (CDCl$_3$) δ: 7.47-7.42 (m, 1H), 7.40 (d, J=3.6 Hz, 1H), 7.30-7.23 (m, 1H), 7.15 (brt, J=8.0 Hz, 1H), 6.97 (brs, 1H), 6.84-6.81 (m, 2H), 4.74 (s, 2H), 3.89-3,83 (m, 2H), 3.73 (s, 2H), 3.41-3.32 (m, 2H), 2.72-2.66 (m, 2H), 2.60-2.52 (m, 2H)

Mass: 462 (M+1)$^+$

Example 90

Synthesis of 6-((4-(3-chloro-2-fluorobenzoyl)piperazin-1-yl)methyl)-N-thiazol-2-yl-4-(1H-1,2,3-triazol-1-ylmethyl)pyridin-2-amine Trifluoroacetate (1) Synthesis of 6-((4-(3-chloro-2-fluorobenzoyl)piperazin-1-yl)methyl)-N-(3-(methoxymethyl)-thiazol-2(3H)-ylidene)-4-(methanesulfonyloxymethyl)pyridin-2-amine

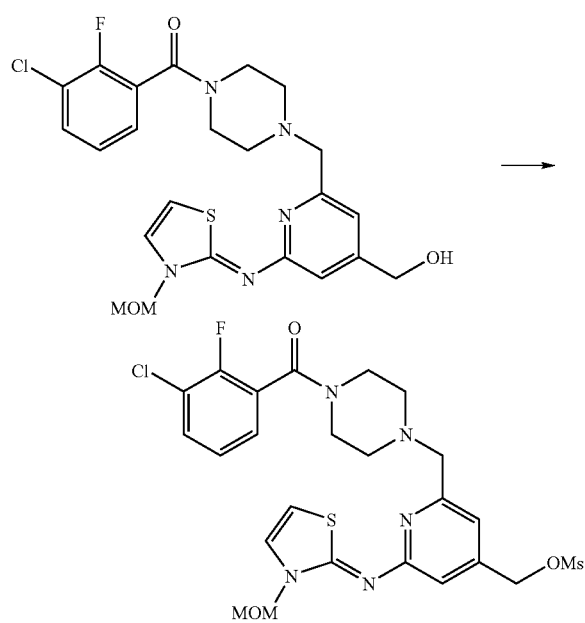

In the same manner as in Example 16-(2), the title compound was obtained using (2-((4-(3-chloro-2-fluorobenzoyl)piperazin-1-yl)methyl)-6-((3-(methoxymethyl)-thiazol-2(3H)-ylidene)amino)pyridin-4-yl)methanol obtained in Example 89-(1).

(2) Synthesis of 6-((4-(3-chloro-2-fluorobenzoyl)piperazin-1-yl)methyl)-N-(3-(methoxymethyl)-thiazol-2(3H)-ylidene)-4-(1H-1,2,3-triazol-1-ylmethyl)pyridin-2-amine and 6-((4-(3-chloro-2-fluorobenzoyl)piperazin-1-yl)methyl)-N-(3-(methoxymethyl)-thiazol-2(3H)-ylidene)-4-(2H-1,2,3-triazol-2-ylmethyl)pyridin-2-amine

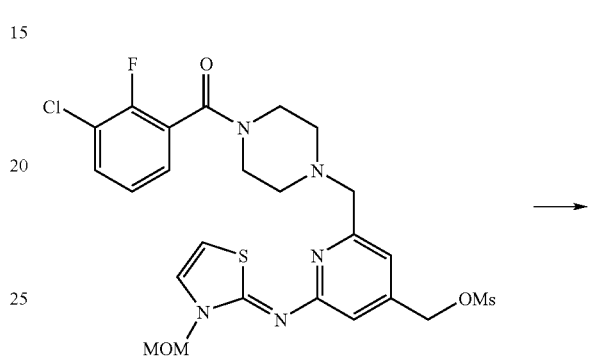

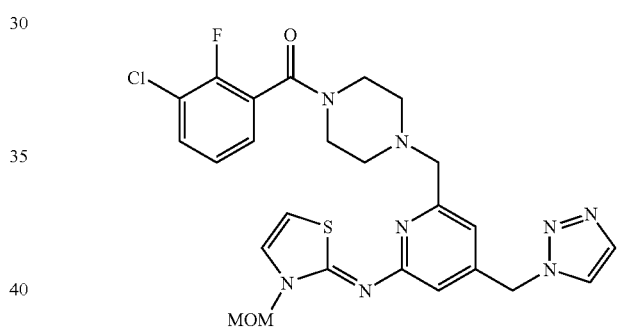

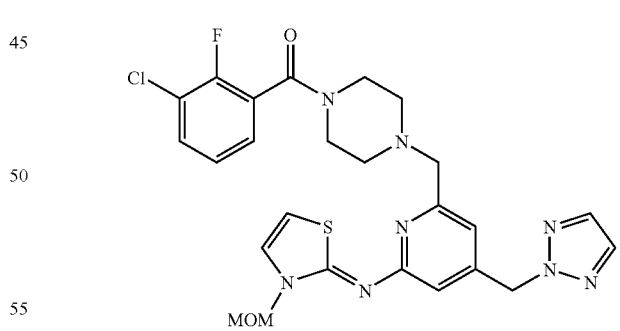

A mixture of 26 mg of 6-((4-(3-chloro-2-fluorobenzoyl)piperazin-1-yl)methyl)-N-(3-(methoxymethyl)-thiazol-2(3H)-ylidene)-4-(methanesulfonyloxymethyl)pyridin-2-amine and 5.2 μl of 1H-1,2,3-triazole, 14 μl of 1,8-diazabicyclo[5.4.0]undeca-7-en and 0.47 ml of chloroform was stirred at room temperature for 19 hours. The reaction solution was purified by a silica gel column chromatography (eluent: chloroform to chloroform/methanol=10/1) to give the title compound.

(3) Synthesis of 6-((4-(3-chloro-2-fluorobenzoyl)piperazin-1-yl)methyl)-N-thiazol-2-yl-4-(1H-1,2,3-triazol-1-ylmethyl)pyridin-2-amine trifluoroacetate

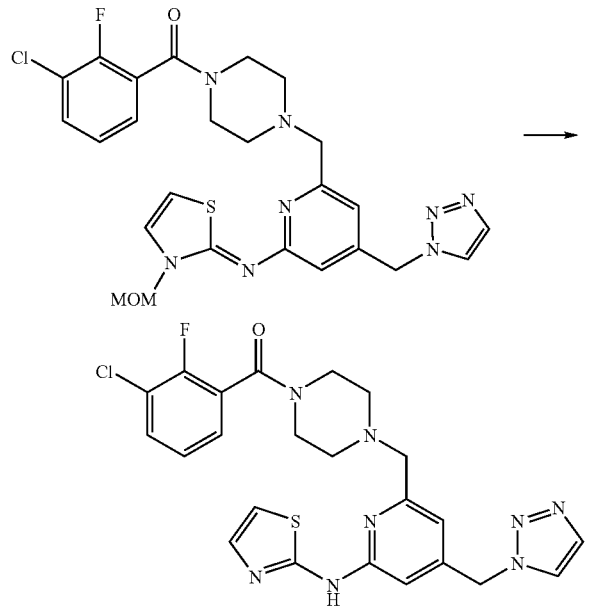

In the same manner as in Example 16-(4), the title compound was obtained using 6-((4-(3-chloro-2-fluorobenzoyl)piperazin-1-yl)methyl)-N-(3-(methoxymethyl)-thiazol-2(3H)-ylidene)-4-(1H-1,2,3-triazol-1-ylmethyl)pyridin-2-amine.

Spectral data of the title compound are as follows.

$^1$H-NMR (CD$_3$OD) δ: 8.13 (s, 1H), 7.84 (d, J=1.2 Hz, 1H), 7.66-7.60 (m, 1H), 7.55 (d, J=3.6 Hz, 1H), 7.42-7.36 (m, 1H), 7.29 (brt, J=7.6 Hz, 1H), 7.22 (d, J=3.6 Hz, 1H), 7.21 (s, 1H), 7.04 (s, 1H), 5.79 (s, 2H), 4.54 (s, 2H), 4.07 (brs, 2H), 3.68 (brs, 2H), 3.57 (brs, 2H), 3.46 (brs, 2H)

Mass: 513 (M+1)$^+$

Example 91

Synthesis of 6-((4-(3-chloro-2-fluorobenzoyl)piperazin-1-yl)methyl)-N-thiazol-2-yl-4-(2H-1,2,3-triazol-2-ylmethyl)pyridin-2-amine Trifluoroacetate

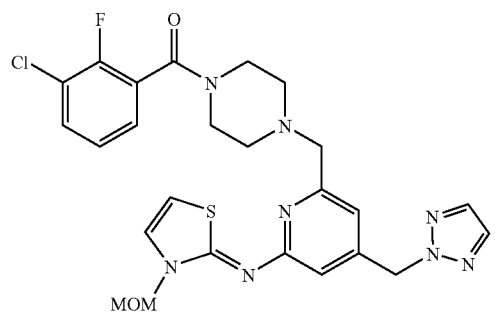

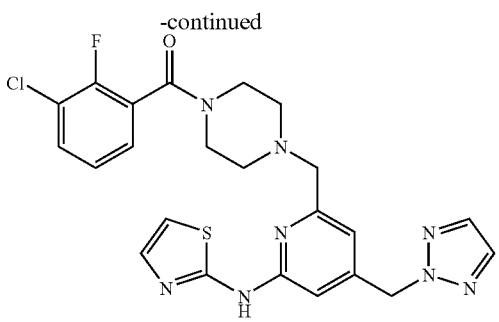

In the same manner as in Example 16-(4), the title compound was obtained using 6-((4-(3-chloro-2-fluorobenzoyl)piperazin-1-yl)methyl)-N-(3-(methoxymethyl)-thiazol-2(3H)-ylidene)-4-(2H-1,2,3-triazol-2-ylmethyl)pyridin-2-amine obtained in Example 90-(2).

Spectral data of the title compound are as follows.

$^1$H-NMR (CD$_3$OD) δ: 7.80 (s, 2H), 7.67-7.61 (m, 1H), 7.46 (d, J=3.6 Hz, 1H), 7.43-7.37 (m, 1H), 7.30 (brt, J=8.0 Hz, 1H), 7.11 (d, J=3.6 Hz, 1H), 7.09 (s, 1H), 6.94 (s, 1H), 5.75 (s, 2H), 4.48 (s, 2H), 4.06 (brs, 2H), 3.67 (brs, 2H), 3.56 (brs, 2H), 3.44 (brs, 2H)

Mass: 513 (M+1)$^+$

Examples 92 to 95 were synthesized in the same manner as in Example 90 as follows.

Example 92

Synthesis of 6-((4-(3-chloro-2-fluorobenzoyl)piperazin-1-yl)methyl)-N-thiazol-2-yl-4-(1H-1,2,4-triazol-1-ylmethyl)pyridin-2-amine Trifluoroacetate $^1$H-NMR (CD$_3$OD) δ: 8.71 (s, 1H), 8.12 (s, 1H), 7.66-7.60 (m, 1H), 7.56 (d, J=3.6 Hz, 1H), 7.44-7.36 (m, 1H), 7.29 (t, J=8.0 Hz, 1H), 7.23 (s, 1H), 7.22 (d, J=3.6 Hz, 1H), 7.07 (s, 1H), 5.60 (s, 2H), 4.54 (s, 2H), 4.07 (brs, 2H), 3.69 (brs, 2H), 3.57 (brs, 2H), 3.46 (brs, 2H)

Mass: 513 (M+1)$^+$

Example 93

Synthesis of 6-((4-(3-chloro-2-fluorobenzoyl)piperazin-1-yl)methyl)-4-((methanesulfonyl)methyl)-N-thiazol-2-ylpyridin-2-amine $^1$H-NMR (CDCl$_3$) δ: 11.37 (brs, 1H), 7.69-7.63 (m, 1H), 7.40-7.34 (m, 2H), 7.30 (t, J=8.0 Hz, 1H), 7.04 (s, 1H), 7.00 (d, J=3.6 Hz, 1H), 6.96 (s, 1H), 4.53 (s, 2H), 3.72-3.64 (m, 4H), 2.97 (s, 3H)

Mass: 524 (M+1)$^+$

Example 94

Synthesis of 6-((4-(3-chloro-2-fluorobenzoyl)piperazin-1-yl)methyl)-4-((dimethylamino)methyl)-N-thiazol-2-ylpyridin-2-amine $^1$H-NMR (CDCl$_3$) δ: 7.48 (d, J=4.0 Hz, 1H), 7.47-7.41 (m, 1H), 7.29-7.24 (m, 1H), 7.14 (brt, J=8.0 Hz, 1H), 6.97 (s, 1H), 6.84 (d, J=4.0 Hz, 1H), 6.81 (s, 1H), 3.86 (brt, J=4.8 Hz, 2H), 3.74 (s, 2H), 3.42 (s, 2H), 3.37 (brs, 2H), 2.70 (brt, J=4.8 Hz, 2H), 2.57 (brs, 2H), 2.27 (s, 6H)

Mass: 489 (M+1)$^+$

Example 95

Synthesis of 6-((4-(3-chloro-2-fluorobenzoyl)piperazin-1-yl)methyl)-4-(methoxymethyl)-N-thiazol-2-ylpyridin-2-amine $^1$H-NMR (CDCl$_3$) δ: 7.49 (brd, J=3.6 Hz, 1H), 7.47-7.41 (m, 1H), 7.30-7.24 (m, 1H), 7.14 (t, J=8.0 Hz, 1H), 6.93 (s, 1H), 6.85 (d, J=3.6 Hz, 1H), 6.83 (s, 1H), 4.47 (s, 2H), 3.87 (brt, J=4.8 Hz, 2H), 3.74 (s, 2H), 3.46 (s, 3H), 3.37 (brs, 2H), 2.71 (brt, J=4.8 Hz, 2H), 2.57 (brs, 2H)

Mass: 476 (M+1)$^+$

Example 96

Synthesis of 1-(2-((4-(3-chloro-2-fluorobenzoyl)piperazin-1-yl)methyl)-6-(thiazol-2-ylamino)pyridin-4-yl)pyrrolidin-2-one

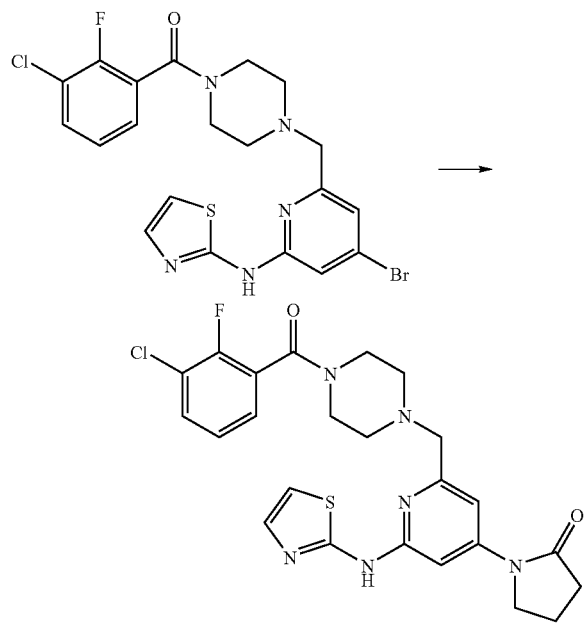

To a solution of 25.5 mg of 4-bromo-6-((4-(3-chloro-2-fluorobenzoyl)piperazin-1-yl)methyl)-N-thiazol-2-ylpyridin-2-amine obtained in Example 81 in 1 mL of 1,4-dioxane was added 0.011 mL of pyrrolidin-2-one, 32 mg of potassium phosphate, 8.7 mg of 9,9-dimethyl-4,5-bis(diphenylphosphino)xanthene and 7.8 mg of tris(dibenzylideneacetone)dipalladium(0)-chloroform complex, successively. The reaction solution was stirred at 100° C. for 3 hours. The reaction solution was cooled, diluted with ethyl acetate, washed with water, and then dried over anhydrous magnesium sulfate. The solvent was concentrated in vacuo and the resulting residue was purified by a reversed phase medium pressure liquid chromatography [ODS-AS-360-CC (manufactured by YMC company), mobile phase: water-acetonitrile-0.1% trifluoroacetic acid]. The obtained fraction was diluted with ethyl acetate, washed with saturated sodium bicarbonate, and then dried over anhydrous magnesium sulfate. The solvent was concentrated in vacuo to give the title compound.

Spectral data of the title compound are as follows.

$^1$H-NMR (CDCl$_3$) δ: 7.62 (s, 1H), 7,50 (s, 1H), 7.44 (t, J=6.8 Hz, 1H), 7.30-7.23 (m, 1H), 7.19-7.11 (m, 2H), 6.85 (s, 1H), 3.94-3.82 (m, 4H), 3.73 (s, 2H), 3.42-3.30 (m, 2H), 2.77-2.45 (m, 6H), 2.26-2.16 (m, 2H)

Mass: 515, 517 (M+1)$^+$

Examples 97 to 103 were synthesized in the same manner as in Example 96 as follows.

Example 97

Synthesis of 3-(2-((4-(3-chloro-2-fluorobenzoyl)piperazin-1-yl)methyl)-6-(thiazol-2-ylamino)pyridin-4-yl)-1,3-oxazolidin-2-one $^1$H-NMR (DMSO-d$_6$) δ: 7.67 (t, J=8.0 Hz, 1H), 7.40-7.25 (m, 4H), 7.13 (s, 1H), 6.99 (d, J=3.3 Hz, 1H), 4.46 (t, J=7.8 Hz, 2H), 4.04 (t, J=7.8 Hz, 2H), 3.72-3.65 (m, 2H), 3.64 (s, 2H), 3.30-3.20 (m, 2H), 2.60-2.41 (m, 4H)

Mass: 517, 519 (M+1)$^+$

Example 98

Synthesis of 3-(2-((4-(3-chloro-2-fluorobenzoyl)piperazin-1-yl)methyl)-6-(thiazol-2-ylamino)pyridin-4-yl)-3-methylimidazolidin-2-one $^1$H-NMR (DMSO-d$_6$) δ: 11.06 (s, 1H), 7.70-7.60 (m, 1H), 7.40-7.20 (m, 5H), 7.03 (s, 1H), 6.95-6.92 (m, 1H), 3.80-3.40 (m, 8H), 3.30-3.15 (m, 2H), 2.77 (s, 3H), 2.65-2.40 (m, 4H)

Mass: 530 (M+1)$^+$

Example 99

Synthesis of 3-(2-((4-(3-chloro-2-fluorobenzoyl)piperazin-1-yl)methyl)-6-(thiazol-2-ylamino)pyridin-4-yl)piperidin-2-one $^1$H-NMR (CDCl$_3$) δ: 7.47-7.40 (m, 2H), 7.29-7.22 (m, 1H), 7.14 (t, J=7.8 Hz, 1H), 6.99 (s, 1H), 6.90 (s, 1H), 6.82 (s, 1H), 3.91-3.80 (m, 2H), 3.75-3.64 (m, 4H), 3.42-3.29 (m, 2H), 2.74-2.46 (m, 6H), 2.03-1.92 (m, 4H)

Mass: 529, 531 (M+1)$^+$

Example 100

Synthesis of 6-((4-(2,3-difluorobenzoyl)piperazin-1-yl)methyl)-N4-(2,2-difluoroethyl)-N2-thiazol-2-ylpyridine-2,4-diamine Mass: 495 (M+1)$^+$

Example 101

Synthesis of 6-((4-(2,3-difluorobenzoyl)piperazin-1-yl)methyl)-4-piperazin-1-yl-N-thiazol-2-ylpyridin-2-amine Mass: 500 (M+1)$^+$

Example 102

Synthesis of 1-(2-((4-(2,3-difluorobenzoyl)piperazin-1-yl)methyl)-6-(thiazol-2-ylamino)pyridin-4-yl)-1,5-dihydro-2H-pyrrol-2-one Mass: 497 (M+1)+

Example 103

Synthesis of 6-((4-(2,3-difluorobenzoyl)piperazin-1-yl)methyl)-4-morpholin-4-yl-N-thiazol-2-ylpyridin-2-amine Mass: 501 (M+1)+

Example 104

Synthesis of 2-((4-(3-chloro-2-fluorobenzoyl)piperazin-1-yl)methyl)-6-(thiazol-2-ylamino)isonicotinonitrile (1) Synthesis of 4-bromo-6-(((tert-butyl(dimethyl)silyl)oxy)methyl)-N-(3-(methoxymethyl)-thiazol-2(3H)-ylidene)pyridin-2-amine In the same manner as in Example 5-(1), the title compound was obtained using (4-bromo-6-((3-(methoxymethyl)-thiazol-2(3H)-ylidene)amino)pyridin-2-yl)methanol obtained in Example 81-(7).

(2) Synthesis of 2-(((tert-butyl(dimethyl)silyl)oxy)methyl)-6-((3-(methoxymethyl)thiazol-2(3H)-ylidene)amino)isonicotinonitrile

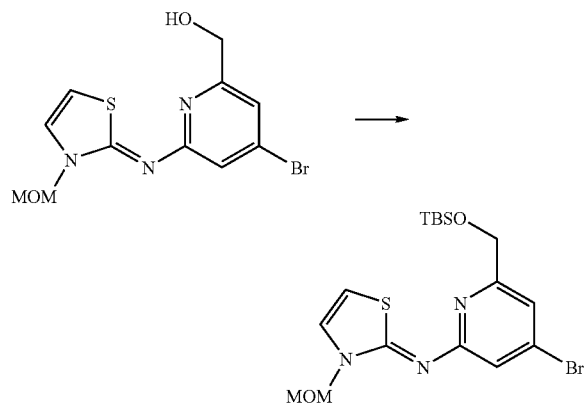

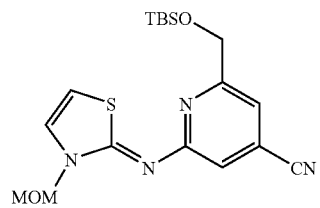

A mixture of 2.04 g of 4-bromo-6-(((tert-butyl(dimethyl)silyl)oxy)methyl)-N-(3-(methoxymethyl)-thiazol-2(3H)-ylidene)pyridin-2-amine, 379 mg of zinc cyanide, 266 mg of 4,5-bis(diphenylphosphino)-9,9-dimethylxanthene, 133 mg of bis(dibenzylideneacetone)palladium(0), 92 mg of zinc and 9.2 ml of N,N-dimethylacetamide was stirred at 140° C. for 3 hours. The resulting reaction mixture was diluted with ethyl acetate, and then an insoluble matter was filtered off using Celite. The filtrate was washed with water and brine. The organic layer was dried over anhydrous magnesium sulfate and filtered, and the filtrate was concentrated. The residue was purified by a silica gel column chromatography (eluent: hexane to hexane/ethyl acetate=3/1) to give the title compound.

(3) Synthesis of 2-((4-(3-chloro-2-fluorobenzoyl)piperazin-1-yl)methyl)-6-(thiazol-2-ylamino)isonicotinonitrile

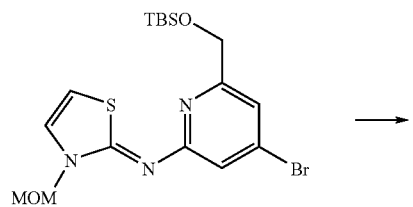

2-(((tert-butyl(dimethyl)silyl)oxy)methyl)-6-((3-(methoxymethyl)thiazol-2(3H)-ylidene)amino)isonicotinonitrile was subjected to the process similar to Example 5-(3) and subsequently the processes similar to Examples 16-(2) to (4) to give the title compound.

Spectral data of the title compound are as follows.

1H-NMR (CDCl$_3$) δ: 7.53 (d, J=3.7 Hz, 1H), 7.50-7.43 (m, 1H), 7.32-7.25 (m, 2H), 7.16 (t, J=7.8 Hz, 1H), 7.05 (s, 1H), 6.97 (d, J=3.5 Hz, 1H), 3.89 (brs, 2H), 3.79 (s, 2H), 3.39 (brs, 2H), 2.69 (t, J=4.9 Hz, 2H), 2.57 (brs, 2H)

Mass: 457 (M+1)+

Example 105

Synthesis of 6-((4-(3-chloro-2-fluorobenzoyl)piper-azin-1-yl)methyl)-4-(2H-tetrazol-5-yl)-N-thiazol-2-ylpyridin-2-amne

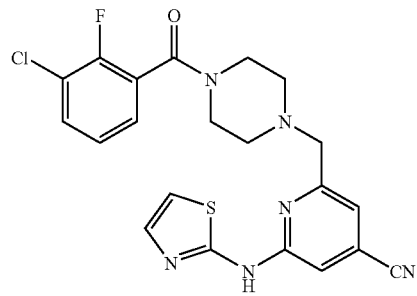

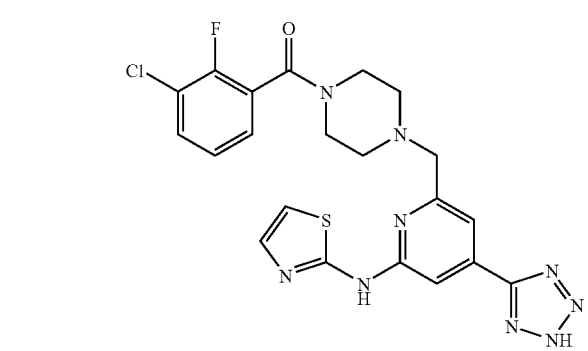

A mixture of 25.2 mg of 2-((4-(3-chloro-2-fluorobenzoyl)piperazin-1-yl)methyl)-6-(thiazol-2-ylamino)isonicotinonitrile obtained in Example 104, 17.9 mg of sodium azide, 38.0 mg of triethylamine hydrochloride and 2 ml of N,N-dimethylformamide was stirred at 110° C. for 13 hours, and then the reaction solution was concentrated. The resulting residue was purified by a thin-layer chromatography for fractionation (eluent: chloroform/methanol=5/1) to give the title compound.

Spectral data of the title compound are as follows.

$^1$H-NMR (CDCl$_3$) δ: 7.84 (s, 1H), 7.43 (dd, J=7.0, 6.3 Hz, 1H), 7.38-7.23 (m, 3H), 7.13 (dd, J=8.0, 7.6 Hz, 1H), 6.85-6.81 (m, 1H), 3.92-3.89 (m, 4H), 3.44-3.30 (m, 2H), 2.81-2.49 (m, 4H)

Mass: 500 (M+1)$^+$

Example 106

Synthesis of 6-((4-(3-chloro-2-fluorobenzoyl)piper-azin-1-yl)methyl)-4-(1-methyl-1H-tetrazol-5-yl)-N-thiazol-2-ylpyridin-2-amine (1) Synthesis of 6-(((tert-butyl(dimethyl)silyl)oxy)methyl)-N-(3-(methoxymethyl)thiazol-2(3H)-ylidene)-4-(2H-tetrazol-5-yl)pyridin-2-amine

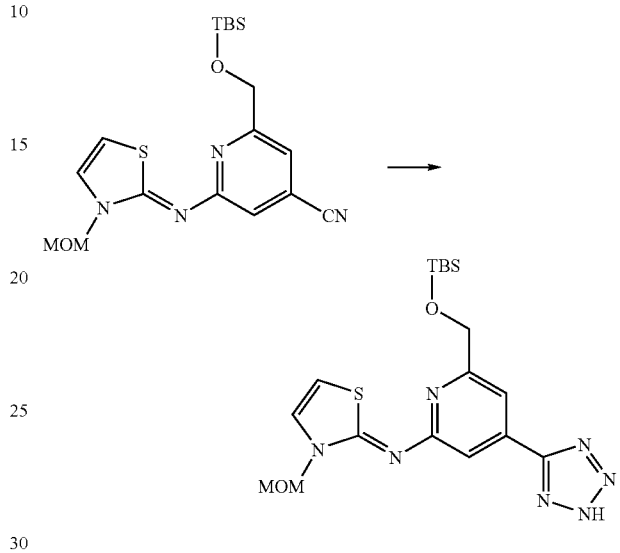

In the same manner as in Example 105, the title compound was obtained using 2-(((tert-butyl(dimethyl)silyl)oxy)methyl)-6-((3-(methoxymethyl)thiazol-2(3H)-ylidene)amino)isonicotinonitrile obtained in Example 104-(2).

(2) Synthesis of 6-(((tert-butyl(dimethyl)silyl)oxy)methyl)-N-(3-(methoxymethyl)thiazol-2(3H)-ylidene)-4-(1-methyl-1H-tetrazol-5-yl)pyridin-2-amine and 6-(((tert-butyl(dimethyl)silyl)oxy)methyl)-N-(3-(methoxymethyl)thiazol-2(3H)-ylidene)-4-(2-methyl-2H-tetrazol-5-yl)pyridin-2-amine

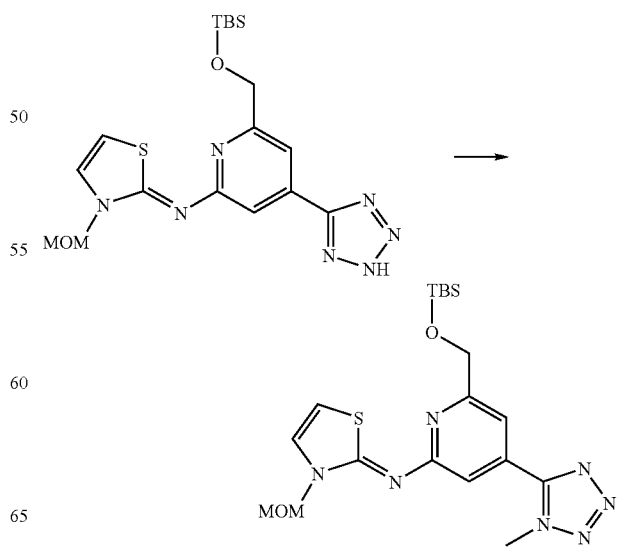

-continued

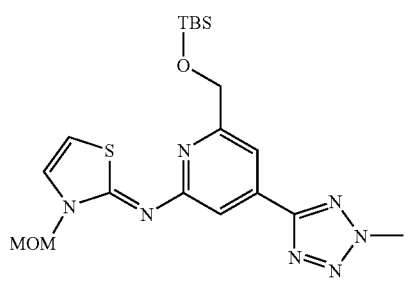

194 mg of 6-(((tert-butyl(dimethyl)silyl)oxy)methyl)-N-(3-(methoxymethyl)thiazol-2(3H)-ylidene)-4-(1H-tetrazol-5-yl)pyridin-2-amine was dissolved in 3 ml of N,N-dimethylformamide, and then 190 mg of cesium carbonate was added thereto. The reaction mixture was stirred at 60° C. for 1.5 hours and cooled to room temperature. 29.3 μl of methyl iodide was added thereto, followed by stirring at room temperature for 1.5 hours. The reaction solution was diluted with ethyl acetate and then washed with water and brine. The resulting organic layer was dried over magnesium sulfate and filtered, and the filtrate was concentrated. The resulting residue was purified by a silica gel column chromatography (eluent: hexane to hexane/ethyl acetate=2/1) to give the title compound, respectively.

(3) Synthesis of 6-((4-(3-chloro-2-fluorobenzoyl)piperazin-1-yl)methyl)-4-(1-methyl-1H-tetrazol-5-yl)-N-thiazol-2-ylpyridin-2-amine

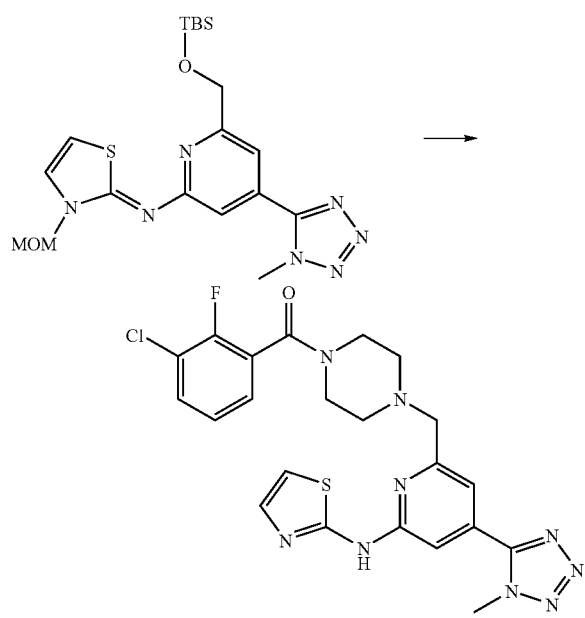

In the same manner as in Example 16, the title compound was obtained using 6-(((tert-butyl(dimethyl)silyl)oxy)methyl)-N-(3-(methoxymethyl)thiazol-2(3H)-ylidene)-4-(1-methyl-1H-tetrazol-5-yl)pyridin-2-amine.

Spectral data of the title compound are as follows.

$^1$H-NMR (DMSO-d$_6$) δ: 11.56 (brs, 1H), 7.68-7.62 (m, 1H), 7.44-7.40 (m, 3H), 7.37 (dd, J=8.0, 7.2 Hz, 1H), 7.30 (d, J=7.8, 7.6 Hz, 1H), 7.07 (d, J=3.3 Hz, 1H), 4.21 (s, 3H), 3.77 (s, 2H), 3.69 (brs, 2H), 3.30-3.23 (m, 2H), 2.64-2.45 (m, 4H)

Mass: 514 (M+1)$^+$

Example 107

Synthesis of 6-((4-(3-chloro-2-fluorobenzoyl)piperazin-1-yl)methyl)-4-(2-methyl-2H-tetrazol-5-yl)-N-thiazol-2-ylpyridin-2-amine

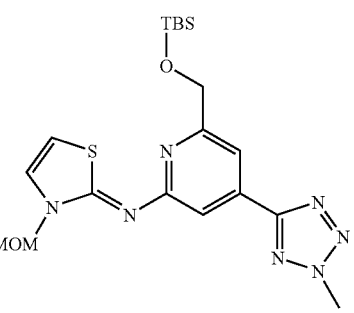

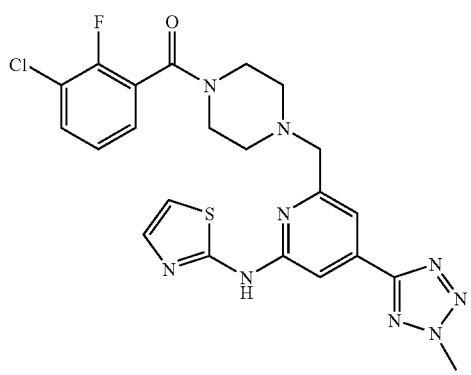

In the same manner as in Example 106, the title compound was obtained using 6-(((tert-butyl(dimethyl)silyl)oxy)methyl)-N-(3-(methoxymethyl)thiazol-2(3H)-ylidene)-4-(2-methyl-2H-tetrazol-5-yl)pyridin-2-amine obtained in Example 106-(2).

Spectral data of the title compound are as follows.

$^1$H-NMR (CDCl$_3$) δ: 7.73 (s, 1H), 7.59 (s, 1H), 7.57-7.41 (m, 2H), 7.30-7.10 (m, 2H), 6.89 (s, 1H), 4.46 (s, 3H), 3.89 (brs, 2H), 3.83 (s, 2H), 3.44-3.36 (m, 2H), 2.80-2.2.51 (m, 4H)

Mass: 514 (M+1)$^+$

Example 108

Synthesis of 6-((4-(3-chloro-2-fluorobenzoyl)piperazin-1-yl)methyl)-N-thiazol-2-yl-4-(1H-1,2,4-triazol-5-yl)pyridin-2-amine

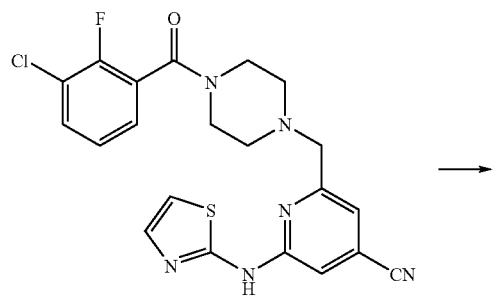

To a mixture of 25.2 mg of 2-((4-(3-chloro-2-fluorobenzoyl)piperazin-1-yl)methyl)-6-(thiazol-2-ylamino)isonicotinonitrile obtained in Example 104 and 1 ml of methanol was added 0.3 ml of a 28% sodium methoxide-methanol solution, followed by stirring at room temperature for 5 hours. To the reaction solution was added a solution of 3.3 mg of formohydrazide in 1 ml of methanol. The reaction mixture was stirred at room temperature for 17 hours, and then heated under reflux for 24 hours. To the reaction solution was added a solution of 16.6 mg of formohydrazide in 1.5 ml of methanol, and further heated under reflux for 22 hours. The reaction solution was cooled to room temperature, and then concentrated. The resulting residue was purified by a thin-layer chromatography for fractionation (eluent: chloroform/methanol=7/1) to give the title compound.

Spectral data of the title compound are as follows.

$^1$H-NMR (DMSO-$d_6$) δ: 8.59 (s, 1H), 7.69-7.58 (m, 3H), 7.41-7.28 (m, 3H), 7.03-6.98 (m, 1H), 3.72 (s, 2H), 3.60-3.05 (m, 6H), 2.63-2.45 (m, 2H)

Mass: 499 (M+1)$^+$

Example 109

Synthesis of 6-((4-(3-chloro-2-fluorobenzoyl)piperazin-1-yl)methyl)-4-(5-methyl-1,2,4-oxadiazol-3-yl)-N-thiazol-2-ylpyridin-2-amine (1) Synthesis of 6-((4-(3-chloro-2-fluorobenzoyl)piperazin-1-yl)methyl)-N-(3-(methoxymethyl)thiazol-2(3H)-ylidene)-4-(5-methyl-1,2,4-oxadiazol-3-yl)pyridin-2-amine

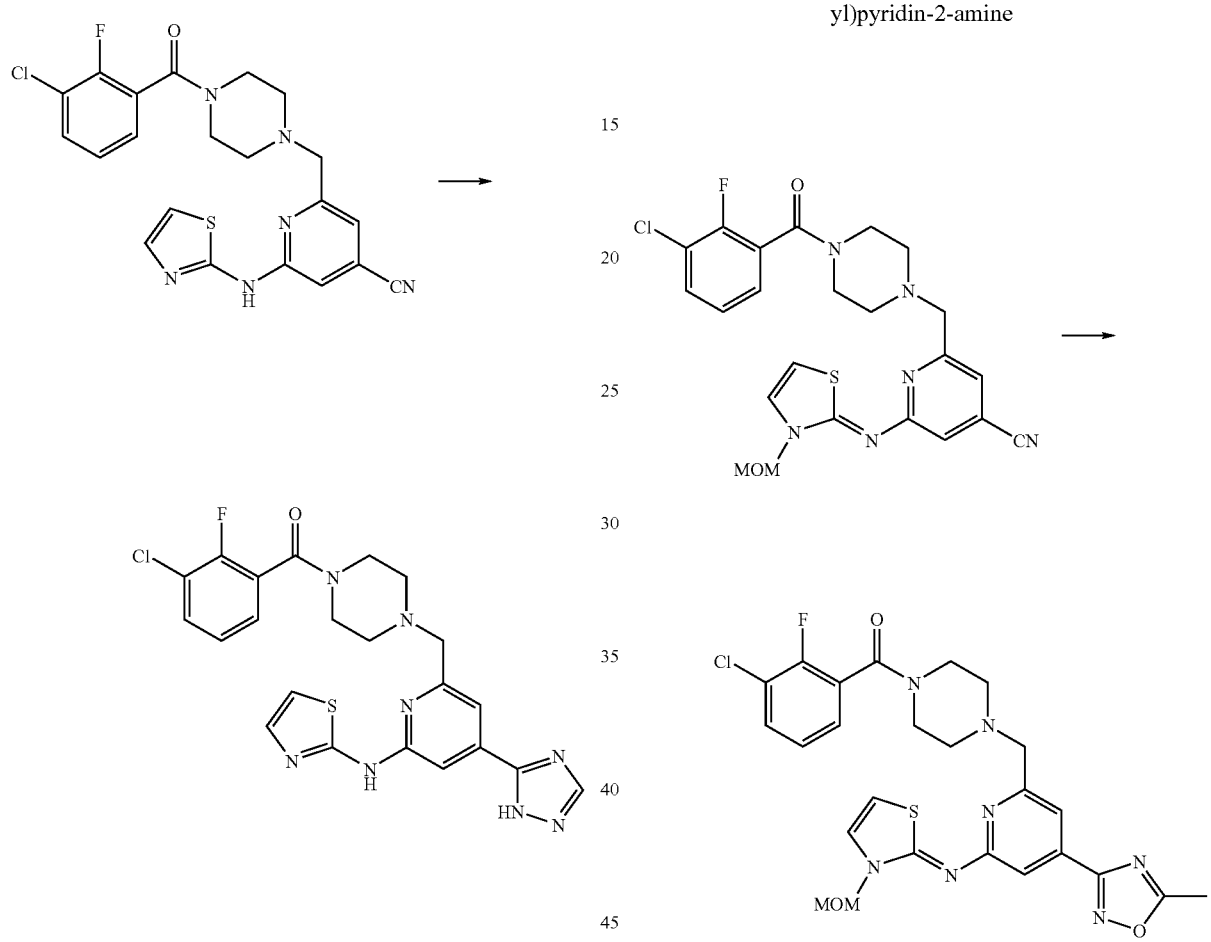

A mixture of 31.1 mg of 2-((4-(3-chloro-2-fluorobenzoyl)piperazin-1-yl)methyl)-6-((3-(methoxymethyl)-thiazol-2(3H)-ylidene)amino)isonicotinonitrile obtained in Example 104-(3), 13.0 mg of hydroxylammonium chloride, 17.2 mg of potassium carbonate and 3 ml of ethanol was heated under reflux for 18 hours. The reaction solution was cooled to room temperature, and then concentrated. To the residue was added 3.0 ml of acetic anhydride followed by heating under reflux for 4 hours. The reaction solution was cooled to room temperature, and then concentrated. The reaction solution was diluted with chloroform and then washed with saturated potassium carbonate. The resulting organic layer was dried over magnesium sulfate and filtered, and the filtrate was concentrated. The resulting residue was purified by a thin-layer chromatography for fractionation (eluent: chloroform/methanol=10/1) to give the title compound.

117

(2) Synthesis of 6-((4-(3-chloro-2-fluorobenzoyl)piperazin-1-yl)methyl)-4-(5-methyl-1,2,4-oxadiazol-3-yl)-N-thiazol-2-ylpyridin-2-amine

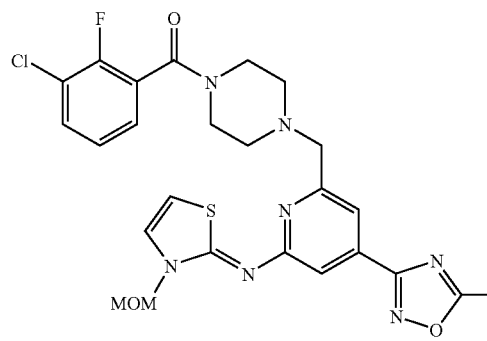

In the same manner as in Example 16-(4), the title compound was obtained using 6-((4-(3-chloro-2-fluorobenzoyl)piperazin-1-yl)methyl)-N-(3-(methoxymethyl)thiazol-2(3H)-ylidene)-4-(5-methyl-1,2,4-oxadiazol-3-yl)pyridin-2-amine.

Spectral data of the title compound are as follows.

$^1$H-NMR (CDCl$_3$) δ: 7.64 (s, 1H), 7.62-7.58 (m, 1H), 7.54 (s, 1H), 7.44 (dd, J=8.0, 7.0 Hz, 1H), 7.28-7.23 (m, 1H), 7.14 (t, J=7.8 Hz, 1H), 6.91 (d, J=3.5 Hz, 1H), 3.91-3.84 (m, 2H), 3.82 (s, 2H), 3.38 (brs, 2H), 2.71 (s, 3H), 2.77-2.50 (m, 4H)

Mass: 514 (M+1)$^+$

Example 110

Synthesis of 6-((4-(3-chloro-2-fluorobenzoyl)piperazin-1-yl)methyl)-4-(3-methyl-1,2,4-oxadiazol-5-yl)-N-thiazol-2-ylpyridin-2-amine (1) Synthesis of 6-((4-(3-chloro-2-fluorobenzoyl)piperazin-1-yl)methyl)-N-(3-(methoxymethyl)thiazol-2(3H)-ylidene)-4-(3-methyl-1,2,4-oxadiazol-5-yl)pyridin-2-amine

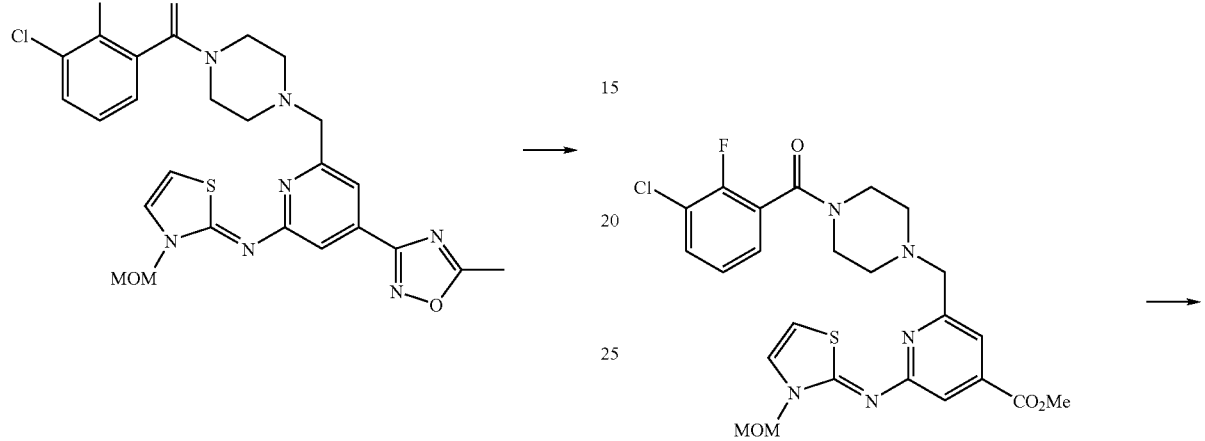

To a mixture of 9.4 mg of N-hydroxyacetamidine, molecular sieves 4A and 1 ml of tetrahydrofuran was added sodium hydride followed by stirring at 65° C. for 1 hour. To the reaction solution was added a solution of 22.6 mg of methyl 2-((4-(3-chloro-2-fluorobenzoyl)piperazin-1-yl)methyl)6-((3-(methoxymethyl)-thiazol-2(3H)-ylidene)amino)isonicotinate in 1 ml of tetrahydrofuran, followed by heating under reflux for 6 hours. The reaction solution was cooled to room temperature, diluted with ethyl acetate, and washed with saturated sodium bicarbonate and brine. The resulting organic layer was dried over magnesium sulfate and filtered, and the filtrate was concentrated. The resulting residue was purified by a thin-layer chromatography for fractionation (eluent: chloroform/methanol=10/1) to give the title compound.

(2) Synthesis of 6-((4-(3-chloro-2-fluorobenzoyl)piperazin-1-yl)methyl)-4-(3-methyl-1,2,4-oxadiazol-5-yl)-N-thiazol-2-ylpyridin-2-amine

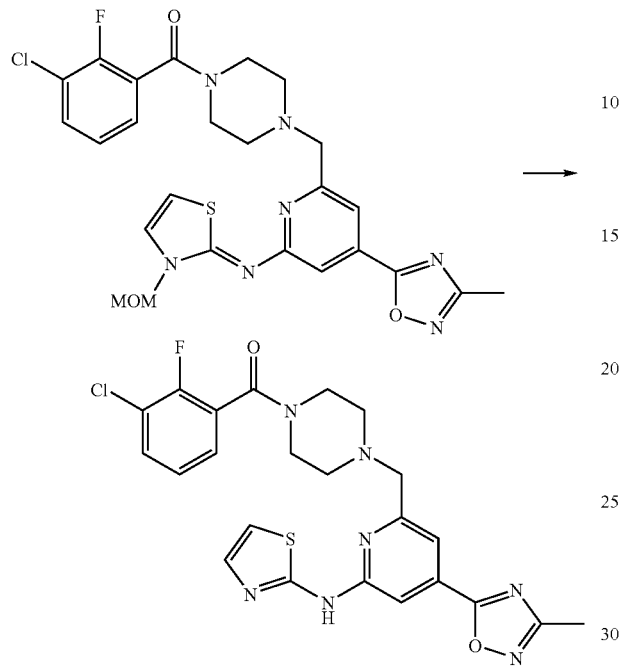

In the same manner as in Example 16-(4), the title compound was obtained using 6-((4-(3-chloro-2-fluorobenzoyl)piperazin-1-yl)methyl)-N-(3-(methoxymethyl)thiazol-2(3H)-ylidene)-4-(3-methyl-1,2,4-oxadiazol-5-yl)pyridin-2-amine.

Spectral data of the title compound are as follows.

$^1$H-NMR (CDCl$_3$) δ: 7.68 (s, 1H), 7.57-7.42 (m, 3H), 7.31-7.10 (m, 2H), 6.95-6.90 (m, 1H), 3.98-3.88 (m, 2H), 3.83 (s, 2H), 3.44-3.36 (m, 2H), 2.80-2.66 (m, 2H), 2.63-2.55 (m, 2H), 2.53 (s, 3H)

Mass: 514 (M+1)$^+$

Example 111

Synthesis of (2-((4-benzoylpiperazin-1-yl)methyl)-6-(1,2,4-thiadiazol-5-ylamino)pyridin-3-yl)methanol (1) Synthesis of (2,6-dibromopyridin-3-yl)methanol

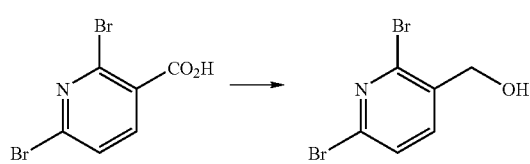

To a mixture of 1.51 g of 2,6-dibromonicotinic acid (Helvetica Chimica Acta, 1976, 59, 229), 0.72 ml of triethylamine and 30 ml of tetrahydrofuran was added 0.57 ml of ethyl chloroformate at 0° C. After stirring at room temperature for 30 minutes, an insoluble matter was filtered. To the filtrate was added 30 ml of tetrahydrofuran, and then 717 mg of sodium borohydride was added thereto. To this mixture was added 13 ml of methanol at 5° C. followed by stirring for 15 minutes. The reaction mixture was diluted with ethyl acetate and then washed with an aqueous solution of saturated ammonium chloride and brine. The organic layer was dried over anhydrous magnesium sulfate and filtered, and the filtrate was concentrated to give the title compound.

(2) Synthesis of 2,6-dibromo-3-(((tert-butyl(dimethyl)silyl)oxy)methyl)pyridine

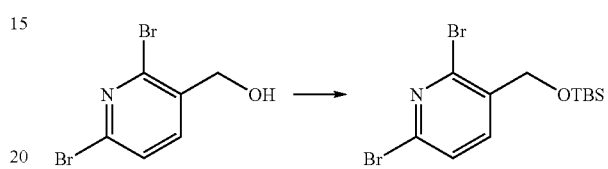

In the same manner as in Example 5-(1), the title compound was obtained using (2,6-dibromopyridin-3-yl)methanol.

(3) Synthesis of 6-bromo-5-(((tert-butyl(dimethyl)silyl)oxy)methyl)-N-(1,2,4-thiadiazol-5-yl)pyridin-2-amine

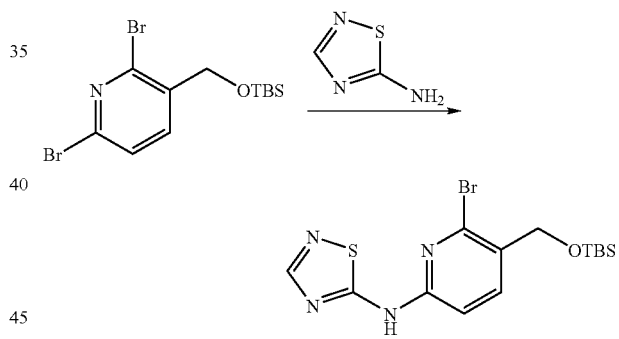

In the same manner as in Example 5-(2), the title compound was obtained using 2,6-dibromo-3-(((tert-butyl(dimethyl)silyl)oxy)methyl)pyridine and 1,2,4-thiadiazol-5-amine.

(4) Synthesis of 6-(methanesulfonyloxymethyl)-5-(((tert-butyl(dimethyl)silyl)oxy)methyl)-N-(1,2,4-thiadiazol-5-yl)pyridin-2-amine

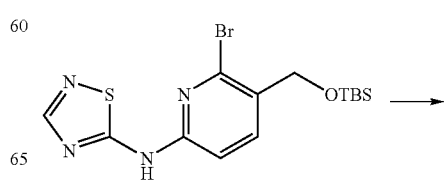

-continued

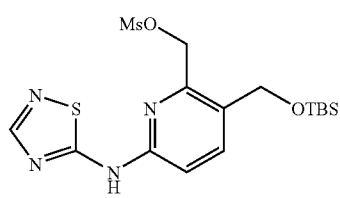

In the same manner as in Examples 1-(2), (5) and 16-(2), the title compound was obtained using 6-bromo-5-(((tert-butyl(dimethyl)silyl)oxy)methyl)-N-(1,2,4-thiadiazol-5-yl)pyridin-2-amine.

(5) Synthesis of (2-((4-benzoylpiperazin-1-yl)methyl)-6-(1,2,4-thiadiazol-5-ylamino)pyridin-3-yl)methanol

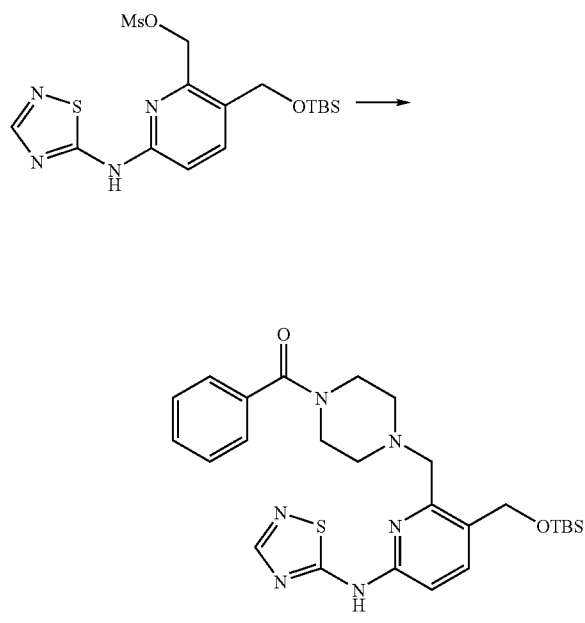

The amination reaction was performed in the same manner as in Example 16-(3) using 6-(methanesulfonyloxymethyl)-5-(((tert-butyl(dimethyl)silyl)oxy)methyl)-N-(1,2,4-thiadiazol-5-yl)pyridin-2-amine and 1-benzoylpiperazine hydrochloride obtained in the same manner as in Reference Example 1. Then, the deprotection reaction was performed in the same manner as in Example 5-(3) to give the title compound.

Spectral data of the title compound are as follows.

$^1$H-NMR (DMSO-d$_6$) δ: 12.11 (brs, 1H), 8.28 (s, 1H), 7.85 (d, J=8.4 Hz, 1H), 7.45-7.35 (m, 5H), 7.07 (d, J=8.4 Hz, 1H), 4.63 (s, 2H), 3.75 (s, 2H), 3.66-3.43 (m, 2H), 3.40-3.20 (m, 2H), 2.57-2.33 (m, 4H)

Mass: 411 (M+1)$^+$

Example 112

Synthesis of 6-((4-(3-chloro-2-fluorobenzoyl)piperazin-1-yl)methyl)-N-(5-fluorothiazol-2-yl)pyridin-2-amine (1) Synthesis of 6-((((tert-butyl(dimethyl)silyl)oxy)methyl)-N-(3-(methoxymethyl)thiazol-2(3H)-ylidene)pyridin-2-amine

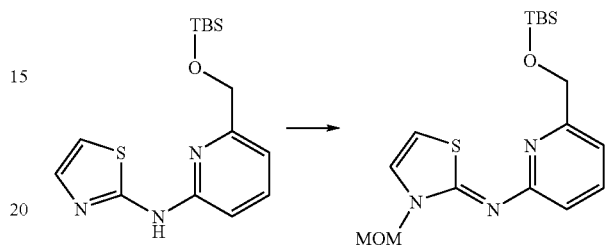

In the same manner as in Example 1-(3), the title compound was obtained using 6-((((tert-butyl(dimethyl)silyl)oxy)methyl)-N-thiazol-2-ylpyridin-2-amine obtained in Example 5-(2).

(2) Synthesis of 6-((((tert-butyl(dimethyl)silyl)oxy)methyl)-N-(5-fluoro-3-(methoxymethyl)thiazol-2(3H)-ylidene)pyridin-2-amine

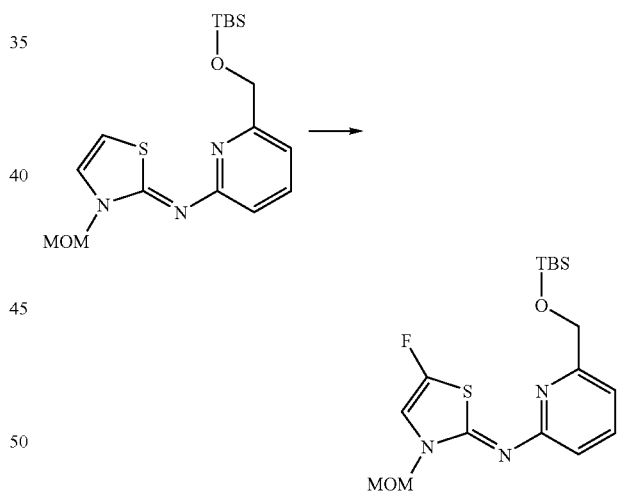

5 ml of tetrahydrofuran was cooled to −78° C., and then 1.05 ml of butyllithium (1.6 M, hexane solution) was dropped thereinto. Into the resulting reaction solution was dropped a solution of 280 mg of 6-((((tert-butyl(dimethyl)silyl)oxy)methyl)-N-(3-(methoxymethyl)thiazol-2(3H)-ylidene)pyridin-2-amine in 5 ml of tetrahydrofuran, followed by stirring at −78° C. for 30 minutes. A solution of N-fluorobenzenesulfonimide in 5 ml of tetrahydrofuran was dropped thereinto. After having the temperature of the resulting reaction solution allowed to −30° C., 230 μl of acetic acid was dropped thereinto. The resulting reaction solution was diluted with ethyl acetate, and then washed with water and brine. The resulting organic layer was dried over anhydrous sodium sulfate and filtered, and the filtrate was concentrated in vacuo. The result-

(3) Synthesis of 6-((4-(3-chloro-2-fluorobenzoyl) piperazin-1-yl)methyl)-N-(5-fluorothiazol-2-yl)pyridin-2-amine

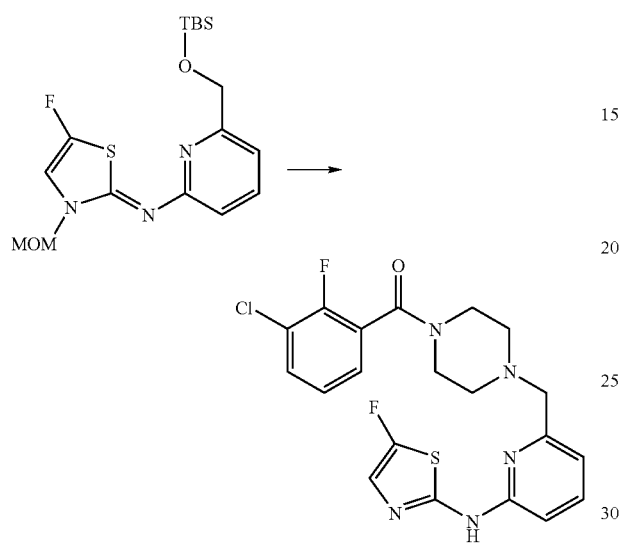

6-(((tert-Butyl(dimethyl)silyl)oxy)methyl)-N-(5-fluoro-3-(methoxymethyl)thiazol-2(3H)-ylidene)pyridin-2-amine was subjected to the process similar to Example 5-(3) and subsequently the processes similar to Examples 16-(2) to (4) to give the title compound.

Spectral data of the title compound are as follows.
Mass: 450 (M+1)+

Example 113

Synthesis of 4-((4-(3-chloro-2-fluorobenzoyl)piperazin-1-yl)methyl)-N-thiazol-2-ylpyrimidin-2-amine ¹H-NMR (CDCl₃) δ: 8.58 (d, J=4.8 Hz, 1H), 7.55 (d, J=3.2 Hz, 1H), 7.48-7.42 (m, 1H), 7.31-7.25 (m, 1H), 7.19-7.13 (m, 1H), 7.06 (d, J=4.8 Hz, 1H), 6.90 (d, J=3.2 Hz, 1H), 3.88 (brs, 2H), 3.70 (s, 2H), 3.39 (brs, 2H), 2.68 (t, J=4.8 Hz, 2H), 2.55 (brs, 2H)
Mass: 433 (M+1)+

Example 114

Synthesis of 6-((4-(2-fluoro-3-(trifluoromethyl)benzoyl)piperazin-1-yl)methyl)-N-(3-methyl-1H-pyrazol-5-yl)pyrazin-2-amine ¹H-NMR (CDCl₃) δ: 8.51 (s, 1H), 8.09 (s, 1H), 7.70-7.56 (m, 2H), 7.52 (s, 1H), 7.37-7.20 (m, 2H), 6.26 (s, 1H), 3.89 (brs, 2H), 3.64 (s, 2H), 3.37 (brs, 2H), 2.66 (dd, J=5.1, 4.9 Hz, 2H), 2.54 (brs, 2H)
Mass: 450 (M+1)+

Example 115

Synthesis of 6-(((1S,4S)-5-(3-chloro-2-fluorobenzoyl)-2,5-diazabicyclo[2.2.1]hept-2-yl)methyl)-N-(3-methyl-1H-pyrazol-5-yl)pyridin-2-amine ¹H-NMR (CDCl₃) δ: 8.45 (s, 1H), 8.08 (s, 1H), 7.47 (t, J=6.8 Hz, 1H), 7.33 (t, J=5.9 Hz, 1H), 7.19-7.14 (m, 2H), 6.07 (s, 1H), 4.94-2.71 (m, 8H), 2.32 (s, 3H), 2.07-1.99 (m, 1H), 1.88-1.79 (m, 1H)
Mass: 442 (M+1)+

Example 116

Synthesis of 2-{[4-(3-chloro-2-fluorobenzoyl)piperazin-1-yl]methyl}-N,N-dimethyl-6-(1H-pyrazol-3-ylamino)isonicotinamide Trifluoroacetate (1) Synthesis of dimethyl 4-hydroxypyridine-2,6-dicarboxylate hydrochloride

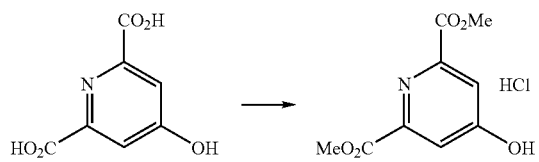

The tile compound was prepared from chelidamic acid in accordance with the method disclosed in J. Am. Chem. Soc., 70, 3908 (1948).

(2) Synthesis of dimethyl 4-benzyloxypyridine-2,6-dicarboxylate

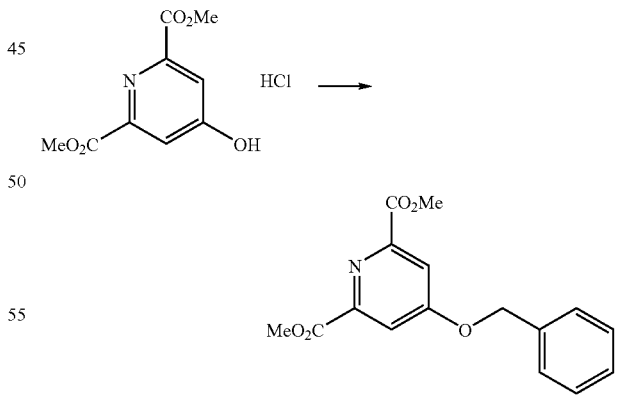

To a solution of 100 g of dimethyl 4-hydroxypyridine-2,6-dicarboxylate hydrochloride dissolved in 500 ml of N,N-dimethylformamide, 122 g of potassium carbonate was added, and the mixture was stirred at room temperature for 1 hour. 52.5 ml of benzyl bromide was added to the resulting reaction mixture, and it was stirred at 50° C. overnight. The reaction mixture was poured into water; and then the resulting

(3) Synthesis of monomethyl 4-benzyloxypyridine-2,6-dicarboxylate

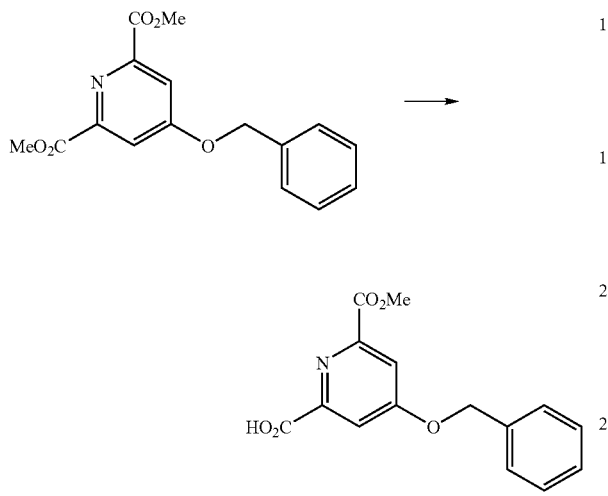

To a solution of 97 g of dimethyl 4-benzyloxypyridine-2,6-dicarboxylate dissolved in 1.5 l of methanol, 18.0 g of potassium hydroxide was added at 50° C., and the mixture was stirred at 60° C. for 2 hours. The resulting reaction mixture was poured into a mixture of diethyl ether, hexane and water. The aqueous layer was separated, washed with diethyl ether, and neutralized with concentrated hydrochloric acid. The resulting white solid was collected after filtration, washed with water, and dried in vacuo to afford the title compound.

(4) Synthesis of methyl 6-amino-4-(benzyloxy)pyridine-2-carboxylate

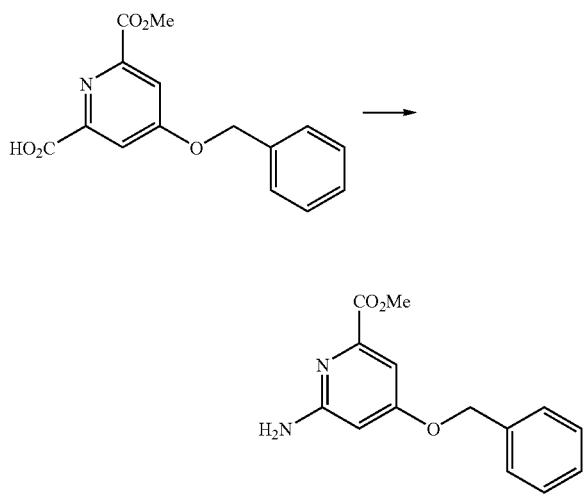

white solid was collected after filtration, washed with water, and dried in vacuo to afford the title compound.

In accordance with the same manner as in Example 81-(3) and 81-(4), the title compound was obtained using monomethyl 4-benzyloxypyridine-2,6-dicarboxylate.

(5) Synthesis of methyl 4-(benzyloxy)-6-chloropyridine-2-carboxylate

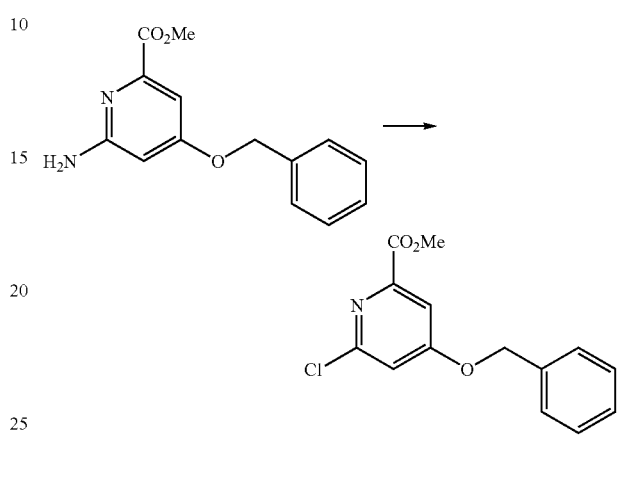

To a solution of 258 mg of methyl 6-amino-4-(benzyloxy)pyridine-2-carboxylate dissolved in 5 ml of chloroform, 170 mg of tert-butyl nitrate and 210 mg of copper(II) chloride were added, and the mixture was stirred for 6 hours with the light being shut out. Then saturated sodium bicarbonate was added to the resulting reaction mixture, and then the mixture was extracted with ethyl acetate. The organic layer was concentrated under a reduced pressure. The resulting residue was purified by flash chromatography (eluent: hexane/ethyl acetate) to yield the title compound.

(6) Synthesis of methyl 4-(benzyloxy)-6-((1-((2-(trimethylsilyl)ethoxy)methyl)-1H-pyrazol-3-yl)amino)pyridine-2-carboxylate

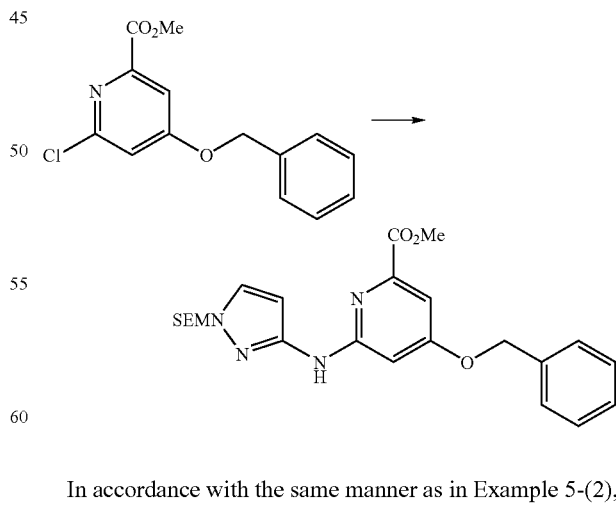

In accordance with the same manner as in Example 5-(2), the title compound was obtained using methyl 4-(benzyloxy)-6-chloropyridine-2-carboxylate and 1-((2-(trimethylsilyl)ethoxy)methyl)-1-H-pyrazol-3-amine obtained in Reference Example 2.

(7) Synthesis of methyl 4-hydroxy-6-((1-((2-(trimethylsilyl)ethoxy)methyl)-1H-pyrazol-3-yl)amino)pyridine-2-carboxylate

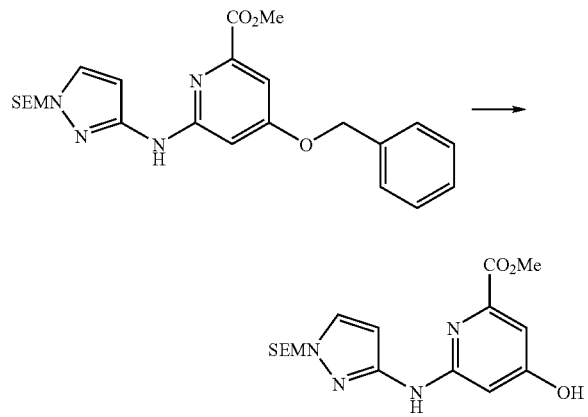

A mixture of 18 g of methyl 4-(benzyloxy)-6-((1-((2-(trimethylsilyl)ethoxy)methyl)-1H-pyrazol-3-yl)amino)pyridine-2-carboxylate dissolved in 200 ml of methanol with 200 ml of tetrahydrofuran was charged with 1.8 g of 20% palladium hydroxide on carbon catalyst, and the mixture was stirred at room temperature for 2 hours under hydrogen atmosphere at 1 atm. The reaction mixture was filtered and concentrated to give crude title compound.

(8) Synthesis of 2-(hydroxymethyl)-6-((1-((2-(trimethylsilyl)ethoxy)methyl)-1H-pyrazol-3-yl)amino)pyridin-4-ol

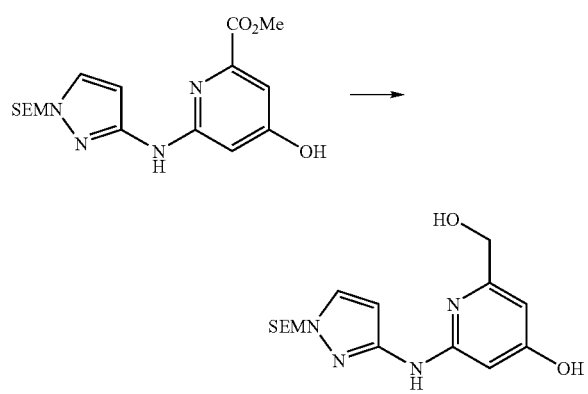

To 16 g of methyl 4-hydroxy-6-((1-((2-(trimethylsilyl)ethoxy)methyl)-1H-pyrazol-3-yl)amino)pyridine-2-carboxylate dissolved in 200 ml of tetrahydrofuran, 2.0 M of lithium borohydride dissolved in 30 ml of tetrahydrofuran solution was added, and the mixture was stirred at 60° C. for 1 hour. The resulting mixture was cooled to 0° C., and then 10% hydrochrolic acid in methanol was added thereto to adjust the pH of the solution to 4. After stirred 30 minutes at room temperature, the mixture was concentrated to give the title compound.

(9) Synthesis of 2-(((tert-butyl(dimethyl)silyl)oxy)methyl)-6-((1-((2-(trimethylsilyl)ethoxy)methyl)-1H-pyrazol-3-yl)amino)pyridin-4-ol

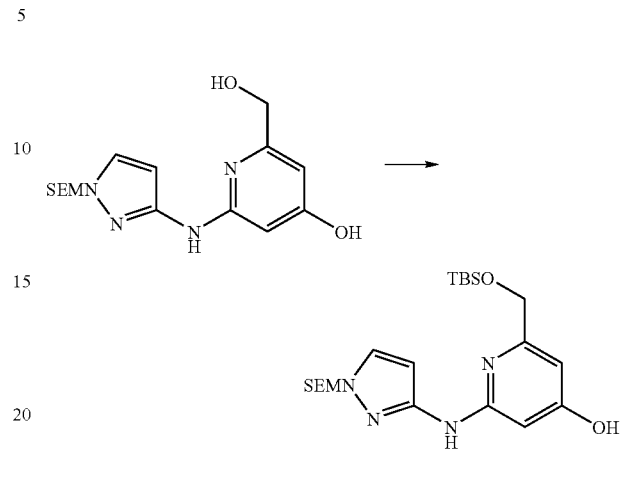

In the same manner as in Example 5-(1), the title compound was obtained using 2-(hydroxymethyl)-6-[(1-{[2-(trimethylsilyl)ethoxy]methyl}-1H-pyrazol-3-yl)amino]pyridin-4-ol.

(10) Synthesis of 2-(((tert-butyl(dimethyl)silyl)oxy)methyl)-6-((1-((2-(trimethylsilyl)ethoxy]methyl)-1H-pyrazol-3-yl)amino)pyridin-4-yl trifluoromethanesulfonate

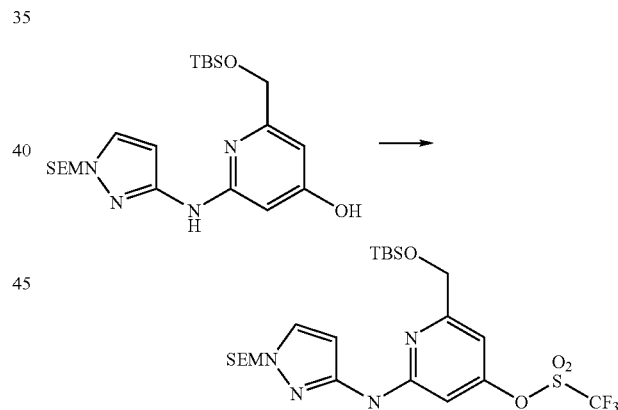

9.7 ml of trifluoromethanesulfonic anhydride was added to a mixture of 12.9 g of 2-(((tert-butyl(dimethyl)silyl)oxy)methyl)-6-((1-((2-(trimethylsilyl)ethoxy)methyl)-1H-pyrazol-3-yl)amino)pyridin-4-ol, 14.2 g of 4-(dimethylamino)pyridine and 290 ml of chloroform at 0° C. The resulting mixture was stirred for 2 hours at room temperature and then diluted with ethyl acetate. The resulting solution was charged with 100 ml of 0.1 mol/l hydrochloric acid at 0° C. The organic layer separated was washed with saturated sodium bicarbonate, water and brine. The resulting organic layer was dried over magnesium sulfate and filtered, and the filtrate was concentrated under a reduced pressure. The resulting residue was purified by a silica gel column chromatography (eluent: hexane/ethyl acetate=10/1 to 1/1) to give the title compound.

(11) Synthesis of methyl 2-(((tert-butyl(dimethyl) silyl)oxy)methyl)-6-((1-((2-(trimethylsilyl)ethoxy] methyl)-1H-pyrazol-3-yl)amino)isoniotinate

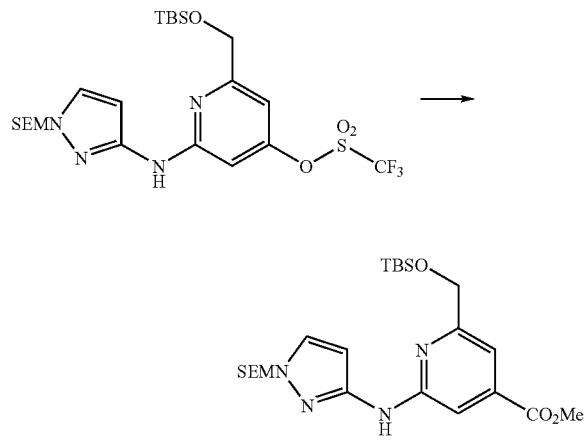

In the same manner as in Example 1-(2), the title compound was obtained using 2-(((tert-butyl(dimethyl)silyl)oxy) methyl)-6-((1-((2-(trimethylsilyl)ethoxy)methyl)-1H-pyrazol-3-yl)amino)pyridin-4-yl trifluoromethanesulfonate.

(12) Synthesis of 2-(((tert-butyl(dimethyl)silyl)oxy) methyl)-N,N-dimethyl-6-((1-((2-(trimethylsilyl) ethoxy)methyl)-1H-pyrazol-3-yl)amino)isonicotinamide

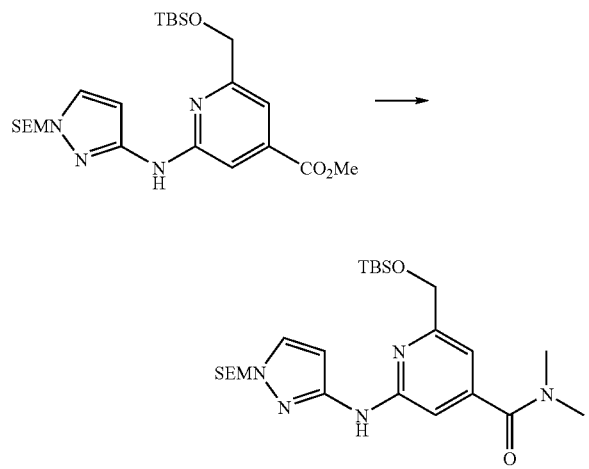

In the same manner as in Example 84, the title compound was obtained using methyl 2-(((tert-butyl(dimethyl)silyl) oxy)methyl)-6-((1-((2-(trimethylsilyl)ethoxy]methyl)-1H-pyrazol-3-yl)amino)isonicotinate.

(13) Synthesis of 2-((4-(3-chloro-2-fluorobenzoyl) piperazin-1-yl)methyl)-N,N-dimethyl-6-(1H-pyrazol-3-ylamino)isonicotinamide

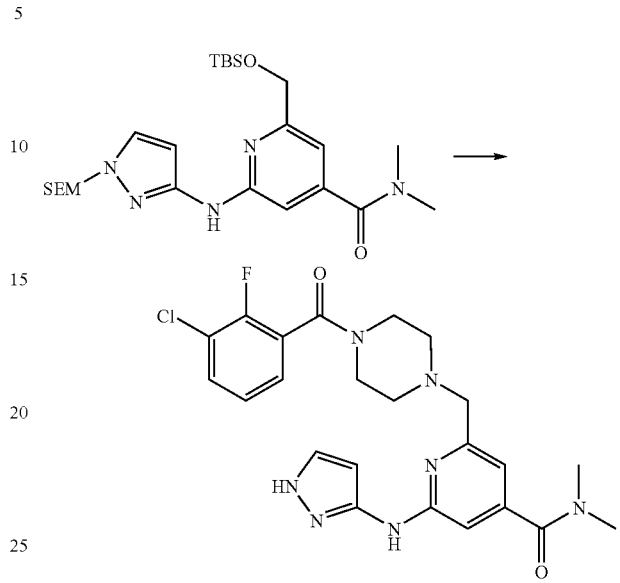

In the same manner as in Example 16, the title compound was obtained using 2-(((tert-butyl(dimethyl)silyl)oxy)methyl)-N,N-dimethyl-6-((1-((2-(trimethylsilyl)ethoxy)methyl)-1H-pyrazol-3-yl)amino)isonicotinamide.

Spectral data of the title compound are as follows.

$^1$H-NMR (CDCl$_3$) δ: 7.91 (brs, 1H), 7.47-7.41 (m, 2H), 7.29-7.24 (m, 1H), 7.15 (t, J=8.0 Hz, 1H), 6.99 (brs, 1H), 6.78 (s, 1H), 6.01 (brs, 1H), 3.85 (brs, 2H), 3.60 (s, 2H), 3.35 (brs, 2H), 3.10 (s, 3H), 2.95 (s, 3H), 2.61 (brt, J=5.2 Hz, 2H), 2.48 (brs, 2H)

Mass: 486 (M+1)$^+$

Examples 117 to 121 were synthesized in the same manner as in Example 116 as follows.

Example 117

Synthesis of 2-((4-(2-fluoro-3-(trifluoromethyl)benzoyl)piperazin-1-yl}methyl)-N,N-dimethyl-6-(1H-pyrazol-3-ylamino)isonicotinamide $^1$H-NMR (CDCl$_3$) δ: 7.71-7.65 (m, 1H), 7.63-7.58 (m, 1H), 7.48 (brs, 1H), 7.33 (t, J=8.0 Hz, 1H), 6.84 (s, 1H), 6.13 (brs, 1H), 3.90 (brs, 2H), 3.70 (s, 2H), 3.40 (brs, 2H), 3.11 (s, 3H), 2.98 (s, 3H), 2.74-2.67 (m, 2H), 2.59 (brs, 2H)

Mass: 520 (M+1)$^+$

Example 118

Synthesis of 6-((4-(2-fluoro-3-(trifluoromethyl)benzoyl)piperazin-1-yl)methyl)-4-((4-methylpiperazin-1-yl)carbonyl)-N-1H-pyrazol-3-ylpyridin-2-amine Trifluoroacetate $^1$H-NMR (CD$_3$OD) δ: 7.85 (brt, J=6.8 Hz, 1H), 7.77 (d, J=2.4 Hz, 1H), 7.74 (brt, J=7.2 Hz, 1H), 7.49 (t, J=8.0 Hz, 1H), 7.19 (s, 1H), 7.01 (s, 1H), 6.21 (d, J=2.4 Hz, 1H), 4.23 (s, 2H), 4.06 (brs, 2H), 3.63 (brs, 2H), 3.18 (brs, 2H), 3.06 (brs, 2H) 2.95 (s, 3H)

Mass: 575 (M+1)$^+$

Example 119

Synthesis of 6-((4-(2-fluoro-3-(trifluoromethyl)benzoyl)piperazin-1-yl)methyl)-4-(piperazin-1-ylcarbonyl)-N-1H-pyrazol-3-ylpyridin-2-amine Trifluoroacetate $^1$H-NMR (CD$_3$OD) δ: 7.85 (brt, J=7.2 Hz, 1H), 7.79 (d, J=2.4 Hz, 1H), 7.74 (brt, J=6.4 Hz, 1H), 7.49 (t, J=8.0 Hz, 1H), 7.18 (s, 1H), 7.03 (s, 1H), 6.22 (d, J=2.4 Hz, 1H), 4.24 (s, 2H), 4.06 (brs, 2H), 3.98 (brs, 2H), 3.71 (brs, 2H), 3.63 (brs, 2H), 3.19 (brs, 2H), 3.07 (brs, 2H)

Mass: 561 (M+1)$^+$

Example 120

Synthesis of 6-((4-(2-fluoro-3-(trifluoromethyl)benzoyl)piperazin-1-yl)methyl)-N-1H-pyrazol-3-yl-4-((4-pyridin-2-ylpiperazin-1-yl)carbonyl)pyridin-2-amine Trifluoroacetate $^1$H-NMR (CD$_3$OD) δ: 8.08 (ddd, J=9.2, 7.2, 1.6 Hz, 1H), 8.01 (dd, J=6.4, 1.6 Hz, 1H), 7.85 (brt, J=7.2 Hz, 1H), 7.79 (d, J=2.4 Hz, 1H), 7.74 (brt, J=6.8 Hz, 1H), 7.49 (t, J=8.0 Hz, 1H), 7.39 (d, J=9.2 Hz, 1H), 7.19 (s, 1H), 7.08-7.02 (m, 2H), 6.22 (d, J=2.4 Hz, 1H), 4.24 (s, 2H), 4.06 (s, 2H), 3.96 (s, 2H), 3.89 (s, 2H), 3.76 (brs, 2H), 3.73 (brs, 2H), 3.63 (brs, 2H), 3.18 (brs, 2H), 3.07 (brs, 2H)

Mass: 638 (M+1)$^+$

Example 121

Synthesis of 6-((4-(2-fluoro-3-(trifluoromethyl)benzoyl)piperazin-1-yl)methyl)-4-(morpholin-4-ylcarbonyl)-N-1H-pyrazol-3-ylpyridin-2-amine Trifluoroacetate $^1$H-NMR (CD$_3$OD) δ: 7.85 (brt, J=7.2 Hz, 1H), 7.79 (d, J=2.4 Hz, 1H), 7.73 (brt, J=6.8 Hz, 1H), 7.49 (t, J=7.6 Hz, 1H), 7.09 (s, 1H), 7.00 (s, 1H), 6.20 (d, J=2.4 Hz, 1H), 4.19 (s, 2H), 4.05 (brs, 2H), 3.75 (brs, 4H), 3.66-3.58 (m, 4H), 3.47-3.41 (m, 2H), 3.16-3.10 (m, 2H), 3.03-2.97 (m, 2H)

Mass: 562 (M+1)$^+$

Example 122

Synthesis of 2-((4-(2-fluoro-3-(trifluoromethyl)benzoyl)piperazin-1-yl)methyl)-6-(1H-pyrazol-3-ylamino)isonicotinonitrile In the same manner as in Example 104-(2) to (3), the title compound was obtained using 2-(((tert-butyl(dimethyl)silyl)oxy)methyl)-6-((1-((2-(trimethylsilyl)ethoxy]methyl)-1H-pyrazol-3-yl)amino)pyridin-4-yl trifluoromethanesulfonate obtained in Example 116-(10).

Spectral data of the title compound are as follows.

$^1$H-NMR (CDCl$_3$) δ: 7.71 (brs, 1H), 7.68 (brt, J=7.6 Hz, 1H), 7.61 (brt, J=6.4 Hz, 1H), 7.51 (brd, J=2.0 Hz, 1H), 7.46 (brs, 1H), 7.33 (t, J=7.6 Hz, 1H), 7.05 (brs, 1H), 6.15 (brs, 1H), 3.89 (brs, 2H), 3.62 (s, 2H), 3.38 (brs, 2H), 2.64 (brt, J=5.2 Hz, 2H), 2.52 (brs, 2H)

Mass: 474 (M+1)$^+$

Example 123

Synthesis of 6-((4-(2-fluoro-3-(trifluoromethyl)benzoyl)piperazin-1-yl)methyl)-4-(2-methyl-2H-tetrazol-5-yl)-N-1H-pyrazol-3-ylpyridin-2-amine In the same manner as in Example 106, the title compound was obtained using 2-(((tert-butyl(dimethyl)silyl)oxy)methyl)-6-((1-((2-(trimethylsilyl)ethoxy]methyl)-1H-pyrazol-3-yl)amino)isonicotinonitrile obtained in Example 122.

Spectral data of the title compound are as follows.

$^1$H-NMR (CDCl$_3$) δ: 7.71 (brs, 1H), 7.68 (brt, J=7.6 Hz, 1H), 7.61 (brt, J=6.4 Hz, 1H), 7.51 (brd, J=2.0 Hz, 1H), 7.46 (brs, 1H), 7.33 (t, J=7.6 Hz, 1H), 7.05 (brs, 1H), 6.15 (brs, 1H), 3.89 (brs, 2H), 3.62 (s, 2H), 3.38 (brs, 2H), 2.64 (brt, J=5.2 Hz, 2H), 2.52 (brs, 2H)

Mass: 474 (M+1)$^+$

Example 124

Synthesis of (thiazol-2-yl)-(6-(4-(2,3-difluorobenzoyl)-piperazin-1-ylmethyl)-pyridin-2-yl)-amine hydrochloride A mixture of 293 mg of (thiazol-2-yl)-(6-(4-(2,3-difluorobenzoyl)-piperazin-1-ylmethyl)-pyridin-2-yl)-amine (Example 4) with 1 ml of methanol was charged with a hydrochloric acid-1,4-dioxane solution (4 M, 3 ml), followed by stirring at room temperature for 1 hour. The reaction mixture was concentrated in vacuo and the residue was suspended in diethyl ether, filtered and collected to give the title compound.

Spectral data of the title compound are as follows.

$^1$H-NMR (DMSO-d$_6$) δ: 7.88-7.81 (m, 1H), 7.60-7.49 (m, 1H), 7.49-7.43 (m, 1H), 7.36-7.25 (m, 3H), 7.21-7.10 (m, 2H), 4.43 (s, 2H), 3.74-3.23 (m, 8H)

Mass: 416 (M+1)$^+$

Example 125

Synthesis of 6-((4-(3-chloro-2-fluorobenzoyl)piperazin-1-yl)methyl)-N-thiazol-2-ylpyridin-2-amine Hydrochloride 5.09 g of 6-((4-(3-chloro-2-fluorobenzoyl)piperazin-1-yl)methyl)-N-thiazol-2-ylpyridin-2-amine (Example 5) was suspended in 100 ml of ethanol, and aqueous hydrogen chloride solution (1.0 M, 11.8 ml) was added thereto at room temperature. The reaction mixture was stirred at 80° C. for 30 minutes and then cooled and evaporated. The resulting residue was dissolved in 250 ml of ethanol by heating under reflux. Then stirring and heating were stopped and the solution was cooled slowly to room temperature. The precipitate was filtered and dried to give 6-((4-(3-chloro-2-fluorobenzoyl)piperazin-1-yl)methyl)-N-thiazol-2-ylpyridin-2-amine hydrochloride as crystal.

Spectral data of the title compound are as follows.

$^1$H-NMR (DMSO-d$_6$) δ: 11.49 (brs, 1H), 7.79 (t, J=7.8 Hz, 1H), 7.73-7.67 (m, 1H), 7.47-7.41 (m, 2H), 7.32 (t, J=7.8 Hz, 1H), 7.27 (d, J=7.0 Hz, 1H), 7.11 (d, J=8.4 Hz, 1H), 7.07 (d, J=3.5 Hz, 1H), 4.39 (s, 2H), 3.69-3.20 (m, 8H)

Mass: 432 (M+1)$^+$ m.p.: 141-167° C. (ethanol)

Example 126

Synthesis of 6-((4-(3-chloro-2-fluorobenzoyl)piperazin-1-yl)methyl)-N-1H-pyrazol-3-ylpyridin-2-amine hydrochloride In the same manner as in Example 124, the title compound was obtained using the compound of Example 16.

Spectral data of the title compound are as follows.
$^1$H-NMR (DMSO-$d_6$) δ: 10.98 (brs, 1H), 7.91 (d, J=2.3 Hz, 1H), 7.82 (dd, J=8.5, 7.3 Hz, 1H), 7.77-7.65 (m, 1H), 7.47-7.41 (m, 1H), 7.39-7.30 (m, 1H), 7.15 (d, J=8.6 Hz, 1H), 7.09 (d, J=7.0 Hz, 1H), 6.27 (d, J=2.5 Hz, 1H), 4.34 (s, 2H), 4.30-3.50 (m, 4H), 3.23 (brs, 2H), 3.11 (brs, 2H)
Mass: 415 (M+1)$^+$

Example 127

Synthesis of 6-((4-(3-chloro-2-fluorobenzoyl)piperazin-1-yl)methyl)-N-(5-methyl-1H-pyrazol-3-yl)pyridin-2-amine hydrochloride In the same manner as in Example 124, the title compound was obtained using the compound of Example 25.

Spectral data of the title compound are as follows.
$^1$H-NMR (CD$_3$OD) δ: 7.88 (dd, J=8.0, 7.8 Hz, 1H), 7.66-7.60 (m, 1H), 7.43-7.37 (m, 1H), 7.30 (bt, J=8.8 Hz, 1H), 7.16 (d, J=7.8 Hz, 1H), 7.05 (d, J=8.0 Hz, 1H), 6.02 (s, 1H), 4.40 (bs, 2H), 3.73 (bs, 2H), 3.37-3.14 (m, 6H), 2.41 (s, 3H)
Mass: 429 (M+1)$^+$

Example 128

Synthesis of 6-((4-(2-fluoro-3-(trifluoromethyl)benzoyl)piperazin-1-yl)methyl)-N-1H-pyrazol-3-ylpyrazin-2-amine Hydrochloride 19.8 g of 6-((4-(2-fluoro-3-(trifluoromethyl)benzoyl)piperazin-1-yl)methyl)-N-1H-pyrazol-3-ylpyrazin-2-amine (Example 44) was suspended in 200 ml of ethanol, and aqueous hydrogen chloride solution (1.0 M, 44.1 ml) was added thereto. The reaction mixture was stirred at room temperature for 1 hour and then evaporated. The resulting residue was solidified with 200 ml of heptane, evaporated and dried to give 6-((4-(2-fluoro-3-(trifluoromethyl)benzoyl)piperazin-1-yl)methyl)-N-1H-pyrazol-3-ylpyrazin-2-amine hydrochloride.

Spectral data of the title compound are as follows.
$^1$H-NMR (DMSO-$d_6$) δ: 10.10 (s, 1H), 8.45 (s, 1H), 8.12 (s, 1H), 7.91 (t, J=7.3 Hz, 1H), 7.82 (t, J=7.0 Hz, 1H), 7.64-7.61 (m, 1H), 7.52 (t, J=7.7 Hz, 1H), 6.54 (s, 1H), 4.37 (s, 2H), 3.66-3.18 (m, 8H)
Mass: 450 (M+1)$^+$

Example 129

Synthesis of 6-((4-(3-chloro-2-fluorobenzoyl)piperazin-1-yl)methyl)-N-(5-methyl-1H-pyrazol-3-yl)pyrazin-2-amine Hydrochloride In the same manner as in Example 124, the title compound was obtained using the compound of Example 56.

Spectral data of the title compound are as follows.
$^1$H-NMR (CD$_3$OD) δ: 8.41 (s, 1H), 8.31 (s, 1H), 7.67-7.61 (m, 1H), 7.42 (t, J=6.8 Hz, 1H), 7.31 (t, J=7.8 Hz, 1H), 6.17 (s, 1H), 4.57 (s, 2H), 3.83-3.77 (m, 2H), 3.76-3.25 (m, 6H), 2.44 (s, 3H)
Mass: 430 (M+1)$^+$

Example 130

Synthesis of 6-((4-(3-chloro-2-fluorobenzoyl)piperazin-1-yl)methyl)-N-(5-chlorothiazol-2-yl)pyridin-2-amine hydrochloride In the same manner as in Example 124, the title compound was obtained using the compound of Example 75.

Spectral data of the title compound are as follows.
$^1$H-NMR (DMSO-$d_6$) δ: 11.68 (brs, 1H), 7.83 (dd, J=8.0, 7.6 Hz, 1H), 7.70 (dd, J=7.4, 7.0 Hz, 1H), 7.50-7.30 (m, 4H), 7.09 (d, J=8.4 Hz, 1H), 4.44 (s, 2H), 3.90-3.18 (m, 8H)
Mass: 466 (M+1)$^+$

Example 131

Synthesis of 2-((4-(2-fluoro-3-(trifluoromethyl)benzoyl)piperazin-1-yl}methyl)-N,N-dimethyl-6-(1H-pyrazol-3-ylamino)isonicotinamide Hydrochloride In the same manner as in Example 128, the title compound was obtained using the compound of Example 117.

Spectral data of the title compound are as follows.
$^1$H-NMR (CD$_3$OD) δ: 7.85 (brt, J=7.2 Hz, 1H), 7.82 (d, J=2.4 Hz, 1H), 7.77-7.71 (m, 1H), 7.49 (brt, J=8.0 Hz, 1H), 7.07 (s, 1H), 7.02 (s, 1H), 6.21 (d, J=2.4 Hz, 1H), 4.21 (s, 2H), 4.07 (brs, 2H), 3.67-3.60 (m, 2H), 3.17-3.08 (m, 5H), 3.04-2.97 (m, 5H)
Mass: 520 (M+1)$^+$

REFERENCE EXAMPLE

Reference Example 1

Synthesis of 1-(3-chloro-2-fluorobenzoyl)piperazine hydrochloride (1) Synthesis of tert-butyl 4-(3-chloro-2-fluorobenzoyl)piperazine-1-carboxylate

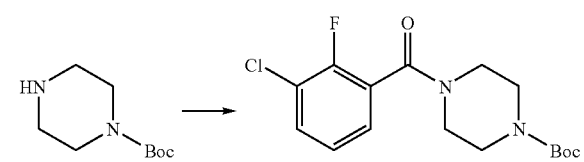

A mixture of 19.4 g of 1-Boc-piperazine, 24.0 g of 1-(3-dimethylaminopropyl)-3-ethylcarbodiimide hydrochloride, 19.1 g of 1-hydroxybenzotriazole, 20.0 g of 3-chloro-2-fluorobenzoic acid and 200 ml of chloroform was stirred at room temperature for 4 hours. The resulting mixture was diluted with chloroform, and an insoluble matter was filtered off using Celite. Then, the filtrate was washed with water and brine. The resulting organic layer was dried over magnesium sulfate and filtered, and the filtrate was concentrated in vacuo. The resulting residue was purified by a silica gel column chromatography (eluent: hexane/ethyl acetate=9/1 to 1/1) to give title compound.

(2) Synthesis of 1-(3-chloro-2-fluorobenzoyl)piperazine Hydrochloride

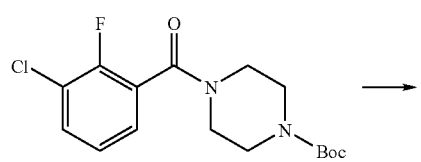

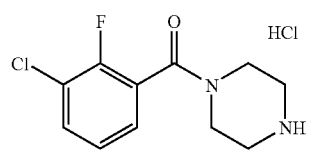

To a mixture of 35.1 g of tert-butyl 4-(3-chloro-2-fluorobenzoyl)piperazine-1-carboxylate and 50 ml of methanol was added a hydrochloric acid-1,4-dioxane solution (4 M, 100 ml) followed by stirring at room temperature for 2.5 hours. The reaction mixture was concentrated in vacuo and the residue was suspended in diethyl ether, filtered and collected to give the title compound.

Spectral data of the title compound are as follows.
$^1$H-NMR (DMSO-$d_6$) δ: 9.68 (br, 1H), 7.74-7.65s (m, 1H), 7.50-7.41 (m, 1H), 7.37-7.28 (m, 1H), 3.88 (br, 2H), 3.57-3.30 (m, 2H), 3.16 (br, 2H), 3.03 (br, 2H)
Mass: 243 (M+1)$^+$

Reference Example 2

Synthesis of 1-((2-(trimethylsilyl)ethoxy)methyl)-1H-pyrazol-3-amine

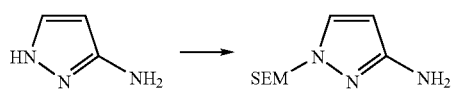

To a solution of 10 g of 1H-pyrazol-3-amine in 100 ml of N,N-dimethylformamide was added 9.6 g of sodium hydride (60%, in oil) under cooling with ice. The reaction mixture was stirred for 30 minutes, and then 21.3 ml of 2-(trimethylsilyl)ethoxymethyl chloride was added thereto. After stirring the resulting mixture at room temperature for 1 hour, aqueous ammonium chloride was added thereto, and the mixture was extracted with chloroform. The resulting organic layer was washed with water and brine, and then dried over magnesium sulfate. The organic layer was filtered and concentrated in vacuo. The resulting residue was purified by a silica gel column chromatography (eluent: hexane/ethyl acetate=4/1 to 1/2) to give the title compound.

Reference Example 3

Synthesis of 5-methyl-1-((2-(trimethylsilyl)ethoxy)methyl)-1H-pyrazol-3-amine

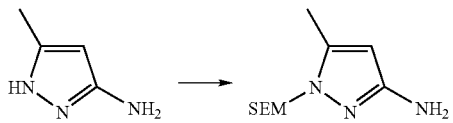

In accordance with the manner of Reference Example 2, the title compound was obtained from 5-methyl-1H-pyrazol-3-amine.

Reference Example 4

Synthesis of 5-cyclopropyl-1-((2-(trimethylsilyl)ethoxy)methyl)-1-H-pyrazol-3-amine or 3-cyclopropyl-1-((2-(trimethylsilyl)ethoxy)methyl)-1H-pyrazol-5-amine

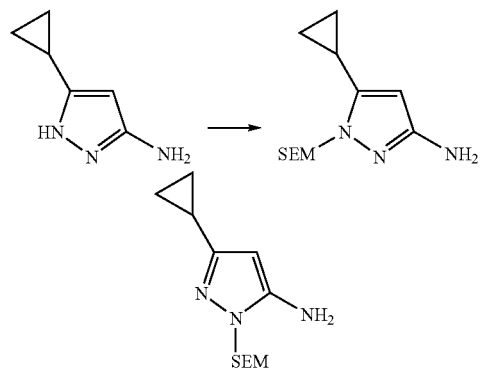

In accordance with the manner of Reference Example 2, the title compound was obtained from 5-cyclopropyl-1H-pyrazol-3-amine.

Spectral data of the title compound are as follows.
$^1$H-NMR (CDCl$_3$) δ: 5.31 (s, 2H), 5.26 (s, 1H), 3.62-3.56 (m, 2H), 1.84-1.76 (m, 1H), 0.97-0.88 (m, 4H), 0.67-0.62 (m, 2H), −0.02s (s, 9H)
Mass: 254 (M+1)$^+$

Reference Example 5

Synthesis of 6-(tetrahydro-2H-pyran-2-yloxy)-1,4-diazepane (1) Synthesis of 2-(2-bromo-1-(bromomethyl)ethoxy)tetrahydro-2H-pyran

To a mixture of 10 g of 1,3-dibromopropan-2-ol, 5.0 ml of 3,4-dihydro-2H-pyran and 50 ml of chloroform was added a catalytic amount of p-toluenesulfonic acid monohydrate followed by stirring at room temperature for 3 hours. The reaction solution was concentrated, diluted with diethyl ether and washed with saturated sodium bicarbonate and brine. The resulting organic layer was dried over magnesium sulfate and filtered, and the filtrate was concentrated to give the title compound.

(2) Synthesis of 1,4-dibenzyl-6-(tetrahydro-2H-pyran-2-yloxy)-1,4-diazepane

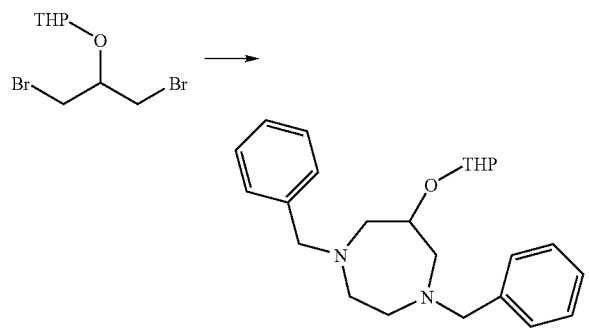

A mixture of 2-(2-bromo-1-(bromomethyl)ethoxy)tetrahydro-2H-pyran obtained above, 10.8 ml of N,N'-dibenzylethane-1,2-diamine, 19.0 g of potassium carbonate and 50 ml of N,N'-dimethylformamide was stirred at 120° C. for 3 hours. The reaction solution was diluted with diethyl ether and washed with water and brine. The resulting organic layer was dried over magnesium sulfate and filtered, and the filtrate was concentrated. The resulting residue was purified by a silica gel column chromatography (eluent: hexane to hexane/ethyl acetate=4/1) to give the title compound.

(3) Synthesis of 6-(tetrahydro-2H-pyran-2-yloxy)-1,4-diazepane

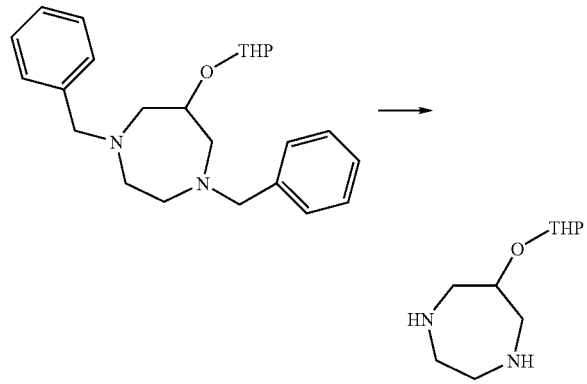

3.06 g of 1,4-dibenzyl-6-(tetrahydro-2H-pyran-2-yloxy)-1,4-diazepane was dissolved in 50 ml of methanol and 1 g of a 20% palladium hydroxide on carbon catalyst was added thereto. The resulting mixture was stirred under a hydrogen atmosphere at ordinary pressure and room temperature for 5 hours. The reaction solution was filtered and the solvent was concentrated to give the title compound.

Reference Example 6

Synthesis of 1-(2-fluoro-3-(difluoromethyl)benzoyl)piperazine hydrochloride (1) Synthesis of tert-butyl 4-(3-bromo-2-fluorobenzoyl)piperazine-1-carboxylate

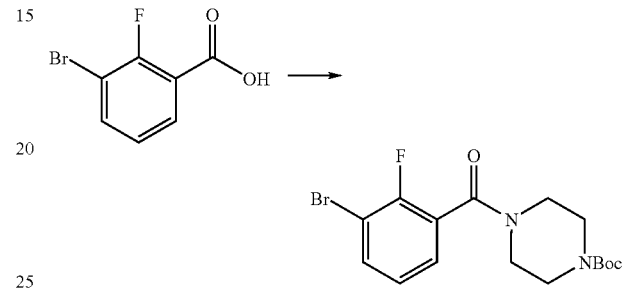

To a mixture of 220 mg of 3-bromo-2-fluorobenzoic acid, 199 mg of tert-butyl piperazine-1-carboxylate and 5.0 ml of chloroform was added 171 mg of hydroxybenzotriazole monohydrate and 215 mg of 1-(3-dimethylaminopropyl)-3-ethylcarbodiimide hydrochloride under cooling with ice, successively. After stirring at room temperature for 4 hours, saturated sodium bicarbonate was added to the reaction mixture, and the resulting mixture was extracted with chloroform. The organic layer was dried over anhydrous magnesium sulfate and filtered, and the filtrate was concentrated. The residue was purified by a silica gel column chromatography (eluent: hexane/ethyl acetate=9/1 to 1/1) to give the title compound.

(2) Synthesis of tert-butyl 4-(2-fluoro-3-formylbenzoyl)piperazine-1-carboxylate

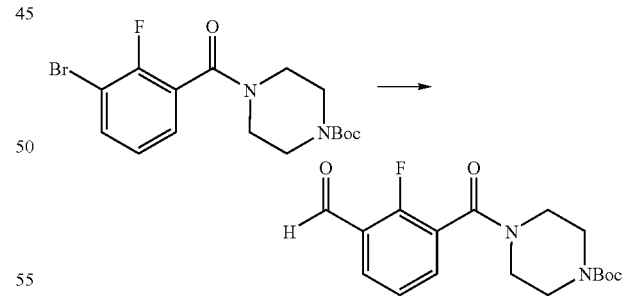

194 mg of tert-butyl 4-(3-bromo-2-fluorobenzoyl)piperazine-1-carboxylate was dissolved in 5.0 ml of tetrahydrofuran, and 1.25 ml of a solution of isobutyl magnesium chloride in tetrahydrofuran (2.0 M) was added thereto at −78° C. After stirring at the same temperature for 2 hours, 0.39 ml (5.0 mmol) of N,N-dimethylformamide was added thereto. The resulting mixture was stirred at the same temperature for 30 minutes and further stirred at 0° C. for 30 minutes. To the reaction mixture was added saturated ammonium chloride, and the mixture was extracted with chloroform. The organic layer was washed with brine and then concentrated. The residue was purified by a silica gel column chromatography (eluent: hexane/ethyl acetate=9/1 to 1/1) to give the title compound.

(3) Synthesis of tert-butyl 4-(3-difluoromethyl-2-fluorobenzoyl)piperazine-1-carboxylate

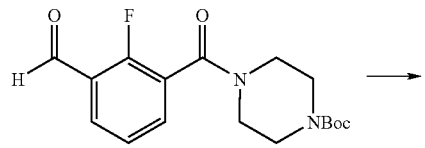

130 mg of tert-butyl 4-(2-fluoro-3-formylbenzoyl)piperazine-1-carboxylate was dissolved in 4.8 ml of dichloromethane, and 0.13 ml of diethylaminosulfur trifluoride was added thereto at room temperature. After stirring at the same temperature for 2 hours, 0.13 ml of diethylaminosulfur trifluoride was added thereto and the resulting mixture was further stirred at the same temperature for 2 hours. The reaction mixture was purified by a silica gel column chromatography (eluent: hexane/ethyl acetate=9/1 to 1/1) to give the title compound.

(4) Synthesis of 1-(3-(difluoromethyl)-2-fluorobenzoyl)piperazine Hydrochloride

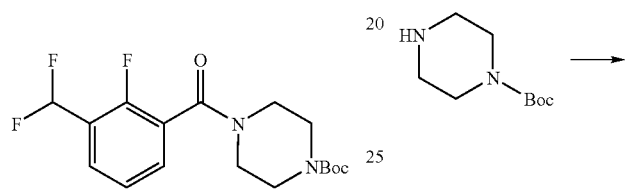

In accordance with the manner of Reference Example 1-(2), the title compound was obtained from tert-butyl 4-(3-(difluoromethyl)-2-fluorobenzoyl)piperazine-1-carboxylate.

Reference Example 7

Synthesis of 1-(2-fluoro-3-(trifluoromethyl)benzoyl)piperazine Hydrochloride (1) Synthesis of tert-butyl 4-(2-fluoro-3-(trifluoromethyl)benzoyl)piperazine-1-carboxylate

A mixture of 3.66 g of 1-Boc-piperazine, 4.53 g of 1-(3-dimethylaminopropyl)-3-ethylcarbodiimide hydrochloride, 3.61 g of 1-hydroxybenzotriazole, 4.50 g of 2-fluoro-3-(trifluoromethyl)benzoic acid and 40 ml of chloroform was stirred at room temperature for 4 hours. The reaction mixture was diluted with chloroform and then was washed with water and brine. The resulting organic layer was dried over magnesium sulfate and filtered, and the filtrate was concentrated in vacuo. The resulting residue was purified by a silica gel column chromatography (eluent: hexane/ethyl acetate=4/1 to 2/1) to give the title compound.

(2) Synthesis of 1-(2-fluoro-3-(trifluoromethyl)benzoyl)piperazine Hydrochloride

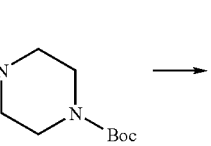

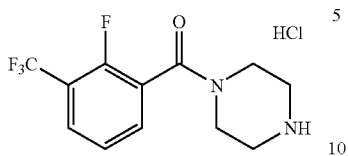

To a mixture of 7.74 g of tert-butyl 4-(2-fluoro-3-(trifluoromethyl)benzoyl)piperazine-1-carboxylate and 10 ml of methanol was added a hydrochloric acid-1,4-dioxane solution (4 M, 20 ml) followed by stirring at room temperature for 4 hours. The reaction mixture was concentrated in vacuo to give the title compound.

Spectral data of the title compound are as follows.

$^1$H-NMR (DMSO-$d_6$) δ: 7.95-7.81 (m, 2H), 7.56-7.49 (m, 1H), 3.92-3.79 (m, 2H), 3.45 (br, 2H), 3.19 (br, 2H), 3.04 (br, 2H)

Mass: 277 (M+1)$^+$

Reference Example 8

Synthesis of tert-butyl 4-(3-cyclopropyl-2-fluorobenzoyl)piperazine-1-carboxylate

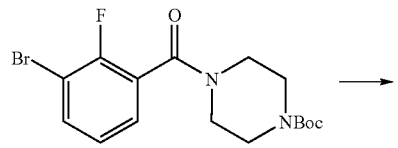

To a solution of 107 mg of tert-butyl 4-(3-bromo-2-fluorobenzoyl)piperazine-1-carboxylate in 2.0 ml of toluene and 0.1 ml of water was added 72 mg of cyclopropylboronic acid, 3.2 mg of palladium acetate, 0.052 ml of tricyclohexylphosphine (15% toluene solution) and 207 mg of potassium phosphate, successively. The reaction solution was stirred at 150° C. for 10 minutes using a microwave reaction apparatus. Water was added to the reaction mixture, and the mixture was extracted with ethyl acetate. The organic layer was washed with brine and then concentrated. The residue was purified by a silica gel column chromatography (eluent: hexane to hexane/ethyl acetate=1/1) to give the title compound.

INDUSTRIAL APPLICABILITY

The compound of the invention is characterized in that it has cell growth inhibitory action as well as synergistic action with other antitumor agents, based on excellent Aurora A selective inhibitory action, and thus it is expected as a useful antitumor agent in the field of pharmaceuticals.

What is claimed is:

1. A compound of general formula I:

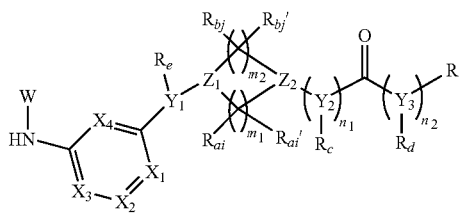

wherein:
- $m_1$ is 2;
- $m_2$ is 2;
- $n_1$ is 0 or 1;
- $n_2$ is 0 or 1;
- i is an integer of any of 1 to $m_1$;
- j is an integer of any of 1 to $m_2$;
- R is phenyl which may be substituted;
- $R_{ai}$ and $R_{ai}'$ are each independently hydrogen atom and lower alkyl;
- $R_{bj}$ and $R_{bj}'$ are each independently hydrogen atom and lower alkyl;

wherein:
- if $m_1$ is 2 and i is $i_0$ wherein $i_0$ is an integer of any of 1 to $m_1$, and further if $m_2$ is 2 and j is $j_0$ wherein $j_0$ is an integer of any of 1 to $m_2$, then one of $R_{ai0}$ and $R_{ai0}'$ and one of $R_{bj0}$ and $R_{bj0}'$ may be combined to form —$(CH_2)_n$— wherein n is 1 or 2; and
- $R_c$, $R_d$, and $R_e$ are each independently hydrogen atom or lower alkyl;
- $X_1$ is CH, $CX_{1a}$, wherein $X_{1a}$ is lower alkyl which may be substituted;
- $X_2$ is CH;
- $X_3$ is CH, or $CX_{3a}$, wherein $X_{3a}$ is lower alkyl which may be substituted;
- $X_4$ is N;
- the number of nitrogen atoms among $X_1$, $X_2$, and $X_3$, and $X_4$ is one or two;
- $Y_1$, $Y_2$, and $Y_3$ are each independently CH or N; however, if $Y_1$ is CH and $R_e$ is hydrogen atom, then the two hydrogen atoms may be substituted with oxo;
- $Z_1$ and $Z_2$ are N;
- W is:

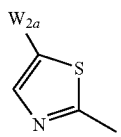

wherein $W_{2a}$ is a hydrogen atom, halogen atom, cyano, $C_{1-2}$ lower alkyl, $C_{3-5}$ cycloalkyl, or $C_{1-2}$ lower alkyl which may be substituted with one or more halogen atoms.

2. The compound according to claim 1 or a pharmaceutically acceptable salt or ester thereof, wherein:
- $n_1$ is 0;
- $n_2$ is 0; and
- R is phenyl wherein the phenyl may be substituted with one or more of the same or different substituents selected from the following:
  1) lower alkyl;
  2) a substituent selected from <substituent group $A_2$>; and
  3) lower alkyl which substituted with one or more of the same or different substituents selected from <substituent group $A_2$>, wherein:
     <substituent group $A_2$> is halogen atom, cyano, hydroxyl, amino, lower alkyl amino, di-lower alkyl amino, lower alkanoyl, lower alkanoylamino, carbamoyl, lower alkyl carbamoyl, and lower alkyl sulfonyl.

3. The compound according to claim 2 or a pharmaceutically acceptable salt or ester thereof, wherein:
- $Y_1$ is CH; and
- $R_e$ is hydrogen atom.

4. The compound according to claim 3 or a pharmaceutically acceptable salt or ester thereof, wherein:
$R_{a1}$, $R_{a1}'$, $R_{a2}$, $R_{a2}'$, $R_{b1}$, $R_{b1}'$, $R_{b2}$, and $R_{b2}'$ are hydrogen atom.

5. The compound according to claim 4 or a pharmaceutically acceptable salt or ester thereof, wherein:
R is phenyl of which $2^{nd}$ and $3^{rd}$ positions are substituted with the same or different halogen atoms or alternatively substituted with halogen atom and methyl substituted with one to three of the same or different halogen atoms, respectively.

6. The compound according to claim 5 or a pharmaceutically acceptable salt or ester thereof, wherein:
$W_{2a}$ is a hydrogen atom, halogen atom, cyano, methyl which may be substituted with one to three fluorine atoms.

7. A compound which is:
(a) 6-((4-(3-chloro-2-fluorobenzoyl)piperazin-1-yl)methyl)-N-thiazol-2-ylpyridin-2-amine,
(b) 6-((4-(2,3-dichlorobenzoyl)piperazin-1-yl)methyl)-N-thiazol-2-ylpyridin-2-amine,
(r) 6-((4-(3-chloro-2-fluorobenzoyl)piperazin-1-yl)methyl)-N-(5-chlorothiazol-2-yl)pyridin-2-amine, or
(s) 6-((4-(3-chloro-2-fluorobenzoyl)piperazin-1-yl)methyl)-N-(5-fluorothiazol-2-yl) pyridin-2-amine;
or a pharmaceutically acceptable salt or ester thereof.

8. A pharmaceutical composition comprising, together with pharmaceutically acceptable carrier or diluent, at least one compound according to claim 1 as active ingredient.

* * * * *